US012747212B2

(12) United States Patent
Collingwood et al.

(10) Patent No.: US 12,747,212 B2
(45) **Date of Patent: *Sep. 29, 2026**

(54) PYRIDINE DERIVATIVES AS TMEM16A MODULATORS FOR USE IN THE TREATMENT OF RESPIRATORY CONDITIONS

(71) Applicant: TMEM16A LIMITED, Welwyn Garden City (GB)

(72) Inventors: Stephen Collingwood, Brighton (GB); Craig Buxton, Abingdon (GB); Jonathan David Hargrave, Abingdon (GB); Peter Ingram, Abingdon (GB); Thomas Beauregard Schofield, Abingdon (GB); Abdul Shaikh, Abingdon (GB); Christopher Stimson, Abingdon (GB)

(73) Assignee: TMEM16A Limited, Welwyn Garden City (GB)

( * ) Notice: Subject to any disclaimer, the term of this patent is extended or adjusted under 35 U.S.C. 154(b) by 1064 days.

This patent is subject to a terminal disclaimer.

(21) Appl. No.: 17/581,504

(22) Filed: Jan. 21, 2022

(65) Prior Publication Data

US 2022/0235006 A1 Jul. 28, 2022

Related U.S. Application Data

(63) Continuation of application No. PCT/GB2020/051778, filed on Jul. 24, 2020.

(30) Foreign Application Priority Data

Jul. 24, 2019 (GB) ..................................... 1910607
Apr. 20, 2020 (GB) ..................................... 2005739

(51) Int. Cl.
*C07D 213/81* (2006.01)

(52) U.S. Cl.
CPC ................................. *C07D 213/81* (2013.01)

(58) Field of Classification Search
CPC .................................................. C07D 213/81
See application file for complete search history.

(56) References Cited

U.S. PATENT DOCUMENTS 11,364,246 B2 * 6/2022 Collingwood ..... A61K 31/5377
2020/0123128 A1 4/2020 Anderson et al.

FOREIGN PATENT DOCUMENTS

CL 2020001945 A1 1/2021
CL 2021003155 A1 7/2022
CL 2022000176 A1 9/2022
CN 111683926 A 9/2020
WO 2005/042524 A1 5/2005
WO 2018/195127 A1 10/2018
WO 2019/145726 A1 8/2019
WO WO-2021014166 A1 1/2021

OTHER PUBLICATIONS

Silverman, Richard B. “2.2 Lead Modification: Drug Design and Development.” The Organic Chemistry of Drug Design and Drug Action, Second ed., Elsevier Academic Press, Burlington , MA, 2004, pp. 29-34. (Year: 2004).*

Silverman, R. B., & Holladay, M. W. (2014). The Organic Chemistry of drug design and Drug Action. Academic Press. (Year: 2014).*

Accurso et al., Denufosol Tetrasodium in Patients with Cystic Fibrosis and Normal to Mildly Impaired Lung Function, Am J Respir Crit Care Med, 2011, 183(5):627-634.

Boucher, R. C., Evidence for airway surface dehydration as the initiating event in CF airway disease, J Intern Med., 2007, 261(1):5-16.

Caputo et al., TMEM16A, A Membrane Protein Associated with Calcium-Dependent Chloride Channel Activity, Science, Oct. 24, 2008, 322(5901):590-594.

De La Fuente et al., Small Molecule Screen Identifies Inhibitors of a Human Intestinal Calcium-Activated Chloride Channel, Mol Pharmacol, 2008, 73(3):758-768.

Gupta et al., Salts of Therapeutic Agents: Chemical, Physicochemical, and Biological Considerations, Molecules, 2018, vol. 23, 1719.

Kellerman et al., Denufosol: A review of studies with inhaled $P2Y_2$ agonists that led to Phase 3, Pulm Pharmacol Ther, 2008, 21(4):600-607.

Kunzelmann et al., Pharmacotherapy of the Ion Transport Defect in Cystic Fibrosis: Role of Purinergic Receptor Agonists and Other Potential Therapeutics, Am J Respir Med, 2003, 2(4):299-309.

Matsui et al., Evidence for Periciliary Liquid Layer Depletion, Not Abnormal Ion Composition, in the Pathogenesis of Cystic Fibrosis Airways Disease, Cell, Dec. 23, 1998, 95(7):1005-15.

Moss, Richard B., Pitfalls of Drug Development: Lessons Learned from Trials of Denufosol in Cystic Fibrosis, J Pediatr, Apr. 2013, 162(4):676-680.

(Continued)

*Primary Examiner* — Andrew D Kosar
*Assistant Examiner* — Connor K English
(74) *Attorney, Agent, or Firm* — Robert C. Hall

(57) ABSTRACT

Compounds of general formula (I), wherein $R^1$, $R^2$, $R^3$, $R^4$, $R^5$, $R^6$, $R^7$, $R^8$, $R^9$ and $R^{10}$ are as defined herein are useful for treating respiratory disease and other diseases and conditions modulated by TMEM16A.

(I)

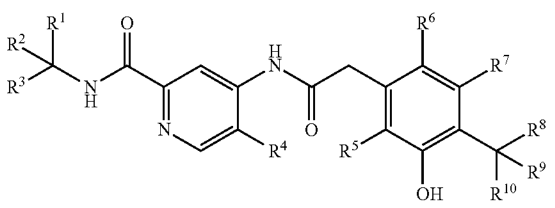

14 Claims, 1 Drawing Sheet

(56) References Cited

OTHER PUBLICATIONS

Pedemonte et al., Structure and function of TMEM16 proteins (anoctamins), Physiol Rev, 2014, 94(2):419-459.
Pezzulo et al., Reduced airway surface pH impairs bacterial killing in the porcine cystic fibrosis lung, Nature, Jul. 5, 2012, 487(7405):109-113.
Yang et al., TMEM16A confers receptor-activated calcium-dependent chloride conductance, Nature, Oct. 30, 2008, 455(7217):1210-1215.
International Search Report and Written Opinion received for PCT Application No. PCT/GB2020/051778, mailed on Oct. 19, 2020, 10 pages.
Namkung et al. "TMEM16A Inhibitors Reveal TMEM16A as a Minor Component of Calcium-activated Chloride Channel Conductance in Airway and Intestinal Epithelial Cells", *J. Biol. Chem.*, 2011, 286,2365-2374.

* cited by examiner

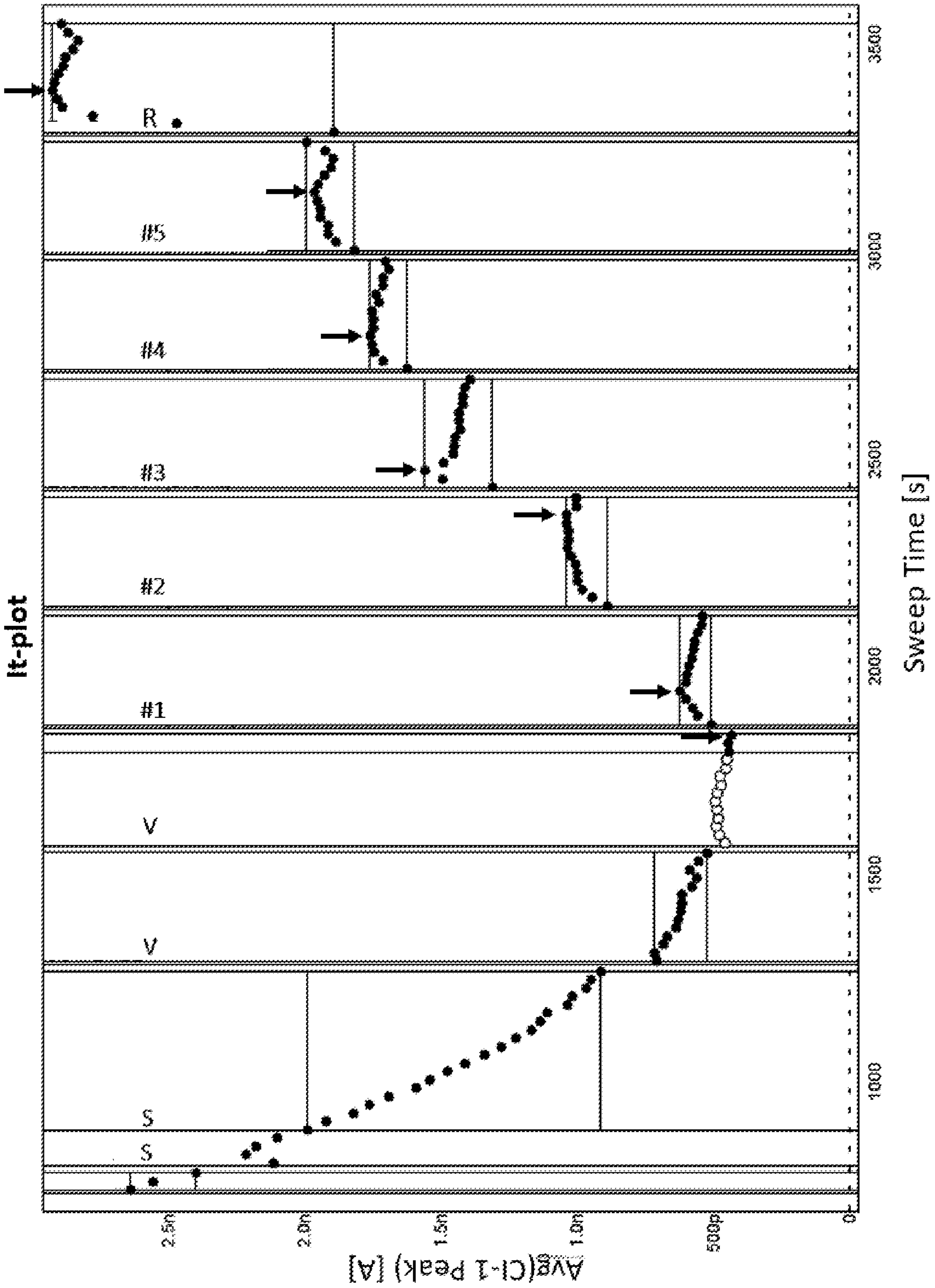
It-plot
Sweep Time [s]
Avg(Cl-1 Peak) [A]
1000
1500
2000
2500
3000
3500
0
500p
1.0n
1.5n
2.0n
2.5n
S
S
V
V
#1
#2
#3
#4
#5
R

PYRIDINE DERIVATIVES AS TMEM16A MODULATORS FOR USE IN THE TREATMENT OF RESPIRATORY CONDITIONS

This application is a continuation of the International Application No. PCT/GB2020/051778, filed Jul. 24, 2020, which claims the benefit of GB Application No. 1910607.9, filed Jul. 24, 2019 and GB Application No. 2005739.4, filed Apr. 20, 2020, which are incorporated herein by reference in their entirety for all purposes.

The present invention relates to novel compounds which have activity as positive modulators of the calcium-activated chloride channel (CaCC), TMEM16A. The invention also relates to methods of preparing the compounds and pharmaceutical compositions containing them as well as to the use of these compounds in treating diseases and conditions modulated by TMEM16A, particularly respiratory diseases and conditions.

BACKGROUND

Humans can inhale up to 12,000 L of air each day and with it comes the potential for airborne pathogens (such as bacteria, viruses and fungal spores) to enter the airways. To protect against these airborne pathogens, the lung has evolved innate defence mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% w/v solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates the ability of the airway to secrete fluid, the % solids can be increased to 15% which is believed to contribute towards the plugging of small airways and failure of mucus clearance. Strategies to increase the hydration of the airway mucus include either the stimulation of anions and thereby fluid secretion or the inhibition of $Na^+$ absorption. To this end, stimulating the activity of TMEM16A channels will increase anion secretion and therefore increase fluid accumulation in the airway mucosa, hydrate mucus and enhance mucus clearance mechanisms.

TMEM16A, also referred to as Anoctamin-1 (Ano1), is the molecular identity of calcium-activated chloride channels (Caputo et al, 2008; Yang et al, 2008). TMEM16A channels open in response to elevation of intracellular calcium levels and allow the bidirectional flux of chloride, bicarbonate and other anions across the cell membrane. Functionally TMEM16A channels have been proposed to modulate transepithelial ion transport, gastrointestinal peristalsis, nociception and cell migration/proliferation (Pedemonte & Galietta, 2014).

TMEM16A channels are expressed by the epithelial cells of different organs including the lungs, liver, kidney, pancreas and salivary glands. In the airway epithelium TMEM16A is expressed at high levels in mucus producing goblet cells, ciliated cells and in submucosal glands. Physiologically TMEM16A is activated by stimuli which mobilise intracellular calcium, particularly purinergic agonists (ATP, UTP), which are released by the respiratory epithelium in response to cyclical shear stress caused by breathing and other mechanical stimuli such as cough. In addition to increasing anion secretion leading to enhanced hydration of the airways, activation of TMEM16A plays an important role in bicarbonate secretion. Bicarbonate secretion is reported to be an important regulator of mucus properties and in controlling airway lumen pH and hence the activity of native antimicrobials such as defensins (Pezzulo et al, 2012).

Indirect modulation of TMEM16A, via elevation of intracellular calcium, has been clinically explored eg. denufosol (Kunzelmann & Mall, 2003). Although encouraging initial results were observed in small patient cohorts this approach did not deliver clinical benefit in larger patient cohorts (Accurso et al 2011; Kellerman et al 2008). This lack of clinical effect was ascribed to only a transient elevation in anion secretion, the result of a short half-life of denufosol on the surface of the epithelium and receptor/pathway desensitisation, and unwanted effects of elevating intracellular calcium such as increased release of mucus from goblet cells (Moss, 2013). Compounds which act directly upon TMEM16A to enhance channel opening at low levels of calcium elevation are expected to durably enhance anion secretion and mucociliary clearance in patients and improve innate defence. As TMEM16A activity is independent of CFTR function, TMEM16A positive modulators have the potential to deliver clinical benefit to all CF patients and non-CF respiratory diseases characterised by mucus congestion including chronic bronchitis and severe asthma.

TMEM16A modulation has been implicated as a therapy for dry mouth (xerostomia), resultant from salivary gland dysfunction in Sjorgen's syndrome and radiation therapy, dry eye, cholestasis and gastrointestinal motility disorders.

Our application, WO2019/145726 relates to compounds which are positive modulators of TMEM16A and which are therefore of use in the treatment of diseases and conditions in which modulation of TMEM16A plays a role, particularly respiratory diseases and conditions.

The present inventors have developed further compounds which are positive modulators of TMEM16A. Many of the compounds of the present invention have advantages over related compounds exemplified in WO2019/145726. These advantages include reduced lipophilicity (as represented by reduced log D values) and lower metabolic clearance, properties which lead to improved pharmacokinetics (PK) when the compounds are administered systemically, including orally. In particular, reduced lipophilicity leads to increased solubility in water. Several of the compounds of the present invention have either or both improved solubility and lower metabolic clearance than the compounds exemplified in WO2019/145726. This leads to advantages such as lower efficacious dose, longer half-life following administration or, in the case of oral administration, higher bioavailability.

SUMMARY OF THE INVENTION

In a first aspect of the present invention there is provided a compound of general formula (I) including all tautomeric forms, all enantiomers, isotopic variants, and salts and solvates thereof:

(I)

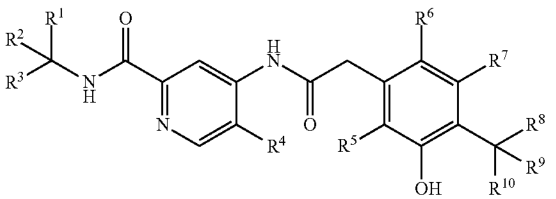

wherein:

$R^1$ is selected from methyl, fluoromethyl, difluoromethyl, trifluoromethyl, chlorodifluoromethyl, dichlorofluoromethyl, ethynyl and CN; or when $R^2$ and $R^3$ together with the carbon atom to which they are attached form a 4- to 6-membered carbocyclic ring substituted in addition to the $R^1$ group, with OH, halo, methyl or $CH_2OH$, $R^1$ may also be H; or when $R^2$ and $R^3$ together with the carbon atom to which they are attached form a 4- to 6-membered carbocyclic ring, which is unsubstituted apart from the $R^1$ group; $R^1$ may also be $CH_2OH$;

$R^2$ is selected from methyl and $CH_2OH$;

$R^3$ is selected from H and methyl; or $R^2$ and $R^3$ together with the carbon atom to which they are attached form a 3- to 10-membered carbocyclic or oxygen-containing heterocyclic ring system either of which is optionally substituted, in addition to the $R^1$ group, with one or more substituents selected from OH, halo, $C_{1-4}$ alkyl, $C_{1-4}$ alkyl substituted with one or more OH substituents, and $C_{1-4}$ haloalkyl; or $R^1$, $R^2$ and $R^3$ together with the carbon atom to which they are attached combine to form a 5- to 8-membered bridged carbocyclic or heterocyclic ring system optionally substituted with one or more substituents selected from OH, halo, $C_{1-4}$ alkyl and $C_{1-4}$ haloalkyl;

$R^4$ is H or halo;

each of $R^5$ and $R^7$ is independently selected from H, halo, $C_{1-3}$ alkyl and $C_{1-3}$ haloalkyl;

$R^6$ is selected from H, halo, CN and $C_{1-4}$ alkyl optionally substituted with one or more substituents selected from halo and OH;

$R^8$ is methyl or ethyl, either of which is optionally substituted with one or more halogen substituents;

$R^9$ is OH, $CH_2OH$ or methyl or ethyl, either of which is optionally substituted with one or more halogen substituents; or $R^8$ and $R^9$ together with the carbon atom to which they are attached form either a 3- to 6-membered cycloalkyl or oxygen-containing heterocyclic ring optionally substituted, in addition to the $R^{10}$ group, with one or more substituents selected from OH, F and $CH_2OH$; or an ethenyl group optionally substituted with one or two halogen substituents;

$R^{10}$ is selected from H, CN, OH, cycloalkyl optionally substituted with OH, and $C_{1-4}$ alkyl optionally substituted with one or more substituents selected from halo, OH and a 3- to 6-membered cycloalkyl or heterocyclic group, either of which is optionally substituted with OH; or $R^8$, $R^9$ and $R^{10}$ together with the carbon atom to which they are attached form a 5- to 8-membered fused or bridged carbocyclic ring system optionally substituted with one or more substituents selected from OH, F and $CH_2OH$;

provided that:

i. when $R^5$ and $R^7$ are H and $R^6$ is H or F, $R^1$, $R^2$, $R^3$, $R^8$, $R^9$ and $R^{10}$ are not all methyl; and ii. when $R^2$, $R^3$, $R^8$, $R^9$ and $R^{10}$ are all methyl, $R^5$, $R^6$ and $R^7$ are not all H; and iii. when $R^1$ is CN and $R^2$ and $R^3$ together with the carbon atom to which they are attached form a 3- to 10-membered oxygen-containing heterocyclic ring, $R^8$, $R^9$ and $R^{10}$ are not all methyl; and iv. $R^9$ and $R^{10}$ are not both OH.

Suitably there is provided a compound of general formula (I). There is also provided salts, such as pharmaceutically acceptable salts, of a compound of formula (I). There is also provided solvates, such as hydrates, or a compound of formula (I).

Since the compounds of general formula (I) are positive modulators of TMEM16A, they are useful for treating diseases and conditions in which modulation of TMEM16A plays a role, especially respiratory diseases and conditions.

DETAILED DESCRIPTION OF THE INVENTION

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All literature and patent documents referred to herein are incorporated by reference to the fullest extent possible.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

Salts and solvates (such as hydrates) of the compounds of general formula (I) are suitably pharmaceutically acceptable. Suitable pharmaceutically acceptable salts are well known to those of skill in the art and are described, for example by Gupta et al (2018). Some particularly suitable salts of the compounds of general formula (I) include basic addition salts such as sodium, potassium, calcium, aluminium, zinc, magnesium and other metal salts as well as choline, diethanolamine, ethanolamine, ethyl diamine and meglumine salts. Alternatively, acid addition salts may be formed, for example hydrochloride, mesylate, hydrobromide, sulphate, and fumarate salts. Salts of synthetic intermediates need not be pharmaceutically acceptable.

In the present specification, the term "$C_{1-4}$ alkyl" refers to a straight or branched fully saturated hydrocarbon group having from 1 to 4 carbon atoms. The term encompasses methyl, ethyl, n-propyl, isopropyl, n-butyl, s-butyl and t-butyl. Other alkyl groups, for example $C_{1-6}$ alkyl and $C_{1-3}$ alkyl are as defined above but contain the stated number of carbon atoms.

The term "3- to 10-membered carbocyclic" refers to a non-aromatic hydrocarbon ring system containing from 3 to 10 ring carbon atoms. The carbocyclic ring system may contain one or more carbon-carbon double bonds but preferably is a cycloalkyl group. The carbocyclic ring system may be a single ring or may contain two rings which may be fused or in a spiro arrangement or bridged, where carbon atoms in a bridge are included in the number of ring carbon atoms. Carbocyclic ring systems may contain other numbers of ring atoms as specified, for example 5 to 8 ring atoms or 3 to 6 ring atoms.

In the context of the present specification, the term "cycloalkyl" refers to a fully saturated carbocyclic ring system as defined above. Examples of cycloalkyl groups include cyclopropyl, cyclobutyl, cyclopentyl, cyclohexyl, as well as bridged cycloalkyl systems such as bicyclo[1.1.1]pentyl.

In the context of the present specification, the terms "3- to 10-membered heterocyclic" and "3- to 10-membered heterocyclyl" refer to a non-aromatic ring system containing 3 to 10 ring atoms, including at least one heteroatom selected from N, O and S. A heterocyclic ring system may contain one or more carbon-carbon double bonds but preferably is fully saturated. The heterocyclic ring system may be a single ring or may contain two or three rings which may be fused or in a spiro arrangement or bridged, where bridge atoms are included in the number of ring atoms. An oxygen-containing heterocyclic ring contains at least one oxygen as a ring atom and optionally one or two further heteroatoms selected from O, N and S. Examples of 3- to 6-membered heterocyclic ring systems include oxetanyl, tetrahydrofuranyl, tetrahydropyranyl, pyrrolidinyl, piperidinyl, morpholinyl, piperazinyl and 2-oxaspiro[3.3]heptan-6-yl. Heterocyclic ring systems may contain other numbers of ring atoms as specified, for example 5 to 8 ring atoms or 3 to 6 ring atoms.

The term "halogen" refers to fluorine, chlorine, bromine or iodine and the term "halo" to fluoro, chloro, bromo or iodo groups. Similarly, "halide" refers to fluoride, chloride, bromide or iodide.

The term "$C_{1-4}$ haloalkyl" as used herein refers to a $C_{1-4}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl. A fluoroalkyl group is a haloalkyl group in which halo is fluoro. Other haloalkyl groups, for example $C_{1-3}$ haloalkyl, are as defined above but contain the stated number of carbon atoms.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

In particularly suitable isotopic variants of the compounds of general formula (I), some or all methyl groups are replaced by $CD_3$. For example, one of, two of or all of $R^8$, $R^9$ and $R^{10}$ may be $CD_3$.

In some suitable compounds of general formula (I):

$R^1$ is selected from methyl, fluoromethyl, difluoromethyl, trifluoromethyl, chlorodifluoromethyl, dichlorofluoromethyl, ethynyl, and CN;

$R^2$ is selected from methyl and $CH_2OH$;

$R^3$ is selected from H and methyl; or $R^2$ and $R^3$ together with the carbon atom to which they are attached form a 3- to 10-membered carbocyclic or oxygen-containing heterocyclic ring system either of which is optionally substituted, in addition to the $R^1$ group, with one or more substituents selected from OH, halo, $C_{1-4}$ alkyl and $C_{1-4}$ haloalkyl; or $R^1$, $R^2$ and $R^3$ together with the carbon atom to which they are attached combine to form a 5- to 8-membered bridged carbocyclic or heterocyclic ring system optionally substituted with one or more substituents selected from OH, halo, $C_{1-4}$ alkyl and $C_{1-4}$ haloalkyl;

$R^4$ is H or halo;

each of $R^5$ and $R^7$ is independently selected from H, halo, $C_{1-3}$ alkyl and $C_{1-3}$ haloalkyl;

$R^6$ is selected from H, halo, CN and $C_{1-4}$ alkyl optionally substituted with one or more substituents selected from halo and OH;

$R^8$ is methyl or ethyl, either of which is optionally substituted with one or more halogen substituents;

$R^9$ is OH, $CH_2OH$ or methyl or ethyl, either of which is optionally substituted with one or more halogen substituents; or $R^8$ and $R^9$ together with the carbon atom to which they are attached form either a 3- to 6-membered cycloalkyl or oxygen-containing heterocyclic ring optionally substituted, in addition to the $R^{10}$ group, with one or more substituents selected from OH, F and $CH_2OH$; or an ethenyl group optionally substituted with one or two halogen substituents;

$R^{10}$ is selected from H, CN, OH, cycloalkyl optionally substituted with OH, and $C_{1-4}$ alkyl optionally substituted with one or more substituents selected from halo, OH and a 3- to 6-membered cycloalkyl or heterocyclic group, either of which is optionally substituted with OH; or $R^8$, $R^9$ and $R^{10}$ together with the carbon atom to which they are attached form a 5- to 8-membered fused or bridged carbocyclic ring system optionally substituted with one or more substituents selected from OH, F and $CH_2OH$;

provided that:

i. when $R^5$ and $R^7$ are H and $R^6$ is H or F, $R^1$, $R^2$, $R^3$, $R^8$, $R^9$ and $R^{10}$ are not all methyl; and ii. when $R^2$, $R^3$, $R^8$, $R^9$ and $R^{10}$ are all methyl, $R^5$, $R^6$ and $R^7$ are not all H; and iii. when $R^1$ is CN and $R^2$ and $R^3$ together with the carbon atom to which they are attached form a 3- to 10-membered oxygen-containing heterocyclic ring, $R^8$, $R^9$ and $R^{10}$ are not all methyl; and iv. $R^9$ and $R^{10}$ are not both OH.

In other suitable compounds of general formula (I):

$R^1$ is selected from methyl, fluoromethyl, difluoromethyl, trifluoromethyl, chlorodifluoromethyl, dichlorofluoromethyl, ethynyl and CN; or when $R^2$ and $R^3$ together with the carbon atom to which they are attached form a 4- to 6-membered carbocyclic ring substituted with OH, halo, methyl or $CH_2OH$, $R^1$ may also be H;

$R^2$ is selected from methyl and $CH_2OH$;

$R^3$ is selected from H and methyl; or $R^2$ and $R^3$ together with the carbon atom to which they are attached form a 3- to 10-membered carbocyclic or oxygen-containing heterocyclic ring system either of which is optionally substituted, in addition to the $R^1$ group, with one or more substituents selected from OH, halo, $C_{1-4}$ alkyl, $C_{1-4}$ alkyl substituted with one or more OH substituents, and $C_{1-4}$ haloalkyl; or $R^1$, $R^2$ and $R^3$ together with the carbon atom to which they are attached combine to form a 5- to 8-membered bridged carbocyclic or heterocyclic ring system optionally substituted with one or more substituents selected from OH, halo, $C_{1-4}$ alkyl and $C_{1-4}$ haloalkyl;

$R^4$ is H or halo;

each of $R^5$ and $R^7$ is independently selected from H, halo, $C_{1-3}$ alkyl and $C_{1-3}$ haloalkyl;

$R^6$ is selected from H, halo, CN and $C_{1-4}$ alkyl optionally substituted with one or more substituents selected from halo and OH;

$R^8$ is methyl or ethyl, either of which is optionally substituted with one or more halogen substituents;

$R^9$ is OH, $CH_2OH$ or methyl or ethyl, either of which is optionally substituted with one or more halogen substituents; or $R^8$ and $R^9$ together with the carbon atom to which they are attached form either a 3- to 6-membered cycloalkyl or oxygen-containing heterocyclic ring optionally substituted, in addition to the $R^{10}$ group, with one or more substituents selected from OH, F and $CH_2OH$; or an ethenyl group optionally substituted with one or two halogen substituents;

$R^{10}$ is selected from H, CN, OH, cycloalkyl optionally substituted with OH, and $C_{1-4}$ alkyl optionally substituted with one or more substituents selected from halo, OH and a 3- to 6-membered cycloalkyl or heterocyclic group, either of which is optionally substituted with OH; or $R^8$, $R^9$ and $R^{10}$ together with the carbon atom to which they are attached form a 5- to 8-membered fused or bridged carbocyclic ring system optionally substituted with one or more substituents selected from OH, F and $CH_2OH$;

provided that:

i. when $R^5$ and $R^7$ are H and $R^6$ is H or F, $R^1$, $R^2$, $R^3$, $R^8$, $R^9$ and $R^{10}$ are not all methyl; and ii. when $R^2$, $R^3$, $R^8$, $R^9$ and $R^{10}$ are all methyl, $R^5$, $R^6$ and $R^7$ are not all H; and iii. when $R^1$ is CN and $R^2$ and $R^3$ together with the carbon atom to which they are attached form a 3- to 10-membered oxygen-containing heterocyclic ring, $R^8$, $R^9$ and $R^{10}$ are not all methyl; and iv. $R^9$ and $R^{10}$ are not both OH.

In some compounds of general formula (I) either:

$R^8$ and $R^9$ together with the carbon atom to which they are attached form a 3- to 6-membered cycloalkyl or oxygen-containing heterocyclic ring substituted, in addition to the $R^{10}$ group, with one or more $CH_2OH$ substituents and optionally with one or more further substituents selected from OH and F; or $R^8$ and $R^9$ together with the carbon atom to which they are attached form a 3- to 6-membered cycloalkyl or oxygen-containing heterocyclic ring optionally substituted, in addition to the $R^{10}$ group, with one or more substituents selected from OH and F; and $R^{10}$ is CN or $C_{1-4}$ alkyl substituted with one or more substituents selected from OH, a 3- to 6-membered cycloalkyl group optionally substituted with OH and a 3- to 6-membered heterocyclic group optionally substituted with OH; or $R^8$ and $R^9$ together with the carbon atom to which they are attached form an ethenyl group optionally substituted with one or two halogen substituents; or $R^8$, $R^9$ and $R^{10}$ together with the carbon atom to which they are attached form a 5- to 8-membered fused or bridged carbocyclic ring system substituted with one or more $CH_2OH$ substituents and optionally with one or more further substituents selected from OH and F.

In these compounds, more suitably either:

$R^8$ and $R^9$ together with the carbon atom to which they are attached form a 3- to 6-membered cycloalkyl or oxygen-containing heterocyclic ring system which is unsubstituted except for the $R^{10}$ group; and $R^{10}$ is selected from CN and $CH_2OH$; or $R^8$, $R^9$ and $R^{10}$ together with the carbon atom to which they are attached form a 5- to 8-membered fused or bridged carbocyclic ring system substituted with $CH_2OH$.

In some compounds of general formula (I):

$R^8$ is methyl or ethyl, either of which is optionally substituted with one or more halogen substituents; and $R^9$ is OH, $CH_2OH$ or methyl or ethyl, either of which is optionally substituted with one or more halogen substituents; or $R^8$ and $R^9$ together with the carbon atom to which they are attached form a 3- to 6-membered cycloalkyl or oxygen-containing heterocyclic ring optionally substituted, in addition to the $R^{10}$ group, with one or more substituents selected from OH and F, and $R^{10}$ is H, OH or $C_{1-4}$ alkyl optionally substituted with one or more halo substituents; or $R^8$, $R^9$ and $R^{10}$ together with the carbon atom to which they are attached form a 5- to 8-membered fused or bridged carbocyclic ring system optionally substituted with one or more substituents selected from OH and F.

In some more suitable compounds of this type:

$R^8$ is methyl or ethyl, $R^9$ is OH or $CH_2OH$ and $R^{10}$ is methyl or ethyl. More suitably, $R^8$ is methyl, $R^9$ OH or $CH_2OH$ and $R^{10}$ is methyl or ethyl. Still more suitably either $R^8$ is methyl, $R^9$ is OH, and $R^{10}$ is methyl or ethyl; or $R^8$ is methyl, $R^9$ is $CH_2OH$ and $R^{10}$ is methyl.

Alternatively, $R^8$ is methyl or ethyl, $R^9$ is methyl or ethyl and $R^{10}$ is OH or $C_{1-4}$ alkyl substituted with OH. More suitably, $R^8$ is methyl, $R^9$ is methyl or ethyl and $R^{10}$ is OH or $CH_2CH_2OH$. Still more suitably either $R^8$ is methyl, $R^9$ is methyl or ethyl, and $R^{10}$ is OH; or $R^8$ is methyl, $R^9$ is methyl and $R^{10}$ is $CH_2OH$.

In other more suitable compounds of this type, $R^8$ and $R^9$ together with the carbon atom to which they are attached form a 3- to 6-membered cycloalkyl ring, which is unsubstituted except for the $R^{10}$ substituent; and $R^{10}$ is OH or $CH_2OH$. Still more suitably, $R^8$ and $R^9$ together with the carbon atom to which they are attached form a cyclopropyl or cyclobutyl ring, which is unsubstituted except for the $R^{10}$ substituent; and $R^{10}$ is $CH_2OH$.

In other more suitable compounds of this type, $R^8$, $R^9$ and $R^{10}$ are all methyl.

In some compounds of general formula (I), $R^1$, $R^2$ and $R^3$ are not all methyl.

In some compounds of general formula (I), $R^8$, $R^9$ and $R^{10}$ are not all methyl.

In some compounds of general formula (I), $R^1$, $R^2$, $R^3$, $R^8$, $R^9$ and $R^{10}$ are not all methyl Suitably, in the compounds of general formula (I), $R^1$ is methyl, difluoromethyl, trifluoromethyl, ethynyl or CN.

In some compounds of general formula (I), $R^1$ is methyl.

In other compounds of general formula (I), $R^1$ is ethynyl.

In some more suitable compounds of general formula (I), $R^1$ is difluoromethyl or trifluoromethyl, especially trifluoromethyl.

In other more suitable compounds of general formula (I), $R^1$ is CN.

In some suitable compounds of general formula (I), $R^2$ is methyl.

In other compounds of general formula (I), $R^2$ is $CH_2OH$.

In compounds of general formula (I) where $R^2$ is methyl or $CH_2OH$, $R^3$ is H or methyl.

In some such compounds, $R^3$ is H. However, more suitably, $R^3$ is methyl.

In some suitable compounds of general formula (I), $R^2$ is methyl and $R^3$ is H. In some suitable compounds of general formula (I), $R^2$ is methyl and $R^3$ is methyl.

Alternatively, as described above, $R^2$ and $R^3$ together with the carbon atom to which they are attached form a 3- to 10-membered carbocyclic or oxygen-containing heterocyclic ring system, optionally substituted as described above. In some suitable compounds of general formula (I), the ring system is a 3- to 6-membered cycloalkyl or oxygen-containing heterocyclic ring. In this case, the ring may be a cycloalkyl ring, for example cyclopropyl, cyclobutyl or cyclopentyl and especially cyclopropyl. Alternatively, the ring may be a fully saturated 3- to 6-membered oxygen-containing heterocyclic ring, for example a tetrahydropyran, tetrahydrofuran or oxetane ring. The 3- to 6-membered cycloalkyl or oxygen-containing heterocyclic ring may be substituted, in addition to $R^1$, with one or more substituents selected from OH, halo, $C_{1-4}$ alkyl and $C_{1-4}$ haloalkyl, more suitably OH, halo, methyl, difluoromethyl or trifluoromethyl, still more suitably OH and halo, for example OH and fluoro.

Suitably, when $R^2$ and $R^3$ form a ring system of this type, $R^1$ is H, methyl, trifluoromethyl, difluoromethyl or CN, more suitably methyl, difluoromethyl, trifluoromethyl or CN, still more suitably trifluoromethyl or CN, and especially trifluoromethyl. The ring system formed by $R^2$ and $R^3$ together with the carbon atom to which they are attached is suitably unsubstituted apart from the group $R^1$.

In compounds of general formula (I) in which $R^1$ is H and $R^2$ and $R^3$ together with the carbon atom to which they are attached form a 4- to 6-membered carbocyclic ring substituted with OH, halo, methyl or $CH_2OH$, a preferred substituent for the 4- to 6-membered carbocyclic ring is OH. Suitably, the ring is a cyclopentyl ring.

In some suitable compounds, $R^2$ and $R^3$ together with the carbon atom to which they are attached form a 4- to 6-membered carbocyclic ring, which is unsubstituted apart from the $R^1$ group.

In some suitable compounds of this type, $R^1$ is $CH_2OH$. In this case, $R^2$ and $R^3$ together with the carbon atom to which they are attached suitably form a cyclobutyl or cyclopentyl ring, most suitably a cyclobutyl ring which is unsubstituted apart from the $R^1$ group.

In some particularly suitable compounds, $R^1$ is trifluoromethyl; and $R^2$ and $R^3$ together with the carbon atom to which they are attached form a cyclopropyl ring which is unsubstituted except for $R^1$.

In some suitable compounds of general formula (I), $R^1$, $R^2$ and $R^3$ together with the carbon atom to which they are attached combine to form a 5- to 8-membered bridged carbocyclic or heterocyclic ring system optionally substituted with one or more substituents selected from OH, halo, $C_{1-4}$ alkyl and $C_{1-4}$ haloalkyl.

In some suitable compounds $R^4$ is H or halo such as F. In particularly suitable compounds, $R^4$ is H.

In some suitable compounds, each of $R^5$ and $R^7$ is H.

In suitable compounds of general formula (I), $R^6$ is selected from H, halo, CN and methyl optionally substituted with one or more substituents selected from halo and OH. More suitably, $R^6$ is H, halo, CN, $CH_3$, $CF_3$, $CHF_2$, $CH_2F$ or $CH_2OH$, still more suitably halo or methyl and particularly halo such as fluoro or chloro.

In suitable compounds of general formula (I), $R^4$ is H; and/or each of $R^5$ and $R^7$ is H; and/or $R^6$ is H, halo, CN, $CH_3$, $CF_3$, $CHF_2$, $CH_2F$ or $CH_2OH$. Suitably, $R^4$ is H and each of $R^5$ and $R^7$ is H. Suitably, $R^4$ is H and $R^6$ is H, halo, CN, $CH_3$, $CF_3$, $CHF_2$, $CH_2F$ or $CH_2OH$. Suitably, each of $R^5$ and $R^7$ is H and $R^6$ is H, halo, CN, $CH_3$, $CF_3$, $CHF_2$, $CH_2F$ or $CH_2OH$. Suitably, $R^4$ is H, each of $R^5$ and $R^7$ is H, and $R^6$ is H, halo, CN, $CH_3$, $CF_3$, $CHF_2$, $CH_2F$ or $CH_2OH$.

In some suitable compounds of general formula (I), $R^8$ is methyl or ethyl, especially methyl. In some suitable compounds of the present invention, $R^8$ is methyl or ethyl, especially methyl, and $R^9$ is methyl, $CH_2OH$ or OH. In particular, $R^8$ is methyl and $R^9$ is OH In other suitable compounds of the invention $R^8$ and $R^9$ are each independently methyl or ethyl. More suitably, one of $R^8$ and $R^9$ is methyl and the other of $R^8$ and $R^9$ is methyl or ethyl.

Alternatively, when $R^8$ and $R^9$ together with the carbon atom to which they are attached form a 3- to 6-membered cycloalkyl or oxygen-containing heterocyclic ring, the ring is suitably unsubstituted except for the $R^{10}$ moiety. The ring formed by $R^8$ and $R^9$ together with the carbon atom to which they are attached is suitably selected from cycloalkyl rings and heterocyclic rings having a single ring oxygen atom, for example cyclopropyl, cyclobutyl, tetrahydropyranyl, tetrahydrofuranyl and oxetanyl.

$R^{10}$ is suitably selected from H, CN, cyclopropyl, cyclobutyl and methyl or ethyl, wherein the methyl or ethyl is unsubstituted or is substituted with one or more substituents selected from fluoro, OH and a 3- to 6-membered cycloalkyl or heterocyclyl group.

More suitably, $R^{10}$ is CN, cyclopropyl, cyclobutyl, unsubstituted methyl or methyl substituted with one or more substituents selected from fluoro, OH and a 3- to 6-membered cycloalkyl or heterocyclyl group.

When $R^{10}$ is methyl or ethyl substituted with a heterocyclic group, it is suitably a 5- or 6-membered nitrogen containing heterocycle optionally containing one or more additional heteroatom and bound to the carbon atom in the methyl or ethyl group via a ring nitrogen atom. Examples of such heterocyclic groups include morpholinyl, pyrrolidinyl, piperidinyl and piperazinyl.

In particularly suitable compounds of general formula (I), $R^{10}$ is CN, methyl, $CF_3$, $CH_2OH$, cyclopropylmethyl or morpholinylmethyl, for example morpholin-4-ylmethyl, and especially $CH_2OH$.

When $R^8$ is methyl or ethyl and $R^9$ is OH or $CH_2OH$, $R^{10}$ is suitably methyl or ethyl.

When $R^8$ is methyl or ethyl, $R^9$ is methyl or ethyl, $R^{10}$ is suitably OH or $C_{1-4}$ alkyl substituted with OH; more suitably OH or $CH_2OH$.

When $R^8$ and $R^9$ together with the carbon atom to which they are attached form a 3- to 6-membered cycloalkyl or oxygen-containing heterocyclic ring, $R^{10}$ is more suitably methyl, ethyl, $CH_2OH$, $CH_2CH_2OH$, trifluoromethyl or CN.

In some particularly suitable compounds, $R^{10}$ is $CH_2OH$

In some compounds of general formula (I), $R^8$ and $R^9$ together with the carbon atom to which they are attached form a cyclopropyl, cyclobutyl, cyclopentyl or oxetanyl ring, especially a cyclopropyl, cyclobutyl or oxetanyl ring, which may be unsubstituted except for the $R^{10}$ group or may have a single $CH_2OH$ substituent in addition to the $R^{10}$ group; and $R^{10}$ is methyl, $CH_2OH$, trifluoromethyl or cyano.

In some such compounds, $R^{10}$ is $CH_2OH$ or cyano.

In some such compounds, the ring is unsubstituted except for the $R^{10}$ group and $R^{10}$ is $CH_2OH$ or cyano, especially $CH_2OH$.

In other such compounds, the ring is unsubstituted except for the $R^{10}$ group and $R^{10}$ is methyl or trifluoromethyl.

When $R^8$, $R^9$ and $R^{10}$ together with the carbon atom to which they are attached form an unsubstituted 5- to 8-membered fused or bridged carbocyclic ring system, it is suitably a bridged ring system such as bicyclo[1.1.1]pentane, bicyclo[2.1.1]hexane or bicyclo[2.2.1]heptane. Suitably, the ring is unsubstituted or is substituted with a single $CH_2OH$ substituent.

Specific examples of compounds of general formula (I) include the following:

4-[[2-(4-tert-Butyl-2-fluoro-5-hydroxy-phenyl)acetyl]amino]-N-(1-methylcyclopropyl)pyridine-2-carboxamide (Compound 1);

4-[[2-(4-tert-Butyl-2-fluoro-5-hydroxy-phenyl)acetyl]amino]-N-(1,1-dimethylprop-2-ynyl)pyridine-2-carboxamide (Compound 1.1);

4-[[2-(4-tert-Butyl-2-fluoro-5-hydroxy-phenyl)acetyl]amino]-N-(1-ethynylcyclopentyl)pyridine-2-carboxamide (Compound 1.2);

4-[[2-(4-tert-Butyl-2-fluoro-5-hydroxy-phenyl)acetyl]amino]-N-(1-cyanoethyl)pyridine-2-carboxamide (Compound 1.3);

4-[[2-(4-tert-Butyl-2-fluoro-5-hydroxy-phenyl)acetyl]amino]-N-[(1R)-1-cyanoethyl]pyridine-2-carboxamide (Compound 1.3a/b);

4-[[2-(4-tert-butyl-2-fluoro-5-hydroxy-phenyl)acetyl]amino]-N-[(1S)-1-cyanoethyl]pyridine-2-carboxamide (Compound 1.3 a/b);

4-[[2-(4-tert-Butyl-2-fluoro-5-hydroxy-phenyl)acetyl]amino]-N-(1-cyano-1-methyl-ethyl)pyridine-2-carboxamide (Compound 1.4);

4-[[2-(4-tert-Butyl-2-fluoro-5-hydroxy-phenyl)acetyl]amino]-N-(1-cyanocyclopropyl)pyridine-2-carboxamide (Compound 1.5);

4-[[2-(4-tert-Butyl-2-fluoro-5-hydroxy-phenyl)acetyl]amino]-N-(1-cyano-2-hydroxy-1-methyl-ethyl)pyridine-2-carboxamide (Compound 1.6);

4-[[2-(4-tert-Butyl-2-fluoro-5-hydroxy-phenyl)acetyl]amino]-N-[(1R)-1-cyano-2-hydroxy-1-methyl-ethyl]pyridine-2-carboxamide (Compound 1.6 a/b);

4-[[2-(4-tert-butyl-2-fluoro-5-hydroxy-phenyl)acetyl]amino]-N-[(1S)-1-cyano-2-hydroxy-1-methyl-ethyl]pyridine-2-carboxamide (Compound 1.6 a/b);

4-[[2-(4-tert-Butyl-2-fluoro-5-hydroxy-phenyl)acetyl]amino]-N-[1-(trifluoromethyl)cyclopropyl]pyridine-2-carboxamide (Compound 1.7);

4-[[2-[2-Fluoro-5-hydroxy-4-(1-hydroxy-1-methyl-ethyl)phenyl]acetyl]amino]-N-[1-(trifluoromethyl)cyclopropyl]pyridine-2-carboxamide (Compound 2);

N-(1-Cyano-1-methyl-ethyl)-4-[[2-[2-fluoro-5-hydroxy-4-(1-hydroxy-1-methyl-ethyl)phenyl]acetyl]amino]pyridine-2-carboxamide (Compound 2.1);

N-tert-Butyl-4-[[2-[4-(1-cyano-1-methyl-ethyl)-2-fluoro-5-hydroxy-phenyl]acetyl]amino]pyridine-2-carboxamide (Compound 2.2);

4-[[2-[4-(1-Cyano-1-methyl-ethyl)-2-fluoro-5-hydroxy-phenyl]acetyl]amino]-N-[1-(trifluoromethyl)cyclopropyl]pyridine-2-carboxamide (Compound 2.3);

N-tert-Butyl-4-[[2-[4-(1-cyanocyclopropyl)-2-fluoro-5-hydroxy-phenyl]acetyl] amino]pyridine-2-carboxamide (Compound 2.4);

N-(1-Cyano-1-methyl-ethyl)-4-[[2-[4-(1,1-dimethyl-2-morpholino-ethyl)-2-fluoro-5-hydroxy-phenyl]acetyl]amino]pyridine-2-carboxamide (Compound 2.5);

4-[[2-[2-fluoro-5-hydroxy-4-(2-hydroxy-1,1-dimethyl-ethyl)phenyl]acetyl]amino]-N-[1-(trifluoromethyl)cyclopropyl]pyridine-2-carboxamide (Compound 2.6);

N-(1-Cyano-1-methyl-ethyl)-4-[[2-[2-fluoro-5-hydroxy-4-(2,2,2-trifluoro-1-hydroxy-1-methyl-ethyl)phenyl]acetyl]amino]pyridine-2-carboxamide (Compound 2.7);

4-[[2-[4-(1-Cyclopropyl-1-hydroxy-ethyl)-2-fluoro-5-hydroxy-phenyl]acetyl]amino]-N-[1-(trifluoromethyl)cyclopropyl]pyridine-2-carboxamide (Compound 2.8);

4-[[2-[4-(4-Cyanotetrahydropyran-4-yl)-2-fluoro-5-hydroxy-phenyl]acetyl]amino]-N-[1-(trifluoromethyl)cyclopropyl]pyridine-2-carboxamide (Compound 2.9);

4-[[2-[2-Fluoro-5-hydroxy-4-[2-(trifluoromethyl)oxetan-2-yl]phenyl]acetyl]amino]-N-[1-(trifluoromethyl)cyclopropyl]pyridine-2-carboxamide (Compound 2.10);

4-[[2-[2-Fluoro-5-hydroxy-4-(1-hydroxy-1-methyl-propyl)phenyl]acetyl]amino]-N-[1-(trifluoromethyl)cyclopropyl]pyridine-2-carboxamide (Compound 2.11);

4-[[2-[2-Fluoro-5-hydroxy-4-[(1S)-1-hydroxy-1-methyl-propyl]phenyl]acetyl]amino]-N-[1-(trifluoromethyl)cyclopropyl]pyridine-2-carboxamide (Compound 2.11 a/b);

4-[[2-[2-fluoro-5-hydroxy-4-[(1R)-1-hydroxy-1-methyl-propyl]phenyl]acetyl]amino]-N-[1-(trifluoromethyl)cyclopropyl] pyridine-2-carboxamide (Compound 2.11 a/b);

4-[[2-[5-Hydroxy-4-(1-hydroxy-1-methyl-ethyl)-2-methyl-phenyl]acetyl]amino]-N-[1-(trifluoromethyl)cyclopropyl]pyridine-2-carboxamide (Compound 2.12);

4-[[2-[2-Fluoro-5-hydroxy-4-[1-(hydroxymethyl)cyclobutyl]phenyl]acetyl]amino]-N-[1-(trifluoromethyl)cyclopropyl]pyridine-2-carboxamide (Compound 2.13);

N-(1-Cyano-1-methyl-ethyl)-4-[[2-[2-fluoro-5-hydroxy-4-[2-(trifluoromethyl)oxetan-2-yl]phenyl]acetyl]amino]pyridine-2-carboxamide (Compound 2.14);

4-[[2-[2-Fluoro-5-hydroxy-4-[4-(hydroxymethyl)tetrahydropyran-4-yl]phenyl]acetyl] amino]-N-[1-(trifluoromethyl)cyclopropyl]pyridine-2-carboxamide (Compound 2.15);

4-[[2-[2-Fluoro-5-hydroxy-4-[1-(hydroxymethyl)cyclopropyl]phenyl]acetyl]amino]-N-[1-(trifluoromethyl)cyclopropyl]pyridine-2-carboxamide (Compound 2.16);

4-[[2-(4-tert-Butyl-2-fluoro-5-hydroxy-phenyl)acetyl]amino]-N-(1-cyano-1-methyl-ethyl)-5-fluoro-pyridine-2-carboxamide (Compound 3);

N-(1-Cyanocyclopropyl)-4-[[2-[2-deuterio-6-fluoro-3-hydroxy-4-[2,2,2-trideuterio-1,1-bis(trideuteriomethyl)ethyl]phenyl]acetyl]amino]pyridine-2-carboxamide (Compound 4);

N-(1-Cyano-1-methyl-ethyl)-4-[[2-[2-fluoro-5-hydroxy-4-(1-methylcyclo butyl)phenyl]acetyl]amino]pyridine-2-carboxamide (Compound 5);

N-tert-Butyl-4-[[2-(4-tert-butyl-5-hydroxy-2-isopropyl-phenyl)acetyl]amino]pyridine-2-carboxamide (Compound 6);

N-tert-Butyl-4-[[2-[2-fluoro-5-hydroxy-4-(1-hydroxy-1-methyl-ethyl)phenyl] acetyl]amino]pyridine-2-carboxamide (Compound 7);
4-[[2-(2-Fluoro-5-hydroxy-4-isopropenyl-phenyl)acetyl]amino]-N-[1-(trifluoromethyl) cyclopropyl]pyridine-2-carboxamide (Compound 7.1);
N-tert-Butyl-4-[[2-[2-fluoro-5-hydroxy-4-(1-methylcyclopropyl)phenyl] acetyl]amino]pyridine-2-carboxamide (Compound 8);
N-(1-Cyanocyclopropyl)-4-[[2-[2-fluoro-5-hydroxy-4-[1-(trifluoromethyl) cyclopropyl]phenyl]acetyl]amino]pyridine-2-carboxamide (Compound 9);
4-[[2-(4-tert-Butyl-2-chloro-5-hydroxy-phenyl)acetyl]amino]-N-(1-cyano-1-methyl-ethyl)pyridine-2-carboxamide (Compound 10);
4-[[2-(4-tert-Butyl-2-chloro-5-hydroxy-phenyl)acetyl]amino]-N-[1-(trifluoromethyl) cyclopropyl]pyridine-2-carboxamide (Compound 10.1);
4-[[2-(4-tert-Butyl-2-chloro-5-hydroxy-phenyl)acetyl]amino]-N-(1-cyanocyclopropyl) pyridine-2-carboxamide (Compound 10.2);
4-[[2-[2-Fluoro-5-hydroxy-4-(3-hydroxy-1,1-dimethyl-propyl)phenyl]acetyl]amino]-N-[1-(trifluoromethyl)cyclopropyl]pyridine-2-carboxamide (Compound 11);
N-(4-Cyanotetrahydropyran-4-yl)-4-[[2-[2-fluoro-5-hydroxy-4-(2-hydroxy-1,1-dimethyl-ethyl)phenyl]acetyl]amino]pyridine-2-carboxamide (Compound 12);
4-[[2-[2-Fluoro-5-hydroxy-4-(2-hydroxy-1,1-dimethyl-ethyl)phenyl]acetyl]amino]-N-[3-(trifluoromethyl) oxetan-3-yl]pyridine-2-carboxamide (Compound 12.1);
4-[[2-[2-Fluoro-5-hydroxy-4-(2-hydroxy-1,1-dimethyl-ethyl)phenyl]acetyl]amino]-N-[(1S,2S)-2-hydroxycyclopentyl]pyridine-2-carboxamide (Compound 12.2);
4-[[2-[2-Fluoro-5-hydroxy-4-(2-hydroxy-1,1-dimethyl-ethyl)phenyl]acetyl]amino]-N-(2-hydroxy-1,1-dimethyl-ethyl)pyridine-2-carboxamide (Compound 12.3);
4-[[2-[2-Fluoro-5-hydroxy-4-(2-hydroxy-1,1-dimethyl-ethyl)phenyl]acetyl]amino]-N-[1-(hydroxymethyl)cyclobutyl]pyridine-2-carboxamide (Compound 12.4);
4-[[2-[2-Fluoro-5-hydroxy-4-(4-hydroxytetrahydropyran-4-yl)phenyl]acetyl]amino]-N-[1-(trifluoromethyl)cyclopropyl]pyridine-2-carboxamide (Compound 13);
4-[[2-[2-Chloro-5-hydroxy-4-(2-hydroxy-1,1-dimethyl-ethyl)phenyl]acetyl]amino]-N-[1-(trifluoromethyl)cyclopropyl]pyridine-2-carboxamide (Compound 14);
4-[[2-[5-Hydroxy-4-(2-hydroxy-1,1-dimethyl-ethyl)-2-methyl-phenyl]acetyl]amino]-N-[1-(trifluoromethyl)cyclopropyl]pyridine-2-carboxamide (Compound 14.1);
N-(3,3-Difluoro-1-methyl-cyclobutyl)-4-[[2-[2-fluoro-5-hydroxy-4-(2-hydroxy-1,1-dimethyl-ethyl)phenyl]acetyl]amino]pyridine-2-carboxamide (Compound 15);
4-[[2-[2-Chloro-5-hydroxy-4-(2-hydroxy-1,1-dimethyl-ethyl)phenyl]acetyl]amino]-N-(1,1-dimethylprop-2-ynyl) pyridine-2-carboxamide (Compound 15.1);
4-[[2-[2-Chloro-5-hydroxy-4-(2-hydroxy-1,1-dimethyl-ethyl)phenyl]acetyl]amino]-N-(3,3-difluoro-1-methyl-cyclobutyl)pyridine-2-carboxamide (Compound 15.2);
4-[[2-[2-Chloro-5-hydroxy-4-(2-hydroxy-1,1-dimethyl-ethyl)phenyl]acetyl]amino]-N-[1-(difluoromethyl)cyclopropyl]pyridine-2-carboxamide (Compound 15.3);
N-[1-(Difluoromethyl)cyclopropyl]-4-[[2-[2-fluoro-5-hydroxy-4-(2-hydroxy-1,1-dimethyl-ethyl)phenyl]acetyl]amino]pyridine-2-carboxamide (Compound 15.4);
N-(1,1-Dimethylprop-2-ynyl)-4-[[2-[2-fluoro-5-hydroxy-4-(2-hydroxy-1,1-dimethyl-ethyl)phenyl]acetyl]amino]pyridine-2-carboxamide (Compound 16);
4-[[2-[2-Fluoro-5-hydroxy-4-(2-hydroxy-1,1-dimethyl-ethyl)phenyl]acetyl]amino]-N-(4-methyltetrahydropyran-4-yl)pyridine-2-carboxamide (Compound 16.1);
N-(1-Cyano-1-methyl-ethyl)-4-[[2-[2-fluoro-5-hydroxy-4-(2-hydroxy-1,1-dimethyl-ethyl)phenyl]acetyl]amino]pyridine-2-carboxamide (Compound 16.2);
4-[[2-[2-Fluoro-5-hydroxy-4-(2-hydroxy-1-methyl-ethyl)phenyl]acetyl]amino]-N-(4-methyltetrahydropyran-4-yl)pyridine-2-carboxamide (Compound 16.3);
4-[[2-[2,6-Difluoro-3-hydroxy-4-(2-hydroxy-1,1-dimethyl-ethyl)phenyl]acetyl]amino]-N-[1-(trifluoromethyl)cyclopropyl]pyridine-2-carboxamide (Compound 16.4);
4-[[2-[2-Fluoro-5-hydroxy-4-[2,2,2-trifluoro-1-(hydroxymethyl)ethyl]phenyl]acetyl]amino]-N-[1-(trifluoromethyl)cyclopropyl]pyridine-2-carboxamide (Compound 17);
4-[[2-[2-Chloro-6-fluoro-3-hydroxy-4-(1-hydroxy-1-methyl-ethyl)phenyl]acetyl]amino]-N-[1-(trifluoromethyl)cyclopropyl]pyridine-2-carboxamide (Compound 18);
4-[[2-[2-Chloro-5-hydroxy-4-(1-hydroxy-1-methyl-ethyl)phenyl]acetyl]amino]-N-[1-(trifluoromethyl)cyclopropyl]pyridine-2-carboxamide (Compound 19);
4-[[2-[2-Fluoro-5-hydroxy-4-(2-hydroxy-1-methyl-ethyl)phenyl]acetyl]amino]-N-[1-(trifluoromethyl)cyclopropyl]pyridine-2-carboxamide (Compound 20);
4-[[2-[2-Fluoro-5-hydroxy-4-[(1S)-2-hydroxy-1-methyl-ethyl]phenyl]acetyl]amino]-N-[1-(trifluoromethyl)cyclopropyl]pyridine-2-carboxamide (Compound 20a/b);
4-[[2-[2-fluoro-5-hydroxy-4-[(1R)-2-hydroxy-1-methyl-ethyl]phenyl]acetyl]amino]-N-[1-(trifluoromethyl)cyclopropyl] pyridine-2-carboxamide (Compound 20a/b);

and salts and solvates of the above.

Compounds of general formula (I) may be prepared by reacting a compound of general formula (II):

(II)

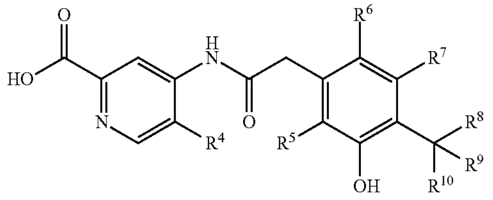

wherein $R^4$, $R^5$, $R^6$, $R^7$, $R^8$, $R^9$ and $R^{10}$ are as defined for general formula (I); with a compound of general formula (III):

(III)

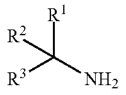

wherein $R^1$, $R^2$ and $R^3$ are as defined in general formula (I).

Suitably, the reaction is conducted in the presence of a coupling reagent and under basic conditions, for example in the presence of an amine such as diisopropylethylamine (DIPEA) and in an organic solvent such as DMF.

Suitable coupling reagents include known peptide coupling agents such as O-(Benzotriazol-1-yl)-N,N,N',N'-tetramethyluronium hexafluorophosphate (HBTU), O-(Benzotriazol-1-yl)-N,N,N',N'-tetramethyluronium tetrafluoroborate (TBTU), O-(7-Azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP) carbodiimides such as 1-ethyl-3-(3-dimethylaminopropyl)carbodiimide (EDCI) and triazoles such as 1-hydroxy-7-azabenzotriazole (HOAt) or hydroxybenzotriazole (HOBt).

Suitably, when these coupling agents are used, the reaction is conducted under basic conditions, for example in the presence of an amine such as diisopropylethylamine (DIPEA) and in an organic solvent such as DMF.

Alternatively, the coupling reagent may be propylphosphonic anhydride (T3P®). When T3P is used as the coupling reagent, the reaction may be conducted under basic conditions, for example in the presence of an amine such as diisopropylethylamine (DIPEA) or triethylamine (TEA) and in an organic solvent such as dioxane.

Coupling agents such as HATU, HBTU, TBTU and TATU are particularly suitable for this reaction.

Compounds of general formula (III) are readily available or may be synthesised by known methods.

A compound of general formula (II) may be prepared by deprotecting a compound of general formula (IV):

(IV)

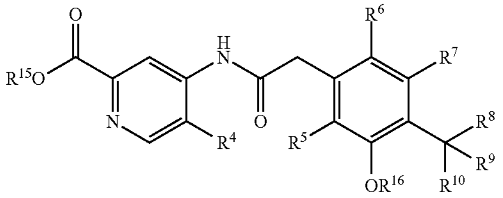

wherein $R^4$, $R^5$, $R^6$, $R^7$, $R^8$, $R^9$ and $R^{10}$ are as defined for general formula (I) and each of $R^{15}$ and $R^{16}$ is independently $C_{1-6}$ alkyl.

Suitably, deprotection is carried out by reaction with boron tribromide, which is particularly useful when both $R^{15}$ and $R^{16}$ are methyl.

Boron tribromide deprotection may be carried out in a polar organic solvent such as dichloromethane. Cooling may be required initially, for example to about −5 to 5° C., and the reaction may subsequently be allowed to warm to a temperature of about 15 to 25° C., typically room temperature.

A compound of general formula (IV) may be prepared by reacting a compound of general formula (V):

(V)

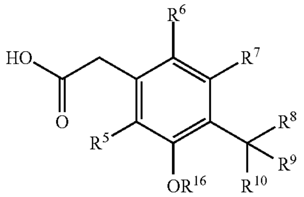

wherein $R^5$, $R^6$, $R^7$, $R^8$, $R^9$ and $R^{10}$ are as defined for general formula (I) and $R^{16}$ is as defined for general formula (IV);

with a compound of general formula (VI):

(VI)

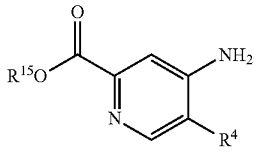

wherein $R^4$ is as defined for general formula (I) and $R^{15}$ is as defined for general formula (IV).

Suitably, the reaction takes place in the presence of a coupling agent as described above, with T3P® being particularly suitable.

Compounds of general formula (VI) are known and are readily available or may be synthesised by known methods.

The synthesis of compounds of general formula (V) will be discussed in greater detail below.

An alternative method for the synthesis of a compound of general formula (IV) is by carbonylation of a compound of general formula (VII):

(VII)

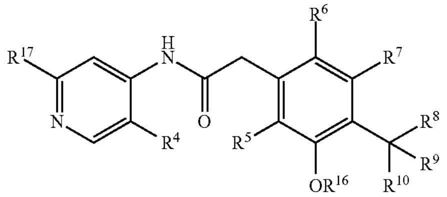

wherein $R^4$, $R^5$, $R^6$, $R^7$, $R^8$, $R^9$ and $R^{10}$ are as defined for general formula (I), $R^{16}$ is as defined for general formula (IV) and $R^{17}$ is halo, for example bromo.

Carbonylation may be carried out by reaction with carbon monoxide in the presence of a palladium catalyst such as $Pd(dppf)Cl_2$ ([1,1'-Bis(diphenylphosphino)ferrocene]dichloropalladium(II)) and a base such as trimethylamine and in an alcoholic solvent such as methanol. Carbon monoxide may be generated in situ by reaction with formic acid and methane sulfonyl chloride with triethylamine.

A compound of general formula (VII) may be prepared by reacting a compound of general formula (V) as defined above with a compound of general formula (VIII):

(VIII)

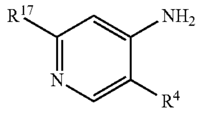

wherein $R^4$ is as defined for general formula (I) and $R^{17}$ is as defined for general formula (VII).

Suitably, the reaction is carried out in the presence of a coupling reagent as defined above, with T3P® being particularly suitable.

Compounds of general formula (VIII) are known and are readily available or may be prepared by known methods.

A compound of general formula (IV) in which $R^8$ and $R^9$ together with the carbon atom to which they are attached form a cycloalkyl group and $R^{10}$ is methyl may be prepared by reacting a compound of general formula (XXXI):

(XXXI)

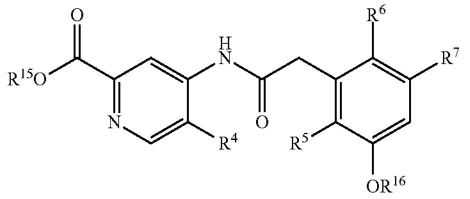

wherein $R^4$, $R^5$, $R^6$ and $R^7$ are as defined for general formula (I) and $R^{15}$ and $R^{16}$ are as defined for general formula (IV);

with a compound of general formula (XXXII):

(XXXII)

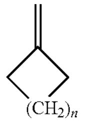

wherein n is 0 to 3.

Suitably, the reaction takes place in the presence of concentrated sulfuric acid.

Compounds of general formula (XXXII) are known and are readily available or may be synthesised by those of skill in the art.

A compound of general formula (XXXI) may be prepared by reacting a compound of general formula (IX):

(IX)

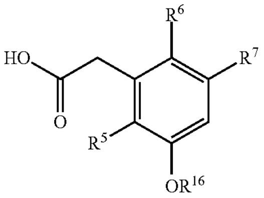

wherein $R^5$, $R^6$ and $R^7$ are as defined for general formula (I) and $R^{16}$ is as defined for general formula (IV);

with a compound of general formula (VI) as defined above.

Suitably, the reaction takes place in the presence of a coupling agent as described above, with T3P® being particularly suitable.

Compounds of general formulae (VI) and (IX) are known and are readily available or may be synthesised by known methods.

There are a number of methods for preparing compounds of general formula (V) depending on the nature of the substituents.

For example, a compound of general formula (V) in which $R^8$ and $R^9$ are methyl and $R^{10}$ is methyl or halomethyl can be prepared by the alkylation of a compound of general formula (IX) as defined above.

Suitable alkylation reactions include Friedel-Crafts alkylation, with a compound of general formula (X):

(X)

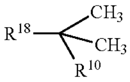

wherein $R^{10}$ is methyl optionally substituted with halo and $R^{18}$ is halo, for example chloro or bromo;

in the presence of a Lewis acid catalyst, for example $FeCl_3$. This method is particularly suitable for compounds in which $R^6$ is F.

Alternatively, for a compound of general formula (IX) in which $R^6$ is halo, alkylation may be carried out by reaction of the with a compound of general formula (XI):

(XI)

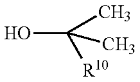

wherein $R^{10}$ is methyl optionally substituted with halo.

Suitably, the reaction is carried out in the presence of concentrated sulfuric acid.

Alternatively, the alkylation can be carried out by reaction with a compound of general formula (XIII):

(XIII)

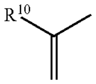

wherein $R^{10}$ is methyl optionally substituted with halo;

in the presence of concentrated sulfuric acid.

Compounds of general formulae (X), (XI) and (XIII) are known and are readily available or may be prepared by known methods.

Compounds of general formula (IX) are also known and are readily available or may be prepared by known methods. For example, a compound of general formula (IX) in which $R^6$ is Cl or Br can be prepared by the chlorination or bromination of a compound of general formula (XII):

(XII)

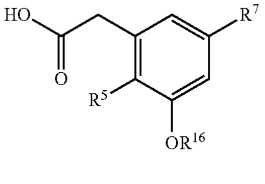

wherein $R^5$ and $R^7$ are as defined for general formula (I) and $R^{16}$ is as defined for general formula (IV).

Suitable halogenating agents include N-chloro succinimide and N-bromosuccinimide.

Compounds of general formula (XII) are known and are readily available or may be prepared by known methods.

An alternative method for the preparation of compounds of general formula (I) is by the deprotection of a compound of general formula (XXI):

(XXI)

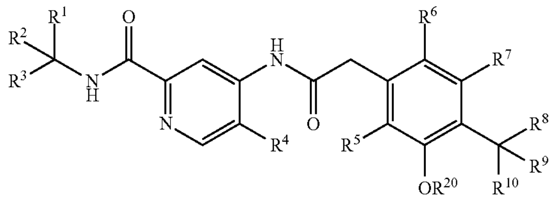

wherein $R^1$, $R^2$, $R^3$, $R^4$, $R^5$, $R^6$, $R^7$, $R^8$, $R^9$ and $R^{10}$ are as defined for general formula (I);

and $R^{20}$ is benzyl optionally substituted with one or more methoxy groups.

Suitably, deprotection can be achieved by catalytic hydrogenation, for example using a palladium catalyst, typically palladium on carbon. The reaction may be carried out in an alcoholic solvent, for example methanol or ethanol. When $R^{20}$ is benzyl substituted with one or more methoxy groups, deprotection can also be achieved by treatment with a strong acid such as hydrochloric acid or trifluoroacetic acid. Further deprotection methods include treatment with sodium borohydride in the presence of a Nickel (II) salt, for example under the conditions set out in Example 19 below.

This method is particularly suitable for compounds of general formula (I) in which $R^{10}$ is OH, CN, halomethyl (e.g. $CF_3$) or methyl substituted with OH or a heterocyclic ring, particularly when the heterocyclic ring is bound to $CH_2$ via a nitrogen atom. In addition, it is suitable for compounds of general formula (I) in which $R^8$ and $R^9$ together with the carbon atom to which they are attached form a 3- to 6-membered cycloalkyl or oxygen-containing heterocyclic ring (either alone or in combination with the $R^{10}$ groups just mentioned).

A compound of general formula (XXI) may be prepared by reacting a compound of general formula (XXII):

(XXII)

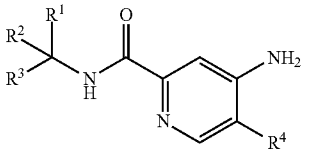

wherein $R^1$, $R^2$, $R^3$ and $R^4$ are as defined for general formula (I);

with a compound of general formula (XXV):

(XXV)

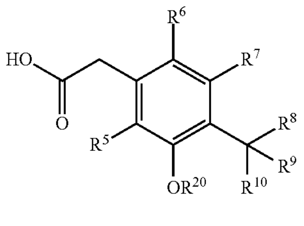

wherein $R^5$, $R^6$, $R^7$, $R^8$, $R^9$ and $R^{10}$ are as defined for general formula (I); and $R^{20}$ is as defined for general formula (XXI).

Suitably, the reaction is carried out in the presence of a coupling reagent as described above. Typically, T3P® may be used as the coupling reagent.

A compound of general formula (XXII) may be prepared by reacting a compound of general formula (III) as defined above with a compound of general formula (XXIII):

(XXIII)

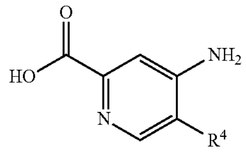

wherein $R^4$ is as defined for general formula (I).

Suitably, the reaction is carried out in the presence of a coupling reagent as described above, for example a coupling reagent such as HATU.

Compounds of general formula (XXIII) are known and are readily available or may be prepared by known methods.

Some compounds of general formula (XXV) are known, while others may be synthesised by those of skill in the art.

For example, a compound of general formula (XXV) in which each of $R^8$ and $R^9$ is independently methyl or ethyl and $R^{10}$ is OH can be prepared from a compound of general formula (XXVI):

(XXVI)

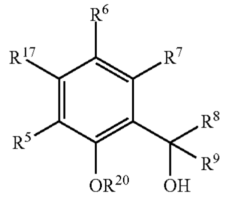

wherein $R^5$, $R^6$ and $R^7$ are as defined for general formula (I); $R^{17}$ is as defined for general formula (VII); each of $R^8$ and $R^9$ is independently methyl or ethyl; and $R^{20}$ is as defined for general formula (XXI);

by reaction with the alkali metal salt of a malonic acid monoester (such as methyl potassium malonate) or the alkali metal salt of cyanoacetic acid (such as potassium 2-cyanoacetate) in the presence of a Pd catalyst (such as $[Pd(allyl)Cl]_2$), a phosphine ligand (such as BINAP) and an organic base (such as DMAP). The resulting ester or nitrile can then be hydrolysed with aqueous base.

A compound of general formula (XXVI) may be prepared from a compound of general formula (XXVII):

(XXVII)

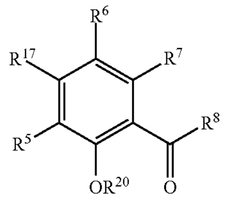

wherein $R^5$, $R^6$ and $R^7$ are as defined for general formula (I); $R^{17}$ is as defined for general formula (VII); $R^8$ is methyl or ethyl and $R^{20}$ is as defined for general formula (XXI);

by reaction with an alkyl Grignard reagent, as $R^9$—MgBr, where $R^9$ is methyl or ethyl, under appropriate conditions.

A compound of general formula (XXVII) may be prepared by protection of a compound of general formula (XXVIII):

(XXVIII)

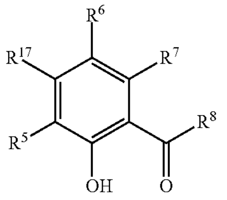

wherein $R^5$, $R^6$ and $R^7$ are as defined for general formula (I); $R^8$ is methyl or ethyl; and $R^{17}$ is as defined for general formula (VII);

by reaction with a compound $R^{20}$—Br, wherein $R^{20}$ is as defined for general formula (XXI), suitably in the presence of a weak base such as potassium carbonate.

A compound of general formula (XXVIII) may be prepared from a compound of general formula (XXIX):

(XXIX)

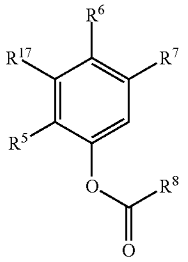

wherein $R^5$, $R^6$ and $R^7$ are as defined for general formula (I); $R^8$ is methyl or ethyl; and $R^{17}$ is as defined for general formula (VII);

by reaction with aluminium chloride in a solvent free reaction at elevated temperature, typically about 150 to 200° C.

A compound of general formula (XXIX) may be prepared from a compound of general formula (XXX):

(XXX)

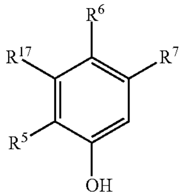

wherein $R^5$, $R^6$ and $R^7$ are as defined for general formula (I); and $R^{17}$ is as defined for general formula (VII);

by reaction with ethanoyl chloride for compounds for compounds of general formula (XXIX) in which $R^8$ is methyl or propanoyl chloride for compounds for compounds of general formula (XXIX) in which $R^8$ is ethyl.

Compounds of general formula (XXX) are known and are readily available or may be prepared by known methods.

A compound of general formula (XXV) in which $R^9$ is methyl or halomethyl and $R^{10}$ is CN may be prepared from a compound of general formula (XXXV):

(XXXV)

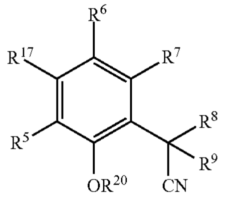

wherein $R^5$, $R^6$, $R^7$ and $R^8$ are as defined for general formula (I), $R^9$ is methyl; $R^{17}$ is as defined for general formula (VII) and $R^{20}$ is as defined for general formula (XXI);

by reaction with the alkali metal salt of a malonic acid monoester (such as methyl potassium malonate) in the presence of a Pd catalyst (such as $[Pd(allyl)Cl]_2$), a phosphine ligand (such as BINAP) and an organic base (such as DMAP). The resulting ester can then be hydrolysed with aqueous base.

A compound of general formula (XXXV) in which $R^8$ and $R^9$ are independently methyl or ethyl may be prepared from a compound of general formula (XXXVI):

(XXXVI)

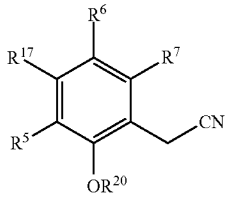

wherein $R^5$, $R^6$ and $R^7$ are as defined for general formula (I); $R^{17}$ is as defined for general formula (VII) and $R^{20}$ is as defined for general formula (XXI).

For compounds in which $R^8$ and $R^9$ are the same, the compound of general formula (XXXVI) may be reacted with a compound of general formula:

$R^8$—I;

wherein $R^8$ is methyl or ethyl;

in the presence of strong base such as sodium hydride.

When $R^8$ and $R^9$ are not the same, sequential reactions may be carried out with compounds of general formulae:

$R^8$—I and $R^9$—I;

wherein one of $R^8$ and $R^9$ is methyl and the other is ethyl;

again in the presence of a strong base such as sodium hydride.

A compound of general formula (XXXVI) may be prepared by reacting a compound of general formula (XXXVII):

(XXXVII)

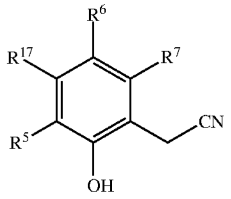

wherein $R^5$, $R^6$ and $R^7$ are as defined for general formula (I); and $R^{17}$ is as defined for general formula (VII);

with a compound $R^{20}$—Br, wherein $R^{20}$ is as defined for general formula (XXI).

Compounds $R^{20}$—Br are known and are readily available or may be prepared by known methods.

Compounds of general formula (XXXVII) may be prepared by reacting a protected compound of general formula (XXXVIII):

(XXXVIII)

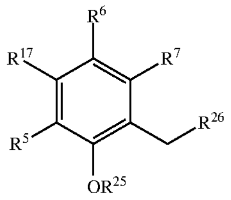

wherein $R^5$, $R^6$ and $R^7$ are as defined for general formula (I); $R^{17}$ is as defined for general formula (VII); $R^{25}$ is an OH protecting group, for example tri($C_{1-6}$ alkyl) silyl or benzyl and $R^{26}$ is halo, for example chloro or bromo;

with sodium cyanide followed by aqueous workup to remove the silyl protecting group.

Compounds of general formula (XXXVI) can also be made directly from a compound of general formula (XXXVIII) in which $R^{25}$ is benzyl by reaction with sodium cyanide.

A compound of general formula (XXXVIII) can be prepared from a compound of general formula (XXXIX):

(XXXIX)

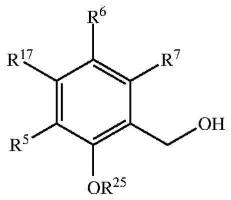

wherein $R^5$, $R^6$ and $R^7$ are as defined for general formula (I); $R^{17}$ is as defined for general formula (VII); and $R^{25}$ is as defined for general formula (XXXVIII);

by reaction with an appropriate halogenating agent. For example, when $R^{26}$ is chloro, thionyl chloride may be used.

A compound of general formula (XXXIX) may be prepared from a compound of general formula (XL):

(XL)

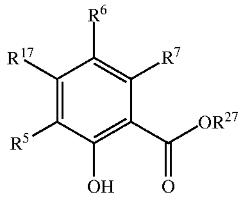

wherein $R^5$, $R^6$ and $R^7$ are as defined for general formula (I); $R^{17}$ is as defined for general formula (VII) and $R^{27}$ is $C_{1-6}$ alkyl or benzyl;

by protecting the OH group with a group $R^{25}$ as defined above for general formula (XXXVIII) followed by reaction with a reducing agent, typically a hydride such as sodium or lithium borohydride.

Compounds of general formula (XL) are readily available or may be synthesised by known methods.

A compound of general formula (XXV) in which $R^8$ and $R^9$ together with the atom to which they are attached form a carbocyclic ring and $R^{10}$ is CN can be prepared from a compound of general formula (XXXVa):

(XXXVa)

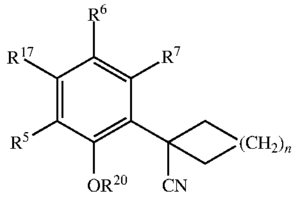

wherein $R^5$, $R^6$ and $R^7$ are as defined for general formula (I); $R^{17}$ is as defined for general formula (VII); $R^{20}$ is as defined for general formula (XXI); and n is 0, 1, 2 or 3;

by reaction with the alkali metal salt of a malonic acid monoester (such as methyl potassium malonate) in the presence of a Pd catalyst (such as $[Pd(allyl)Cl]_2$), a phosphine ligand (such as BINAP) and an organic base (such as DMAP), followed by hydrolysis with aqueous base as described above for the conversion of the compound of general formula (XXXV) to the compound of general formula (XXV).

A compound of general formula (XXXVa) can be prepared from a compound of general formula (XXXVI) as defined above by reaction with a compound of general formula (XLIa):

$$R^{28}-CH_2-(CH_2)_n-CH_2-R^{29} \quad \text{(XLIa)}$$

wherein n is as defined above for general formula (XXXVa) and each of $R^{28}$ and $R^{29}$ is independently halo such as chloro, bromo or iodo.

A compound of general formula (XXV) in which $R^8$ and $R^9$ together with the atom to which they are attached form 3- to 6-membered oxygen-containing heterocyclic ring and $R^{10}$ is CN can be prepared from a compound of general formula (XXXVc):

(XXXVc)

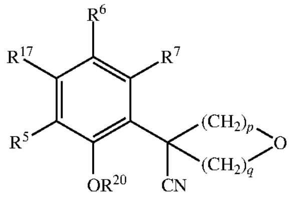

wherein $R^5$, $R^6$ and $R^7$ are as defined for general formula (I); $R^{17}$ is as defined for general formula (VII); $R^{20}$ is as defined for general formula (XXI); and each p and q is 0, 1, 2, 3 or 4 provided that the sum of p and q is from 1 to 4.

The method is analogous to that described above for the reaction of the compounds of general formulae (XXV) and (XXXVa).

A compound of general formula (XXXVa) can be prepared from a compound of general formula (XXXVI) as defined above by reaction with a compound of general formula (XLIc):

$$R^{28}-(CH_2)_p-O-(CH_2)_q-R^{29} \quad \text{(XLIc)}$$

wherein p and q are as defined above for general formula (XXXVc) and each of $R^{28}$ and $R^{29}$ is independently as defined above for general formula (XLIa)

Compounds of general formula (XLIa) and (XLIc) are known and are either readily available or may be prepared by known methods.

A compound of general formula (XXV) in which $R^8$ and $R^9$ are methyl and $R^{10}$ is methyl substituted with a heterocyclic group, especially a nitrogen-containing heterocyclic group bound to the methyl carbon via a ring nitrogen atom, may be prepared from a compound of general formula (XXXVb):

(XXXVb)

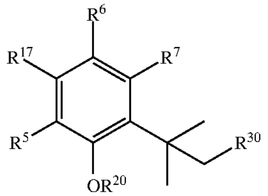

wherein $R^5$, $R^6$ and $R^7$ are as defined for general formula (I); $R^{17}$ is as defined for general formula (VII); $R^{20}$ is as defined for general formula (XXI); and $R^{30}$ is a heterocyclic group, especially a nitrogen-containing heterocyclic group bound to the methyl carbon via a ring nitrogen atom;

by reaction with the alkali metal salt of a malonic acid monoester (such as methyl potassium malonate) in the presence of a Pd catalyst (such as $[Pd(allyl)Cl]_2$), a phosphine ligand (such as BINAP) and an organic base (such as DMAP), followed by hydrolysis with aqueous base as described above.

A compound of general formula (XXXVb) may be prepared from a compound of general formula (XXXV) as defined above in two steps. Firstly, the compound of general formula (XXXV) is reduced, for example using a hydride reducing agent such as diisobutyl aluminium hydride (DIBAL) to convert the cyano group to an aldehyde. Then the aldehyde moiety is reacted with a compound of formula $R^{30}$—H, where $R^{30}$ is as defined above for general formula (XXXVb) under acidic conditions (e.g. acetic acid) and in the presence of a reducing agent such as sodium triacetoxyborohydride (STAB).

A compound of general formula (XXV) in which $R^8$ and $R^9$ together with the carbon atom to which they are attached form an oxetane ring and $R^{10}$ is methyl optionally substituted with halo may be prepared from a compound of general formula (L):

(L)

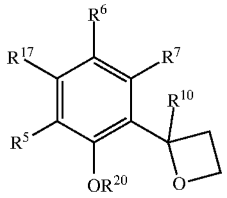

wherein $R^5$, $R^6$ and $R^7$ are as defined for general formula (I), $R^{10}$ is methyl optionally substituted with halo; $R^{17}$ is as defined for general formula (VII); $R^{20}$ is as defined for general formula (XXI);

by reaction with a halo-(2-alkoxy-2-oxo-ethyl)zinc (such as bromo-(2-tert-butoxy-2-oxo-ethyl)zinc) in the presence of a palladium catalyst (such as $[Pd(allyl)Cl]_2$), a phosphine ligand (such as QPhos) and an organic base such as DMAP, followed by hydrolysis of the resulting ester using an aqueous base.

The compound of general formula (L) may be prepared from a compound of general formula (LI):

(LI)

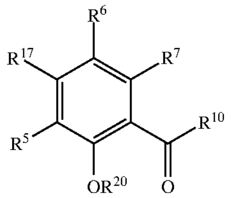

wherein $R^5$, $R^6$ and $R^7$ are as defined for general formula (I), $R^{10}$ is methyl optionally substituted with halo; $R^{17}$ is as defined for general formula (VII); and $R^{20}$ is as defined for general formula (XXI);

by reaction with a sulfur ylide such as trimethylsulfoxonium iodide in a Corey Chaykovsky type reaction.

A compound of general formula (LI) may be obtained by oxidation of a compound of general formula (LII):

(LII)

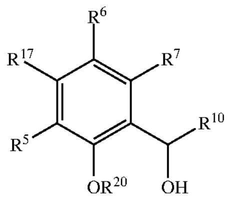

wherein $R^5$, $R^6$ and $R^7$ are as defined for general formula (I), $R^{10}$ is methyl optionally substituted with halo; $R^{17}$ is as defined for general formula (VII); and $R^{20}$ is as defined for general formula (XXI).

The oxidation may be carried out using Dess-Martin periodinane under acidic conditions, for example in the presence of trifluoroacetic acid.

A compound of general formula (LII) in which $R^{10}$ is $CF_3$ or $CHF_2$ may be prepared from a compound of general formula (LIII):

(LIII)

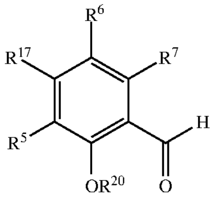

wherein $R^5$, $R^6$ and $R^7$ are as defined for general formula (I); $R^{17}$ is as defined for general formula (VII); and $R^{20}$ is as defined for general formula (XXI);

by reaction with a compound of general formula (LIV):

$$(CH_3)_3\text{-}Si-R^{10} \quad \text{(LIV)}$$

wherein $R^{10}$ is methyl optionally substituted with halo; or an alternative trialkyl silane.

The reaction may be conducted at about 15 to 25° C., typically at room temperature in an organic solvent such as dichloromethane.

Compounds of general formula (LIV) are readily available or may be synthesised by known methods.

A compound of general formula (LIII) may be prepared from a compound of general formula (LIX):

(LIX)

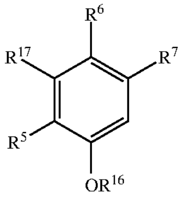

wherein $R^5$, $R^6$ and $R^7$ are as defined for general formula (I); $R^{17}$ is as defined for general formula (VII) and $R^{16}$ is as defined for general formula (IV);

by reaction with dichloro(methoxy)methane in the presence of a Lewis acid such as titanium tetrachloride, followed by removal of the group $R^{16}$, for example using boron tribromide and reprotection with a group $R^{20}$, for example by reaction with a compound $R^{20}$—Br, Br, wherein $R^{20}$ is as defined for general formula (XXI), suitably in the presence of a weak base such as potassium carbonate.

Compounds of general formula (LIX) are known and are readily available or may be synthesised by known methods.

Compounds of general formula (LIII) may be modified by treating the aldehyde in an olefination reaction, for example a Wittig type reaction and the product may be further modified to produce compounds which are similar in structure to the compounds of general formulae (XXXV), (XXXVa), (XXXVb), (XXXVc), (XXXVI), (XXXVII) and (L) but which have alternative substituents at the position between the $R^7$ and OH substituents (see preparation of Intermediate R below). The syntheses of further similar compounds with alternative substituents are also given below (see preparation of Intermediates B, BA, BB, BC, BD, BE, C, CA, CB, D, E, M, N and W.

To obtain a compound of general formula (LII) in which $R^{10}$ is $C_{1-4}$ alkyl, an appropriate Grignard reagent may be reacted with the compound of general formula (LIII).

A compound of general formula (LIII) may be obtained by oxidation of a compound of general formula (LV):

(LV)

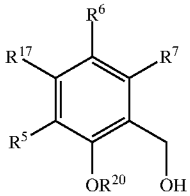

wherein $R^5$, $R^6$ and $R^7$ are as defined for general formula (I); $R^{17}$ is as defined for general formula (VII); and $R^{20}$ is as defined for general formula (XXI).

A suitable oxidising agent for this reaction is manganese dioxide and the reaction may be conducted in an organic solvent such as toluene at the reflux temperature of the solvent.

A compound of general formula (LV) may be prepared from a compound of general formula (LVI):

(LVI)

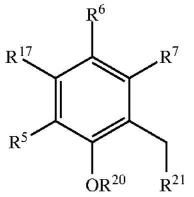

wherein $R^5$, $R^6$ and $R^7$ are as defined for general formula (I); $R^{17}$ is as defined for general formula (VII); $R^{20}$ is as defined for general formula (XXI) and $R^{21}$ is halo, for example chloro or bromo;

by reaction with a hydroxide, suitably an alkali metal hydroxide such as sodium or potassium hydroxide in an organic solvent such as dioxane. Suitably, the reaction is carried out at the reflux temperature of the solvent.

Compounds of general formula (LV) can also be prepared directly from a compound of general formula (XL) via protection of the phenol followed by reduction of the ester using a reducing agent such as $NaBH_4$.

A compound of general formula (LVI) may be prepared from a compound of general formula (XL) as defined above by protecting the OH group with a group $R^{20}$ as defined above for general formula (XXI) followed by reduction of the ester then conversion of the resulting alcohol to the alkyl halide (e.g. using thionyl chloride).

A further method for preparing a compound of general formula (XXV) is by reaction of a compound of general formula (LVII):

(LVII)

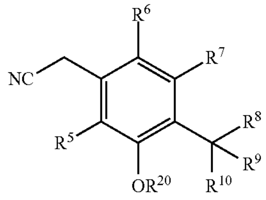

wherein $R^5$, $R^6$, $R^7$, $R^8$, $R^9$ and $R^{10}$ are as defined for general formula (I); and $R^{20}$ is as defined for general formula (XXI);

with a hydroxide, for example an aqueous base, for example an alkali metal hydroxide such as sodium or potassium hydroxide in a solvent such as THF. The reaction may be carried out in an organic solvent such as tetrahydrofuran at elevated temperature, for example at the reflux temperature of the solvent.

This method is particularly suitable for compounds in which $R^8$, $R^9$ and $R^{10}$ together with the carbon atom to which they are attached form a fused or bridged ring system.

When $R^8$, $R^9$ and $R^{10}$ together with the carbon atom to which they are attached form a fused or bridged ring system, the compound of general formula (LVII) may be prepared from a compound of formula (LVIII):

(LVIII)

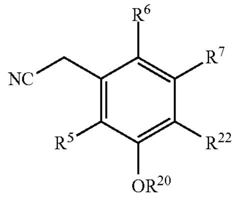

wherein $R^5$, $R^6$ and $R^7$ are as defined for general formula (I); $R^{20}$ is as defined for general formula (XXI); and $R^{22}$ is halo, for example bromo or chloro.

The compound of general formula (LVIII) may be reacted with a halide of a suitable bridged or fused ring and the substituents on the ring may be manipulated as required.

Compounds of general formula (LVIII) are readily available or may be synthesised by known methods.

A compound of general formula (I) in which $R^9$ is OH and $R^{10}$ is methyl optionally substituted with halo may be prepared from a compound of general formula (LX), which is a compound of general formula (I) in which $R^8$ and $R^9$ combine to form an ethenyl group and $R^{10}$ is methyl optionally substituted with halo:

(LX)

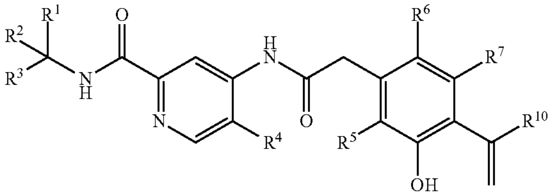

wherein $R^1$, $R^2$, $R^3$, $R^4$, $R^5$, $R^6$ and $R^7$ are as defined for general formula (I); and $R^{10}$ is methyl optionally substituted with halo;

by reaction with an aqueous acid such as methanesulfonic acid in a mixture of 1,4-dioxane and water.

A compound of general formula (LX) can be prepared from a compound of general formula (LXI):

(LXI)

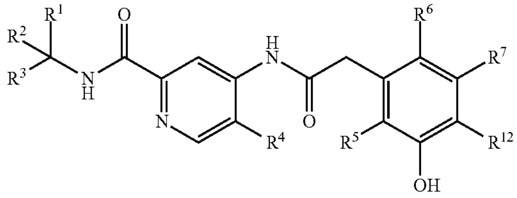

wherein $R^1$, $R^2$, $R^3$, $R^4$, $R^5$, $R^6$ and $R^7$ are as defined for general formula (I); and $R^{12}$ is halo, for example chloro or bromo;

by reaction with 2-isopropenyl-4,4,5,5-tetramethyl-1,3,2-dioxaborolane in the presence of tripotassium phosphate, tricyclohexylphosphine and palladium acetate ($Pd(OAc)_2$).

An analogous method may be used to prepare a compound of general formula (I) in which $R^8$ and $R^9$ combine to form a 3- to 6-membered cycloalkyl or oxygen-containing heterocyclic ring and $R^{10}$ is OH. In this method, the compound of general formula (LXI) is reacted with an appropriate cyclic 1,3,2-dioxaborolane to give a compound similar to that of general formula (LX) but in which the moiety $—C(=CH_2)—R^{10}$ is replaced with a cyclic group containing a C=C double bond at the position at which the cyclic group is connected to the remainder of the molecule. This can hydrated under reducing conditions, for example as described in Example 13 below, to give the required product.

A compound of general formula (LXI) may be prepared by deprotecting a compound of general formula (LXI I):

(LXII)

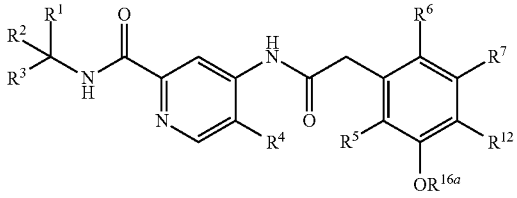

wherein $R^1$, $R^2$, $R^3$, $R^4$, $R^5$, $R^6$ and $R^7$ are as defined for general formula (I); $R^{16a}$ is $C_{1-6}$ alkyl or benzyl; and $R^{12}$ is as defined for general formula (LXI).

Deprotection is suitably achieved by treatment with boron tribromide as described above for the deprotection of a compound of general formula (IV).

A compound of general formula (LXI I) may be prepared by reacting a compound of general formula (XXII) as defined above with a compound of general formula (LXIII):

(LXIII)

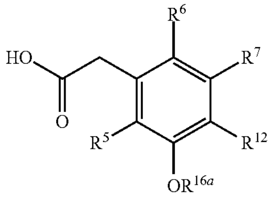

wherein $R^5$, $R^6$ and $R^7$ are as defined for general formula (I); $R^{16a}$ is as defined for general formula (LXII); and $R^{12}$ is as defined for general formula (LXI).

Suitably, the reaction is carried out under similar conditions to those described above for the reaction of the compound of general formula (V) with the compound of general formula (VI).

Compounds of general formula (LXIII) are known and are readily available or may be prepared by known methods.

For example, a compound of general formula (LXIII) may be prepared by brominating or chlorinating a compound of general formula (LXIV):

(LXIV)

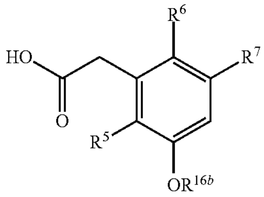

wherein $R^5$, $R^6$ and $R^7$ are as defined for general formula (I); $R^{16b}$ is H or $C_{1-6}$ alkyl.

Bromination or chlorination may be carried out using any suitable agent, for example N-bromo succinimide, N-chlorosuccinimide or bromine. Where $R^{16b}$ is H, reaction with a suitable protecting reagent may be carried out to obtain the compound of general formula (LXIII). For example, reaction with benzyl bromide gives a compound of general formula (LXIII) in which $R^{16a}$ is benzyl.

A method for the preparation of a compound of general formula (XXI) in which $R^8$ and $R^9$ combine with the carbon atom to which they are attached to form a cyclopropyl ring and $R^{10}$ is methyl optionally substituted with halo is by reaction of a compound of general formula (LXV):

(LXV)

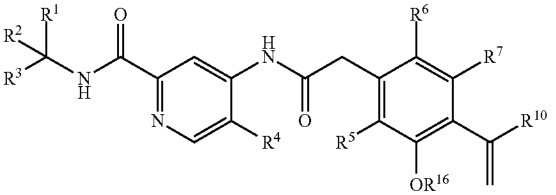

wherein $R^1$, $R^2$, $R^3$, $R^4$, $R^5$, $R^6$ and $R^7$ are as defined for general formula (I); $R^{16}$ is as defined for general formula (IV) and $R^{10}$ is methyl optionally substituted with halo;

with 8-(iodomethyl)-8,8'-spirobi[7,9-dioxa-8-silanuidabicyclo[4.3.0]nona-1,3,5-triene];

triethylammonium in the presence of (4,4'-di-t-butyl-2,2'-bipyridine)bis[3,5-difluoro-2-[5-trifluoromethyl-2-pyridinyl-kN)phenyl-kC]iridium(III) hexafluorophosphate;

under irradiation with blue light.

Suitably, the process is as described in Example 8 below and takes place under an inert atmosphere such as nitrogen in an anhydrous organic solvent such as dimethylsulfoxide.

A compound of general formula (LXV) in which $R^{10}$ is methyl may be prepared from a compound of general formula (LXII) as defined above by reaction with 2-isopropenyl-4,4,5,5-tetramethyl-1,3,2-dioxaborolane and tripotassium phosphate followed by tricyclohexylphosphine and palladium acetate.

In some cases, the introduction of the cyclopropyl group may take place at an earlier stage of the process. For example, a compound of general formula (LXX):

(LXX)

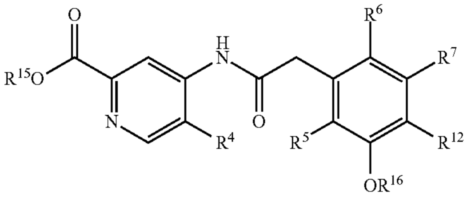

wherein $R^4$, $R^5$, $R^6$ and $R^7$ are as defined for general formula (I); $R^{15}$ and $R^{16}$ are as defined for general formula (IV) and $R^{12}$ is halo, for example chloro or bromo;

may be treated with bis(pinacolato)diboron in the presence of a palladium catalyst such as $Pd(dppf)Cl_2$. The boronic ester product of this reaction may then be treated with a compound of general formula (LXXI):

(LXXI)

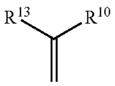

wherein $R^{10}$ is methyl optionally substituted with halo and $R^{13}$ is halo, for example chloro or bromo to yield a product of general formula (LXXII):

(LXXII)

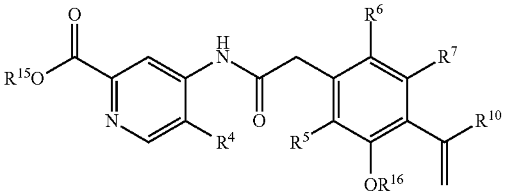

wherein $R^4$, $R^5$, $R^6$ and $R^7$ are as defined for general formula (I); $R^{15}$ and $R^{16}$ are as defined for general formula (IV) and $R^{10}$ is methyl optionally substituted with halo;

The compound of general formula (LXXII) can be converted to a compound of general formula (IV) in which $R^8$ and $R^9$ together with the carbon atom to which they are attached form a cylopropyl group and $R^{10}$ is methyl optionally substituted with halo by reaction with with 8-(iodomethyl)-8,8'-spirobi[7,9-dioxa-8-silanuidabicyclo[4.3.0]nona-1,3,5-triene];

triethylammonium and (4,4'-di-t-butyl-2,2'-bipyridine)bis[3,5-difluoro-2-[5-trifluoromethyl-2-pyridinyl-kN)phenyl-kC]iridium(III) hexafluorophosphate;

under irradiation with blue light as described for the reaction of the compound of general formula (LXV) above.

A compound of general formulae (LXI) can be prepared by methods analogous to those described above for compounds of general formula (I) except that the intermediates analogous to the compounds of general formulae (V) and (XXV) will have a group $R^{12}$ in place of the —C($R^8$) ($R^9$) ($R^{10}$) substituent.

Compounds of general formula (I) in which $R^8$ and $R^8$ are methyl or ethyl and $R^{10}$ is $CH_2OH$ or $CH_2CH_2OH$ may be prepared from compounds of general formula (LXXV):

(LXXV)

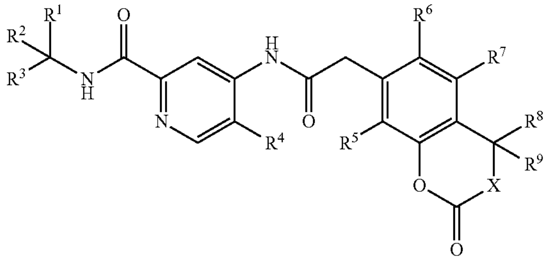

wherein $R^5$, $R^6$ and $R^7$ are as defined for general formula (I); each of $R^8$ and $R^9$ is independently methyl or ethyl and X is a bond or —$CH_2$—;

by reduction, for example using a hydride reducing agent such as lithium borohydride.

Suitably, the reaction is carried out in an organic solvent such as tetrahydrofuran and the reducing agent is added with cooling, for example at −78° C.

A compound of general formula (LXXV) may be prepared by reacting a compound of general formula (XXII) as defined above with a compound of general formula (LXXX):

(LXXX)

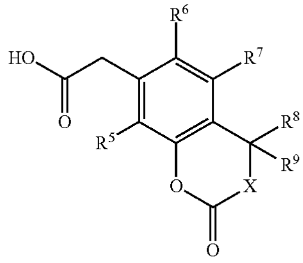

wherein $R^5$, $R^6$ and $R^7$ are as defined for general formula (I); each of $R^8$ and $R^9$ is independently methyl or ethyl and X is as defined for general formula (LXXV).

Suitably, the reaction is carried out in the presence of a coupling reagent as described above. T3P® is particularly suitable.

In some cases, the compound of general formula (LXXV) is isolated and purified before reduction to give the compound of general formula (I). In other cases, however, the compounds of general formulae (LXXX) and (XXII) react to give a compound of general formula (LXXX), which is then reduced to give a compound of general formula (I) without further purification. This is more usually the case for 5-membered lactone intermediates (LXXX), i.e. when X is a bond.

In a variation of this method, a compound of general formula (LXXV) may be prepared by reacting a compound of general formula (III) as defined above with a compound of general formula (LXXVI):

(LXXVI)

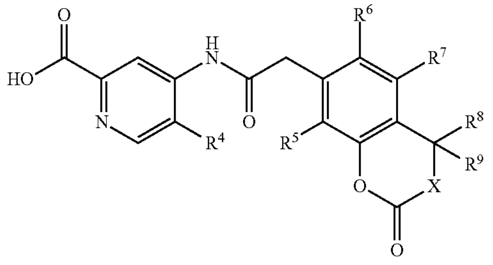

wherein $R^4$, $R^5$, $R^6$ and $R^7$ are as defined for general formula (I); each of $R^8$ and $R^9$ is independently methyl or ethyl and X is as defined for general formula (LXXV).

Suitably, the reaction is carried out in the presence of a coupling reagent as described above, with HATU being an example of a suitable coupling reagent.

The compound of general formula (LXXV) may be reduced to a compound of general formula (I) without further purification.

A compound of general formula (LXXVI) may be prepared by hydrolysis of a compound of general formula (LXXVII):

(LXXVII)

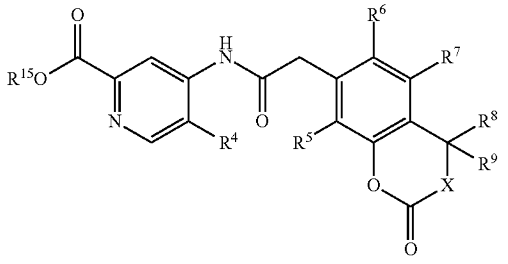

wherein $R^4$, $R^5$, $R^6$ and $R^7$ are as defined for general formula (I); $R^{15}$ is as defined for general formula (IV); each of $R^8$ and $R^9$ is independently methyl or ethyl and X is as defined for general formula (LXXV).

Suitably, the hydrolysis is base hydrolysis, for example carried out using lithium hydroxide in a solvent such as tetrahydrofuran.

A compound of general formula (LXXVII) may be prepared by reacting a compound of general formula (VI) as defined above with a compound of general formula (LXXX) as defined above.

Suitably, the reaction is carried out in the presence of a coupling reagent as described above. T3P® is particularly suitable.

A compound of general formula (LXXX) in which X is $—CH_2—$ may be prepared from a compound of general formula (LXXXI):

(LXXXI)

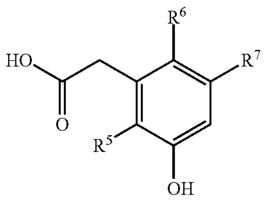

wherein $R^5$, $R^6$ and $R^7$ are as defined for general formula (I);

by reaction with a compound of general formula (LXXXII):

(LXXXII)

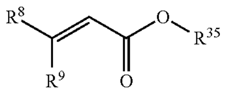

wherein $R^8$ and $R^9$ are as defined for general formula (I) and $R^{35}$ is $C_{1-6}$ alkyl.

Suitably, the reaction is carried out in the presence of a strong acid such as methane sulfonic acid.

Compounds of general formulae (LXXXI) and (LXXXII) are known and are readily available or may be prepared by methods known to those of skill in the art.

A compound of general formula (LXXX) in which X is a bond may be prepared from a compound of general formula (LXXXIII):

(LXXXIII)

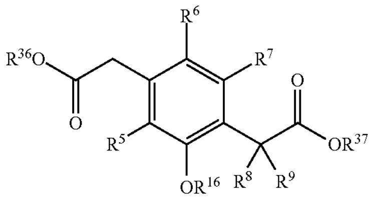

wherein $R^5$, $R^6$ and $R^7$ are as defined for general formula (I); $R^{16}$ is as defined for general formula (IV); $R^{36}$ is $C_{1-6}$ alkyl or benzyl; $R^{37}$ is $C_{1-6}$ alkyl; and each of $R^8$ and $R^9$ is independently methyl or ethyl;

by reaction with boron tribromide. Typically, the reaction is carried out a temperature of about −5 to 5° C. in a solvent such as dichloromethane.

A compound of general formula (LXXXIII) can be prepared by reacting a compound of general formula (LXXXIV):

(LXXXIV)

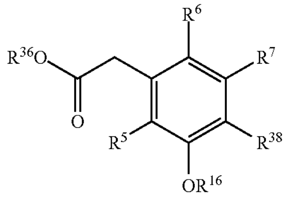

wherein $R^5$, $R^6$ and $R^7$ are as defined for general formula (I); $R^{16}$ is as defined for general formula (IV); $R^{36}$ is as defined for general formula (LXXXIII); and $R^{38}$ is a halogen, especially bromine or chlorine and more especially bromine;

with a compound of general formula (LXXXV):

(LXXXV)

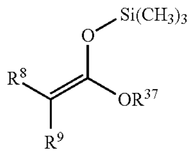

wherein $R^{37}$ is as defined for general formula (LXXXIII) and each of $R^8$ and $R^9$ is independently methyl or ethyl.

The reaction may be carried out in the presence of zinc fluoride and a palladium/platinum catalyst such as $Pd(P^tBu_3)_2$. Suitably, the reaction is conducted under an inert atmosphere, for example under nitrogen.

Compounds of general formula (LXXXV) are known and are readily available or may be prepared by methods familiar to those of skill in the art.

A compound of general formula (LXXXIV) may be prepared by esterification a compound of general formula (LXXXVI):

(LXXXVI)

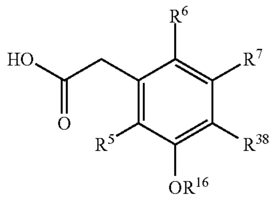

wherein $R^5$, $R^6$ and $R^7$ are as defined for general formula (I); $R^{16}$ is as defined for general formula (IV); and $R^{38}$ is a halogen, especially bromine or chlorine and more especially bromine;

for example by reaction with a compound $R^{36}$-Hal, where Hal is bromine or chlorine, especially bromine.

The reaction may be conducted under mildly basic conditions, for example in the presence of potassium carbonate, and in a solvent such as N,N-dimethylformamide.

A compound of general formula (LXXXVI) may be prepared by halogenation of a compound of general formula (IX) as defined above. Suitable halogenating agents include bromine in a solvent such as acetonitrile. Alternatively, N-chlorosuccinimide or N-bromosuccinimide may be used.

An alternative method for the preparation of a compound of general formula (LXXV) in which X is a bond is by the reaction of a compound of general formula (XC):

(XC)

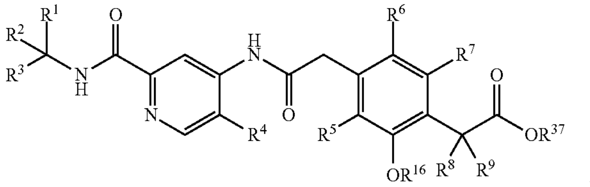

wherein $R^1$, $R^2$, $R^3$, $R^4$, $R^5$, $R^6$ and $R^7$ are as defined for general formula (I); $R^{16}$ is as defined for general formula (IV); $R^{37}$ is as defined for general formula (LXXXIII); and each of $R^8$ and $R^9$ is independently methyl or ethyl;

with boron tribromide.

Typically, the reaction is conducted in a solvent such as dichloromethane.

An alternative procedure for the synthesis of a compound of general formula (XXI) in which $R^8$ is methyl or ethyl, $R^9$ is $CH_2OH$ and $R^{10}$ is H is by the reduction of a compound of general formula (XCV):

(XCV)

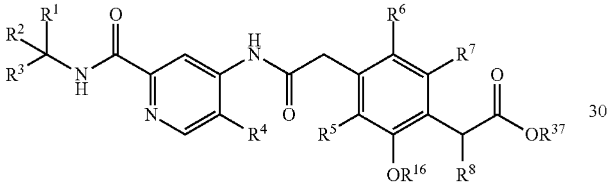

wherein $R^1$, $R^2$, $R^3$, $R^4$, $R^5$, $R^6$ and $R^7$ are as defined for general formula (I); $R^{37}$ is as defined for general formula (LXXXIII); and $R^8$ is methyl or ethyl;

typically using a hydride reducing agent such as lithium aluminium hydride.

Suitably, the reaction is carried out at reduced temperature, typically −78° C. in a solvent such as tetrahydrofuran.

A compound of general formula (XCV) may be prepared by reacting a compound of general formula (LXII) as defined above with a compound of general formula (XCVI):

(XCVI)

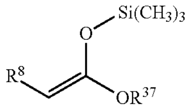

wherein $R^8$ is methyl or ethyl and $R^{37}$ is as defined for general formula (LXXXIII).

The reaction may be carried out in the presence of zinc fluoride and a palladium/platinum catalyst such as Pd$(P^tBu_3)_2$. Suitably, the reaction is conducted under an inert atmosphere, for example under nitrogen.

Compounds of general formula (I) may also be converted to other compounds of general formula (I). For example, a compound of general formula (I) in which $R^6$ is halo, especially bromo or chloro, can be converted to a compound of general formula (I) in which $R^6$ is alkyl in a Suzuki type reaction with an appropriate alkyl- or alkenyl-boronic acid ester, for example an alkyl- or alkenyl-4,4,5,5-tetramethyl-1,3,2-dioxaborolane in the presence of tricyclohexylphosphine and palladium acetate and a base (such as $K_2CO_3$).

A compound of general formula (I) in which $R^5$ is H may be converted to a compound of general formula (I) in which $R^5$ is halo, for example chloro or bromo, by reaction with a suitable halogenating agent such as N-chlorosuccinimide or N-bromosuccinimide, suitably at a temperature of about 15 to 25° C., for example at room temperature, and in a solvent such as N,N-dimethylformamide.

The compounds of general formula (I) are positive modulators of TMEM16A and therefore, in a further aspect of the invention, there is provided a compound of general formula (I) as defined above for use in medicine, particularly in the treatment or prophylaxis of diseases and conditions affected by modulation of TMEM16A.

There is also provided the use of a compound of general formula (I) as defined above in the manufacture of a medicament for the treatment or prophylaxis of diseases and conditions affected by modulation of TMEM16A.

There is also provided a method for the treatment or prophylaxis of diseases and conditions affected by modulation of TMEM16A, the method comprising administering to a patient in need of such treatment an effective amount of a compound of general formula (I) as defined above.

The diseases and conditions affected by modulation of TMEM16A include respiratory diseases and conditions, dry mouth (xerostomia), intestinal hypermobility, cholestasis and ocular conditions.

There is also provided:

A compound of general formula (I) as defined above for use in the treatment or prophylaxis of respiratory diseases and conditions.

A compound of general formula (I) as defined above for use in the treatment or prophylaxis of dry mouth (xerostomia).

A compound of general formula (I) as defined above for use in the treatment or prophylaxis of intestinal hypermobility.

A compound of general formula (I) as defined above for use in the treatment or prophylaxis of cholestasis.

A compound of general formula (I) as defined above for use in the treatment or prophylaxis of ocular conditions.

The invention also provides:

The use of a compound of general formula (I) as defined above in the manufacture of a medicament for the treatment or prophylaxis of respiratory diseases and conditions.

The use of a compound of general formula (I) as defined above in the manufacture of a medicament for the treatment or prophylaxis of dry mouth (xerostomia).

The use of a compound of general formula (I) as defined above in the manufacture of a medicament for the treatment or prophylaxis of intestinal hypermobility.

The use of a compound of general formula (I) as defined above in the manufacture of a medicament for the treatment or prophylaxis of cholestasis.

The use of a compound of general formula (I) as defined above in the manufacture of a medicament for the treatment or prophylaxis of ocular conditions.

There is further provided:

A method for the treatment or prophylaxis of respiratory diseases and conditions, the method comprising administering to a patient in need of such treatment an effective amount of a compound of general formula (I) as defined above.

A method for the treatment or prophylaxis of dry mouth (xerostomia), the method comprising administering to a patient in need of such treatment an effective amount of a compound of general formula (I) as defined above.

A method for the treatment or prophylaxis of intestinal hypermobility, the method comprising administering to a patient in need of such treatment an effective amount of a compound of general formula (I) as defined above.

A method for the treatment or prophylaxis of cholestasis, the method comprising administering to a patient in need of such treatment an effective amount of a compound of general formula (I) as defined above.

A method for the treatment or prophylaxis of ocular conditions, the method comprising administering to a patient in need of such treatment an effective amount of a compound of general formula (I) as defined above.

Respiratory diseases and conditions which may be treated or prevented by the compounds of general formula (I) include cystic fibrosis, chronic obstructive pulmonary disease (COPD), chronic bronchitis, emphysema, bronchiectasis, including non-cystic fibrosis bronchiectasis, asthma and primary ciliary dyskinesia.

Dry mouth (xerostomia) which may be treated or prevented by the compounds of general formula (I) may result from Sjorgens syndrome, radiotherapy treatment and xerogenic drugs.

Intestinal hypermobility which may be treated or prevented by the compounds of general formula (I) may be associated with gastric dyspepsia, gastroparesis, chronic constipation and irritable bowel syndrome.

Ocular conditions which may be treated or prevented by the compounds of by the compounds of general formula (I) include dry eye disease.

The compounds of the present invention will generally be administered as part of a pharmaceutical composition and therefore the invention further provides a pharmaceutical composition comprising a compound of general formula (I) together with a pharmaceutically acceptable excipient.

The pharmaceutical composition may be formulated for oral, rectal, nasal, topical (including topical administration to the lung, dermal, transdermal, eye drops, buccal and sublingual), vaginal or parenteral (including subcutaneous, intramuscular, intravenous and intradermal) administration and may be prepared by any methods well known in the art of pharmacy.

The compounds of the invention are especially well adapted for oral administration.

The composition may be prepared by bringing into association the above defined active agent with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac® 70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®.

Further examples of dry powder delivery systems include ECLIPSE, NEXT, ROTAHALER, HAN DI HALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of general formula (I) is provided as a micronized dry powder formulation, for example comprising lactose of a suitable grade.

Thus, as an aspect of the invention there is provided a pharmaceutical composition comprising a compound of general formula (I) in particulate form in combination with particulate lactose, said composition optionally comprising magnesium stearate.

In one embodiment a compound of general formula (I) is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of general formula (I) is provided as a micronized dry powder formulation, for example comprising lactose of a suitable grade, filled into hard shell capsules for use in a single dose device such as AEROLISER.

In another embodiment a compound of general formula (I) is provided as a micronized dry powder formulation, comprising lactose of a suitable grade and magnesium stearate, filled into hard shell capsules for use in a single dose device such as AEROLISER.

In another embodiment a compound of general formula (I) is provided as a fine powder for use in an inhalation dosage form wherein the powder is in fine particles with a $D_{50}$ of 0.5-10 μm e.g. around 1-5 μm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 μm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of general formula (I) will be about 0.0001 to less than 4.0% (w/w).

Preferably, for topical ocular administration, the compositions administered according to general formula (I) will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of general formula (I). In addition, the compound of general formula (I) may also be introduced by means of ocular implants or inserts.

The compositions administered according to general formula (I) may also include various other ingredients, including, but not limited to, tonicity agents, buffers, surfactants, stabilizing polymer, preservatives, co-solvents and viscosity building agents. Suitable pharmaceutical compositions of general formula (I) include a compound of the invention formulated with a tonicity agent and a buffer. The pharmaceutical compositions of general formula (I) may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of general formula (I). The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as TritonX114 and tyloxapol.

Additional agents that may be added to the ophthalmic compositions of compounds of general formula (I) are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of general formula (I) to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of general formula (I) will be sterile, but typically unpreserved. Such compositions, therefore, generally will not contain preservatives.

Parenteral formulations will generally be sterile.

The medical practitioner, or other skilled person, will be able to determine a suitable dosage for the compound of general formula (I) and hence the amount of the compound of the invention that should be included in any particular pharmaceutical formulation (whether in unit dosage form or otherwise).

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore, in a further aspect of the present invention there is provided a product comprising a compound of general formula (I) and an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

There is also provided a compound of general formula (I) in combination with an additional agent useful in the treatment or prevention of respiratory conditions as a combined preparation for simultaneous, sequential or separate use in the treatment of a disease or condition affected by modulation of TMEM16A and especially a respiratory disease or condition, for example one of the diseases and conditions mentioned above.

Suitable additional active agents which may be included in a pharmaceutical composition or a combined preparation with the compounds of general formula (I), (Ix), (IA), (IB), (IC), (ID) or (IE) include:

- β2 adrenoreceptor agonists such as metaproterenol, isoproterenol, isoprenaline, albuterol, salbutamol, formoterol, salmeterol, indacaterol, terbutaline, orciprenaline, bitolterol mesylate, pirbuterol, olodaterol, vilanterol and abediterol;
- antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;
- dornase alpha;

corticosteroids such as prednisone, prednisolone, flunisolide, triamcinolone acetonide, beclomethasone dipropionate, budesonide, fluticasone propionate mometasone furoate and fluticasone furoate;

Leukotriene antagonists such as montelukast and zafirlukast;

anticholinergic compounds, particularly muscarinic antagonists such as ipratropium, tiotropium, glycopyrrolate, aclidinium and umeclidinium;

CFTR repair therapies (e.g. CFTR potentiators, correctors or amplifiers) such as Ivacaftor, QBW251, Bamacaftor (VX659), Elexacaftor (VX445), VX561/CPT-656, VX152, VX440, GLP2737, GLP2222, GLP2451, PTI438, PTI801, PTI808, FDL-169 and FDL-176 and CFTR correctors such as Lumacaftor and Tezacaftor or combinations thereof (for example a combination of Ivacaftor, Tezacaftor and Elexacaftor);

ENaC modulators, particularly ENaC inhibitors;

Antibiotics;

Antivirals such as ribavirin and neuraminidase inhibitors such as zanamivir;

Antifungals such as PUR1900;

Airway hydrating agents (osmoloytes) such as hypertonic saline and mannitol (Bronchitol®); and Mucolytic agents such as. N-acetyl cysteine.

When the additional active agent is an ENaC modulator, it may be an ENaC inhibitor such as amiloride, VX-371, AZD5634, QBW276, SPX-101, BI443651, BI1265162 and ETD001.

Other suitable ENaC blockers are disclosed in our applications WO 2017/221008, WO 2018/096325, WO 2019/077340 and WO 2019/220147 and any of the example compounds of those applications may be used in combination with the compounds of general formula (I). Particularly suitable compounds for use in combination with the compounds of general formula (I) include compounds having a cation selected from:

2-[({3-amino-5H-pyrrolo[2,3-b]pyrazin-2-yl}formamido)ethyl]-6-(4-{bis[(2S,3R,4R,5R)-2,3,4,5,6-pentahydroxyhexyl]amino}piperidine-1-carbonyl)-1,3-diethyl-1H-1,3-benzodiazol-3-ium;

2-[({3-amino-5H-pyrrolo[2,3-b]pyrazin-2-yl}formamido)methyl]-6-{[2-(4-{bis[(2S,3R,4R,5R)-2,3,4,5,6-pentahydroxyhexyl]amino}piperidin-1-yl)ethyl]carbamoyl}-1,3-diethyl-1H-1,3-benzodiazol-3-ium;

2-[({3-amino-5H-pyrrolo[2,3-b]pyrazin-2-yl}formamido)methyl]-5-[4-({bis[(2S,3R,4R,5R)-2,3,4,5,6-pentahydroxyhexyl]amino}methyl)piperidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3R)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-6-[(3S)-3-{bis[(2S,3R,4R,5R)-2,3,4,5,6-pentahydroxyhexyl]amino}pyrrolidine-1-carbonyl]-1,3-diethyl-1H-1,3-benzodiazol-3-ium;

2-[({3-amino-5H-pyrrolo[2,3-b]pyrazin-2-yl}formamido)methyl]-1,3-diethyl-6-{[(1r,4r)-4-{bis[(2S,3R,4R,5R)-2,3,4,5,6-pentahydroxyhexyl]amino}cyclohexyl]carbamoyl}-1H-1,3-benzodiazol-3-ium;

2-[({3-amino-5H-pyrrolo[2,3-b]pyrazin-2-yl}formamido)methyl]-1,3-diethyl-6-{[(1s,4s)-4-{bis[(2S,3R,4R,5R)-2,3,4,5,6-pentahydroxyhexyl]amino}cyclohexyl]carbamoyl}-1H-1,3-benzodiazol-3-ium;

and a suitable anion, for example halide, sulfate, nitrate, phosphate, formate, acetate, trifluoroacetate, fumarate, citrate, tartrate, oxalate, succinate, mandelate, methane sulfonate or p-toluene sulfonate.

DESCRIPTION OF THE DRAWINGS

FIG. 1 is an example trace from a whole-cell patch clamp (Qpatch) TMEM16A potentiator assay as used in Biological Example 21 and illustrates the methodology used in the assay.

EXAMPLES

General Conditions:

Mass spectra were run on LC-MS systems using electrospray ionization. These were run using either a Waters Acquity uPLC system with Waters PDA and ELS detectors or Shimadzu LCMS-2010EV systems. [M+H]+ refers to mono-isotopic molecular weights.

NMR spectra were recorded on a Bruker Avance III HD 500 MHz with a 5 mm Broad Band Inverse probe, a Bruker Avance III HD 250 MHz, a 400 MHz Avance III HD Nanobay fitted with a 5 mm Broad Band Observed SmartProbe using the solvent as internal deuterium lock. Spectra were recorded at room temperature unless otherwise stated and were referenced using the solvent peak.

Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

Compounds were purified by flash column chromatography on normal phase silica on Biotage® Isolera systems using the appropriate SNAP cartridge or Sfär cartridge and gradient. Alternatively, compounds were purified on reverse phase silica using either Biotage® Isolera or Biotage® Selekt systems with the appropriate SNAP C18 or Sfär C18 cartridges and reverse phase eluent or by preparative HPLC (if stated otherwise).

Preparative HPLC Using Acidic pH, Early Elution Method

Purifications by were performed on a Gilson LC system using Waters Sunfire C18 columns (30 mm×100 mm, 10 μM; temperature: RT) and a gradient of 10-95% B (A=0.1% formic acid in water; B=0.1% formic acid in acetonitrile) over 14.44 min then 95% B for 2.11 min, with an injection volume of 1500 μL and a flow rate of 40 mL/min. UV spectra were recorded at 215 nm using a Gilson detector.

Preparative HPLC Using Acidic pH, Standard Elution Method

Purifications by preparative HPLC (acidic pH, standard elution method) were performed on a Gilson LC system using Waters Sunfire C18 columns (30 mm×100 mm, 10 μM; temperature: RT) and a gradient of 30-95% B (A=0.1% formic acid in water; B=0.1% formic acid in acetonitrile) over 11 min then 95% B for 2.11 min, with an injection volume of 1500 μL and a flow rate of 40 mL/min. UV spectra were recorded at 215 nm using a Gilson detector.

Preparative HPLC Using Basic pH, Early Elution Method

Purifications by preparative HPLC (basic pH, early elution method) were performed on a Gilson LC system using Waters Xbridge C18 columns (30 mm×100 mm, 10 μM;

temperature: RT) and a gradient of 10-95% (A=0.2% ammonium hydroxide in water; B=0.2% ammonium hydroxide in acetonitrile) over 14.44 min then 95% B for 2.11 min, with an injection volume of 1500 μL and a flow rate of 40 mL/min. UV spectra were recorded at 215 nm using a Gilson detector.

Preparative HPLC Using Basic pH, Standard Elution Method

Purifications by preparative HPLC (basic pH, standard elution method) were performed on a Gilson LC system using Waters Xbridge C18 columns (30 mm×100 mm, 10 μM; temperature: RT) and a gradient of 30-95% (A=0.2% ammonium hydroxide in water; B=0.2% ammonium hydroxide in acetonitrile) over 11 min then 95% B for 2.11 min, with an injection volume of 1500 μL and a flow rate of 40 mL/min. UV spectra were recorded at 215 nm using a Gilson detector.

If not indicated otherwise, the analytical HPLC conditions are as follows:

| Method A | |
|---|---|
| Column: | Phenomenex Kinetix-XB C18 2.1 × 100 mm, 1.7 μm |
| Column Temp: | 40° C. |
| Eluents: | A: $H_2O$ + 0.1% formic acid, B: acetonitrile + 0.1% formic acid |
| Flow Rate: | 0.6 mL/min |
| Gradient: | 0-5.3 min 5-100% B, 5.3-5.8 min 100% B, 5.8-5.82 min 100-5% B, 5.82-7.00 min 5% B |

| Method C | |
|---|---|
| Column: | Waters UPLC ® BEH ™ C18 2.1 × 100 mm, 1.7 μm |
| Column Temp: | 40° C. |
| Eluents: | A: 2 mM ammonium bicarbonate, buffered to pH 10, B: acetonitrile |
| Flow Rate: | 0.6 mL/min |
| Gradient: | 0-5.3 min 5-100% B, 5.3-5.8 min 100% B, 5.8-5.82 min 100-5% B, 5.82-7.00 min 5% B |

| Method E | |
|---|---|
| Column: | Kinetex Core-Shell C18 2.1 × 50 mm, 5 μm |
| Column Temp: | 40° C. |
| Eluents: | A: $H_2O$ + 0.1% formic acid, B: acetonitrile + 0.1% formic acid |
| Flow Rate: | 1.2 mL/min |
| Gradient: | 0-1.20 min 5-100% B, 1.20-1.30 min 100% B, 1.30-1.31 min 100-5% B, 1.31-1.7 min 5% B |

| Method F | |
|---|---|
| Column: | Phenomenex Gemini-NX C18 2.0 × 50 mm, 3 μm |
| Column Temp: | 40° C. |
| Eluents: | A: 2 mM ammonium bicarbonate, buffered to pH 10, B: acetonitrile |
| Flow Rate: | 1 mL/min |
| Gradient: | 0-1.80 min 1-100% B, 1.80-2.10 min 100% B, 2.10-2.30 min 100-1% B, 2.30-3.50 min 1% B |

| Method G | |
|---|---|
| Column: | Waters UPLC ® BEH ™ C18, 2.1 × 50 mm, 1.7 μm |
| Column Temp: | 40° C. |
| Eluents: | A: $H_2O$ + 0.1% formic acid, B: acetonitrile + 0.1% formic acid |
| Flow Rate: | 0.9 mL/min |
| Gradient: | 0-1.10 min 5-100% B, 1.10-1.35 min 100% B, 1.35-1.40 min 100-5% B, 1.40-1.50 min 5% B |

| Method H | |
|---|---|
| Column: | Kinetex Core-Shell C18 2.1 × 50 mm, 5 μm |
| Column Temp: | 40° C. |
| Eluents: | A: $H_2O$ + 0.1% formic acid, B: acetonitrile + 0.1% formic acid |
| Flow Rate: | 1.2 mL/min |
| Gradient: | 0-1.83 min 5-100% B, 1.83-2.25 min 100% B, 2.25-2.26 min 100-5% B, 2.26-2.8 min 5% B |

-continued

| Method I | |
|---|---|
| Column: | Waters UPLC ® BEH ™ C18 2.1 × 30 mm, 1.7 μm |
| Column Temp: | 40° C. |
| Eluents: | A: 2 mM ammonium bicarbonate, buffered to pH 10, B: acetonitrile |
| Flow Rate: | 1.0 mL/min |
| Gradient: | 0-0.75 min 5-100% B, 0.75-0.85 min 100% B, 0.85-0.9 min 100-5% B, 0.9-1.0 min 5% B |

The following example are intended to illustrate the invention and are not to be construed as being limitations thereon. Temperatures are given in degrees centigrade. If not mentioned otherwise, all evaporations are performed in vacuo, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS and NMR. Abbreviations used are those conventional in the art. If not defined, the terms have their generally accepted meanings.

Abbreviations aq. aqueous
br broad
Cy cyclohexyl
d doublet
dd doublet of doublets
DIBAL diisobutylaluminium hydride
DCM dichloromethane
DCE 1,2-dichloroethane
DIPEA diisopropylethylamine
DMAP 4-dimethylaminopyridine
DMF N,N-dimethylformamide
DMSO dimethyl sulfoxide
EtOH ethanol
EtOAc ethyl acetate
HATU 2-(7-aza-1H-benzotriazole-1-yl)-1,1,3,3-tetramethyluronium hexafluorophosphate
HPLC high pressure liquid chromatography
IPA isopropyl alcohol
MeCN acetonitrile
MeOH methanol
MS mass spectrometry
m multiplet
min minute(s)
mL millilitre(s)
m/z mass to charge ratio
NMR nuclear magnetic resonance
Q-Phos 1,2,3,4,5-pentaphenyl-1'-(di-tert-butylphosphino)ferrocene
Rt retention time
s singlet
t triplet
T3P® 1-propanephosphonic anhydride solution
TBAF tetra-n-butylammonium fluoride
TBTU N,N,N',N'-tetramethyl-O-(benzotriazol-1-yl)uronium tetrafluoroborate
TEA TEA
TFA trifluoroacetic acid
THF tetrahydrofuran
μL microlitre(s)

Preparation Examples

Example 1

4-[[2-(4-tert-Butyl-2-fluoro-5-hydroxy-phenyl) acetyl]amino]-N-(1-methylcyclopropyl)pyridine-2-carboxamide

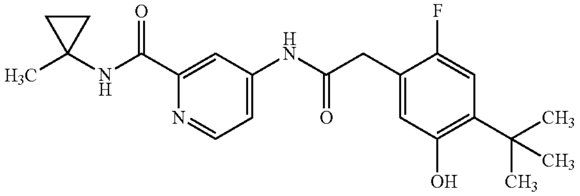 [SMILES: CC1(NC(=O)c2cc(NC(=O)Cc3cc(O)c(C(C)(C)C)cc3F)ccn2)CC1]

Step 1: Methyl 4-[[2-(4-tert-butyl-2-fluoro-5-methoxy-phenyl)acetyl]amino]pyridine-2-carboxylate

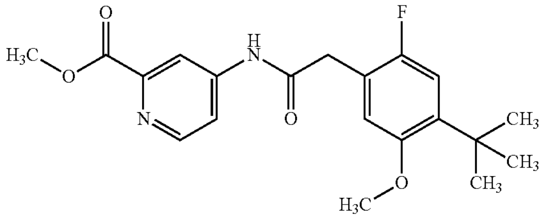 [SMILES: COC(=O)c1cc(NC(=O)Cc2cc(OC)c(C(C)(C)C)cc2F)ccn1]

To a stirred solution of 2-(4-tert-butyl-2-fluoro-5-methoxy-phenyl)acetic acid (Intermediate G) (120 mg, 0.5 mmol), methyl 4-aminopyridine-2-carboxylate (76 mg, 0.5 mmol) and DIPEA (96 μL, 0.55 mmol) in 1,4-dioxane (1 mL) was added 50% T3P® solution in EtOAc (297 μL, 0.5 mmol) and the mixture was stirred at room temperature for 45 min. The resulting mixture was partitioned between EtOAc (20 mL) and water (20 mL). The organic portion was separated, dried over $Na_2SO_4$ and concentrated in vacuo. The crude material was purified by chromatography on silica eluting with 0-100% EtOAc in heptanes to afford the title compound as an off-white solid.

LC-MS (Method E): Rt 1.20 min; MS m/z 375.2=[M+H]+ (100% @215 nm)

$^1$H NMR (500 MHz, Chloroform-d) δ 8.61 (d, J=5.5 Hz, 1H), 8.05-7.84 (m, 2H), 7.60 (s, 1H), 7.07 (d, J=11.9 Hz, 1H), 6.77 (d, J=6.6 Hz, 1H), 3.99 (s, 3H), 3.83 (s, 3H), 3.73 (d, J=1.0 Hz, 2H), 1.36 (s, 9H).

Step 2: 4-[[2-(4-tert-Butyl-2-fluoro-5-hydroxy-phenyl)acetyl]amino]pyridine-2-carboxylic acid

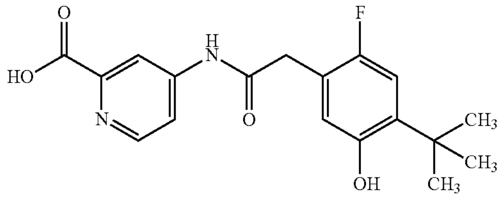 [SMILES: CC(C)(C)c1cc(F)c(CC(=O)Nc2ccnc(C(=O)O)c2)cc1O]

1M $BBr_3$ in DCM (0.21 mL, 2.24 mmol) was added dropwise to a cooled (0° C.), stirred suspension of methyl 4-[[2-(4-tert-butyl-2-fluoro-5-methoxy-phenyl)acetyl]amino]pyridine-2-carboxylate (step 1) (140 mg, 0.37 mmol) in DCM (4 mL). After 30 min, the ice bath was removed and the reaction mixture was stirred at room temperature for 6 h. The resulting mixture was concentrated in vacuo and the residue partitioned between EtOAc (10 mL) and sat. $NaHCO_3$ (10 mL). The aqueous portion was separated and the pH was adjusted to pH~3 using 2M aq. HCl. The mixture was extracted with EtOAc (2×10 mL) and the combined organic extracts were dried over $Na_2SO_4$ and concentrated in vacuo to afford the title compound as an off-white solid.

LC-MS (Method E): Rt 0.98 min; MS m/z 347.1=[M+H]+ (94% @215 nm)

$^1$H NMR (500 MHz, DMSO-d6) δ 11.26 (s, 1H), 9.33 (s, 1H), 8.62 (d, J=6.1 Hz, 1H), 8.40 (d, J=2.1 Hz, 1H), 8.00 (dd, J=6.1, 2.1 Hz, 1H), 6.88 (d, J=11.9 Hz, 1H), 6.74 (d, J=6.9 Hz, 1H), 3.72 (s, 2H), 1.32 (s, 9H)

Step 3: 4-[[2-(4-tert-Butyl-2-fluoro-5-hydroxy-phenyl)acetyl]amino]-N-(1-methylcyclopropyl)pyridine-2-carboxamide To a solution of 4-[[2-(4-tert-butyl-2-fluoro-5-hydroxy-phenyl)acetyl]amino]pyridine-2-carboxylic acid (step 2) (80 mg, 0.21 mmol), 1-methylcyclopropanamine (15 mg, 0.21 mmol) and DIPEA (73 μL, 0.42 mmol) in DMF (1 mL) was added HATU (75 mg, 0.2 mmol) and the resulting mixture was stirred at room temperature for 1 hour. The resulting mixture was concentrated in vacuo and the residue was partitioned between EtOAc (5 mL) and water (5 mL). The organic layer was washed with water (2×5 mL), brine (5 mL), dried over $Na_2SO_4$ and concentrated in vacuo. The crude material was purified by preparative HPLC (acidic pH, early elution method) and the desired fractions were combined and lyophilised overnight to afford the title compound as an off-white powder.

LC-MS (Method A): Rt 3.51 min; MS m/z 400.2=[M+H]+ (96% @215 nm)

$^1$H NMR (500 MHz, DMSO-d6) δ 10.74 (s, 1H), 9.29 (s, 1H), 8.76 (s, 1H), 8.44 (d, J=5.5 Hz, 1H), 8.17 (d, J=2.0 Hz, 1H), 7.80 (dd, J=5.5, 2.2 Hz, 1H), 6.87 (d, J=11.9 Hz, 1H), 6.73 (d, J=6.9 Hz, 1H), 3.64 (s, 2H), 1.35 (s, 3H), 1.31 (s, 9H), 0.82-0.70 (m, 2H), 0.66-0.55 (m, 2H).

The compounds of the following tabulated Examples (Table 1) were prepared analogously to Example 1 by replacing 1-methylcyclopropanamine (step 3) with the appropriate commercially available amine.

TABLE 1

| Ex. | Structure and Name | Retention Time, [M + H]+, 1H NMR |
|---|---|---|
| 1.1 | 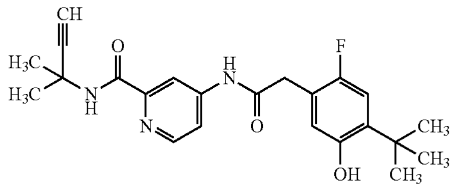 4-[[2-(4-tert-Butyl-2-fluoro-5-hydroxy-phenyl)acetyl]amino]-N-(1,1-dimethylprop-2-ynyl)pyridine-2-carboxamide | LC-MS (Method A): Rt 3.68 min; MS m/z 412.2 = [M + H]+ (100% @ 215 nm) $^{1}$H NMR (500 MHz, DMSO-d6) δ 10.79 (s, 1H), 9.30 (s, 1H), 8.48 (d, J = 5.5 Hz, 1H), 8.32 (s, 1H), 8.21 (d, J = 2.0 Hz, 1H), 7.82 (dd, J = 5.5, 2.2 Hz, 1H), 6.88 (d, J = 11.9 Hz, 1H), 6.74 (d, J = 6.9 Hz, 1H), 3.65 (s, 2H), 3.21 (s, 1H), 1.65 (s, 6H), 1.32 (s, 9H). |
| 1.2 | 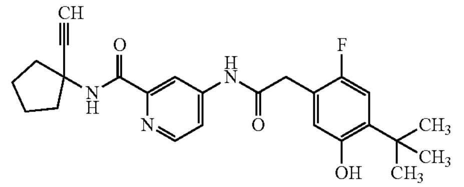 4-[[2-(4-tert-Butyl-2-fluoro-5-hydroxy- phenyl)acetyl]amino]-N-(1-ethynylcyclopentyl)pyridine-2-carboxamide | LC-MS (Method A): Rt 3.89 min; MS m/z 438.3 = [M + H]+ (100% @ 215 nm) $^{1}$H NMR (400 MHz, DMSO-d6) δ 10.79 (s, 1H), 9.30 (s, 1H), 8.53 – 8.37 (m, 2H), 8.20 (d, J = 1.9 Hz, 1H), 7.82 (dd, J = 5.5, 2.2 Hz, 1H), 6.88 (d, J = 11.9 Hz, 1H), 6.74 (d, J = 7.0 Hz, 1H), 3.65 (s, 2H), 3.16 (s, 1H), 2.30 – 2.20 (m, 2H), 2.14 – 2.04 (m, 2H), 1.77 – 1.65 (m, 4H), 1.32 (s, 9H). |
| 1.3 | 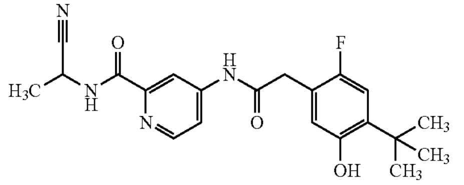 4-[[2-(4-tert-Butyl-2-fluoro-5-hydroxy-phenyl)acetyl]amino]-N-(1-cyanoethyl)pyridine-2-carboxamide | LC-MS (Method A): Rt 3.30 min; MS m/z 399.2 = [M + H]+ (100% @ 215 nm) $^{1}$H NMR (500 MHz, DMSO-d6) δ 10.80 (s, 1H), 9.48 (d, J = 8.1 Hz, 1H), 9.30 (s, 1H), 8.53 (d, J = 5.5 Hz, 1H), 8.25 (d, J = 2.1 Hz, 1H), 7.85 (dd, J = 5.5, 2.2 Hz, 1H), 6.88 (d, J = 11.9 Hz, 1H), 6.74 (d, J = 7.0 Hz, 1H), 5.06 – 4.98 (m, 1H), 3.65 (s, 2H), 1.55 (d, J = 7.2 Hz, 3H), 1.32 (s, 9H). |
| 1.4 | 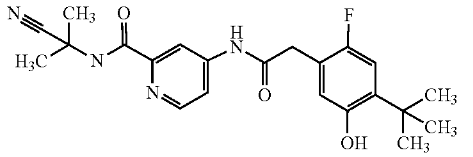 4-[[2-(4-tert-Butyl-2-fluoro-5-hydroxy-phenyl)acetyl]amino]-N-(1-cyano-1-methyl-ethyl)pyridine-2-carboxamide | LC-MS (Method A): Rt 3.45 min; MS m/z 413.2 = [M + H]+ (100% @ 215 nm) $^{1}$H NMR (400 MHz, DMSO-d6) δ 10.83 (s, 1H), 9.32 (s, 1H), 8.83 (s, 1H), 8.52 (d, J = 5.4 Hz, 1H), 8.24 (s, 1H), 7.85 (d, J = 4.0 Hz, 1H), 6.88 (d, J = 11.9 Hz, 1H), 6.75 (d, J = 6.8 Hz, 1H), 3.66 (s, 2H), 1.72 (s, 6H), 1.32 (s, 9H). |
| 1.5 | 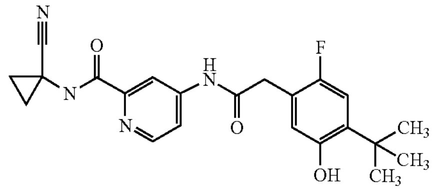 4-[[2-(4-tert-Butyl-2-fluoro-5-hydroxy-phenyl)acetyl]amino]-N-(1-cyanocyclopropyl)pyridine-2-carboxamide | LC-MS (Method A): Rt 3.29 min; MS m/z 411.3 = [M + H]+ (100% @ 215 nm) $^{1}$H NMR (500 MHz, DMSO-d6) δ 10.81 (s, 1H), 9.66 (s, 1H), 9.30 (s, 1H), 8.50 (d, J = 5.5 Hz, 1H), 8.23 (d, J = 2.0 Hz, 1H), 7.85 (dd, J = 5.5, 2.2 Hz, 1H), 6.88 (d, J = 11.9 Hz, 1H), 6.74 (d, J = 7.0 Hz, 1H), 3.65 (s, 2H), 1.56 – 1.51 (m, 2H), 1.36 – 1.28 (m, 11H). |
| 1.6 | 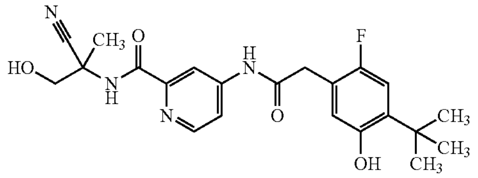 4-[[2-(4-tert-Butyl-2-fluoro-5-hydroxy-phenyl)acetyl]amino]-N-(1-cyano-2-hydroxy-1-methyl-ethyl)pyridine-2-carboxamide | LC-MS (Method A): Rt 3.16 min; MS m/z 429.2 = [M + H]+ (99% @ 215 nm) $^{1}$H NMR (500 MHz, DMSO-d6) δ 10.84 (s, 1H), 9.31 (s, 1H), 8.74 (s, 1H), 8.53 (d, J = 5.5 Hz, 1H), 8.26 (d, J = 2.1 Hz, 1H), 7.86 (dd, J = 5.5, 2.2 Hz, 1H), 6.89 (d, J = 11.9 Hz, 1H), 6.75 (d, J = 6.9 Hz, 1H), 5.94 – 5.86 (m,1H), 3.88 – 3.78 (m, 1H), 3.78 – 3.70 (m, 1H), 3.67 (s, 2H), 1.67 (s, 3H), 1.33 (s, 9H). |

TABLE 1-continued

| Ex. | Structure and Name | Retention Time, [M + H]+, 1H NMR |
|---|---|---|
| 1.7 | 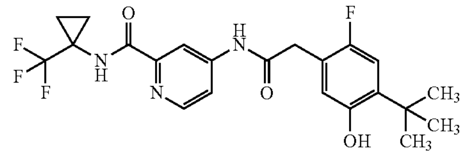 4-[[2-(4-tert-Butyl-2-fluoro-5-hydroxy-phenyl)acetyl]amino]-N-[1-(trifluoromethyl)cyclopropyl]pyridine-2-carboxamide | LC-MS (Method A): Rt 3.72 min; MS m/z 454.3 = [M + H]+ (100% @ 215 nm) $^1$H NMR (400 MHz, DMSO-d6) δ 10.79 (s, 1H), 9.38 (s, 1H), 9.30 (s, 1H), 8.51 (d, J = 5.6 Hz, 1H), 8.22 (d, J = 1.8 Hz, 1H), 7.84 (dd, J = 5.5, 2.2 Hz, 1H), 6.88 (d, J = 11.9 Hz, 1H), 6.74 (d, J = 7.0 Hz, 1H), 3.65 (s, 2H), 1.35 - 1.27 (m, 11H), 1.23 - 1.15 (m, 2H). |

Example 1.3a and 1.3b

Chiral separation of racemic 4-[[2-(4-tert-Butyl-2-fluoro-5-hydroxy-phenyl)acetyl]amino]-N-(1-cyanoethyl)pyridine-2-carboxamide (Example 1.3) using Supercritical Fluid Chromatography [chiral phase column 7% MeOH:93% $CO_2$ with Chiralcel OJ-H @15 ml/min] afforded the individual enantiomers:

Example 1.3a

4-[[2-(4-tert-Butyl-2-fluoro-5-hydroxy-phenyl)acetyl]amino]-N-[(1R)-1-cyanoethyl]pyridine-2-carboxamide or 4-[[2-(4-tert-butyl-2-fluoro-5-hydroxy-phenyl)acetyl]amino]-N-[(1S)-1-cyanoethyl]pyridine-2-carboxamide

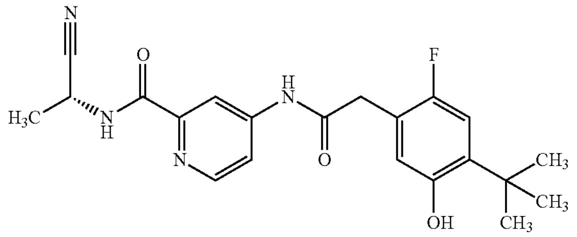

(R)-isomer

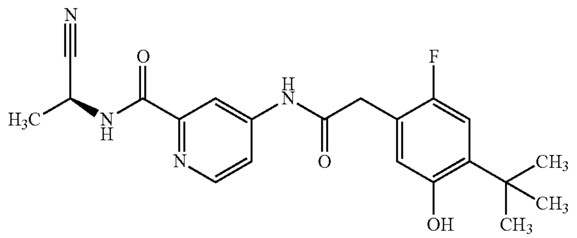

(S)-isomer

First eluted Peak: SFC retention time=3.48 mins

LC-MS (Method A): Rt 3.35 min; MS m/z 399.2=[M+H]+ (100% @215 nm)

$^1$H NMR (500 MHz, DMSO-d6) δ 10.82 (s, 1H), 9.49 (d, J=8.1 Hz, 1H), 9.32 (s, 1H), 8.53 (d, J=5.5 Hz, 1H), 8.25 (d, J=2.0 Hz, 1H), 7.85 (dd, J=5.5, 2.2 Hz, 1H), 6.88 (d, J=11.9 Hz, 1H), 6.74 (d, J=6.9 Hz, 1H), 5.07-4.99 (m, 1H), 3.65 (s, 2H), 1.55 (d, J=7.2 Hz, 3H), 1.32 (s, 9H).

Example 1.3b

4-[[2-(4-tert-Butyl-2-fluoro-5-hydroxy-phenyl)acetyl]amino]-N-[(1R)-1-cyanoethyl]pyridine-2-carboxamide or 4-[[2-(4-tert-butyl-2-fluoro-5-hydroxy-phenyl)acetyl]amino]-N-[(1S)-1-cyanoethyl]pyridine-2-carboxamide

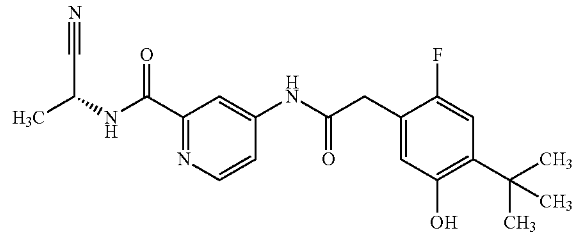

(R)-isomer

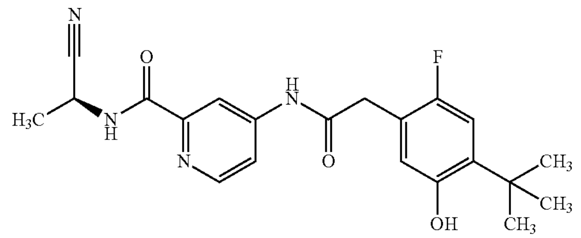

(S)-isomer

Second eluted Peak: SFC retention time=4.36 mins

LC-MS (Method A): Rt 3.35 min; MS m/z 399.2=[M+H]+ (100% @215 nm)

$^1$H NMR (500 MHz, DMSO-d6) δ 10.83 (s, 1H), 9.49 (d, J=8.1 Hz, 1H), 9.33 (s, 1H), 8.53 (d, J=5.5 Hz, 1H), 8.25 (d, J=2.0 Hz, 1H), 7.85 (dd, J=5.5, 2.2 Hz, 1H), 6.88 (d, J=11.9 Hz, 1H), 6.74 (d, J=6.9 Hz, 1H), 5.07-4.99 (m, 1H), 3.65 (s, 2H), 1.55 (d, J=7.2 Hz, 3H), 1.32 (s, 9H).

Example 1.6a and 1.6b

Chiral separation of racemic 4-[[2-(4-tert-Butyl-2-fluoro-5-hydroxy-phenyl)acetyl]amino]-N-(1-cyano-2-hydroxy-1-methyl-ethyl)pyridine-2-carboxamide (Example 1.6) using Supercritical Fluid Chromatography [chiral phase column 25% IPA:75% $CO_2$ with Chiralpak IC 25 cm @4 ml/min] afforded the individual enantiomers:

Example 1.6a

4-[[2-(4-tert-Butyl-2-fluoro-5-hydroxy-phenyl)acetyl]amino]-N-[(1R)-1-cyano-2-hydroxy-1-methyl-ethyl]pyridine-2-carboxamide or 4-[[2-(4-tert-butyl-2-fluoro-5-hydroxy-phenyl)acetyl]amino]-N-[(1S)-1-cyano-2-hydroxy-1-methyl-ethyl]pyridine-2-carboxamide

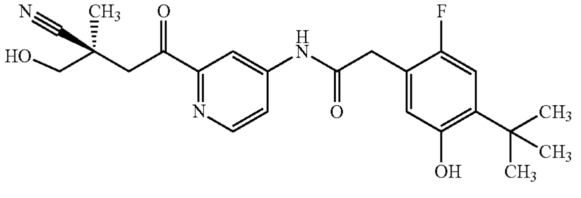

(R)-isomer

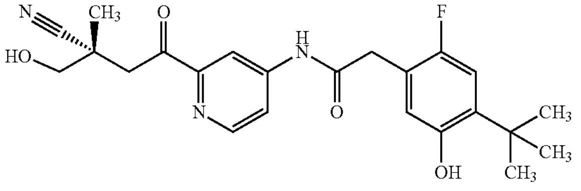

(S)-isomer

First Eluted Peak: SFC retention time=2.33 mins

LC-MS (Method A): Rt 3.16 min; MS m/z 429.3=[M+H]+ (98% @215 nm)

$^1$H NMR (500 MHz, DMSO-d6) δ 10.84 (s, 1H), 9.32 (s, 1H), 8.74 (s, 1H), 8.52 (d, J=5.5 Hz, 1H), 8.25 (d, J=2.0 Hz, 1H), 7.86 (dd, J=5.5, 2.1 Hz, 1H), 6.88 (d, J=11.9 Hz, 1H), 6.75 (d, J=6.9 Hz, 1H), 5.91 (s, 1H), 3.82 (d, J=10.8 Hz, 1H), 3.73 (d, J=10.9 Hz, 1H), 3.66 (s, 2H), 1.66 (s, 3H), 1.32 (s, 9H).

Example 1.6b

4-[[2-(4-tert-Butyl-2-fluoro-5-hydroxy-phenyl)acetyl]amino]-N-[(1R)-1-cyano-2-hydroxy-1-methyl-ethyl]pyridine-2-carboxamide or 4-[[2-(4-tert-butyl-2-fluoro-5-hydroxy-phenyl)acetyl]amino]-N-[(1S)-1-cyano-2-hydroxy-1-methyl-ethyl]pyridine-2-carboxamide

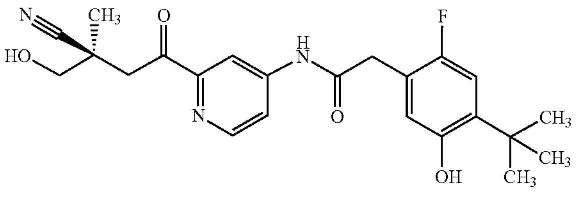

(R)-isomer

-continued

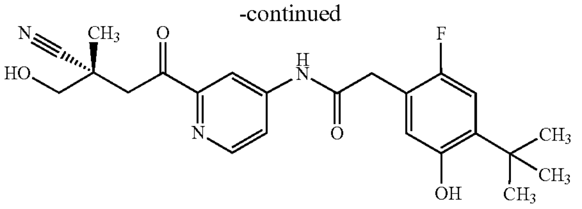

(S)-isomer

Second Eluted Peak: SFC retention time=4.26 mins

LC-MS (Method A): Rt 3.16 min; MS m/z 429.3=[M+H]+ (99% @215 nm)

$^1$H NMR (500 MHz, DMSO-d6) δ 10.85 (s, 1H), 9.30 (s, 1H), 8.74 (s, 1H), 8.52 (d, J=5.5 Hz, 1H), 8.25 (d, J=2.0 Hz, 1H), 7.86 (dd, J=5.5, 2.1 Hz, 1H), 6.88 (d, J=11.9 Hz, 1H), 6.75 (d, J=6.9 Hz, 1H), 5.91 (s, 1H), 3.82 (d, J=11.0 Hz, 1H), 3.73 (d, J=10.9 Hz, 1H), 3.66 (s, 2H), 1.66 (s, 3H), 1.32 (s, 9H).

Example 2

4-[[2-[2-Fluoro-5-hydroxy-4-(1-hydroxy-1-methyl-ethyl)phenyl]acetyl]amino]-N-[1-(trifluoromethyl)cyclopropyl]pyridine-2-carboxamide

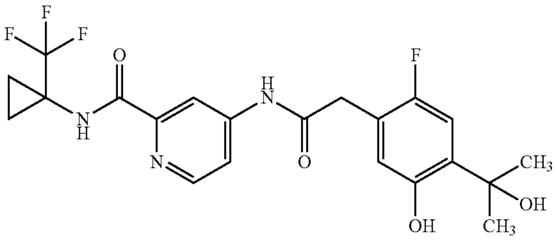 [SMILES: CC(C)(O)c1cc(F)c(CC(=O)Nc2ccnc(C(=O)NC3(C(F)(F)F)CC3)c2)cc1O]

Step 1: 4-[[2-[5-Benzyloxy-2-fluoro-4-(1-hydroxy-1-methyl-ethyl)phenyl]acetyl]amino]-N-[1-(trifluoromethyl)cyclopropyl]pyridine-2-carboxamide

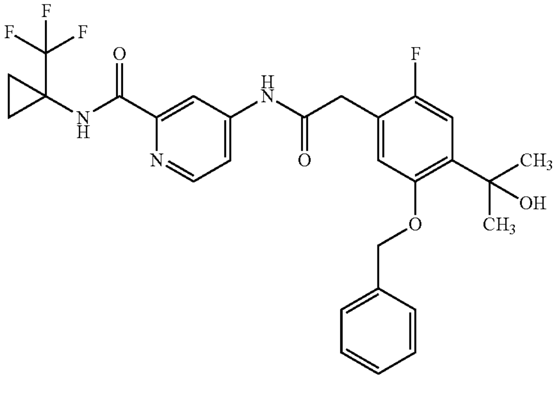 [SMILES: CC(C)(O)c1cc(F)c(CC(=O)Nc2ccnc(C(=O)NC3(C(F)(F)F)CC3)c2)cc1OCc1ccccc1]

To a stirred solution of 2-[5-benzyloxy-2-fluoro-4-(1-hydroxy-1-methyl-ethyl)phenyl]acetic acid (Intermediate B) (38 mg, 0.12 mmol), 4-amino-N-[1-(trifluoromethyl)cyclopropyl]pyridine-2-carboxamide (Intermediate A) (29 mg, 0.12 mmol) and DIPEA (23 μL, 0.13 mmol) in 1,4-dioxane (0.5 mL) was added 50% T3P® solution in EtOAc (71 μL, 0.12 mmol) and the reaction mixture was stirred at room temperature for 1.5 h. The resulting mixture was partitioned between EtOAc (5 mL) and water (5 mL). The organic layer was separated, dried over $Na_2SO_4$ and concentrated in vacuo to afford the title compound as an off-white solid.

LC-MS (Method E): Rt 1.24 mins; MS m/z 546.3=[M+H]+ (93% @215 nm)

$^1$H NMR (500 MHz, MeOD) δ 8.49 (d, J=5.3 Hz, 1H), 8.19 (s, 1H), 7.90 (d, J=4.8 Hz, 1H), 7.46-7.42 (m, 2H), 7.37-7.26 (m, 4H), 7.02 (d, J=6.0 Hz, 1H), 5.12 (s, 2H), 3.77 (s, 2H), 1.57 (s, 6H), 1.42-1.18 (m, 4H).

Step 2: 4-[[2-[2-Fluoro-5-hydroxy-4-(1-hydroxy-1-methyl-ethyl)phenyl]acetyl]amino]-N-[1-(trifluoromethyl)cyclopropyl]pyridine-2-carboxamide To a solution of 4-[[2-[5-benzyloxy-2-fluoro-4-(1-hydroxy-1-methyl-ethyl) phenyl]acetyl]amino]-N-[1-(trifluoromethyl)cyclopropyl]pyridine-2-carboxamide (step 1) (45 mg, 0.08 mmol) in EtOH (2 mL) was added 10% Pd—C (9 mg, 0.01 mmol). The mixture was placed under a hydrogen atmosphere and stirred for 2 h. The resulting mixture was filtered through Celite® (filter material), rinsing with EtOH (10 mL). The filtrate was concentrated in vacuo and the crude material was purified by preparative HPLC (acidic pH, early elution method) to afford the title compound as an off-white solid.

LC-MS (Method A): Rt 2.95 mins; MS m/z 456.2=[M+H]+ (98% @215 nm)

$^1$H NMR (500 MHz, DMSO-d6) δ 10.82 (s, 1H), 9.58 (br s, 1H), 9.40 (s, 1H), 8.51 (d, J=5.5 Hz, 1H), 8.22 (d, J=2.0 Hz, 1H), 7.85 (dd, J=5.5, 2.2 Hz, 1H), 7.11 (d, J=11.4 Hz, 1H), 6.73 (d, J=6.6 Hz, 1H), 5.63 (br s, 1H), 3.68 (s, 2H), 1.49 (s, 6H), 1.35-1.27 (m, 2H), 1.24-1.14 (m, 2H).

The title compound was also prepared according to the following method:

A cooled (0° C.) solution of 4-[[2-(2-fluoro-5-hydroxy-4-isopropenyl-phenyl)acetyl]amino]-N-[1-(trifluoromethyl) cyclopropyl]pyridine-2-carboxamide (Example 7.1) (1.0 g, 2.29 mmol) in IPA (20 mL) and DCM (4 mL) purged with an atmosphere of air was treated with tris(2,2,6,6-tetramethyl-3,5-heptanedionato)manganese(III) (0.14 g, 0.23 mmol) followed by dropwise addition of phenylsilane (0.56 mL, 4.57 mmol). The reaction mixture was stirred at room temperature for 2 h with continuous air purging. The reaction was quenched with 20% aqueous sodium thiosulfate (100 mL) and stirred at room temperature for 30 min. The resulting mixture was extracted with EtOAc (3×100 mL) and the combined organic extracts were washed with brine (100 mL), dried over $MgSO_4$ and concentrated in vacuo. Purification by chromatography on silica eluting with 0 to 100% EtOAc in heptane followed by 0 to 100% MeOH in EtOAc afforded a yellow solid. The solid was further purified by C18 reverse phase chromatography eluting with 10-100% MeCN in water (+0.1% formic acid) to yield a white solid. The solid was recrystallised from MeCN (12 mL) to afford the title compound as a white solid.

LCMS (Method A—MSQ2, 7 min) Rt 2.92 mins; MS m/z 456.2=[M+H]+ (100% @215 nm)

1H NMR (500 MHz, DMSO-d6) δ 10.79 (s, 1H), 9.56 (bs, 1H), 9.39 (s, 1H), 8.50 (d, J=5.5 Hz, 1H), 8.21 (d, J=1.9 Hz, 1H), 7.84 (dd, J=5.5, 2.1 Hz, 1H), 7.10 (d, J=11.4 Hz, 1H), 6.72 (d, J=6.6 Hz, 1H), 5.63 (bs, 1H), 3.67 (s, 2H), 1.48 (s, 6H), 1.35-1.23 (m, 2H), 1.25-1.10 (m, 2H).

Example 2.1

N-(1-Cyano-1-methyl-ethyl)-4-[[2-[2-fluoro-5-hydroxy-4-(1-hydroxy-1-methyl-ethyl)phenyl]acetyl]amino]pyridine-2-carboxamide

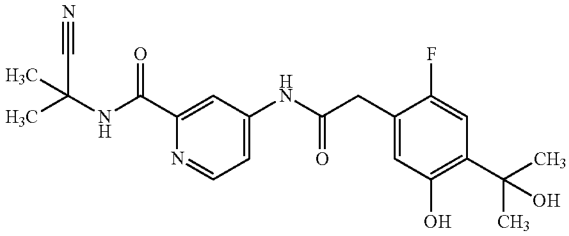 [SMILES: CC(C)(C#N)NC(=O)c1cc(NC(=O)Cc2cc(O)c(C(C)(C)O)cc2F)ccn1]

The title compound was prepared from 2-[5-benzyloxy-2-fluoro-4-(1-hydroxy-1-methyl-ethyl)phenyl]acetic acid (Intermediate B) and 4-amino-N-(1-cyano-1-methyl-ethyl) pyridine-2-carboxamide (Intermediate AB) analogously to Example 2 steps 1 and 2.

LC-MS (Method A): Rt 2.57 mins; MS m/z 415.3=[M+H]+ (95% @215 nm)

(500 MHz, DMSO-d6) δ 10.83 (s, 1H), 9.57 (br s, 1H), 8.84 (s, 1H), 8.53 (d, J=5.5 Hz, 1H), 8.24 (d, J=2.1 Hz, 1H), 7.86 (dd, J=5.5, 2.2 Hz, 1H), 7.11 (d, J=11.4 Hz, 1H), 6.73 (d, J=6.7 Hz, 1H), 5.63 (s, 1H), 3.69 (s, 2H), 1.73 (s, 6H), 1.50 (s, 6H).

Example 2.2

N-tert-Butyl-4-[[2-[4-(1-cyano-1-methyl-ethyl)-2-fluoro-5-hydroxy-phenyl]acetyl]amino]pyridine-2-carboxamide

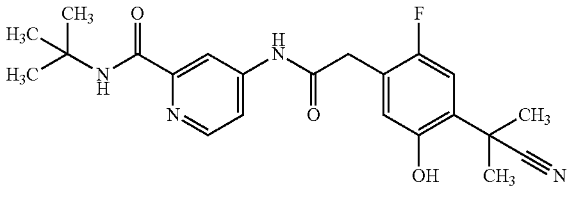 [SMILES: CC(C)(C)NC(=O)c1cc(NC(=O)Cc2cc(O)c(C(C)(C)C#N)cc2F)ccn1]

The title compound was prepared from 2-[5-benzyloxy-4-(1-cyano-1-methyl-ethyl)-2-fluoro-phenyl]acetic acid (Intermediate C) and 4-amino-N-tert-butyl-pyridine-2-carboxamide analogously to Example 2 steps 1 and 2.

LC-MS (Method C): Rt 3.27 mins; MS m/z 411.5=[M−H]− (99% @215 nm)

$^1$H NMR (500 MHz, DMSO-d6) δ 10.82 (s, 1H), 10.10 (s, 1H), 8.46 (d, J=5.5 Hz, 1H), 8.18 (d, J=2.1 Hz, 1H), 8.03 (s, 1H), 7.80 (dd, J=5.5, 2.2 Hz, 1H), 7.04 (d, J=11.0 Hz, 1H), 6.87 (d, J=6.7 Hz, 1H), 3.72 (s, 2H), 1.69 (s, 6H), 1.40 (s, 9H).

Example 2.3

4-[[2-[4-(1-Cyano-1-methyl-ethyl)-2-fluoro-5-hydroxy-phenyl]acetyl]amino]-N-[1-(trifluoromethyl)cyclopropyl]pyridine-2-carboxamide

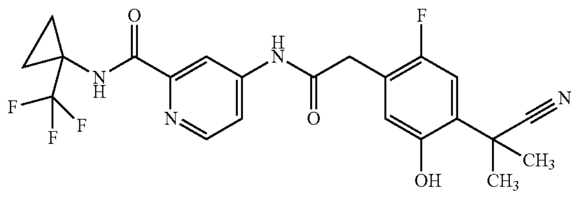 [SMILES: CC(C)(C#N)c1cc(F)c(CC(=O)Nc2ccnc(C(=O)NC3(C(F)(F)F)CC3)c2)cc1O]

The title compound was prepared from 2-[5-benzyloxy-4-(1-cyano-1-methyl-ethyl)-2-fluoro-phenyl]acetic acid (Intermediate C) and 4-amino-N-[1-(trifluoromethyl)cyclopropyl]pyridine-2-carboxamide (Intermediate A) analogously to Example 2 steps 1 and 2.

LC-MS (Method C): Rt 3.20 mins; MS m/z 465.3=[M+H]+ (96% @215 nm)

$^1$H NMR (500 MHz, DMSO-d6) δ 10.82 (s, 1H), 10.05 (br. s, 1H), 9.39 (s, 1H), 8.51 (d, J=5.4 Hz, 1H), 8.21 (s, 1H), 7.87-7.78 (m, 1H), 7.04 (d, J=10.9 Hz, 1H), 6.87 (d, J=6.5 Hz, 1H), 3.72 (s, 2H), 1.69 (s, 6H), 1.33-1.26 (m, 2H), 1.20-1.12 (m, 2H).

Example 2.4

N-tert-Butyl-4-[[2-[4-(1-cyanocyclopropyl)-2-fluoro-5-hydroxy-phenyl]acetyl] amino]pyridine-2-carboxamide

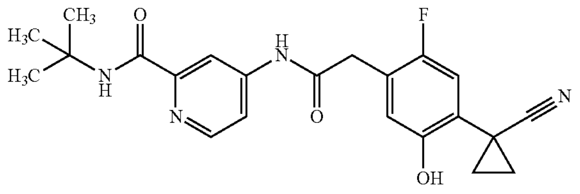 [SMILES: CC(C)(C)NC(=O)c1cc(NC(=O)Cc2cc(O)c(C3(C#N)CC3)cc2F)ccn1]

The title compound was prepared from 2-[5-benzyloxy-4-(1-cyanocyclopropyl)-2-fluoro-phenyl]acetic acid (Intermediate D) and 4-amino-N-tert-butyl-pyridine-2-carboxamide analogously to Example 2 steps 1 and 2.

LC-MS (Method A): Rt 3.05 mins; MS m/z 411.3=[M+H]+ (96% @215 nm)

$^1$H NMR (500 MHz, DMSO-d6) δ 10.80 (s, 1H), 9.96 (br s, 1H), 8.46 (d, J=5.5 Hz, 1H), 8.18 (d, J=2.1 Hz, 1H), 8.03 (s, 1H), 7.80 (dd, J=5.5, 2.2 Hz, 1H), 7.08 (d, J=10.1 Hz, 1H), 6.85 (d, J=6.5 Hz, 1H), 3.71 (s, 2H), 1.59-1.52 (m, 2H), 1.40 (s, 9H), 1.33-1.26 (m, 2H).

Example 2.5

N-(1-Cyano-1-methyl-ethyl)-4-[[2-[4-(1,1-dimethyl-2-morpholino-ethyl)-2-fluoro-5-hydroxy-phenyl]acetyl]amino]pyridine-2-carboxamide

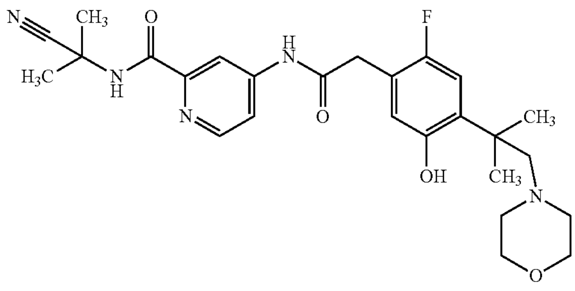 [SMILES: CC(C)(C#N)NC(=O)c1cc(NC(=O)Cc2cc(O)c(C(C)(C)CN3CCOCC3)cc2F)ccn1]

The title compound was prepared from 2-[5-benzyloxy-4-(1,1-dimethyl-2-morpholino-ethyl)-2-fluoro-phenyl]acetic acid (Intermediate E) and 4-amino-N-(1-cyano-1-methyl-ethyl)pyridine-2-carboxamide (Intermediate AB) analogously to Example 2 steps 1 and 2.

LC-MS (Method A): Rt 1.70 mins; MS m/z 498.3=[M+H]+ (99% @215 nm)

$^1$H NMR (500 MHz, DMSO-d6) δ 11.56 (s, 1H), 10.82 (s, 1H), 8.84 (s, 1H), 8.52 (d, J=5.5 Hz, 1H), 8.23 (d, J=2.0 Hz, 1H), 7.85 (dd, J=5.5, 2.2 Hz, 1H), 6.86 (d, J=12.1 Hz, 1H), 6.71 (d, J=7.1 Hz, 1H), 3.66 (s, 2H), 3.57-3.49 (m, 4H), 2.64 (s, 2H), 2.48-2.41 (m, 4H), 1.72 (s, 6H), 1.31 (s, 6H).

Example 2.6

4-[[2-[2-Fluoro-5-hydroxy-4-(2-hydroxy-1,1-dimethyl-ethyl)phenyl]acetyl]amino]-N-[1-(trifluoromethyl)cyclopropyl]pyridine-2-carboxamide

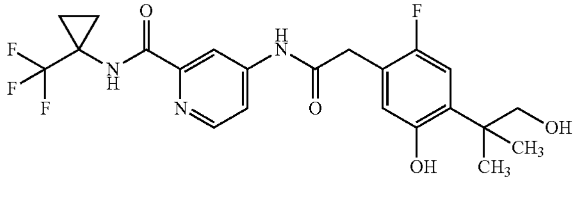

The title compound was prepared from 4-amino-N-[1-(trifluoromethyl)cyclopropyl]pyridine-2-carboxamide (Intermediate A) and 2-[5-benzyloxy-2-fluoro-4-(2-hydroxy-1,1-dimethyl-ethyl)phenyl]acetic acid (Intermediate L) analogously to Example 2 steps 1 and 2.

LC-MS (Method A): Rt 2.99 mins; MS m/z 470.2=[M+H]+ (99% @215 nm)

$^1$H NMR (500 MHz, DMSO-d6) δ 10.79 (s, 1H), 9.39 (s, 1H), 9.38 (s, 1H), 8.50 (d, J=5.5 Hz, 1H), 8.21 (d, J=2.0 Hz, 1H), 7.84 (dd, J=5.5, 2.2 Hz, 1H), 6.90 (d, J=12.1 Hz, 1H), 6.72 (d, J=7.0 Hz, 1H), 4.75 (t, J=5.3 Hz, 1H), 3.64 (s, 2H), 3.60 (d, J=5.0 Hz, 2H), 1.32-1.28 (m, 2H), 1.25 (s, 6H), 1.21-1.16 (m, 2H).

The title compound was also prepared according to the following method:

Step 1: 4-[[2-(5-Fluoro-3,3-dimethyl-2-oxo-benzofuran-6-yl)acetyl]amino]-N-[1-(trifluoro methyl) cyclopropyl]pyridine-2-carboxamide

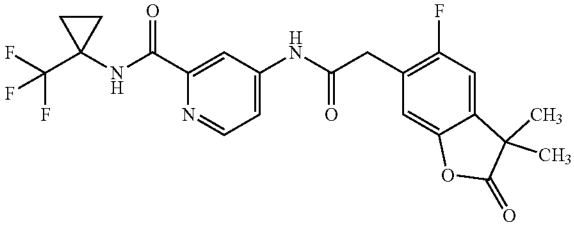 [SMILES: CC1(C)C(=O)Oc2cc(CC(=O)Nc3ccnc(C(=O)NC4(C(F)(F)F)CC4)c3)c(F)cc21]

To a solution of 2-(5-fluoro-3,3-dimethyl-2-oxo-benzofuran-6-yl)acetic acid (Intermediate U) (98%, 1.82 g, 7.5 mmol) and 4-amino-N-[1-(trifluoromethyl)cyclopropyl] pyridine-2-carboxamide (Intermediate A) (96%, 2.11 g, 8.25 mmol) in DMF (40 mL) was added DIPEA (3.93 mL, 22.49 mmol) followed by 50% T3P® solution in EtOAc (8.93 mL, 14.99 mmol) and the reaction mixture was stirred at room temperature for 2 h. The resulting mixture was diluted with EtOAc (150 mL) and washed with brine (3×150 mL). The combined aqueous washes were extracted with EtOAc (80 mL) and the organic extract washed with brine (3×80 mL). The organic extracts were combined, dried over $Na_2SO_4$ and concentrated in vacuo to afford the title compound as a pale yellow solid.

LC-MS (Method E): Rt 1.24 min; MS m/z 466.2=[M+H]+ (92% @215 nm)

$^1$H NMR (500 MHz, DMSO-d6) δ 10.84 (s, 1H), 9.39 (s, 1H), 8.51 (d, J=5.5 Hz, 1H), 8.19 (d, J=2.0 Hz, 1H), 7.84 (dd, J=5.5, 2.2 Hz, 1H), 7.45 (d, J=8.9 Hz, 1H), 7.31 (d, J=5.8 Hz, 1H), 3.83 (s, 2H), 1.45 (s, 6H), 1.32-1.28 (m, 2H), 1.21-1.16 (m, 2H).

Step 2: 4-[[2-[2-Fluoro-5-hydroxy-4-(2-hydroxy-1,1-dimethyl-ethyl)phenyl]acetyl]amino]-N-[1-(trifluoromethyl)cyclopropyl]pyridine-2-carboxamide To a cooled (−78° C.) solution of 4-[[2-(5-fluoro-3,3-dimethyl-2-oxo-benzofuran-6-yl)acetyl]amino]-N-[1-(trifluoromethyl)cyclopropyl]pyridine-2-carboxamide (step 1) (92%, 3.46 g, 6.84 mmol) in THF (65 mL) was added 4M $LiBH_4$ in THF (1.88 mL, 7.53 mmol). The mixture was stirred for 30 min then allowed to gradually warm to room temperature and stirred for 4 h. The resulting mixture was poured onto ice cold 1M HCl (150 mL), allowed to stand for 20 min and then partitioned between EtOAc (200 mL) and water (100 mL). The phases were separated and the aqueous portion was further extracted with EtOAc (200 mL). The combined organic extracts were washed with saturated $NaHCO_3$ solution (2×150 mL), brine (150 mL), dried over $Na_2SO_4$ and concentrated in vacuo. The crude residue was suspended in EtOAc (~19 mL) and filtered, washing the solids with EtOAc (3×10 mL). The solids were dried under vacuum for 1 h and then azeotroped with MeCN (2×100 mL) to give a white solid. The filtrate from the EtOAc filtration was concentrated in vacuo to give a yellow solid which was purified by C18 reverse phase chromatography eluting with MeCN/water 10-100% (0.1% formic acid) to afford an off-white solid. The solids from the EtOAc filtration and from the reverse phase purification were combined and recrystallised from MeCN to afford the title compound as colourless crystalline solid.

LC-MS (Method A): Rt 2.96 min; MS m/z 470.2=[M+H]+ (99% @215 nm)

1H NMR (500 MHz, DMSO-d6) δ 10.80 (s, 1H), 9.57-9.20 (m, 2H), 8.50 (d, J=5.5 Hz, 1H), 8.21 (d, J=1.9 Hz, 1H), 7.84 (dd, J=5.5, 2.1 Hz, 1H), 6.90 (d, J=12.1 Hz, 1H), 6.72 (d, J=7.0 Hz, 1H), 4.76 (s, 1H), 3.65 (s, 2H), 3.60 (s, 2H), 1.32-1.28 (m, 2H), 1.25 (s, 6H), 1.21-1.16 (m, 2H).

Example 2.7

N-(1-Cyano-1-methyl-ethyl)-4-[[2-[2-fluoro-5-hydroxy-4-(2,2,2-trifluoro-1-hydroxy-1-methyl-ethyl) phenyl]acetyl]amino]pyridine-2-carboxamide

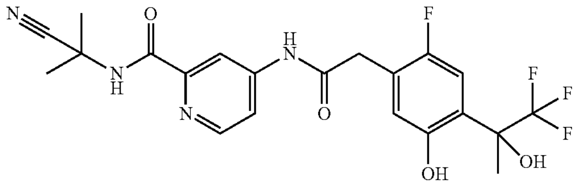 [SMILES: CC(C)(C#N)NC(=O)c1cc(NC(=O)Cc2cc(O)c(C(C)(O)C(F)(F)F)cc2F)ccn1]

The title compound was prepared from 2-[5-benzyloxy-2-fluoro-4-(2,2,2-trifluoro-1-hydroxy-1-methyl-ethyl)phenyl]acetic acid (Intermediate BA) and 4-amino-N-(1-cyano-1-methyl-ethyl)pyridine-2-carboxamide (Intermediate AB) analogously to Example 2 steps 1 and 2.

LC-MS (Method A): Rt 2.91 mins; MS m/z 469.2=[M+H]+ (97% @215 nm)

$^1$H NMR (400 MHz, DMSO-d6) δ 10.86 (s, 1H), 8.84 (s, 1H), 8.52 (d, J=5.5 Hz, 1H), 8.23 (d, J=1.9 Hz, 1H), 7.85 (dd, J=5.5, 2.2 Hz, 1H), 7.24 (d, J=11.4 Hz, 1H), 6.80 (d, J=6.6 Hz, 1H), 3.72 (s, 2H), 1.79 (s, 3H), 1.72 (s, 6H).

Example 2.8

4-[[2-[4-(1-Cyclopropyl-1-hydroxy-ethyl)-2-fluoro-5-hydroxy-phenyl]acetyl]amino]-N-[1-(trifluoromethyl)cyclopropyl]pyridine-2-carboxamide

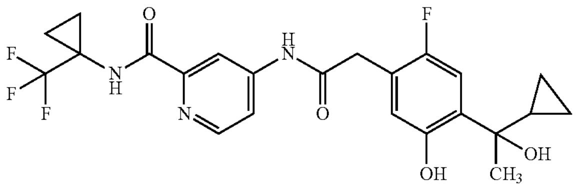 [SMILES: CC(O)(c1cc(F)c(CC(=O)Nc2ccnc(C(=O)NC3(C(F)(F)F)CC3)c2)cc1O)C1CC1]

The title compound was prepared from 2-[5-benzyloxy-4-(1-cyclopropyl-1-hydroxy-ethyl)-2-fluoro-phenyl]acetic acid (Intermediate BB) and 4-amino-N-[1-(trifluoromethyl) cyclopropyl]pyridine-2-carboxamide (Intermediate A) analogously to Example 2 steps 1 and 2.

LC-MS (Method A): Rt 3.23 mins; MS m/z 482.3=[M+H]+ (98% @215 nm)

$^1$H NMR (500 MHz, DMSO-d6) δ 10.80 (s, 1H), 9.61 (s, 1H), 9.39 (s, 1H), 8.50 (d, J=5.5 Hz, 1H), 8.21 (d, J=2.0 Hz, 1H), 7.84 (dd, J=5.5, 2.2 Hz, 1H), 7.08 (d, J=11.4 Hz, 1H), 6.72 (d, J=6.7 Hz, 1H), 5.36 (s, 1H), 3.67 (s, 2H), 1.55-1.48

(m, 4H), 1.32-1.27 (m, 2H), 1.21-1.16 (m, 2H), 0.48-0.41 (m, 1H), 0.36-0.23 (m, 2H), 0.19-0.13 (m, 1H).

Example 2.9

4-[[2-[4-(4-Cyanotetrahydropyran-4-yl)-2-fluoro-5-hydroxy-phenyl]acetyl]amino]-N-[1-(trifluoromethyl)cyclopropyl]pyridine-2-carboxamide

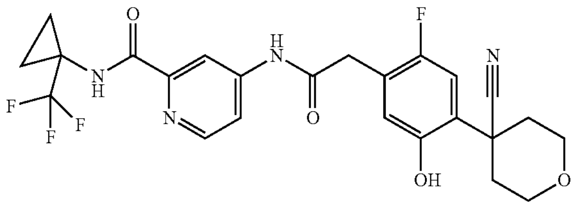 [SMILES: N#CC1(c2cc(F)c(CC(=O)Nc3ccnc(C(=O)NC4(C(F)(F)F)CC4)c3)cc2O)CCOCC1]

The title compound was prepared from 2-[5-benzyloxy-4-(4-cyanotetrahydropyran-4-yl)-2-fluoro-phenyl]acetic acid (Intermediate M) and 4-amino-N-[1-(trifluoromethyl)cyclopropyl]pyridine-2-carboxamide (Intermediate A) analogously to Example 2 steps 1 and 2.

LC-MS (Method A): Rt 2.92 mins; MS m/z 507.2=[M+H]+ (100% @215 nm)

$^1$H NMR (500 MHz, DMSO-d6) δ 10.84 (s, 1H), 10.16 (s, 1H), 9.40 (s, 1H), 8.51 (d, J=5.5 Hz, 1H), 8.21 (d, J=2.1 Hz, 1H), 7.84 (dd, J=5.5, 2.1 Hz, 1H), 7.06 (d, J=11.0 Hz, 1H), 6.90 (d, J=6.7 Hz, 1H), 4.01-3.93 (m, 2H), 3.73 (s, 2H), 3.68 (m, 2H), 2.32-2.27 (m, 2H), 2.00 (td, J=13.2, 4.2 Hz, 2H), 1.32-1.28 (m, 2H), 1.21-1.16 (m, 2H).

Example 2.10

4-[[2-[2-Fluoro-5-hydroxy-4-[2-(trifluoromethyl)oxetan-2-yl]phenyl]acetyl]amino]-N-[1-(trifluoromethyl)cyclopropyl]pyridine-2-carboxamide

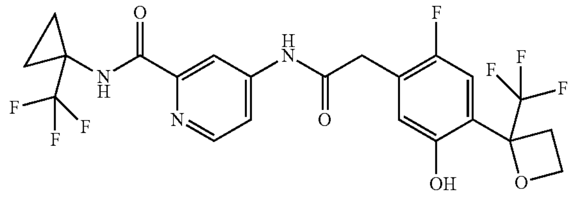 [SMILES: O=C(Cc1cc(O)c(C2(C(F)(F)F)CCO2)cc1F)Nc1ccnc(C(=O)NC2(C(F)(F)F)CC2)c1]

The title compound was prepared from 2-[5-benzyloxy-2-fluoro-4-[2-(trifluoromethyl)oxetan-2-yl]phenyl]acetic acid (Intermediate N) and 4-amino-N-[1-(trifluoromethyl)cyclopropyl]pyridine-2-carboxamide (Intermediate A) analogously to Example 2 steps 1 and 2.

LC-MS (Method A): Rt 3.41 mins; MS m/z 522.4=[M+H]+ (95% @215 nm)

$^1$H NMR (400 MHz, DMSO-$d_6$) δ 10.86 (s, 1H), 9.88 (br. s, 1H), 9.38 (s, 1H), 8.51 (d, J=5.5 Hz, 1H), 8.22 (d, J=2.0 Hz, 1H), 7.84 (dd, J=5.5, 2.2 Hz, 1H), 6.96 (d, J=10.2 Hz, 1H), 6.88 (d, J=6.3 Hz, 1H), 4.75-4.65 (m, 1H), 4.55-4.46 (m, 1H), 3.74 (s, 2H), 3.19-3.05 (m, 2H), 1.34-1.27 (m, 2H), 1.22-1.16 (m, 2H).

Example 2.11

4-[[2-[2-Fluoro-5-hydroxy-4-(1-hydroxy-1-methyl-propyl)phenyl]acetyl]amino]-N-[1-(trifluoromethyl)cyclopropyl]pyridine-2-carboxamide

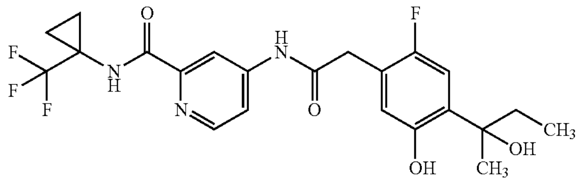

The title compound was prepared from 2-[5-benzyloxy-2-fluoro-4-(1-hydroxy-1-methyl-propyl)phenyl]acetic acid (Intermediate BC) and 4-amino-N-[1-(trifluoromethyl)cyclopropyl]pyridine-2-carboxamide (Intermediate A) analogously to Example 2 steps 1 and 2.

LC-MS (Method A): Rt 3.12 mins; MS m/z 470.2=[M+H]+ (100% @215 nm)

$^1$H NMR (500 MHz, DMSO-d6) δ 10.80 (s, 1H), 9.58 (s, 1H), 9.39 (s, 1H), 8.50 (d, J=5.5 Hz, 1H), 8.21 (d, J=2.0 Hz, 1H), 7.84 (dd, J=5.5, 2.2 Hz, 1H), 7.06 (d, J=11.5 Hz, 1H), 6.70 (d, J=6.7 Hz, 1H), 5.43 (s, 1H), 3.67 (s, 2H), 1.95 (dq, J=14.8, 7.4 Hz, 1H), 1.70 (dq, J=14.5, 7.2 Hz, 1H), 1.46 (s, 3H), 1.33-1.27 (m, 2H), 1.22-1.16 (m, 2H), 0.69 (t, J=7.4 Hz, 3H).

Example 2.11a and 2.11b

Chiral separation of racemic 4-[[2-[2-fluoro-5-hydroxy-4-(1-hydroxy-1-methyl-propyl)phenyl] acetyl]amino]-N-[1-(trifluoromethyl)cyclopropyl]pyridine-2-carboxamide (Example 2.11) using Chiral HPLC [chiral phase column 95% heptanes:5% EtOH with Chiralcel OD-H, 4.6×250 mm, 5 μL, @0.5 mL/min] afforded the individual enantiomers:

Example 2.11a

4-[[2-[2-Fluoro-5-hydroxy-4-[(1S)-1-hydroxy-1-methyl-propyl]phenyl]acetyl]amino]-N[1-(trifluoromethyl)cyclopropyl]pyridine-2-carboxamide or 4-[[2-[2-fluoro-5-hydroxy-4-[(1R)-1-hydroxy-1-methyl-propyl]phenyl]acetyl]amino]-N-[1-(trifluoromethyl)cyclopropyl] pyridine-2-carboxamide

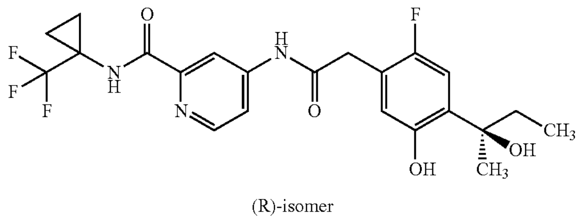

(R)-isomer

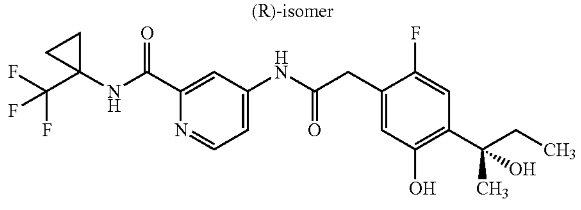

(S)-isomer

First Eluted Peak: Chiral HPLC Retention Time=44.37 min

LC-MS (Method A): Rt 3.15 min; MS m/z 470.4=[M+H]+ (98% @215 nm)

$^{1}$H NMR (500 MHz, DMSO-d6) δ 10.80 (s, 1H), 9.58 (br. s, 1H), 9.39 (s, 1H), 8.50 (d, J=5.5 Hz, 1H), 8.21 (d, J=2.1 Hz, 1H), 7.84 (dd, J=5.5, 2.2 Hz, 1H), 7.06 (d, J=11.5 Hz, 1H), 6.70 (d, J=6.7 Hz, 1H), 5.45 (br. s, 1H), 3.66 (s, 2H), 1.95 (dq, J=14.8, 7.4 Hz, 1H), 1.70 (dq, J=14.4, 7.2 Hz, 1H), 1.46 (s, 3H), 1.36-1.25 (m, 2H), 1.25-1.16 (m, 2H), 0.69 (t, J=7.4 Hz, 3H).

Example 2.11b

4-[[2-[2-Fluoro-5-hydroxy-4-[(1S)-1-hydroxy-1-methyl-propyl]phenyl]acetyl]amino]-N-[1-(trifluoromethyl)cyclopropyl]pyridine-2-carboxamide or 4-[[2-[2-fluoro-5-hydroxy-4-[(1R)-1-hydroxy-1-methyl-propyl]phenyl]acetyl]amino]-N-[1-(trifluoromethyl)cyclopropyl] pyridine-2-carboxamide

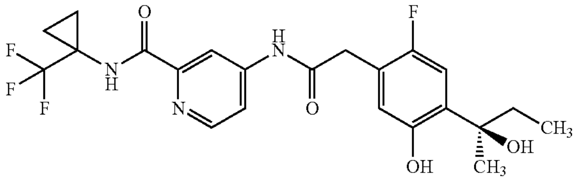

(R)-isomer

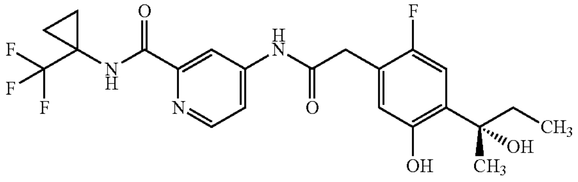 [SMILES: CCC(C)(O)c1cc(F)c(CC(=O)Nc2ccnc(C(=O)NC3(C(F)(F)F)CC3)c2)cc1O]

(S)-isomer

Second Eluted Peak: Chiral HPLC Retention Time=50.81 min

LC-MS (Method A): Rt 3.15 min; MS m/z 470.4=[M+H]+ (98% @215 nm)

$^{1}$H NMR (500 MHz, DMSO-d6) δ 10.80 (s, 1H), 9.60 (br. s, 1H), 9.39 (s, 1H), 8.50 (d, J=5.5 Hz, 1H), 8.21 (d, J=2.0 Hz, 1H), 7.84 (dd, J=5.5, 2.2 Hz, 1H), 7.06 (d, J=11.5 Hz, 1H), 6.70 (d, J=6.7 Hz, 1H), 5.44 (br. s, 1H), 3.67 (s, 2H), 1.95 (dq, J=14.7, 7.4 Hz, 1H), 1.70 (dq, J=14.6, 7.3 Hz, 1H), 1.46 (s, 3H), 1.32-1.26 (m, 2H), 1.23-1.15 (m, 2H), 0.69 (t, J=7.4 Hz, 3H).

Example 2.12

4-[[2-[5-Hydroxy-4-(1-hydroxy-1-methyl-ethyl)-2-methyl-phenyl]acetyl]amino]-N-[1-(trifluoromethyl)cyclopropyl]pyridine-2-carboxamide

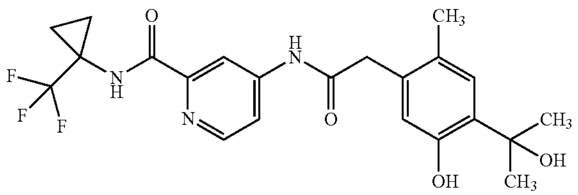 [SMILES: Cc1cc(C(C)(C)O)c(O)cc1CC(=O)Nc1ccnc(C(=O)NC2(C(F)(F)F)CC2)c1]

The title compound was prepared from 2-[5-benzyloxy-4-(1-hydroxy-1-methyl-ethyl)-2-methyl-phenyl]acetic acid (Intermediate BD) and 4-amino-N-[1-(trifluoromethyl)cyclopropyl]pyridine-2-carboxamide (Intermediate A) analogously to Example 2 steps 1 and 2.

LC-MS (Method A): Rt 3.00 min; MS m/z 452.2=[M+H]+ (100% @215 nm)

$^{1}$H NMR (400 MHz, DMSO-d6) δ 10.72 (s, 1H), 9.50 (s, 1H), 9.37 (s, 1H), 8.49 (d, J=5.5 Hz, 1H), 8.21 (d, J=1.9 Hz, 1H), 7.85 (dd, J=5.5, 2.2 Hz, 1H), 7.04 (s, 1H), 6.63 (s, 1H), 5.76 (s, 1H), 3.61 (s, 2H), 2.16 (s, 3H), 1.48 (s, 6H), 1.33-1.27 (m, 2H), 1.22-1.15 (m, 2H).

Example 2.13

4-[[2-[2-Fluoro-5-hydroxy-4-[1-(hydroxymethyl)cyclobutyl]phenyl]acetyl]amino]-N-[1-(trifluoromethyl)cyclopropyl]pyridine-2-carboxamide

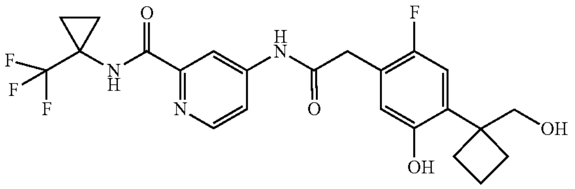 [SMILES: O=C(Cc1cc(O)c(C2(CO)CCC2)cc1F)Nc1ccnc(C(=O)NC2(C(F)(F)F)CC2)c1]

Step 1: [1-[2-Benzyloxy-5-fluoro-4-[2-oxo-2-[[2-[[1-(trifluoromethyl)cyclopropyl]carbamoyl]-4-pyridyl]amino]ethyl]phenyl]cyclobutyl]methyl acetate

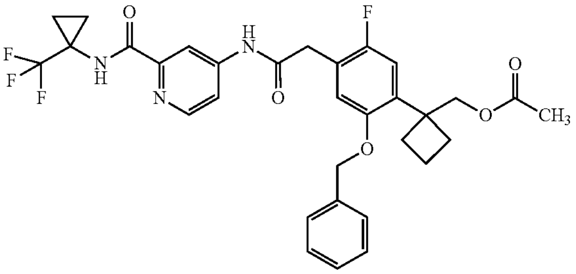 [SMILES: CC(=O)OCC1(c2cc(F)c(CC(=O)Nc3ccnc(C(=O)NC4(C(F)(F)F)CC4)c3)cc2OCc2ccccc2)CCC1]

To a solution of 2-[4-[1-(acetoxymethyl)cyclobutyl]-5-benzyloxy-2-fluoro-phenyl]acetic acid (Intermediate CA) (94%, 142 mg, 0.35 mmol) and 4-amino-N-[1-(trifluoromethyl) cyclopropyl]pyridine-2-carboxamide (Intermediate A) (93 mg, 0.38 mmol) in 1,4-dioxane (2 mL) was added DIPEA (91 μL, 0.52 mmol) followed by 50% T3P® solution in EtOAc (0.31 mL, 0.52 mmol) and the mixture was stirred at room temperature overnight. The resulting mixture was diluted with EtOAc (10 mL) and washed sequentially with 1M HCl (10 mL), sat. $NaHCO_3$ (10 mL) solution and brine (10 mL). The organic portion was dried over $Na_2SO_4$ and concentrated in vacuo. The crude material was purified by chromatography on silica eluting with 0-50% EtOAc in heptanes to afford the title compound as a pale yellow powder.

LC-MS (Method E): Rt 1.44 min; MS m/z 614.4=[M+H]+ (99% @215 nm)

$^1$H NMR (400 MHz, DMSO-d6) δ 10.81 (s, 1H), 9.38 (s, 1H), 8.51 (d, J=5.5 Hz, 1H), 8.21 (d, J=2.1 Hz, 1H), 7.85 (dd, J=5.5, 2.2 Hz, 1H), 7.46-7.41 (m, 2H), 7.40-7.35 (m, 2H), 7.34-7.29 (m, 1H), 7.09 (d, J=6.3 Hz, 1H), 6.82 (d, J=10.4 Hz, 1H), 5.04 (s, 2H), 4.31 (s, 2H), 3.76 (s, 2H), 2.35-2.27 (m, 2H), 2.18-2.11 (m, 2H), 2.07-1.97 (m, 1H), 1.90 (s, 3H), 1.78-1.70 (m, 1H), 1.31-1.17 (m, 4H).

Step 2: 4-[[2-[2-Fluoro-5-hydroxy-4-[1-(hydroxymethyl)cyclobutyl]phenyl]acetyl]amino]-N-[1-(trifluoromethyl)cyclopropyl]pyridine-2-carboxamide To a solution of [1-[2-benzyloxy-5-fluoro-4-[2-oxo-2-[[2-[[1-(trifluoromethyl)cyclopropyl] carbamoyl]-4-pyridyl] amino]ethyl]phenyl]cyclobutyl]methyl acetate (step 1) (99%, 135 mg, 0.22 mmol) in MeOH (1 mL) was added $K_2CO_3$ (33 mg, 0.24 mmol) and the mixture stirred at room temperature for 2 h. The resulting mixture was filtered through Celite® and washed through with MeOH (1 mL). To the filtrate was added 10% Pd/C (14 mg, 0.01 mmol) and the mixture placed under an atmosphere of $H_2$ and stirred for 2 h. The resulting mixture was filtered through Celite® and washed through with MeOH. The filtrate was concentrated in vacuo and purification of the crude material by chromatography on silica eluting with 50-100% EtOAc in heptanes afforded the title compound as a colourless powder.

LC-MS (Method A): Rt 3.10 min; MS m/z 482.3=[M+H]+ (94% @215 nm)

$^1$H NMR (400 MHz, DMSO-d6) δ 10.79 (s, 1H), 9.38 (s, 1H), 9.01 (s, 1H), 8.50 (d, J=5.5 Hz, 1H), 8.22 (d, J=1.9 Hz, 1H), 7.84 (dd, J=5.5, 2.1 Hz, 1H), 6.69 (d, J=6.7 Hz, 1H), 6.65 (d, J=10.8 Hz, 1H), 4.84 (t, J=5.4 Hz, 1H), 3.65 (s, 2H), 3.62 (d, J=5.6 Hz, 2H), 2.21-2.16 (m, 4H), 2.00-1.90 (m, 1H), 1.74-1.67 (m, 1H), 1.32-1.27 (m, 2H), 1.21-1.17 (m, 2H).

Example 2.14

N-(1-Cyano-1-methyl-ethyl)-4-[[2-[2-fluoro-5-hydroxy-4-[2-(trifluoromethyl)oxetan-2-yl]phenyl]acetyl]amino]pyridine-2-carboxamide

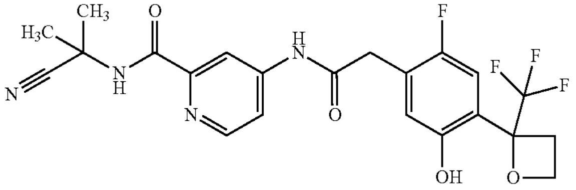 [SMILES: CC(C)(C#N)NC(=O)c1cc(NC(=O)Cc2cc(O)c(C3(C(F)(F)F)CCO3)cc2F)ccn1]

The title compound was prepared from 2-[5-benzyloxy-2-fluoro-4-[2-(trifluoromethyl)oxetan-2-yl]phenyl]acetic acid (Intermediate N) and 4-amino-N-(1-cyano-1-methyl-ethyl)pyridine-2-carboxamide (Intermediate AB) analogously to Example 2 steps 1 and 2.

LC-MS (Method A): Rt 3.11 min; MS m/z 481.4=[M+H]+ (100% @215 nm)

1H NMR (500 MHz, DMSO-d6) δ 10.89 (s, 1H), 9.83 (s, 1H), 8.85 (s, 1H), 8.53 (d, J=5.5 Hz, 1H), 8.24 (d, J=2.0 Hz, 1H), 7.86 (dd, J=5.5, 2.2 Hz, 1H), 6.97 (d, J=10.1 Hz, 1H), 6.88 (d, J=6.3 Hz, 1H), 4.73-4.66 (m, 1H), 4.55-4.48 (m, 1H), 3.76 (s, 2H), 3.18-3.06 (m, 2H), 1.72 (s, 6H).

Example 2.15

4-[[2-[2-Fluoro-5-hydroxy-4-[4-(hydroxymethyl)tetrahydropyran-4-yl]phenyl]acetyl] amino]-N-[1-(trifluoromethyl)cyclopropyl]pyridine-2-carboxamide

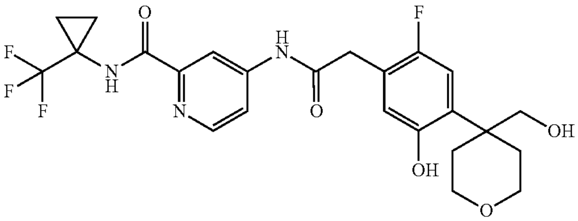 [SMILES: O=C(Cc1cc(O)c(C2(CO)CCOCC2)cc1F)Nc1ccnc(C(=O)NC2(C(F)(F)F)CC2)c1]

The title compound was prepared from 2-[4-[4-(acetoxymethyl)tetrahydropyran-4-yl]-5-benzyloxy-2-fluoro-phenyl]acetic acid (Intermediate CB) and 4-amino-N-[1-(trifluoromethyl)cyclopropyl]pyridine-2-carboxamide (Intermediate A) analogously to Example 2 steps 1 and 2.

LC-MS (Method A): Rt 2.56 min; MS m/z 512.1=[M+H]+ (100% @215 nm)

$^1$H NMR (500 MHz, DMSO-d6) δ 10.82 (s, 1H), 9.40 (d, J=6.9 Hz, 2H), 8.51 (d, J=5.5 Hz, 1H), 8.22 (d, J=1.9 Hz, 1H), 7.84 (dd, J=5.5, 2.2 Hz, 1H), 6.88 (d, J=12.2 Hz, 1H), 6.76 (d, J=7.0 Hz, 1H), 4.61 (t, J=5.2 Hz, 1H), 3.70-3.61 (m, 6H), 3.43-3.37 (m, 2H), 2.26-2.17 (m, 2H), 1.83 (ddd, J=13.3, 9.3, 3.6 Hz, 2H), 1.33-1.27 (m, 2H), 1.22-1.15 (m, 2H).

Example 2.16

4-[[2-[2-Fluoro-5-hydroxy-4-[1-(hydroxymethyl)cyclopropyl]phenyl]acetyl]amino]-N-[1-(trifluoromethyl)cyclopropyl]pyridine-2-carboxamide

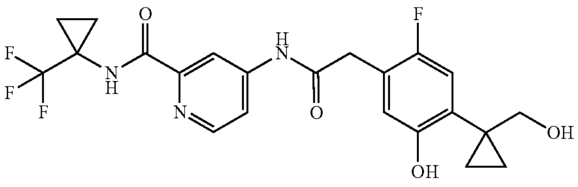 [SMILES: O=C(Cc1cc(O)c(C2(CO)CC2)cc1F)Nc1ccnc(C(=O)NC2(C(F)(F)F)CC2)c1]

Step 1: Methyl 1-[2-benzyloxy-4-(2-benzyloxy-2-oxo-ethyl)-5-fluoro-phenyl]cyclopropanecarboxylate

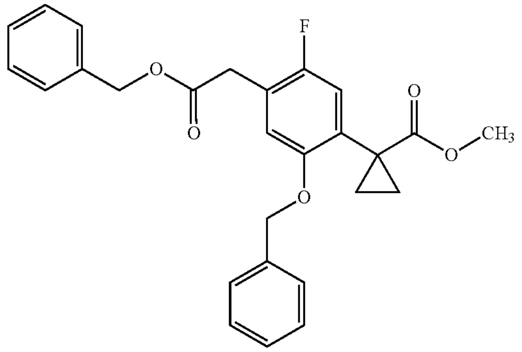 [SMILES: COC(=O)C1(c2cc(F)c(CC(=O)OCc3ccccc3)cc2OCc2ccccc2)CC1]

Activated zinc (1.066 g, 16.31 mmol) in THF (54.35 mL) was heated at 65° C. and treated with bromine (70 μL, 1.22 mmol) and stirred until the red colour had dissipated. Methyl 1-bromocyclopropanecarboxylate (21.89 g, 12.23 mmol) was added and the mixture was heated at 70° C. for 2 h. The mixture was then cooled to room temperature and allowed to settle to help remove any remaining Zn dust.

A separate vessel was charged with $Pd(dba)_2$ (234 mg, 0.41 mmol), Q-Phos (290 mg, 0.41 mmol) and benzyl 2-(5-benzyloxy-4-bromo-2-fluoro-phenyl)acetate (Intermediate S, step 2) (3.5 g, 8.15 mmol) and placed under a nitrogen atmosphere. To this mixture, transferred by syringe, was added the freshly prepared Negishi reagent and the reaction mixture was stirred at 65° C. for 3 h. The resulting mixture was concentrated in vacuo and purification by chromatography on silica eluting with 0-30% EtOAc in heptanes (repeated twice) afforded the title compound as a pale pink solid.

LC-MS (Method I): Rt 0.77 min; MS m/z 466.3=[M+NH4]+ (97% @215 nm)

$^1$H NMR (400 MHz, DMSO-d6) δ 7.40-7.31 (m, 10H), 7.11-7.06 (m, 2H), 5.14 (s, 2H), 5.06 (s, 2H), 3.76 (s, 2H), 3.48 (s, 3H), 1.47-1.41 (m, 2H), 1.18-1.13 (m, 2H).

Step 2: 2-[2-Fluoro-5-hydroxy-4-(1-methoxycarbonylcyclopropyl)phenyl]acetic acid

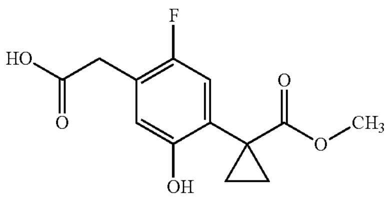 [SMILES: COC(=O)C1(c2cc(F)c(CC(=O)O)cc2O)CC1]

A mixture of methyl 1-[2-benzyloxy-4-(2-benzyloxy-2-oxo-ethyl)-5-fluoro-phenyl]cyclopropanecarboxylate (step 1) (97%, 3.64 g, 7.88 mmol) in EtOH (60 mL) was treated with 10% Pd/C (50% in water) (15.38 g, 0.72 mmol), placed under a hydrogen atmosphere and stirred at room temperature for 4 h. The resulting mixture was filtered through Celite®, washing with EtOAc, and concentrated in vacuo to afford the title compound as a pale yellow soft glass.

LC-MS (Method G): Rt 0.69 min; MS m/z 269.1=[M+H]+ (94% @215 nm)

$^1$H NMR (400 MHz, DMSO-d6) δ 12.42 (br. s, 1H), 9.36 (s, 1H), 6.91 (d, J=10.3 Hz, 1H), 6.69 (d, J=6.7 Hz, 1H), 3.52 (s, 3H), 3.49 (s, 2H), 1.44-1.39 (m, 2H), 1.12-1.06 (m, 2H).

Step 3: 2-(5-Fluoro-2-oxo-spiro[benzofuran-3,1'-cyclopropane]-6-yl)acetic acid

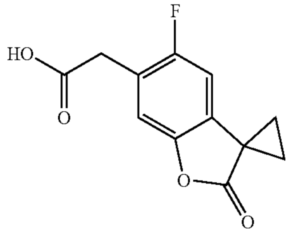 [SMILES: O=C(O)Cc1cc2c(cc1F)C1(CC1)C(=O)O2]

2-[2-Fluoro-5-hydroxy-4-(1-methoxycarbonylcyclopropyl)phenyl]acetic acid (step 2) (94%, 2.8 g, 9.81 mmol) in THF (10 mL) was treated with 1M KOH (29.44 mL, 29.44 mmol) at room temperature and stirred for 2 h. The resulting mixture was treated with 1M aq. HCl (39.25 mL, 39.25 mmol) and extracted with EtOAc (3×20 mL). The combined organic extracts were dried over $Na_2SO_4$ and concentrated in vacuo. The residue was dissolved in THF (20 mL), treated with 4M HCl in dioxane (3.46 mL, 98.12 mmol) and heated at 80° C. for 1 h. Additional 4 M HCl in dioxane (10 mL) was added and stirring continued at 80° C. for 1 h. After cooling to room temperature, the mixture was concentrated in vacuo to afford the title compound as an off-white solid.

LC-MS (Method E): Rt 0.98 min; (83% @215 nm)

$^1$H NMR (400 MHz, DMSO-d6) δ 12.46 (br. s, 1H), 7.27 (d, J=5.8 Hz, 1H), 7.12-7.08 (m, 1H), 3.64 (d, J=1.6 Hz, 2H), 1.89-1.84 (m, 2H), 1.76-1.71 (m, 2H).

Step 4: 4-[[2-(5-Fluoro-2-oxo-spiro[benzofuran-3,1'-cyclopropane]-6-yl)acetyl]amino]-N-[1-(trifluoromethyl)cyclopropyl]pyridine-2-carboxamide

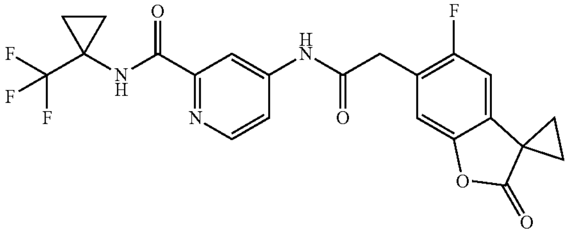 [SMILES: O=C(Cc1cc2c(cc1F)C1(CC1)C(=O)O2)Nc1ccnc(C(=O)NC2(C(F)(F)F)CC2)c1]

2-(5-Fluoro-2-oxo-spiro[benzofuran-3,1'-cyclopropane]-6-yl)acetic acid (step 3) (83%, 1.860 g, 6.54 mmol) and 4-amino-N-[1-(trifluoromethyl)cyclopropyl]pyridine-2-carboxamide (Intermediate A) (1.76 g, 7.19 mmol) in 1,4-dioxane (40 mL) were treated with DIPEA (3.42 mL, 19.61 mmol) and 50% T3P® solution in EtOAc (7.78 mL, 13.07 mmol) and the mixture was stirred at room temperature for 45 min. The resulting mixture was partitioned between water (150 mL) and EtOAc (150 mL) and the phases were separated. The aqueous portion was back-extracted with EtOAc (150 mL) then the combined organic extracts were dried over $Na_2SO_4$ and concentrated in vacuo to afford the title compound as a beige solid.

LC-MS (Method E): Rt 1.20 min; MS m/z 464.2=[M+H]+ (98% @215 nm)

$^{1}$H NMR (400 MHz, DMSO-d6) δ 10.81 (s, 1H), 9.38 (s, 1H), 8.50 (d, J=5.5 Hz, 1H), 8.19 (d, J=2.0 Hz, 1H), 7.84 (dd, J=5.5, 2.1 Hz, 1H), 7.33 (d, J=5.8 Hz, 1H), 7.12 (d, J=9.0 Hz, 1H), 3.83 (s, 2H), 1.90-1.84 (m, 2H), 1.78-1.73 (m, 2H), 1.33-1.26 (m, 2H), 1.21-1.16 (m, 2H).

Step 5: 4-[[2-[2-Fluoro-5-hydroxy-4-[1-(hydroxymethyl)cyclopropyl]phenyl]acetyl]amino]-N-[1-(trifluoromethyl)cyclopropyl]pyridine-2-carboxamide To a cooled (−78° C.) solution of 4-[[2-(5-fluoro-2-oxo-spiro[benzofuran-3,1'-cyclopropane]-6-yl)acetyl]amino]-N-[1-(trifluoromethyl)cyclopropyl]pyridine-2-carboxamide (step 4) (98%, 3.12 g, 6.59 mmol) in THF (70 mL) was added dropwise 4M $LiBH_4$ in THF (1.81 mL, 7.25 mmol). The mixture was stirred at −78° C. for 10 min, then allowed to warm gradually to room temperature and stirred at room temperature for 5 h. The resulting mixture was cooled to 0° C. with an ice bath and quenched by the dropwise addition of 1M HCl (70 mL). The resulting mixture was warmed to room temperature, diluted with EtOAc (300 mL) and water (230 mL) and the phases were separated. The aqueous portion was extracted with EtOAc (300 mL) and the combined organic extracts were dried over $Na_2SO_4$ and concentrated in vacuo to give the crude product as a beige solid. The solid was recrystallised from EtOAc (~25 mL) to afford a white powdery solid. The mother liquor was concentrated in vacuo to give a yellow solid which was purified by C18 reverse phase chromatography eluting with MeCN/water 10-100% (0.1% formic acid) to afford an off-white solid.

The material from the EtOAc crystallization and the reverse phase purification were combined in MeCN and concentrated in vacuo. The solids were azeotroped with MeCN then recrystallised from MeCN and dried in a high vacuum oven at ~40° C. overnight to afford the title compound as a white solid.

LC-MS (Method A): Rt 2.84 min; MS m/z 468.3=[M+H]+ (99% @215 nm)

$^{1}$H NMR (400 MHz, DMSO-d6) δ 10.79 (s, 1H), 9.38 (s, 1H), 9.24 (s, 1H), 8.51 (d, J=5.5 Hz, 1H), 8.21 (d, J=1.9 Hz, 1H), 7.85 (dd, J=5.5, 2.2 Hz, 1H), 6.89 (d, J=10.4 Hz, 1H), 6.75 (d, J=6.7 Hz, 1H), 4.99 (t, J=5.4 Hz, 1H), 3.67 (s, 2H), 3.47 (d, J=5.3 Hz, 2H), 1.35-1.27 (m, 2H), 1.23-1.14 (m, 2H), 0.83-0.73 (m, 2H), 0.68-0.58 (m, 2H).

Example 3

4-[[2-(4-tert-Butyl-2-fluoro-5-hydroxy-phenyl)acetyl]amino]-N-(1-cyano-1-methyl-ethyl)-5-fluoro-pyridine-2-carboxamide

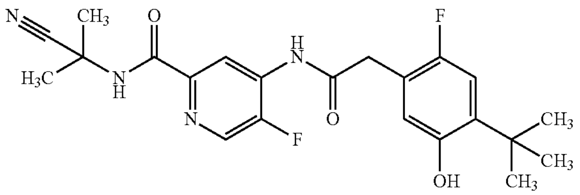 [SMILES: CC(C)(C#N)NC(=O)c1cc(NC(=O)Cc2cc(O)c(C(C)(C)C)cc2F)c(F)cn1]

Step 1: N-(2-Bromo-5-fluoro-4-pyridyl)-2-(4-tert-butyl-2-fluoro-5-methoxy-phenyl) acetamide

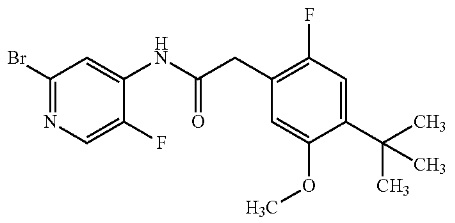 [SMILES: COc1cc(CC(=O)Nc2cc(Br)ncc2F)c(F)cc1C(C)(C)C]

The title compound was prepared from 2-(4-tert-butyl-2-fluoro-5-methoxy-phenyl)acetic acid (Intermediate G) and 2-bromo-5-fluoro-pyridin-4-amine analogously to Example 1 step 1. DIPEA was replaced with TEA.

LC-MS (Method E): Rt 1.38 mins; MS m/z 413.0, 415.0=[M+H]+ (94 @ 215 nm)

$^{1}$H NMR (500 MHz, DMSO-d6) δ 10.67 (s, 1H), 8.41 (d, J=2.6 Hz, 1H), 8.38 (d, J=5.8 Hz, 1H), 6.98 (d, J=6.7 Hz, 1H), 6.95 (d, J=11.8 Hz, 1H), 3.87 (s, 2H), 3.78 (s, 3H), 1.31 (s, 9H).

Step 2: Methyl 4-[[2-(4-tert-butyl-2-fluoro-5-methoxy-phenyl)acetyl]amino]-5-fluoro-pyridine-2-carboxylate

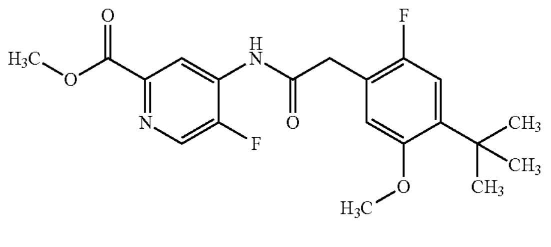 [SMILES: COC(=O)c1cc(NC(=O)Cc2cc(OC)c(C(C)(C)C)cc2F)c(F)cn1]

All reagents charged to COware gas reactor system (two-chamber glass apparatus) according to the following procedure;

Chamber A was charged with N-(2-bromo-5-fluoro-4-pyridyl)-2-(4-tert-butyl-2-fluoro-5-methoxy-phenyl) acetamide (step 1) (500 mg, 1.21 mmol), Pd(dppf)$Cl_2$ (85 mg, 0.12 mmol) and the apparatus was flushed with nitrogen. To chamber B, a solution of formic acid (320 μL, 8.47 mmol) and methanesulfonyl chloride (656 μL, 8.47 mmol) in degassed toluene (5 mL) was added. Then a solution of TEA (423 μL, 2.42 mmol) in MeOH (5 mL) was added to chamber A followed by the addition of TEA (2.96 mL, 16.94 mmol) to chamber B to generate carbon monoxide. The COware equipment was heated to 60° C. for 16 h. The resulting mixture from chamber A was partitioned between EtOAc (100 mL) and brine (100 mL). The phases were separated and the aqueous portion was re-extracted with EtOAc (100 mL). The combined organic extracts were dried over $Na_2SO_4$ and concentrated in vacuo and purification of the crude material by chromatography on silica eluting with 0-100% EtOAc in heptanes afforded the title compound as a pale beige foam.

LC-MS (Method E): Rt 1.25 mins; MS m/z 393.1=[M+H]+ (94% @215 nm)

$^1$H NMR (500 MHz, DMSO-d6) δ 10.67 (s, 1H), 8.91 (d, J=6.4 Hz, 1H), 8.66 (d, J=2.4 Hz, 1H), 6.99 (d, J=6.7 Hz, 1H), 6.96 (d, J=11.8 Hz, 1H), 3.87 (s, 2H), 3.85 (s, 3H), 3.79 (s, 3H), 1.32 (s, 9H).

Step 3: 4-[[2-(4-tert-Butyl-2-fluoro-5-hydroxy-phenyl)acetyl]amino]-5-fluoro-pyridine-2-carboxylic acid

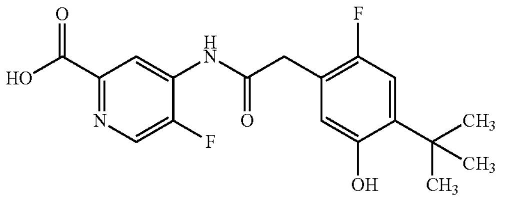 [SMILES: CC(C)(C)c1cc(F)c(CC(=O)Nc2cc(C(=O)O)ncc2F)cc1O]

1M $BBr_3$ in DCM (4.34 mL, 4.34 mmol) was added to a solution of methyl 4-[[2-(4-tert-butyl-2-fluoro-5-methoxy-phenyl)acetyl]amino]-5-fluoro-pyridine-2-carboxylate (step 2) (98%, 348 mg, 0.87 mmol) in DCM (10 mL) and the mixture was stirred at room temperature for 4 h. The resulting mixture was diluted with water (15 mL) and stirred at room temperature for 10 min. The volatile solvent removed in vacuo and the resulting mixture diluted with EtOAc (50 mL) and 1:1 water:brine (30 mL). The phases were separated and the aqueous portion was re-extracted with EtOAc (30 mL). The combined organic extracts were dried over $Na_2SO_4$ and concentrated in vacuo to afford the title compound as an off-white solid.

LC-MS (Method E): Rt 1.08 mins; MS m/z 365.1=[M+H]+ (95% @215 nm)

$^1$H NMR (400 MHz, DMSO-d6) δ 10.61 (s, 1H), 9.30 (s, 1H), 8.90 (d, J=6.5 Hz, 1H), 8.64 (d, J=2.4 Hz, 1H), 6.87 (d, J=11.9 Hz, 1H), 6.73 (d, J=7.0 Hz, 1H), 3.78 (s, 2H), 1.32 (s, 9H).

Step 4: 4-[[2-(4-tert-Butyl-2-fluoro-5-hydroxy-phenyl)acetyl]amino]-N-(1-cyano-1-methyl-ethyl)-5-fluoro-pyridine-2-carboxamide HATU (151 mg, 0.40 mmol) was added to a solution of 4-[[2-(4-tert-butyl-2-fluoro-5-hydroxy-phenyl)acetyl]amino]-5-fluoro-pyridine-2-carboxylic acid (step 3) (145 mg, 0.40 mmol), 2-amino-2-methyl-propanenitrile hydrochloride (72 mg, 0.6 mmol) and DIPEA (0.17 mL, 0.99 mmol) in DMF (3 mL) and the reaction mixture was stirred at room temperature for 2 h. The resulting mixture was diluted with EtOAc (20 mL) and water (20 mL) and the phases were separated. The organic portion was washed with brine (20 mL), dried over $Na_2SO_4$ and concentrated in vacuo. Purification of the crude material by preparative HPLC (acidic pH, standard elution method) afforded the title compound as a white solid.

LC-MS (Method A): Rt 3.54 mins; MS m/z 431.2=[M+H]+ (98% @215 nm)

$^1$H NMR (500 MHz, DMSO-d6) δ 10.63 (s, 1H), 9.31 (s, 1H), 8.88 (d, J=6.5 Hz, 1H), 8.82 (s, 1H), 8.61 (d, J=2.4 Hz, 1H), 6.88 (d, J=11.9 Hz, 1H), 6.74 (d, J=6.9 Hz, 1H), 3.79 (s, 2H), 1.71 (s, 6H), 1.32 (s, 9H).

Example 4

N-(1-Cyanocyclopropyl)-4-[[2-[2-deuterio-6-fluoro-3-hydroxy-4-[2,2,2-trideuterio-1,1-bis(trideuteriomethyl)ethyl]phenyl]acetyl]amino]pyridine-2-carboxamide

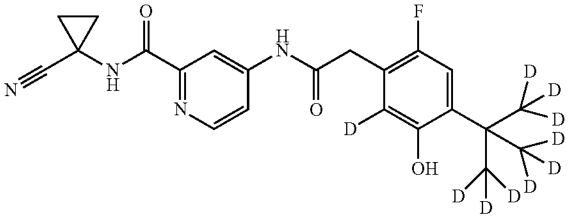 [SMILES: [2H]c1c(O)c(C(C([2H])([2H])[2H])(C([2H])([2H])[2H])C([2H])([2H])[2H])cc(F)c1CC(=O)Nc1ccnc(C(=O)NC2(C#N)CC2)c1]

Step 1: 2-[2-Deuterio-6-fluoro-3-methoxy-4-[2,2,2-trideuterio-1,1-bis(trideuterio methyl) ethyl]phenyl] acetic acid

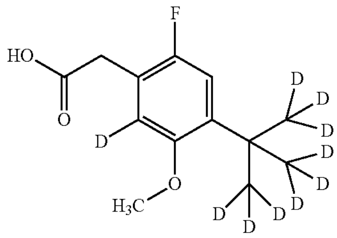 [SMILES: [2H]c1c(CC(=O)O)c(F)cc(C(C([2H])([2H])[2H])(C([2H])([2H])[2H])C([2H])([2H])[2H])c1OC]

A vessel containing 2-(2-fluoro-5-methoxy-phenyl)acetic acid (300 mg, 1.63 mmol) in DCE (16 mL) was treated with 1,1,1,3,3,3-hexadeuterio-2-deuteriooxy-2-(trideuteriomethyl) propane (1.23 mL, 13.03 mmol) and deuterosulfuric acid (0.71 mL, 13.03 mmol) then stirred at room temperature for 3 h. The resulting mixture was diluted with water (20 mL) and the layers separated. The aqueous layer was extracted with DCM (3×20 mL) and the combined organic extracts were dried over $Na_2SO_4$ and concentrated in vacuo. The residue was dissolved in DCM (15 mL), treated with TFA (1.5 mL), stirred for 2 h and concentrated in vacuo. Purification of the resulting mixture by chromatography on silica eluting with 0-100% EtOAc (+1% formic acid) in heptanes (+1% formic acid) afforded the title compound as a colourless solid. (Note: NMR analysis indicated 80% D incorporation in the ortho-position to the phenol, and 97% D incorporation in the tert-butyl group.)

LC-MS (Method E): Rt 1.18 mins; (75% @215 nm)

$^1$H NMR (500 MHz, DMSO-d6) δ 12.41 (s, 1H), 7.08 (d, J=9.4 Hz, 0.2H), 6.92 (d, J=11.7 Hz, 1H), 3.77 (s, 3H), 3.55 (d, J=1.0 Hz, 2H), 1.25 (s, 0.3H).

Step 2: Methyl 4-[[2-[2-deuterio-6-fluoro-3-methoxy-4-[2,2,2-trideuterio-1,1-bis (trideuteriomethyl)ethyl]phenyl]acetyl]amino]pyridine-2-carboxylate

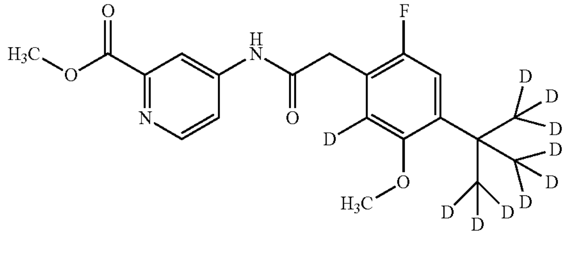 [SMILES: [2H]c1c(CC(=O)Nc2ccnc(C(=O)OC)c2)c(F)cc(C(C([2H])([2H])[2H])(C([2H])([2H])[2H])C([2H])([2H])[2H])c1OC]

A mixture of methyl 4-aminopyridine-2-carboxylate (178 mg, 1.17 mmol) and 2-[2-deuterio-6-fluoro-3-methoxy-4-[2,2,2-trideuterio-1,1-bis(trideuteriomethyl) ethyl]phenyl]acetic acid (step 1) (267 mg, 1.06 mmol) in 1,4-dioxane (10.7 mL) was treated with TEA (0.56 mL, 3.19 mmol) and 50% T3P® solution in EtOAc (0.63 mL, 1.06 mmol) and the mixture was stirred for 16 h. The resulting mixture was concentrated in vacuo and the residue was dissolved in EtOAc (30 mL). The mixture was washed with saturated aqueous sodium bicarbonate (2×20 mL), dried over $Na_2SO_4$ and concentrated in vacuo. Purification of the crude material by chromatography on silica eluting with 0-100% EtOAc in heptanes followed by 0-100% MeOH in EtOAc afforded the title compound as a colourless oil. (Note: NMR analysis indicated 80% D incorporation in the ortho-position to the phenol, and 97% D incorporation in the tert-butyl group.)

LC-MS (Method E): Rt 1.17 mins; MS m/z 385.1=[M+H]+ (69% @215 nm)

$^1$H NMR (500 MHz, DMSO-d6) δ 10.81 (s, 1H), 8.55 (d, J=5.5 Hz, 1H), 8.30 (t, J=2.2 Hz, 1H), 7.77 (dd, J=5.5, 2.1 Hz, 1H), 6.99 (d, J=6.65 Hz, 0.2H), 6.95 (d, J=11.7 Hz, 1H), 3.87 (s, 3H), 3.79 (s, 3H), 3.75 (s, 2H), 1.26 (s, 0.3H).

Step 3: 4-[[2-[2-Deuterio-6-fluoro-3-hydroxy-4-[2,2,2-trideuterio-1,1-bis(trideuteriomethyl) ethyl]phenyl]acetyl]amino]pyridine-2-carboxylic acid

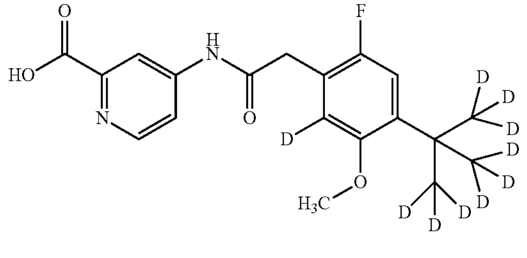 [SMILES: [2H]c1c(CC(=O)Nc2ccnc(C(=O)O)c2)c(F)cc(C(C([2H])([2H])[2H])(C([2H])([2H])[2H])C([2H])([2H])[2H])c1OC]

Methyl 4-[[2-[2-deuterio-6-fluoro-3-methoxy-4-[2,2,2-trideuterio-1,1-bis (trideuteriomethyl) ethyl]phenyl]acetyl] amino]pyridine-2-carboxylate (step 2) (69%, 471 mg, 0.85 mmol) in THF (4 mL) was treated with 1M LiOH (4.23 mL, 4.23 mmol) and stirred for 2 h. The volatile solvents were removed in vacuo and the aqueous phase was acidified to pH 1 by addition of 1M HCl. The resulting suspension was extracted with EtOAc (3×10 mL) and the combined organic extracts were concentrated in vacuo. The crude material was dissolved in DCM (8 mL), cooled in an ice bath and treated with 1M $BBr_3$ in DCM (2.54 mL, 2.54 mmol). After stirring for 3 h, the reaction was quenched with water (10 mL) and the phases separated. The aqueous layer was extracted with DCM (2×20 mL) and EtOAc (2×20 mL) and the combined organic extracts were concentrated in vacuo. Purification of the crude material by C18 reverse phase chromatography eluting with 10-100% MeCN in water afforded the title compound as a colourless solid. (Note: NMR analysis indicated 80% D incorporation in the ortho-position to the phenol, and 97% D incorporation in the tert-butyl group.)

LC-MS (Method E): Rt 0.98 mins; MS m/z 357.1=[M+H]+ (100% @215 nm)

$^1$H NMR (400 MHz, DMSO-d6) δ 10.79 (s, 1H), 9.29 (s, 1H), 8.54 (d, J=5.5 Hz, 1H), 8.27 (s, 1H), 7.79 (dd, J=5.5, 2.1 Hz, 1H), 6.86 (d, J=11.9 Hz, 1H), 6.74 (d, J=7.0 Hz, 0.2H), 3.65 (s, 2H), 1.26 (s, 0.3H).

Step 4: N-(1-Cyanocyclopropyl)-4-[[2-[2-deuterio-6-fluoro-3-hydroxy-4-[2,2,2-trideuterio-1,1-bis(trideuteriomethyl)ethyl]phenyl]acetyl]amino]pyridine-2-carboxamide 4-[[2-[2-Deuterio-6-fluoro-3-hydroxy-4-[2,2,2-trideuterio-1,1-bis(trideuterio methyl)ethyl]phenyl]acetyl]amino] pyridine-2-carboxylic acid (step 3) (50 mg, 0.14 mmol) in DMF (1.4 mL) was treated with 1-aminocyclopropane carbonitrile hydrochloride (20 mg, 0.17 mmol), DIPEA (49 µL, 0.28 mmol) and HATU (50.7 mg, 0.13 mmol) and the mixture was stirred at room temperature for 2 h. Purification of the reaction mixture by preparative HPLC (acidic pH, early elution method) afforded the title compound as a colourless solid. (Note: NMR analysis indicated 80% D incorporation in the ortho-position to the phenol, and 97% D incorporation in the tert-butyl group).

LC-MS (Method C): Rt 3.38 mins; MS m/z 421.3=[M+H]+ (100% @215 nm)

$^1$H NMR (500 MHz, DMSO-d6) δ 10.82 (s, 1H), 9.67 (s, 1H), 9.30 (s, 1H), 8.51 (d, J=5.5 Hz, 1H), 8.24 (d, J=2.1 Hz, 1H), 7.86 (dd, J=5.5, 2.2 Hz, 1H), 6.87 (d, J=11.9 Hz, 1H), 6.75 (d, J=6.9 Hz, 0.2H), 3.66 (s, 2H), 1.57-1.51 (m, 2H), 1.37-1.30 (m, 2H), 1.27 (s, 0.3H).

Example 5

N-(1-Cyano-1-methyl-ethyl)-4-[[2-[2-fluoro-5-hydroxy-4-(1-methylcyclo butyl)phenyl]acetyl]amino] pyridine-2-carboxamide

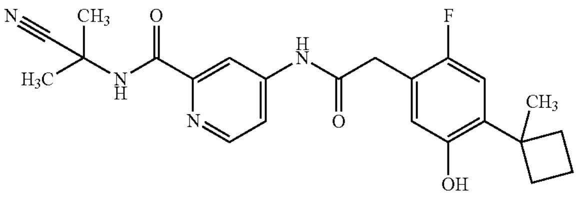 [SMILES: CC(C)(C#N)NC(=O)c1cc(NC(=O)Cc2cc(O)c(C3(C)CCC3)cc2F)ccn1]

Step 1: Methyl 4-[[2-(2-fluoro-5-methoxy-phenyl)acetyl]amino]pyridine-2-carboxylate

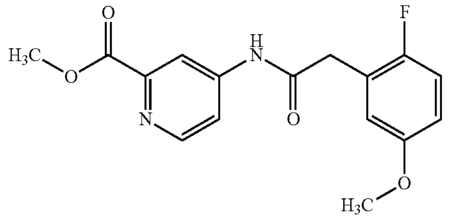 [SMILES: COC(=O)c1cc(NC(=O)Cc2cc(OC)ccc2F)ccn1]

To a solution of methyl 4-aminopyridine-2-carboxylate (3.64 g, 23.89 mmol) and 2-(2-fluoro-5-methoxy-phenyl)acetic acid (4 g, 21.72 mmol) in 1,4-dioxane (108.6 mL) was added TEA (9.48 mL, 54.3 mmol) and 50% T3P® solution in EtOAc (51.67 mL, 43.44 mmol) and the mixture was stirred for 2 h. The resulting mixture was concentrated in vacuo and the residue was dissolved in EtOAc (100 mL) and washed with saturated aqueous sodium bicarbonate (2×100 mL). The organic portion was dried over $Na_2SO_4$ and concentrated in vacuo. Purification by chromatography on silica eluting with 0%-100% EtOAc in heptanes afforded the title compound as an orange gum.

LC-MS (Method E): Rt 1.00 mins; MS m/z 319.1=[M+H]+ (100% @215 nm)

$^1$H NMR (500 MHz, DMSO-d6) δ 10.80 (s, 1H), 8.55 (d, J=5.4 Hz, 1H), 8.30 (d, J=1.8 Hz, 1H), 7.77 (dd, J=5.5, 2.2 Hz, 1H), 7.11 (t, J=9.2 Hz, 1H), 6.96 (dd, J=6.1, 3.2 Hz, 1H), 6.86 (dt, J=8.9, 3.7 Hz, 1H), 3.87 (s, 3H), 3.77 (s, 2H), 3.73 (s, 3H).

Step 2: Methyl 4-[[2-[2-fluoro-5-methoxy-4-(1-methylcyclobutyl)phenyl]acetyl]amino] pyridine-2-carboxylate

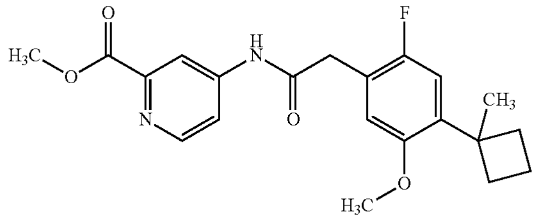 [SMILES: COC(=O)c1cc(NC(=O)Cc2cc(OC)c(C3(C)CCC3)cc2F)ccn1]

A solution of methyl 4-[[2-(2-fluoro-5-methoxy-phenyl)acetyl]amino]pyridine-2-carboxylate (step 1) (200 mg, 0.63 mmol) in DCE (2 mL) was treated with concentrated sulfuric acid (0.27 mL, 5.03 mmol) and the mixture was cooled to 0° C. To this mixture was added dropwise methylenecyclobutane (214 mg, 3.14 mmol) in DCE (2 mL) and the mixture was stirred at room temperature overnight. The resulting mixture was diluted with DCM (10 mL) and water (10 mL). The organic portion was separated, dried over $Na_2SO_4$ and concentrated in vacuo to afford the title compound as yellow solid.

LC-MS (Method E): Rt 1.22 mins; MS m/z 387.1=[M+H]+ (77% @215 nm)

Step 3: N-(1-Cyano-1-methyl-ethyl)-4-[[2-[2-fluoro-5-hydroxy-4-(1-methylcyclobutyl) phenyl]acetyl]amino]pyridine-2-carboxamide A solution of 1M $BBr_3$ in DCM (4.05 mL, 4.05 mmol) was added to a cooled (0° C.), stirred solution of methyl 3-[[2-[2-fluoro-5-methoxy-4-(1-methylcyclobutyl)phenyl]acetyl]amino] benzoate (260 mg, 0.67 mmol) under nitrogen, over 2 min. The mixture was allowed to warm to room temperature and stirred overnight. The reaction was quenched with ice, stirring for 30 min. The organic layer was separated, dried over $Na_2SO_4$ and concentrated in vacuo to afford a brown oil. The oil was dissolved in DMF (1 mL) and 2-amino-2-methyl-propanenitrile hydrochloride (36 mg, 0.29 mmol) and DIPEA (86 μL, 0.49 mmol) were added followed by HATU (80.83 mg, 0.21 mmol) and the reaction mixture was stirred at room temperature overnight. The resulting mixture was diluted with EtOAc (10 mL) and water (10 mL). The organic layer was separated, dried over $Na_2SO_4$ and concentrated in vacuo. Purification of the crude material by preparative HPLC (acidic pH, early elution method) afforded the title compound as an off-white solid.

LC-MS (Method A): Rt 3.52 mins; MS m/z 425.3=[M+H]+ (96% @215 nm)

$^1$H NMR (500 MHz, MeOH -d4) δ 8.47 (d, J=5.5 Hz, 1H), 8.19 (d, J=1.9 Hz, 1H), 7.94 (dd, J=5.5, 2.1 Hz, 1H), 6.69-6.63 (m, 2H), 3.68 (s, 2H), 2.43-2.30 (m, 2H), 2.16-2.02 (m, 3H), 1.80 (s, 6H), 1.80-1.72 (m, 1H), 1.45 (s, 3H).

Example 6

N-tert-Butyl-4-[[2-(4-tert-butyl-5-hydroxy-2-isopropyl-phenyl)acetyl]amino] pyridine-2-carboxamide

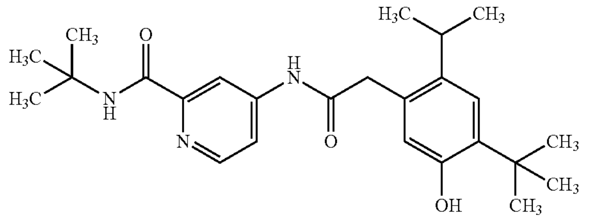 [SMILES: CC(C)c1cc(C(C)(C)C)c(O)cc1CC(=O)Nc1ccnc(C(=O)NC(C)(C)C)c1]

Step 1: 4-[[2-(2-Bromo-4-tert-butyl-5-methoxy-phenyl)acetyl]amino]-N-tert-butyl-pyridine-2-carboxamide

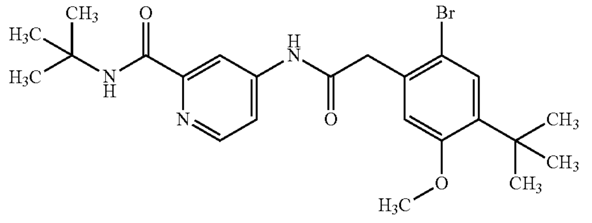 [SMILES: COc1cc(CC(=O)Nc2ccnc(C(=O)NC(C)(C)C)c2)c(Br)cc1C(C)(C)C]

The title compound was prepared from 2-(2-bromo-4-tert-butyl-5-methoxy-phenyl)acetic acid (Intermediate F) and 4-amino-N-tert-butyl-pyridine-2-carboxamide analogously to Example 1 step 1.

LC-MS (Method E): Rt 1.42 mins; MS m/z 476.1, 478.1=[M+H]+ (96% @215 nm)

$^1$H NMR (400 MHz, DMSO-d6) δ 10.80 (s, 1H), 8.45 (d, J=5.5 Hz, 1H), 8.17 (d, J=1.8 Hz, 1H), 8.03 (s, 1H), 7.81 (dd, J=5.5, 2.2 Hz, 1H), 7.30 (s, 1H), 7.09 (s, 1H), 3.86 (s, 2H), 3.81 (s, 3H), 1.40 (s, 9H), 1.32 (s, 9H).

Step 2: 4-[[2-(2-Bromo-4-tert-butyl-5-hydroxy-phenyl)acetyl]amino]-N-tert-butyl-pyridine-2-carboxamide

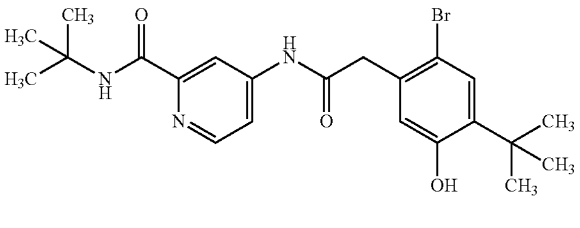 [SMILES: CC(C)(C)NC(=O)c1cc(NC(=O)Cc2cc(O)c(C(C)(C)C)cc2Br)ccn1]

The title compound was prepared from 4-[[2-(2-bromo-4-tert-butyl-5-methoxy-phenyl)acetyl]amino]-N-tert-butyl-pyridine-2-carboxamide (step 1) and 1M $BBr_3$ in DCM analogously to Example 1 step 2.

LC-MS (Method E): Rt 1.32 mins; MS m/z 462.0, 463.9=[M+H]+ (96% @215 nm)

$^1$H NMR (500 MHz, DMSO-d6) δ 10.79 (s, 1H), 9.66 (s, 1H), 8.46 (d, J=5.5 Hz, 1H), 8.20 (d, J=2.0 Hz, 1H), 8.03 (s, 1H), 7.80 (dd, J=5.5, 2.2 Hz, 1H), 7.24 (s, 1H), 6.83 (s, 1H), 3.75 (s, 2H), 1.40 (s, 9H), 1.33 (s, 9H).

Step 3: N-tert-Butyl-4-[[2-(4-tert-butyl-5-hydroxy-2-isopropyl-phenyl)acetyl]amino] pyridine-2-carboxamide A mixture of 4-[[2-(2-bromo-4-tert-butyl-5-hydroxy-phenyl)acetyl]amino]-N-tert-butyl-pyridine-2-carboxamide (step 2) (96%, 170 mg, 0.35 mmol), 2-isopropenyl-4,4,5,5-tetramethyl-1,3,2-dioxaborolane (119 mg, 0.71 mmol), tripotassium phosphate (300 mg, 1.41 mmol), $P(Cy)_3$ (40 mg, 0.14 mmol) and $Pd(OAc)_2$ (16 mg, 0.07 mmol) under nitrogen was dissolved in degassed 10:1 toluene:water (2.2 mL) and the mixture was heated at 100° C. for 4 h. The resulting mixture was concentrated in vacuo and the residue dissolved in EtOAc (10 mL). The mixture was washed with water (10 mL) and the aqueous wash was re-extracted with EtOAc (3×10 mL). The combined organic extracts were dried over $Na_2SO_4$ and concentrated in vacuo. The crude mixture was filtered through a plug of silica, washing through with EtOAc and concentrated in vacuo. The residue was dissolved in EtOH (2 mL) and treated with 10% Pd/C (38 mg, 0.35 mmol). The mixture was placed under a hydrogen atmosphere and stirred for 24 h. The resulting mixture was filtered through a Celite® plug, washing through with EtOAc and the filtrate was concentrated in vacuo. Purification by preparative HPLC (acidic pH, early elution method) afforded the title compound as a colourless solid.

LC-MS (Method A): Rt 4.32 mins; MS m/z 426.4=[M+H]+ (100% @215 nm)

$^1$H NMR (500 MHz, DMSO-d6) δ 10.72 (s, 1H), 9.03 (s, 1H), 8.45 (d, J=5.5 Hz, 1H), 8.20 (d, J=2.0 Hz, 1H), 8.03 (s, 1H), 7.81 (dd, J=5.5, 2.2 Hz, 1H), 7.03 (s, 1H), 6.62 (s, 1H), 3.64 (s, 2H), 3.05 (hept, J=6.9 Hz, 1H), 1.40 (s, 9H), 1.33 (s, 9H), 1.12 (d, J=6.8 Hz, 6H).

Example 7

N-tert-Butyl-4-[[2-[2-fluoro-5-hydroxy-4-(1-hydroxy-1-methyl-ethyl)phenyl] acetyl]amino]pyridine-2-carboxamide

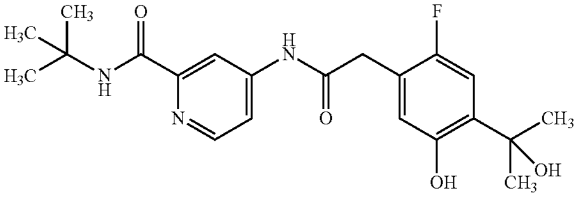 [SMILES: CC(C)(C)NC(=O)c1cc(NC(=O)Cc2cc(O)c(C(C)(C)O)cc2F)ccn1]

Step 1: 4-[[2-(4-Bromo-2-fluoro-5-hydroxy-phenyl) acetyl]amino]-N-tert-butyl-pyridine-2-carboxamide

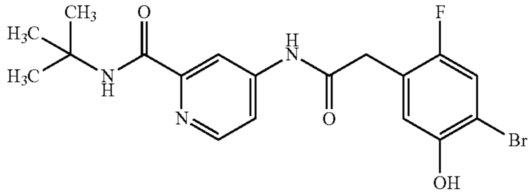 [SMILES: CC(C)(C)NC(=O)c1cc(NC(=O)Cc2cc(O)c(Br)cc2F)ccn1]

The title compound was prepared from 4-[[2-(4-bromo-2-fluoro-5-methoxy-phenyl)acetyl]amino]-N-tert-butyl-pyridine-2-carboxamide (Intermediate I) and 1M $BBr_3$ in DCM analogously to Example 1 step 2.

LC-MS (Method A): Rt 3.28 mins; MS m/z 424.1, 426.1=[M+H]+ (93% @215 nm)

$^1$H NMR (500 MHz, DMSO-d6) δ 10.79 (s, 1H), 10.15 (s, 1H), 8.46 (d, J=5.5 Hz, 1H), 8.18 (d, J=2.1 Hz, 1H), 8.03 (s, 1H), 7.79 (dd, J=5.5, 2.2 Hz, 1H), 7.40 (d, J=9.0 Hz, 1H), 6.95 (d, J=6.9 Hz, 1H), 3.71 (s, 2H), 1.40 (s, 9H).

Step 2: N-tert-Butyl-4-[[2-(2-fluoro-5-hydroxy-4-isopropenyl-phenyl)acetyl]amino]pyridine-2-carboxamide

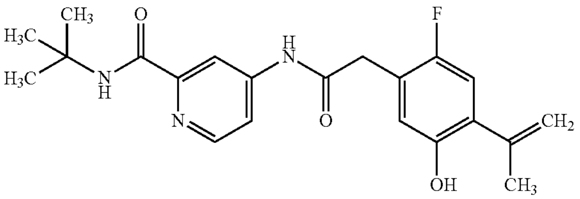 [SMILES: C=C(C)c1cc(F)c(CC(=O)Nc2ccnc(C(=O)NC(C)(C)C)c2)cc1O]

The title compound was prepared from 4-[[2-(4-bromo-2-fluoro-5-hydroxy-phenyl)acetyl]amino]-N-tert-butyl-pyridine-2-carboxamide (step 1) and 2-isopropenyl-4,4,5,5-tetramethyl-1,3,2-dioxaborolane analogously to Example 8 step 1.

LC-MS (Method A): Rt 3.56 mins; MS m/z 386.2=[M+H]+ (91% @215 nm)

$^1$H NMR (500 MHz, DMSO-d6) δ 10.78 (s, 1H), 9.43 (s, 1H), 8.46 (d, J=5.5 Hz, 1H), 8.19 (d, J=2.0 Hz, 1H), 8.03 (s, 1H), 7.81 (dd, J=5.5, 2.2 Hz, 1H), 6.91 (d, J=10.6 Hz, 1H), 6.80 (d, J=6.7 Hz, 1H), 5.22-5.19 (m, 1H), 5.14-5.11 (m, 1H), 3.69 (s, 2H), 2.06 (s, 3H), 1.40 (s, 9H).

Step 3: N-tert-Butyl-4-[[2-[2-fluoro-5-hydroxy-4-(1-hydroxy-1-methyl-ethyl)phenyl]acetyl] amino]pyridine-2-carboxamide A solution of N-tert-butyl-4-[[2-(2-fluoro-5-hydroxy-4-isopropenyl-phenyl) acetyl]amino]pyridine-2-carboxamide (step 2) (50 mg, 0.13 mmol) in water (2.5 mL) and 1,4-dioxane (5 mL) was treated with methanesulfonic acid (842 μL, 12.97 mmol) and stirred at 30° C. for 24 h. After standing at room temperature overnight, the mixture was partitioned between EtOAc (20 mL) and water (20 mL). The layers were separated and the aqueous portion further extracted with EtOAc (2×20 mL). The combined organic extracts were washed with brine (20 mL), dried over $Na_2SO_4$ and concentrated in vacuo. The crude material was purified by preparative HPLC (acidic pH, early elution method) to afford the title compound as a white solid.

LC-MS (Method A): Rt 2.99 mins; MS m/z 404.3=[M+H]+ (100% @215 nm)

$^1$H NMR (500 MHz, MeOH -d4) δ 8.43 (dd, J=5.6, 0.5 Hz, 1H), 8.13 (dd, J=2.2, 0.5 Hz, 1H), 7.90 (dd, J=5.5, 2.2 Hz, 1H), 7.00 (d, J=11.2 Hz, 1H), 6.73 (d, J=6.6 Hz, 1H), 3.70 (s, 2H), 1.58 (s, 6H), 1.47 (s, 9H).

Example 7.1

4-[[2-(2-Fluoro-5-hydroxy-4-isopropenyl-phenyl) acetyl]amino]-N-[1-(trifluoromethyl) cyclopropyl] pyridine-2-carboxamide

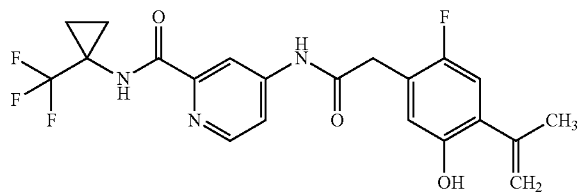 [SMILES: C=C(C)c1cc(F)c(CC(=O)Nc2ccnc(C(=O)NC3(C(F)(F)F)CC3)c2)cc1O]

Step 1: 4-[2-(4-Bromo-2-fluoro-5-hydroxyphenyl) acetamido]-N-[1-(trifluoromethyl) cyclopropyl]pyridine-2-carboxamide

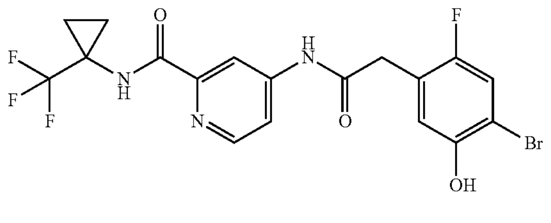 [SMILES: O=C(Cc1cc(O)c(Br)cc1F)Nc1ccnc(C(=O)NC2(C(F)(F)F)CC2)c1]

To a cooled (0° C.) solution of 4-[[2-(4-bromo-2-fluoro-5-methoxy-phenyl)acetyl]amino]-N-[1-(trifluoromethyl)cyclopropyl]pyridine-2-carboxamide (Intermediate H) (19.5 g, 39.78 mmol) in DCM (250 mL) was added dropwise 1M $BBr_3$ in DCM (119.33 mL, 119.33 mmol) over 10 min. The reaction mixture was allowed to warm to room temperature and stirred for 2.5 h. The solvent was removed in vacuo and the crude material was suspended in EtOAc (350 mL) at 0° C. and treated with sat. $NaHCO_3$ (550 mL). The mixture was stirred vigorously for 20 min at room temperature and the organic layer was separated. The aqueous layer was re-extracted with EtOAc (200 mL) and the combined organic extracts were dried over $Na_2SO_4$ and concentrated in vacuo. The crude material was suspended in MeCN (300 mL) and the mixture was heated to 100° C. for 10 min. Water (300 mL) was added and heating continued for 30 min. The resulting hot mixture was filtered and the solid was washed with MeCN (2×70 mL) and dried at 40° C. under high vacuum to afford the title compound as a white solid.

LC-MS (Method E): Rt 1.16 min; MS m/z 476.2, 478.1=[M+H]+ (96% @215 nm)

$^1$H NMR (500 MHz, DMSO-d6) δ 10.82 (s, 1H), 10.17 (s, 1H), 9.39 (s, 1H), 8.51 (d, J=5.5 Hz, 1H), 8.20 (d, J=2.0 Hz, 1H), 7.83 (dd, J=5.5, 2.2 Hz, 1H), 7.40 (d, J=9.0 Hz, 1H), 6.95 (d, J=6.9 Hz, 1H), 3.71 (s, 2H), 1.37-1.23 (m, 2H), 1.22-1.15 (m, 2H).

Step 2: 4-[[2-(2-Fluoro-5-hydroxy-4-isopropenyl-phenyl)acetyl]amino]-N-[1-(trifluoromethyl)cyclopropyl]pyridine-2-carboxamide A solution of 2-isopropenyl-4,4,5,5-tetramethyl-1,3,2-dioxaborolane (12.19 g, 72.57 mmol), $Pd(OAc)_2$ (1.63 g, 7.26 mmol), 4-[[2-(4-bromo-2-fluoro-5-hydroxy-phenyl)acetyl]amino]-N-[1-(trifluoromethyl)cyclopropyl]pyridine-2-carboxamide (step 1) (96%, 18.0 g, 36.29 mmol) in toluene (200 mL) and water (40 mL) was degassed with nitrogen for 10 min and then treated with $P(Cy)_3$ (4.07 g, 14.51 mmol) and tripotassium phosphate (30.81 g, 145.14 mmol). The mixture was sparged with nitrogen, sealed and heated at 100° C. overnight. The resulting mixture was concentrated in vacuo and the crude residue was partitioned between EtOAc (200 mL) and water (200 mL). The organic portion was separated, dried over $Na_2SO_4$ and filtered through a Celite® pad, washing through with 20% MeOH in DCM (100 mL). The filtrate was concentrated in vacuo and the crude material suspended in toluene (200 mL). The mixture was heated to reflux for 20 minutes and then cooled and allowed to stand at 0 degrees overnight. Filtration of the resulting solid and washing with toluene (50 mL) and heptane (100 mL) afforded the title compound as an off-white solid.

The filtrate was concentrated in vacuo and the crude material was dissolved in MeCN (200 mL). Further material was obtained by concentration of the filtrate in vacuo and re-dissolving in MeCN (200 mL). 2,4,6-Trimercapto-s-triazine (1.5 g) and decolorizing charcoal (3.0 g) were added and the mixture was stirred at 20-25° C. for 1 h. Celite® (2.0 g) was added and the mixture was stirred at 0-5° C. for 1 h. The precipitate was removed by suction filtration through filter paper and washed with MeCN (100 mL). The filtrate was concentrated in vacuo and the crude material was suspended in toluene (100 mL) and heated to reflux for 20 min. The mixture was allowed to cool to room temperature and kept at 0° C. overnight. The resulting mixture was filtered, the solid was washed with cold toluene (50 mL) followed by heptane (100 mL) and dried in high vacuum oven at 40° C. to afford the title compound as an off-white solid.

Further material was obtained by concentration of the filtrate and purification of the crude material by chromatography on silica eluting with 0-100% EtOAc in heptane followed by 0-100% MeOH in EtOAc. The purified material from the purification steps were combined and further purified by C18 reverse phase chromatography eluting with 10-100% MeCN in water (+0.1% formic acid). The resulting solid was recrystallised from MeCN (10 mL) to afford the title compound as a white solid.

LC-MS (Method A): Rt 3.32 min; MS m/z 438.1=[M+H]+ (100% @215 nm)

$^1$H NMR (500 MHz, DMSO-d$_6$) δ 10.81 (s, 1H), 9.45 (s, 1H), 9.39 (s, 1H), 8.51 (d, J=5.5 Hz, 1H), 8.22 (d, J=2.0 Hz, 1H), 7.84 (dd, J=5.5, 2.2 Hz, 1H), 6.91 (d, J=10.6 Hz, 1H), 6.80 (d, J=6.7 Hz, 1H), 5.22-5.19 (m, 1H), 5.14-5.11 (m, 1H), 3.69 (s, 2H), 2.11-2.01 (m, 3H), 1.36-1.23 (m, 2H), 1.25-1.11 (m, 2H).

Example 8

N-tert-Butyl-4-[[2-[2-fluoro-5-hydroxy-4-(1-methylcyclopropyl)phenyl] acetyl]amino]pyridine-2-carboxamide

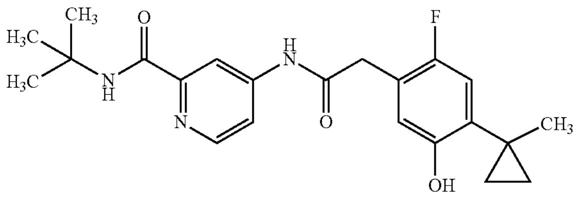 [SMILES: CC(C)(C)NC(=O)c1cc(NC(=O)Cc2cc(O)c(C3(C)CC3)cc2F)ccn1]

Step 1: N-tert-Butyl-4-[[2-(2-fluoro-4-isopropenyl-5-methoxy-phenyl)acetyl]amino]pyridine-2-carboxamide

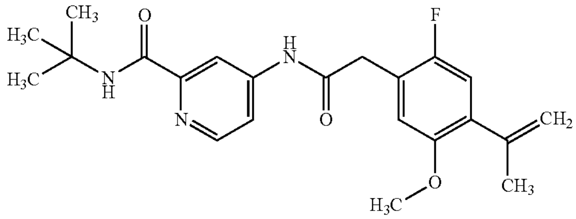 [SMILES: C=C(C)c1cc(F)c(CC(=O)Nc2ccnc(C(=O)NC(C)(C)C)c2)cc1OC]

A solution of 4-[[2-(4-bromo-2-fluoro-5-methoxy-phenyl)acetyl]amino]-N-tert-butyl-pyridine-2-carboxamide (Intermediate I) (850 mg, 1.94 mmol), 2-isopropenyl-4,4,5,5-tetramethyl-1,3,2-dioxaborolane (729 μL, 3.88 mmol) and tripotassium phosphate (1.65 g, 7.76 mmol) in toluene (6 mL) and water (0.6 mL) was degassed with nitrogen for 10 min and then treated with Pd(OAc)$_2$ (87 mg, 0.39 mmol) and P(Cy)$_3$ (217.54 mg, 0.78 mmol). The mixture was sparged with nitrogen, sealed and heated at 100° C. for 3 h. The resulting mixture was concentrated in vacuo and the crude residue was partitioned between EtOAc (50 mL) and water (50 mL). The organic portion was separated, washed with brine (50 mL), dried over $Na_2SO_4$ and concentrated in vacuo. The resulting crude material was purified by chromatography on silica eluting with 0-100% EtOAc in heptanes followed by 0-10% MeOH in EtOAc to afford the title compound as a yellow solid.

LC-MS (Method E): Rt 1.35 mins; MS m/z 400.2=[M+H]+ (91% @215 nm)

$^1$H NMR (500 MHz, DMSO-d6) δ 10.78 (s, 1H), 8.45 (d, J=5.5 Hz, 1H), 8.17 (d, J=2.1 Hz, 1H), 8.03 (s, 1H), 7.81 (dd, J=5.5, 2.2 Hz, 1H), 7.03 (d, J=6.4 Hz, 1H), 6.97 (d, J=10.2 Hz, 1H), 5.16-5.12 (m, 1H), 5.11-5.08 (m, 1H), 3.78 (s, 2H), 3.76 (s, 3H), 2.04 (s, 3H), 1.39 (s, 9H).

Step 2: N-tert-Butyl-4-[[2-[2-fluoro-5-methoxy-4-(1-methylcyclopropyl)phenyl]acetyl] amino]pyridine-2-carboxamide

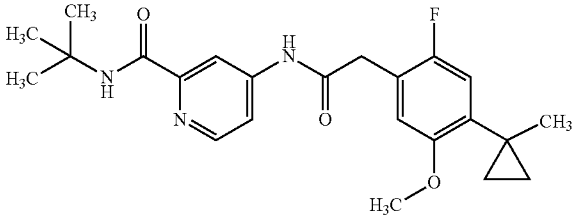 [SMILES: COc1cc(CC(=O)Nc2ccnc(C(=O)NC(C)(C)C)c2)c(F)cc1C1(C)CC1]

To a mixture of triethylammonium bis(catecholato)iodomethylsilicate (Intermediate J) (95%, 193 mg, 0.38 mmol) and (4,4'-di-t-butyl-2,2'-bipyridine)bis[3,5-difluoro-2-[5-trifluoromethyl-2-pyridinyl-kN)phenyl-kC]iridium(III) hexafluorophosphate (14 mg, 0.01 mmol) in anhydrous TEA (6.59 mL) under nitrogen was added a solution of N-tert-butyl-4-[[2-(2-fluoro-4-isopropenyl-5-methoxy-phenyl) acetyl]amino]pyridine-2-carboxamide (step 1) (100 mg, 0.25 mmol) in anhydrous DMSO (1.5 mL). The reaction mixture was sealed with parafilm and irradiated in front of a Kessil A160WE Tuna Blue 40 W LED lamp overnight maintaining the temperature at approximately 20-25° C. with a fan. Additional triethylammonium bis(catecholato) iodomethylsilicate (Intermediate J) (95%, 193 mg, 0.38 mmol) and (4,4'-di-t-butyl-2,2'-bipyridine)bis[3,5-difluoro-2-[5-trifluoromethyl-2-pyridinyl-kN)phenyl-kC]iridium(III) hexafluorophosphate (14 mg, 0.01 mmol) were added, the mixture re-purged with nitrogen and irradiated for a further 8 h. The resulting mixture was diluted in EtOAc (10 mL) and $H_2O$ (10 mL). A precipitate formed which was removed by filtration through a 1 g Celite® Isolute cartridge, washing with EtOAc. The filtrate phases were separated, the organic portion washed with brine (2×10 mL), dried over $Na_2SO_4$, nd concentrated in vacuo. Purification by chromatography on silica eluting with 0-100% EtOAc in heptanes followed by further purification by C18 reverse phase chromatography eluting with 10-100% MeCN (+0.1% formic acid) in $H_2O$ (+0.1% formic acid) afforded the title compound as a yellow viscous oil.

LC-MS (Method E): Rt 1.33 mins; MS m/z 414.1=[M+H]+ (97% @215 nm)

$^1$H NMR (500 MHz, DMSO-d6) δ 10.77 (s, 1H), 8.45 (d, J=5.5 Hz, 1H), 8.17 (d, J=2.0 Hz, 1H), 8.03 (s, 1H), 7.81 (dd, J=5.5, 2.2 Hz, 1H), 6.98 (d, J=5.1 Hz, 1H), 6.97-6.95 (m, 1H), 3.80 (s, 3H), 3.75 (s, 2H), 1.40 (s, 9H), 1.26 (s, 3H), 0.69-0.65 (m, 2H), 0.65-0.59 (m, 2H).

Step 3: N-tert-Butyl-4-[[2-[2-fluoro-5-hydroxy-4-(1-methylcyclopropyl)phenyl]acetyl] amino]pyridine-2-carboxamide 1M $BCl_3$ in DCM (181 μL, 0.18 mmol) was added dropwise to a cooled (0° C.) solution of N-tert-butyl-4-[[2-[2-fluoro-5-methoxy-4-(1-methylcyclopropyl)phenyl] acetyl] amino]pyridine-2-carboxamide (step 2) (30 mg, 0.07 mmol) and tetra-n-butylammonium iodide (67 mg, 0.18 mmol) in DCM (1 mL) under nitrogen and the mixture was stirred at 0° C. for 2 h. Additional 1M $BCl_3$ in DCM (72 μL, 0.07 mmol) was added and stirring continued for 30 min. The reaction was quenched with ice and the organic layer separated through a hydrophobic frit. The remaining aqueous layer was washed with DCM and the organic portions were combined and concentrated in vacuo. Purification of the crude material by C18 reverse phase chromatography eluting with 10-100% MeCN (+0.1% formic acid) in $H_2O$ (+0.1% formic acid) afforded the title compound as an off-white solid.

LC-MS (Method A): Rt 3.56 mins; MS m/z 400.3=[M+H]+ (98% @215 nm)

$^1H$ NMR (500 MHz, DMSO-d6) δ 10.76 (s, 1H), 9.17 (s, 1H), 8.45 (d, J=5.5 Hz, 1H), 8.18 (d, J=2.1 Hz, 1H), 8.03 (s, 1H), 7.80 (dd, J=5.5, 2.2 Hz, 1H), 6.87 (d, J=10.4 Hz, 1H), 6.73 (d, J=6.7 Hz, 1H), 3.64 (s, 2H), 1.40 (s, 9H), 1.26 (s, 3H), 0.69-0.63 (m, 2H), 0.63-0.55 (m, 2H).

Example 9

N-(1-Cyanocyclopropyl)-4-[[2-[2-fluoro-5-hydroxy-4-[1-(trifluoromethyl) cyclopropyl]phenyl]acetyl] amino]pyridine-2-carboxamide

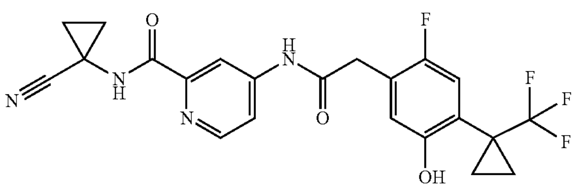 [SMILES: N#CC1(NC(=O)c2cc(NC(=O)Cc3cc(O)c(C4(C(F)(F)F)CC4)cc3F)ccn2)CC1]

Step 1: Methyl 4-[[2-[2-fluoro-5-methoxy-4-(4,4,5,5-tetramethyl-1,3,2-dioxaborolan-2-yl)phenyl] acetyl]amino]pyridine-2-carboxylate

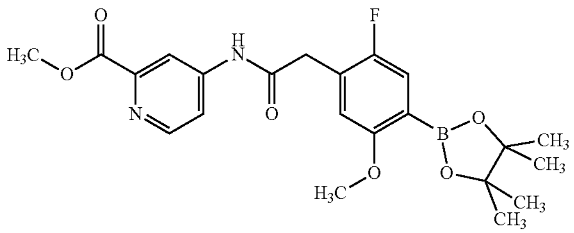

A mixture of methyl 4-[[2-(4-bromo-2-fluoro-5-methoxyphenyl)acetyl]amino]pyridine-2-carboxylate (Intermediate I step 1) (94%, 4.5 g, 10.65 mmol), bis(pinacolato)diboron (4.06 g, 15.97 mmol), KOAc (4.42 g, 31.95 mmol) and Pd(dppf)$Cl_2$ (779 mg, 1.06 mmol) in 1,4-dioxane (45 mL) under nitrogen was heated at 80° C. for 4 h. Additional bis(pinacolato)diboron (4.06 g, 15.97 mmol) was added and the mixture was heated at 80° C. for a further 3.5 h. Additional Pd(dppf)$Cl_2$ (779 mg, 1.06 mmol) was then added and the mixture heated at 80° C. overnight. The resulting mixture was filtered through Celite® (filter material) and concentrated in vacuo. Purification of the crude material by chromatography on silica eluting with 0-100% EtOAc in heptanes followed by 0-10% MeOH in EtOAc afforded the title compound as a dark brown viscous oil.

LC-MS (Method E): Rt 1.11 mins; MS m/z 445.2=[M+H]+ (62% @215 nm)

$^1H$ NMR (400 MHz, DMSO-d6) δ 10.81 (s, 1H), 8.55 (d, J=5.5 Hz, 1H), 8.29 (d, J=1.8 Hz, 1H), 7.77 (dd, J=5.5, 2.2 Hz, 1H), 7.20 (d, J=9.6 Hz, 1H), 7.01 (d, J=5.7 Hz, 1H), 3.87 (s, 3H), 3.81 (s, 2H), 3.73 (s, 3H), 1.27 (s, 12H).

Step 2: Methyl 4-[[2-[2-fluoro-5-methoxy-4-[1-(trifluoromethyl)vinyl]phenyl]acetyl]amino] pyridine-2-carboxylate

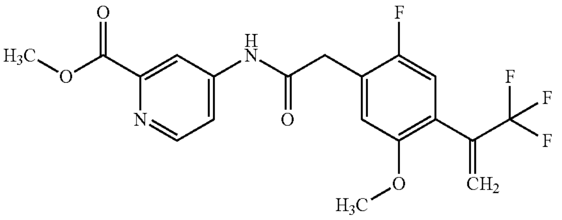 [SMILES: C=C(c1cc(F)c(CC(=O)Nc2ccnc(C(=O)OC)c2)cc1OC)C(F)(F)F]

A mixture of methyl 4-[[2-[2-fluoro-5-methoxy-4-(4,4,5,5-tetramethyl-1,3,2-dioxaborolan-2-yl)phenyl]acetyl] amino]pyridine-2-carboxylate (step 1) (4.5 g, 10.13 mmol), $Cs_2CO_3$ (3.96 g, 12.16 mmol) and Pd(dppf)$Cl_2$ (827 mg, 1.01 mmol) under nitrogen was dissolved in degassed monoglyme (45.5 mL) and degassed, deionised water (13 mL). 2-Bromo-3,3,3-trifluoro-prop-1-ene (2.36 mL, 22.28 mmol) was added and the mixture heated at 80° C. overnight. The resulting mixture was diluted with EtOAc (150 mL) and water (150 mL). The organic portion was separated, washed with brine (150 mL), dried over $Na_2SO_4$ and concentrated in vacuo. Purification by chromatography on silica eluting with EtOAc in heptanes 0-100% followed by MeOH in EtOAc 0-20% with subsequent purification by C18 reverse phase chromatography eluting with 10-100% MeCN (+0.1% formic acid) in $H_2O$ (+0.1% formic acid) afforded the title compound as a colourless viscous oil.

LC-MS (Method G): Rt 0.83 mins; MS m/z 413.2=[M+H]+ (91% @215 nm)

Step 3: Methyl 4-[[2-[2-fluoro-5-methoxy-4-[1-(trifluoromethyl)cyclopropyl]phenyl] acetyl]amino] pyridine-2-carboxylate

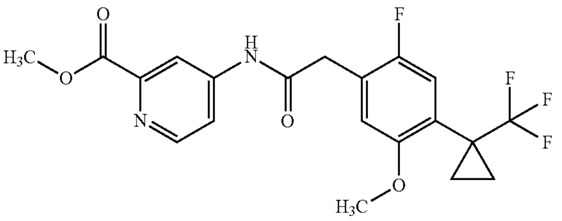 [SMILES: COC(=O)c1cc(NC(=O)Cc2cc(OC)c(C3(C(F)(F)F)CC3)cc2F)ccn1]

The title compound was prepared from methyl 4-[[2-[2-fluoro-5-methoxy-4-[1-(trifluoromethyl)vinyl]phenyl] acetyl]amino]pyridine-2-carboxylate (step 2) and triethylammonium bis(catecholato)iodomethylsilicate (Intermediate J) analogously to Example 8 step 2.

LC-MS (Method A): Rt 3.22 mins; MS m/z 427.2=[M+H]+ (42% @215 nm)

$^1H$ NMR (500 MHz, Chloroform-d) δ 8.62 (s, 1H), 8.01 (d, J=2.1 Hz, 1H), 7.94-7.91 (m, 1H), 7.65 (s, 1H), 7.18 (d, J=9.8 Hz, 1H), 6.86-6.82 (m, 1H), 3.99 (s, 3H), 3.85 (s, 3H), 3.74 (s, 2H), 1.40-1.36 (m, 2H), 1.01-0.97 (m, 2H).

Step 4: 4-[[2-[2-fluoro-5-hydroxy-4-[1-(trifluoromethyl)cyclopropyl]phenyl]acetyl]amino] pyridine-2-carboxylic acid

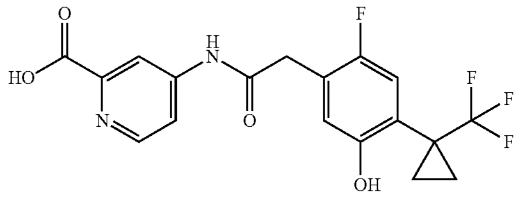 [SMILES: O=C(Cc1cc(O)c(C2(C(F)(F)F)CC2)cc1F)Nc1ccnc(C(=O)O)c1]

The title compound was prepared from methyl 4-[[2-[2-fluoro-5-methoxy-4-[1-(trifluoromethyl)cyclopropyl]phenyl]acetyl]amino]pyridine-2-carboxylate (step 3) and 1M $BBr_3$ in DCM analogously to Example 1 step 2.

LC-MS (Method E): Rt 0.96 mins; MS m/z 399.1=[M+H]+ (76% @215 nm)

$^1$H NMR (500 MHz, DMSO-d6) δ 10.89 (s, 1H), 9.62 (s, 1H), 8.57-8.53 (m, 1H), 8.28 (d, J=2.0 Hz, 1H), 7.83-7.79 (m, 1H), 7.07 (d, J=9.4 Hz, 1H), 6.84 (d, J=6.6 Hz, 1H), 3.72 (s, 2H), 1.32-1.29 (m, 2H), 1.06-1.02 (m, 2H). [acid-OH not observed]

Step 5: N-(1-Cyanocyclopropyl)-4-[[2-[2-fluoro-5-hydroxy-4-[1-(trifluoromethyl) cyclopropyl]phenyl] acetyl]amino]pyridine-2-carboxamide To a solution of 4-[[2-[2-fluoro-5-hydroxy-4-[1-(trifluoromethyl)cyclopropyl] phenyl]acetyl]amino]pyridine-2-carboxylic acid (step 4) (42%, 63 mg, 0.07 mmol) in DMF (1.5 mL) was added DIPEA (23 μL, 0.13 mmol), 1-aminocyclopropanecarbonitrile hydrochloride (9 mg, 0.08 mmol) followed by HATU (24 mg, 0.06 mmol) and the mixture was stirred under nitrogen, at room temperature for 2 h. Additional 1-aminocyclopropanecarbonitrile hydrochloride (9 mg, 0.08 mmol), DIPEA (23 μL, 0.13 mmol) were added followed by HATU (24 mg, 0.06 mmol) and the reaction mixture was stirred overnight. The resulting mixture was concentrated in vacuo and purification of the crude material by preparative HPLC (acidic pH, early elution method) afforded the title compound as a tan solid.

LC-MS (Method A): Rt 3.08 mins; MS m/z 463.2=[M+H]+ (94% @215 nm)

$^1$H NMR (500 MHz, DMSO-d6) δ 10.85 (s, 1H), 9.68 (s, 1H), 9.62 (s, 1H), 8.50 (d, J=5.5 Hz, 1H), 8.22 (d, J=2.0 Hz, 1H), 7.85 (dd, J=5.5, 2.2 Hz, 1H), 7.07 (d, J=10.0 Hz, 1H), 6.84 (d, J=6.6 Hz, 1H), 3.71 (s, 2H), 1.55-1.51 (m, 2H), 1.35-1.28 (m, 4H), 1.07-1.01 (m, 2H).

Example 10

4-[[2-(4-tert-Butyl-2-chloro-5-hydroxy-phenyl) acetyl]amino]-N-(1-cyano-1-methyl-ethyl)pyridine-2-carboxamide

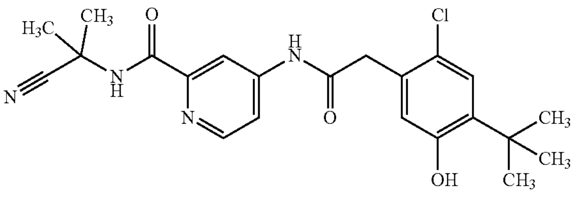 [SMILES: CC(C)(C#N)NC(=O)c1cc(NC(=O)Cc2cc(O)c(C(C)(C)C)cc2Cl)ccn1]

Step 1: Methyl 4-[[2-(4-tert-butyl-2-chloro-5-methoxy-phenyl)acetyl]amino]pyridine-2-carboxylate

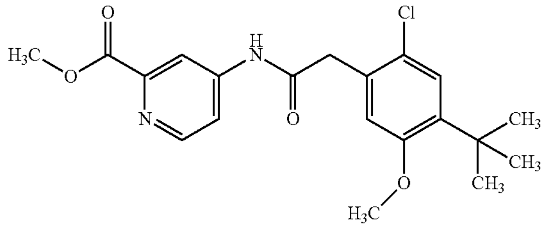 [SMILES: COC(=O)c1cc(NC(=O)Cc2cc(OC)c(C(C)(C)C)cc2Cl)ccn1]

To a stirred solution of 2-(4-tert-butyl-2-chloro-5-methoxy-phenyl)acetic acid (Intermediate K) (1.68 g, 6.54 mmol), methyl 4-aminopyridine-2-carboxylate (1.19 g, 7.85 mmol) and DIPEA (1.49 mL, 8.51 mmol) in 1,4-dioxane (40 mL) was added 50% T3P® solution in EtOAc (5.06 mL, 8.51 mmol). The reaction mixture was stirred at room temperature for 45 min and then partitioned between EtOAc (200 mL) and water (200 mL). The resulting suspension was washed with 1M aq. HCl (100 mL) followed by 20% aqueous NaOH (2×100 mL). The organic layer was separated, dried over $Na_2SO_4$ and concentrated in vacuo. The crude material was purified by chromatography on silica eluting with 20-100% EtOAc in heptanes to afford the title compound as an off-white powder.

LC-MS (Method E): Rt 1.25 mins; MS m/z 391.1, 393.1=[M+H]+ (100% @215 nm)

$^1$H NMR (500 MHz, DMSO-d6) δ 10.82 (s, 1H), 8.55 (d, J=5.45 Hz, 1H), 8.31 (d, J=2.0 Hz, 1H), 7.77 (dd, J=5.5, 2.1 Hz, 1H), 7.16 (s, 1H), 7.08 (s, 1H), 3.86 (s, 3H), 3.85 (s, 2H), 3.81 (s, 3H), 1.32 (s, 9H).

Step 2: 4-[[2-(4-tert-Butyl-2-chloro-5-hydroxy-phenyl)acetyl]amino]pyridine-2-carboxylic acid

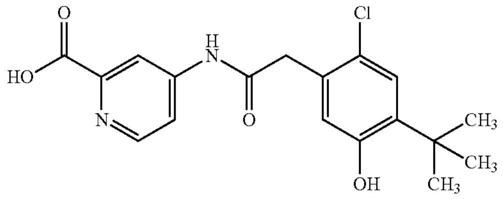

1M $BBr_3$ in DCM (63.71 mL, 63.71 mmol) was added dropwise to a cooled (0° C.), stirred suspension of methyl 4-[[2-(4-tert-butyl-2-chloro-5-methoxy-phenyl)acetyl] amino]pyridine-2-carboxylate (step 1) (4.15 g, 10.62 mmol) in DCM (8 mL). After 30 min, the ice bath was removed and the reaction mixture was stirred at room temperature for 18 h. The resulting mixture was concentrated in vacuo and the crude residue was partitioned between EtOAc (100 mL) and water (100 mL). The organic layer was separated and the aqueous layer back-extracted with EtOAc (50 mL). The combined organic extracts were dried over $Na_2SO_4$ and concentrated in vacuo. The residue was suspended in 1:1 MeCN:water (50 mL) and filtered, washing through with 1:1 MeCN:water. The solid was dried under vacuum to afford the title compound.

LC-MS (Method E): Rt 1.02 mins; MS m/z 363.0, 365.0=[M+H]+ (100% @215 nm)

Step 3: 4-[[2-(4-tert-Butyl-2-chloro-5-hydroxy-phenyl)acetyl]amino]-N-(1-cyano-1-methyl-ethyl) pyridine-2-carboxamide To a solution of 4-[[2-(4-tert-butyl-2-chloro-5-hydroxy-phenyl)acetyl]amino]pyridine-2-carboxylic acid (step 2) (2.5 g, 6.89 mmol) in DMF (25 mL) was added 2-amino-2-methyl-propanenitrile hydrochloride (914 mg, 7.58 mmol), DIPEA (2.41 mL, 13.78 mmol) followed by HATU (2.62 g, 6.89 mmol) and the mixture stirred at room temperature overnight. The resulting mixture was diluted with EtOAc and washed sequentially with 1M HCl (150 mL), sat. $NaHCO_3$ solution (150 mL) and brine (150 mL). The organic portion was dried over $Na_2SO_4$ and concentrated in vacuo. Purification of the crude material by chromatography on silica eluting with 0-100% EtOAc in heptanes afforded the title compound as a colourless powder.

LC-MS (Method A): Rt 3.65 mins; MS m/z 429.2, 431.2=[M+H]+ (99% @215 nm)

$^1$H NMR (500 MHz, DMSO-d6) δ 10.85 (s, 1H), 9.64 (s, 1H), 8.85 (s, 1H), 8.52 (d, J=5.5 Hz, 1H), 8.24 (d, J=2.0 Hz, 1H), 7.85 (dd, J=5.5, 2.1 Hz, 1H), 7.09 (s, 1H), 6.82 (s, 1H), 3.75 (s, 2H), 1.72 (s, 6H), 1.33 (s, 9H).

Example 10.1

4-[[2-(4-tert-Butyl-2-chloro-5-hydroxy-phenyl)acetyl]amino]-N-[1-(trifluoromethyl) cyclopropyl] pyridine-2-carboxamide

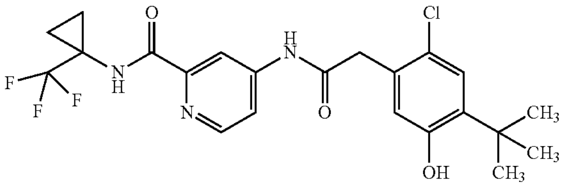 [SMILES: CC(C)(C)c1cc(Cl)c(CC(=O)Nc2ccnc(C(=O)NC3(C(F)(F)F)CC3)c2)cc1O]

The title compound was prepared analogously to Example 10 by replacing 2-amino-2-methyl-propanenitrile hydrochloride (step 3) with 1-(trifluoromethyl)cyclopropanamine hydrochloride.

LC-MS (Method A): Rt 3.92 mins; MS m/z 470.2, 472.2=[M+H]+ (98% @215 nm)

$^1$H NMR (400 MHz, DMSO-d6) δ 10.81 (s, 1H), 9.62 (s, 1H), 9.38 (s, 1H), 8.51 (d, J=5.5 Hz, 1H), 8.22 (d, J=2.0 Hz, 1H), 7.84 (dd, J=5.5, 2.2 Hz, 1H), 7.09 (s, 1H), 6.82 (s, 1H), 3.74 (s, 2H), 1.33 (s, 9H), 1.30-1.14 (m, 4H).

Example 10.2

4-[[2-(4-tert-Butyl-2-chloro-5-hydroxy-phenyl)acetyl]amino]-N-(1-cyanocyclopropyl) pyridine-2-carboxamide

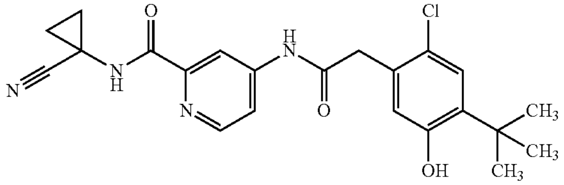 [SMILES: CC(C)(C)c1cc(Cl)c(CC(=O)Nc2ccnc(C(=O)NC3(C#N)CC3)c2)cc1O]

The title compound was prepared analogously to Example 10 by replacing 2-amino-2-methyl-propanenitrile hydrochloride (step 3) with 1-aminocyclopropanecarbonitrile hydrochloride.

LC-MS (Method A): Rt 3.50 mins; MS m/z 427.2, 429.2=[M+H]+ (97% @215 nm)

$^1$H NMR (400 MHz, DMSO-d6) δ 10.82 (br s, 1H), 9.66 (s, 1H), 9.63 (br s, 1H), 8.50 (d, J=5.7 Hz, 1H), 8.24 (d, J=1.8 Hz, 1H), 7.85 (dd, J=5.5, 2.2 Hz, 1H), 7.09 (s, 1H), 6.82 (s, 1H), 3.75 (s, 2H), 1.56-1.50 (m, 2H), 1.39-1.27 (m, 11H).

Example 11

4-[[2-[2-Fluoro-5-hydroxy-4-(3-hydroxy-1,1-dimethyl-propyl)phenyl]acetyl]amino]-N-[1-(trifluoromethyl)cyclopropyl]pyridine-2-carboxamide

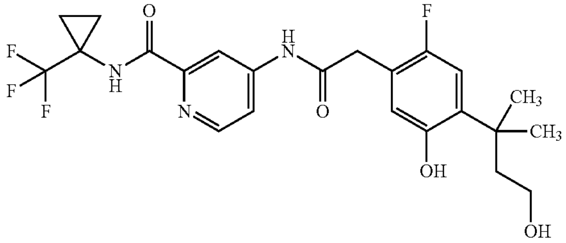 [SMILES: CC(C)(CCO)c1cc(F)c(CC(=O)Nc2ccnc(C(=O)NC3(C(F)(F)F)CC3)c2)cc1O]

Step 1: 4-[[2-(6-Fluoro-4,4-dimethyl-2-oxo-chroman-7-yl)acetyl]amino]-N-[1-(trifluoromethyl) cyclopropyl]pyridine-2-carboxamide

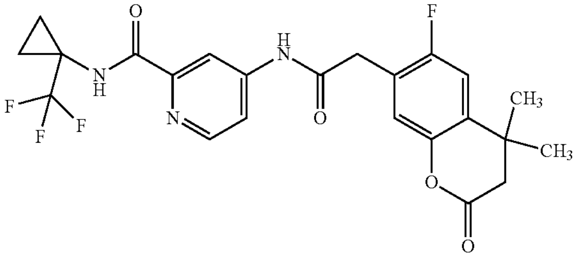 [SMILES: CC1(C)CC(=O)Oc2cc(CC(=O)Nc3ccnc(C(=O)NC4(C(F)(F)F)CC4)c3)c(F)cc21]

The title compound was prepared from 2-(6-fluoro-4,4-dimethyl-2-oxo-chroman-7-yl)acetic acid (Intermediate P)

and 4-amino-N-[1-(trifluoromethyl)cyclopropyl]pyridine-2-carboxamide (Intermediate A) analogously to Example 2 step 1.

LC-MS (Method G): Rt 0.96 min; MS m/z 480.2=[M+H]+ (93% @215 nm)

$^1$H NMR (500 MHz, DMSO-d6) δ 10.84 (s, 1H), 9.39 (s, 1H), 8.51 (d, J=5.5 Hz, 1H), 8.19 (d, J=2.0 Hz, 1H), 7.84 (dd, J=5.5, 2.2 Hz, 1H), 7.28 (d, J=10.2 Hz, 1H), 7.15 (d, J=6.4 Hz, 1H), 3.80 (s, 2H), 2.73 (s, 2H), 1.34-1.21 (m, 8H), 1.21-1.17 (m, 2H).

Step 2: 4-[[2-[2-Fluoro-5-hydroxy-4-(3-hydroxy-1,1-dimethyl-propyl)phenyl]acetyl]amino]-N-[1-(trifluoromethyl)cyclopropyl]pyridine-2-carboxamide To a stirred, cooled (−78° C.) solution of 4-[[2-(6-fluoro-4,4-dimethyl-2-oxo-chroman-7-yl)acetyl]amino]-N-[1-(trifluoromethyl)cyclopropyl]pyridine-2-carboxamide (step 1) (93%, 345 mg, 0.67 mmol) in THF (10 mL) was added 4M $LiBH_4$ in THF (201 µL, 0.8 mmol) and the mixture was stirred at −78° C. for 1 h and then at room temperature overnight.

The reaction was quenched with water (20 mL) and diluted with EtOAc (10 mL). The organic layer was separated, dried over $Na_2SO_4$ and concentrated in vacuo. Purification of the crude residue by C18 reverse phase chromatography eluting with 10-100% MeCN in water (0.1% formic acid) afforded the title compound as a white solid.

LC-MS (Method A): Rt 2.98 min; MS m/z 484.2=[M+H]+ (98% @215 nm)

$^1$H NMR (500 MHz, DMSO-d6) δ 10.81 (s, 1H), 9.39 (s, 1H), 9.30 (s, 1H), 8.50 (d, J=5.5 Hz, 1H), 8.22 (d, J=2.0 Hz, 1H), 7.84 (dd, J=5.5, 2.2 Hz, 1H), 6.82 (d, J=12.0 Hz, 1H), 6.73 (d, J=7.0 Hz, 1H), 4.16 (t, J=4.9 Hz, 1H), 3.65 (s, 2H), 3.20-3.10 (m, 2H), 2.03-1.91 (m, 2H), 1.38-1.22 (m, 8H), 1.21-1.12 (m, 2H).

Example 12

N-(4-Cyanotetrahydropyran-4-yl)-4-[[2-[2-fluoro-5-hydroxy-4-(2-hydroxy-1,1-dimethyl-ethyl)phenyl]acetyl]amino]pyridine-2-carboxamide

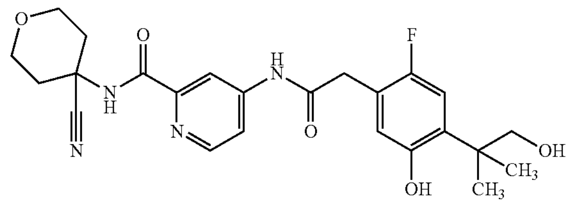 [SMILES: CC(C)(CO)c1cc(F)c(CC(=O)Nc2ccnc(C(=O)NC3(C#N)CCOCC3)c2)cc1O]

Step 1: Methyl 4-[[2-(5-fluoro-3,3-dimethyl-2-oxo-benzofuran-6-yl)acetyl]amino]pyridine-2-carboxylate

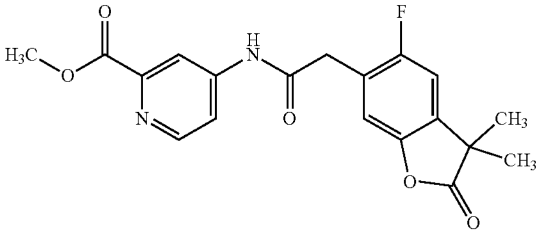

DIPEA (9.0 mL, 51.53 mmol) and 50% T3P0 solution in EtOAc (20.0 mL, 33.6 mmol) were added simultaneously to a stirred solution of 2-(5-fluoro-3,3-dimethyl-2-oxo-benzofuran-6-yl)acetic acid (Intermediate U) (4.0 g, 16.79 mmol) and methyl 4-aminopyridine-2-carboxylate (2.55 g, 16.79 mmol) in DMF (60 mL) and the mixture was stirred at room temperature for 2 h. The resulting mixture was diluted with EtOAc (60 mL) and washed with brine (100 mL). The aqueous was extracted with EtOAc (2×75 mL) and the combined organic extracts were washed with brine (2×100 mL), dried over $Na_2SO_4$ and concentrated in vacuo. Purification of the residue by chromatography on silica eluting with 0-100% EtOAc in heptanes followed by azeotroping of the product fractions with EtOAc (3×100 mL) afforded the title compound as a beige powder.

LC-MS (Method G): Rt 0.81 min; MS m/z 373.2=[M+H]+ (100% @215 nm)

$^1$H NMR (400 MHz, DMSO-d6) δ 10.85 (br. s, 1H), 8.56 (d, J=5.4 Hz, 1H), 8.30 (d, J=1.9 Hz, 1H), 7.77 (dd, J=5.5, 2.1 Hz, 1H), 7.44 (d, J=8.9 Hz, 1H), 7.30 (d, J=5.8 Hz, 1H), 3.86 (s, 3H), 3.83 (s, 2H), 1.45 (s, 6H).

Step 2: 4-[[2-(5-Fluoro-3,3-dimethyl-2-oxo-benzofuran-6-yl)acetyl]amino]pyridine-2-carboxylic acid

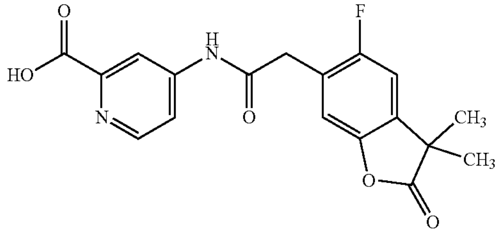 [SMILES: CC1(C)C(=O)Oc2cc(CC(=O)Nc3ccnc(C(=O)O)c3)c(F)cc21]

To a solution of methyl 4-[[2-(5-fluoro-3,3-dimethyl-2-oxo-benzofuran-6-yl)acetyl]amino] pyridine-2-carboxylate (step 1) (2.0 g, 5.37 mmol) in THF (22 mL) was added a solution of lithium hydroxide hydrate (1.13 g, 26.86 mmol) in water (22 mL) and the reaction mixture was stirred at room temperature for 1 h. The pH of the resulting mixture was adjusted to pH 1 using 2M $KHSO_4$ (approx. 45 mL) and stirring continued at room temperature for 1 h. Dioxane (100 mL) was added to aid solubility and the mixture was heating to 50° C. overnight. The mixture was extracted with EtOAc/MeCN (1:1, 4×100 mL) and the combined organic extracts were dried over $Na_2SO_4$ and concentrated in vacuo. The crude residue was dissolved in 4M HCl in dioxane (15 mL)

and heated to 80° C. for 1 h. The resulting emulsion was allowed to cool to room temperature and concentrated in vacuo, azeotroping with EtOAc:MeCN (1:1, 2×100 mL) to afford the title compound as an off-white solid.

LC-MS (Method E): Rt 0.93 min; MS m/z 359.1=[M+H]+ (97% @215 nm)

$^1$H NMR (400 MHz, DMSO-d6) δ 11.26 (br. s, 1H), 8.60 (d, J=5.9 Hz, 1H), 8.36 (d, J=2.1 Hz, 1H), 7.95 (dd, J=5.9, 2.2 Hz, 1H), 7.45 (d, J=8.9 Hz, 1H), 7.32 (d, J=5.8 Hz, 1H), 3.89 (s, 2H), 1.45 (s, 6H).

Step 3: N-(4-Cyanotetrahydropyran-4-yl)-4-[[2-[2-fluoro-5-hydroxy-4-(2-hydroxy-1,1-dimethyl-ethyl)phenyl]acetyl]amino]pyridine-2-carboxamide To a solution of 4-[[2-(5-fluoro-3,3-dimethyl-2-oxo-benzofuran-6-yl)acetyl]amino]pyridine-2-carboxylic acid (step 2) (87%, 150 mg, 0.36 mmol), 4-aminotetrahydropyran-4-carbonitrile (51 mg, 0.40 mmol) and HATU (166 mg, 0.44 mmol) in DMF (3 mL) was added DIPEA (89 μL, 0.51 mmol) and the mixture was stirred at room temperature overnight. Additional HATU (166 mg, 0.44 mmol), 4-aminotetrahydropyran-4-carbonitrile (51 mg, 0.40 mmol) and DIPEA (89 μL, 0.51 mmol) were added and stirring continued for a further hour. The resulting mixture was diluted with EtOAc (8 mL), washed with water (8 mL), brine (2×8 mL), dried over $Na_2SO_4$ and concentrated in vacuo. The crude residue was dissolved in THF (3 mL) and cooled to −78° C. 4M $LiBH_4$ in THF (0.10 mL, 0.40 mmol) was added dropwise and stirring continued whilst gradually warming to room temperature over 45 min. The resulting mixture was re-cooled to 0° C. and the reaction was quenched by the dropwise addition of 1M HCl (5 mL). The mixture was diluted with EtOAc (10 mL) and the phases were separated. The aqueous was extracted with EtOAc (10 mL) and the combined organic extracts were dried over $Na_2SO_4$ and concentrated in vacuo. Purification of the crude product by C18 reverse phase chromatography eluting with 10-100% MeCN in water (+0.1% formic acid) afforded the title compound as a beige solid.

LC-MS (Method A): Rt 2.54 min; MS m/z 471.4=[M+H]+ (100% @215 nm)

$^1$H NMR (500 MHz, DMSO-d6) δ 10.83 (s, 1H), 9.39 (s, 1H), 9.02 (s, 1H), 8.54 (d, J=5.5 Hz, 1H), 8.24 (d, J=2.0 Hz, 1H), 7.86 (dd, J=5.5, 2.2 Hz, 1H), 6.90 (d, J=12.1 Hz, 1H), 6.72 (d, J=7.0 Hz, 1H), 4.77 (t, J=5.3 Hz, 1H), 3.87 (dt, J=12.1, 3.8 Hz, 2H), 3.65 (s, 2H), 3.62-3.55 (m, 4H), 2.40-2.33 (m, 2H), 2.11-2.03 (m, 2H), 1.25 (s, 6H).

Example 12.1

4-[[2-[2-Fluoro-5-hydroxy-4-(2-hydroxy-1,1-dimethyl-ethyl)phenyl]acetyl]amino]-N-[3-(trifluoromethyl)oxetan-3-yl]pyridine-2-carboxamide

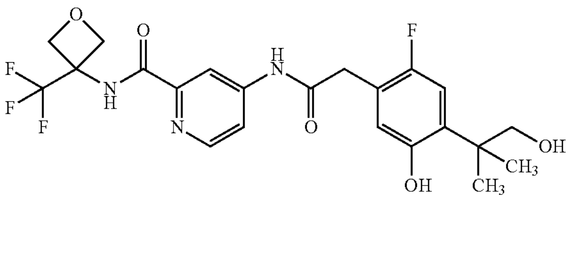 [SMILES: CC(C)(CO)c1cc(F)c(CC(=O)Nc2ccnc(C(=O)NC3(C(F)(F)F)COC3)c2)cc1O]

The title compound was prepared from 4-[[2-(5-fluoro-3,3-dimethyl-2-oxo-benzofuran-6-yl)acetyl]amino]pyridine-2-carboxylic acid (Example 12 step 2) and 3-(trifluoromethyl)oxetan-3-amine hydrochloride analogously to Example 12 step 3.

LC-MS (Method A): Rt 2.75 min; MS m/z 486.3=[M+H]+ (100% @215 nm)

$^1$H NMR (400 MHz, DMSO-d6) δ 10.82 (s, 1H), 9.89 (s, 1H), 9.38 (s, 1H), 8.55 (d, J=5.5 Hz, 1H), 8.22 (d, J=2.0 Hz, 1H), 7.87 (dd, J=5.5, 2.1 Hz, 1H), 6.91 (d, J=12.1 Hz, 1H), 6.73 (d, J=7.0 Hz, 1H), 4.93 (d, J=7.9 Hz, 2H), 4.79-4.69 (m, 3H), 3.66 (s, 2H), 3.61 (d, J=3.3 Hz, 2H), 1.26 (s, 6H).

Example 12.2

4-[[2-[2-Fluoro-5-hydroxy-4-(2-hydroxy-1,1-dimethyl-ethyl)phenyl]acetyl]amino]-N-[(1S,2S)-2-hydroxycyclopentyl]pyridine-2-carboxamide

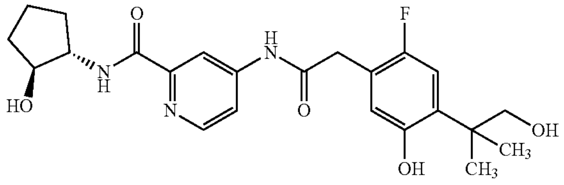 [SMILES: CC(C)(CO)c1cc(F)c(CC(=O)Nc2ccnc(C(=O)N[C@H]3CCC[C@@H]3O)c2)cc1O]

The title compound was prepared from 4-[[2-(5-fluoro-3,3-dimethyl-2-oxo-benzofuran-6-yl)acetyl]amino]pyridine-2-carboxylic acid (Example 12 step 2) and (1S,2S)-2-aminocyclopentanol hydrochloride analogously to Example 12 step 3.

LC-MS (Method A): Rt 2.37 min; MS m/z 446.3=[M+H]+ (100% @215 nm)

$^1$H NMR (500 MHz, Methanol-d4) δ 8.46 (d, J=5.5 Hz, 1H), 8.34 (br. s, 1H), 8.18 (d, J=1.9 Hz, 1H), 7.89 (dd, J=5.5, 2.2 Hz, 1H), 6.95 (d, J=12.0 Hz, 1H), 6.71 (d, J=6.8 Hz, 1H), 4.16-4.08 (m, 2H), 3.79 (s, 2H), 3.69 (s, 2H), 2.23-2.15 (m, 1H), 2.05-1.97 (m, 1H), 1.89-1.73 (m, 2H), 1.70-1.58 (m, 2H), 1.34 (s, 6H).

Example 12.3

4-[[2-[2-Fluoro-5-hydroxy-4-(2-hydroxy-1,1-dimethyl-ethyl)phenyl]acetyl]amino]-N-(2-hydroxy-1,1-dimethyl-ethyl)pyridine-2-carboxamide

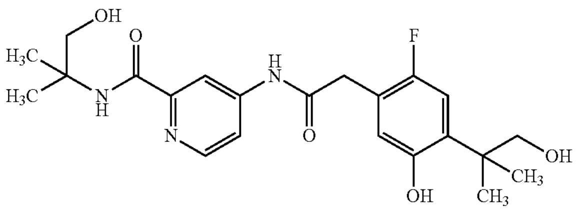 [SMILES: CC(C)(CO)NC(=O)c1cc(NC(=O)Cc2cc(O)c(C(C)(C)CO)cc2F)ccn1]

4-[[2-(5-Fluoro-3,3-dimethyl-2-oxo-benzofuran-6-yl)acetyl]amino]pyridine-2-carboxylic acid ((Example 12 step 2) (87%, 172 mg, 0.42 mmol) and DIPEA (0.22 mL, 1.26 mmol) were suspended in DMF (2 mL) and treated with HATU (191 mg, 0.5 mmol) followed by 2-amino-2-methylpropan-1-ol (49 mg, 0.54 mmol) and the reaction mixture was stirred at room temperature for 2 h. The resulting mixture was diluted with EtOAc (25 mL) and washed with water (2×20 mL), brine (2×20 mL), dried over $Na_2SO_4$ and concentrated in vacuo. The crude intermediate was dissolved in THF (10 mL) and cooled to −78° C. 4M $LiBH_4$ in THF (157 μL, 0.63 mmol) was added and stirring continued whilst gradually warming to room temperature. After stirring for a further 1.5 h, the resulting mixture was re-cooled to 0° C. and the reaction was quenched by the dropwise addition of 1M HCl (10 mL). The mixture was diluted with EtOAc (20 mL) and water (20 mL) and the phases were separated. The aqueous portion was further extracted with EtOAc (2×10 mL) and the combined organic extracts were dried over $Na_2SO_4$ and concentrated in vacuo. Purification of the crude product by preparative HPLC (acidic pH, early elution method) gave a solid which was dried in a vacuum oven at 40° C. to afford the title compound as a colourless solid.

LCMS (Method A) Rt 2.43 mins; MS m/z 434.3=[M+H]+ (100% @215 nm)

1H NMR (400 MHz, DMSO-d6) δ 10.76 (s, 1H), 9.37 (s, 1H), 8.45 (d, J=5.5 Hz, 1H), 8.25 (s, 1H), 8.19 (d, J=1.9 Hz, 1H), 7.80 (dd, J=5.5, 2.2 Hz, 1H), 6.90 (d, J=12.1 Hz, 1H), 6.72 (d, J=7.0 Hz, 1H), 5.13 (t, J=5.5 Hz, 1H), 4.77-4.70 (m, 1H), 3.64 (s, 2H), 3.60 (d, J=3.7 Hz, 2H), 3.44 (d, J=5.5 Hz, 2H), 1.33 (s, 6H), 1.25 (s, 6H).

Example 12.4

4-[[2-[2-Fluoro-5-hydroxy-4-(2-hydroxy-1,1-dimethyl-ethyl)phenyl]acetyl]amino]-N-[1-(hydroxymethyl)cyclobutyl]pyridine-2-carboxamide

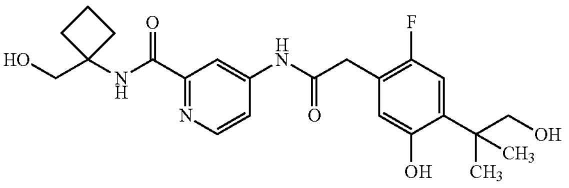 [SMILES: CC(C)(CO)c1cc(F)c(CC(=O)Nc2ccnc(C(=O)NC3(CO)CCC3)c2)cc1O]

To a solution of 4-[[2-(5-fluoro-3,3-dimethyl-2-oxo-benzofuran-6-yl)acetyl]amino]pyridine-2-carboxylic acid (Example 12 step 2) (87%, 160 mg, 0.39 mmol) and DIPEA (0.24 mL, 1.36 mmol) in DMF (3 mL) was added HATU (177 mg, 0.47 mmol) followed by (1-aminocyclobutyl) methanol hydrochloride (70 mg, 0.51 mmol) and the mixture was stirred at room temperature for 40 mins. The resulting mixture was diluted with EtOAc (20 ml) and water (20 mL) and the phases were separated. The organic portion was washed with brine (20 mL), dried over $Na_2SO_4$ and concentrated in vacuo. The crude intermediate was taken up in THF (3 mL) and cooled to −78° C. 4M $LiBH_4$ in THF (107 μL, 0.43 mmol) was added dropwise and the mixture was stirred whilst gradually warming to room temperature over 40 mins. The resulting mixture was re-cooled to 0° C. and the reaction was quenched by the dropwise addition of 1M HCl (5 mL). The mixture was diluted with EtOAc (10 mL) and the phases were separated. The aqueous portion was further extracted with EtOAc (10 mL) and the combined organic extracts were dried over $Na_2SO_4$ and concentrated in vacuo. Purification of the crude product by preparative HPLC (acidic pH, early elution method) afforded the title compound as a colourless solid.

LC-MS (Method A): Rt 2.43 min; MS m/z 446.3=[M+H]+ (100% @215 nm) 1H NMR (500 MHz, DMSO-d6) δ 10.79 (s, 1H), 9.34 (br. s, 1H), 8.48 (d, J=5.5 Hz, 1H), 8.41 (s, 1H), 8.19 (d, J=2.0 Hz, 1H), 7.82 (dd, J=5.5, 2.2 Hz, 1H), 6.91 (d, J=12.1 Hz, 1H), 6.73 (d, J=7.0 Hz, 1H), 5.01 (t, J=5.5 Hz, 1H), 4.76 (br. s, 1H), 3.65 (s, 2H), 3.62 (d, J=5.4 Hz, 2H), 3.61 (s, 2H), 2.09-2.01 (m, 2H), 1.89-1.80 (m, 1H), 1.79-1.66 (m, 1H), 1.26 (s, 6H).

Example 13

4-[[2-[2-Fluoro-5-hydroxy-4-(4-hydroxytetrahydro-pyran-4-yl)phenyl]acetyl]amino]-N-[1-(trifluoromethyl)cyclopropyl]pyridine-2-carboxamide

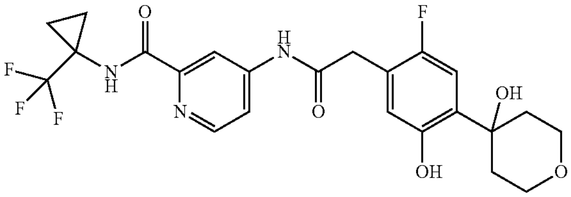 [SMILES: O=C(Cc1cc(O)c(C2(O)CCOCC2)cc1F)Nc1ccnc(C(=O)NC2(C(F)(F)F)CC2)c1]

Step 1: 4-[[2-(5-Benzyloxy-4-bromo-2-fluoro-phenyl)acetyl]amino]-N-[1-(trifluoromethyl) cyclopropyl]pyridine-2-carboxamide

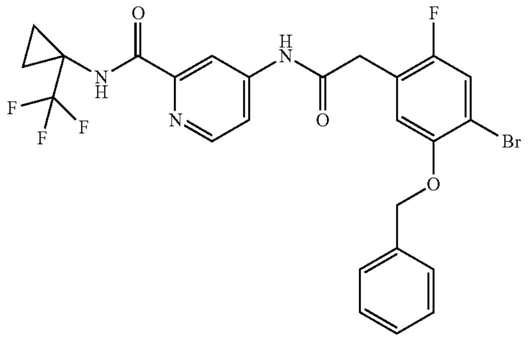 [SMILES: O=C(Cc1cc(OCc2ccccc2)c(Br)cc1F)Nc1ccnc(C(=O)NC2(C(F)(F)F)CC2)c1]

The title compound was prepared from 2-(5-benzyloxy-4-bromo-2-fluoro-phenyl)acetic acid (Intermediate S) and 4-amino-N-[1-(trifluoromethyl)cyclopropyl]pyridine-2-carboxamide (Intermediate A) analogously to Example 2 step 1.

LC-MS (Method G): Rt 1.13 min; MS m/z 566.1, 568.0=[M+H]+ (100% @215 nm)

$^{1}H$ NMR (400 MHz, DMSO-d6) δ 10.82 (s, 1H), 9.39 (s, 1H), 8.51 (d, J=5.5 Hz, 1H), 8.19 (d, J=2.0 Hz, 1H), 7.84 (dd, J=5.5, 2.2 Hz, 1H), 7.56 (d, J=8.9 Hz, 1H), 7.50-7.46 (m, 2H), 7.42-7.36 (m, 2H), 7.35-7.28 (m, 2H), 5.16 (s, 2H), 3.79 (s, 2H), 1.33-1.27 (m, 2H), 1.23-1.15 (m, 2H).

Step 2: 4-[[2-[5-Benzyloxy-4-(3,6-dihydro-2H-pyran-4-yl)-2-fluoro-phenyl]acetyl]amino]-N-[1-(trifluoromethyl)cyclopropyl]pyridine-2-carboxamide

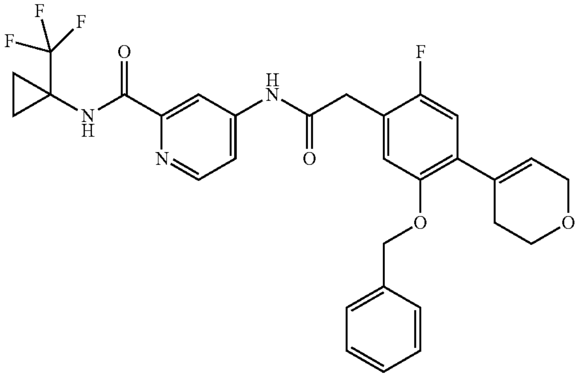 [SMILES: O=C(Cc1cc(OCc2ccccc2)c(C2=CCOCC2)cc1F)Nc1ccnc(C(=O)NC2(C(F)(F)F)CC2)c1]

A solution of 4-[[2-(5-benzyloxy-4-bromo-2-fluoro-phenyl)acetyl]amino]-N-[1-(trifluoromethyl)cyclopropyl]pyridine-2-carboxamide (step 1) (220 mg, 0.39 mmol), dihydro-2H-pyran-4-yl)-4,4,5,5-tetramethyl-1,3,2-dioxaborolane (163 mg, 0.78 mmol), tripotassium phosphate (330 mg, 1.55 mmol) in toluene (5 mL) and water (0.5 mL) was degassed with nitrogen for 10 min and then treated with $Pd(OAc)_2$ (17 mg, 0.08 mmol) and $P(Cy)_3$ (44 mg, 0.16 mmol). The mixture was bubbled with nitrogen for a further 5 min, sealed and heated at 100° C. for 5 h. The resulting mixture was concentrated in vacuo and the residue was partitioned between EtOAc (25 mL) and water (25 mL). The layers were separated and organic portion was washed with brine (25 mL), dried over $Na_2SO_4$ and concentrated in vacuo. The crude material was purified by chromatography on silica eluting with 0-100% EtOAc in heptanes to afford the title compound.

LC-MS (Method E): Rt 1.35 min; MS m/z 570.3=[M+H]+ (100% @215 nm)

$^1$H NMR (400 MHz, DMSO-d6) δ 10.80 (s, 1H), 9.39 (s, 1H), 8.51 (d, J=5.4 Hz, 1H), 8.20 (d, J=1.8 Hz, 1H), 7.85 (dd, J=5.5, 2.2 Hz, 1H), 7.46-7.34 (m, 4H), 7.34-7.28 (m, 1H), 7.15 (d, J=6.4 Hz, 1H), 7.00 (d, J=10.3 Hz, 1H), 5.99-5.95 (m, 1H), 5.07 (s, 2H), 4.19-4.15 (m, 2H), 3.77 (s, 2H), 3.74 (t, J=5.4 Hz, 2H), 2.43-2.38 (m, 2H), 1.33-1.27 (m, 2H), 1.22-1.17 (m, 2H).

Step 3: 4-[[2-[5-Benzyloxy-2-fluoro-4-(4-hydroxytetrahydropyran-4-yl)phenyl]acetyl] amino]-N-[1-(trifluoromethyl)cyclopropyl]pyridine-2-carboxamide

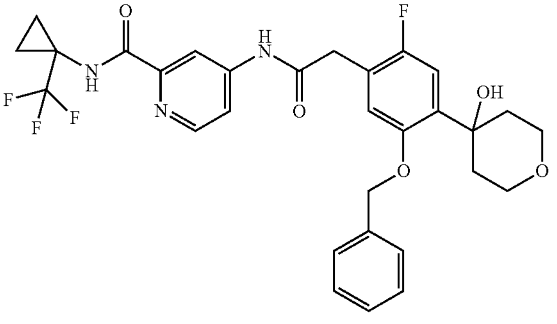 [SMILES: O=C(Cc1cc(OCc2ccccc2)c(C2(O)CCOCC2)cc1F)Nc1ccnc(C(=O)NC2(C(F)(F)F)CC2)c1]

A solution of 4-[[2-[5-benzyloxy-4-(3,6-dihydro-2H-pyran-4-yl)-2-fluoro-phenyl]acetyl]amino]-N-[1-(trifluoromethyl)cyclopropyl]pyridine-2-carboxamide (step 2) (100%, 170 mg, 0.3 mmol), in IPA (5 mL) and DCM (1 mL) was purged with air for 10 min. The mixture was cooled to 0° C. and tris(2,2,6,6-tetramethyl-3,5-heptanedionato)manganese(III) (18 mg, 0.03 mmol) was added followed by phenylsilane (74 μL, 0.6 mmol). The reaction mixture was allowed to warm to room temperature and stirred for 1 h. The reaction was quenched with 20% aqueous solution of sodium thiosulfate (20 mL) and stirred at room temperature for 30 min. The resulting mixture was extracted with EtOAc (2×25 mL), and the combined organic extracts were washed with brine (20 mL), dried over $MgSO_4$ and concentrated in vacuo. Purification of the crude material by chromatography on silica eluting with 0-100% EtOAc in heptanes afforded the title compound as an off-white solid.

LC-MS (Method E): Rt 1.26 min; MS m/z 588.3=[M+H]+ (79% @215 nm)

$^1$H NMR (500 MHz, DMSO-d6) δ 10.80 (s, 1H), 9.38 (s, 1H), 8.51 (d, J=5.5 Hz, 1H), 8.20 (d, J=1.9 Hz, 1H), 7.84 (dd, J=5.5, 2.2 Hz, 1H), 7.52-7.48 (m, 2H), 7.41-7.34 (m, 3H), 7.32-7.28 (m, 1H), 7.13 (d, J=6.3 Hz, 1H), 5.15 (s, 2H), 5.11 (s, 1H), 3.79-3.71 (m, 4H), 3.66 (dd, J=10.7, 5.2 Hz, 2H), 2.68-2.57 (m, 2H), 1.35-1.28 (m, 4H), 1.21-1.17 (m, 2H).

Step 4: 4-[[2-[2-Fluoro-5-hydroxy-4-(4-hydroxytetrahydropyran-4-yl)phenyl]acetyl]amino]-N-[1-(trifluoromethyl)cyclopropyl]pyridine-2-carboxamide The title compound was prepared from 4-[[2-[5-benzyloxy-2-fluoro-4-(4-hydroxytetrahydropyran-4-yl)phenyl]acetyl]amino]-N-[1-(trifluoromethyl)cyclopropyl]pyridine-2-carboxamide (step 3) and 10% Pd—C analogously to Example 2 step 2.

LC-MS (Method A): Rt 2.71 min; MS m/z 498.2=[M+H]+ (100% @215 nm)

$^1$H NMR (500 MHz, DMSO-d6) δ 10.81 (s, 1H), 9.57 (s, 1H), 9.39 (s, 1H), 8.50 (d, J=5.5 Hz, 1H), 8.21 (d, J=2.0 Hz, 1H), 7.84 (dd, J=5.5, 2.2 Hz, 1H), 7.18 (d, J=11.5 Hz, 1H), 6.76 (d, J=6.6 Hz, 1H), 5.35 (s, 1H), 3.77-3.72 (m, 2H), 3.70-3.65 (m, 4H), 2.46 (obscured m, 2H), 1.36 (d, J=12.9 Hz, 2H), 1.32-1.27 (m, 2H), 1.21-1.16 (m, 2H).

Example 14

4-[[2-[2-Chloro-5-hydroxy-4-(2-hydroxy-1,1-dimethyl-ethyl)phenyl]acetyl]amino]-N-[1-(trifluoromethyl)cyclopropyl]pyridine-2-carboxamide

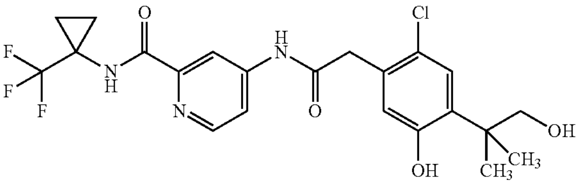 [SMILES: CC(C)(CO)c1cc(Cl)c(CC(=O)Nc2ccnc(C(=O)NC3(C(F)(F)F)CC3)c2)cc1O]

Step 1: Methyl 2-[5-chloro-2-methoxy-4-[2-oxo-2-[[2-[[1-(trifluoromethyl)cyclopropyl] carbamoyl]-4-pyridyl]amino]ethyl]phenyl]-2-methyl-propanoate

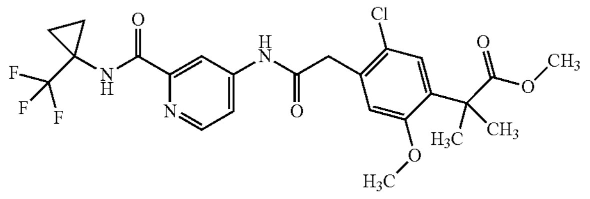 [SMILES: COC(=O)C(C)(C)c1cc(Cl)c(CC(=O)Nc2ccnc(C(=O)NC3(C(F)(F)F)CC3)c2)cc1OC]

To a stirred solution of 2-[2-chloro-5-methoxy-4-(2-methoxy-1,1-dimethyl-2-oxo-ethyl)phenyl]acetic acid (Intermediate T step 5) (771 mg, 2.56 mmol), 4-amino-N-[1-(trifluoromethyl)cyclopropyl]pyridine-2-carboxamide (Intermediate A) (629 mg, 2.56 mmol) and TEA (672 μL, 3.85 mmol) in 1,4-dioxane (10 mL) was added 50% T3P® solution in EtOAc (2.29 mL, 3.85 mmol) and the reaction mixture was stirred at ambient temperature for 1 h.

The resulting mixture was concentrated in vacuo and the crude residue dissolved in EtOAc (20 mL), washed with $NaHCO_3$ (15 mL), brine (15 mL), dried over $Na_2SO_4$ and concentrated in vacuo. Purification of the crude residue by chromatography on silica eluting with 0-100% EtOAc in heptanes yielded the title compound as an off-white solid.

LC-MS (Method G): Rt 1.05 min; MS m/z 528.1, 530.1=[M+H]+ (99% @215 nm)

$^1$H NMR (500 MHz, DMSO-d6) δ 10.87 (s, 1H), 9.40 (s, 1H), 8.51 (d, J=5.5 Hz, 1H), 8.21 (d, J=2.0 Hz, 1H), 7.85 (dd, J=5.5, 2.2 Hz, 1H), 7.28 (s, 1H), 7.11 (s, 1H), 3.89 (s, 2H), 3.73 (s, 3H), 3.55 (s, 3H), 1.42 (s, 6H), 1.32-1.30 (m, 2H), 1.21-1.19 (m, 2H).

Step 2: 4-[[2-(5-Chloro-3,3-dimethyl-2-oxo-benzofuran-6-yl)acetyl]amino]-N-[1-(trifluoromethyl) cyclopropyl]pyridine-2-carboxamide

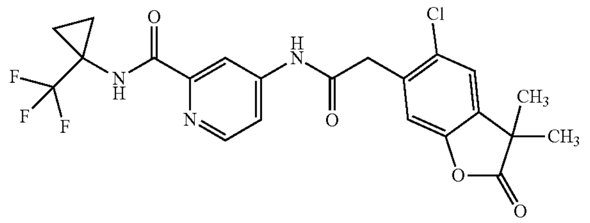 [SMILES: CC1(C)C(=O)Oc2cc(CC(=O)Nc3ccnc(C(=O)NC4(C(F)(F)F)CC4)c3)c(Cl)cc21]

1M $BBr_3$ in DCM (2.81 mL, 2.81 mmol) was added dropwise to a solution of methyl 2-[5-chloro-2-methoxy-4-[2-oxo-2-[[2-[[1-(trifluoromethyl)cyclopropyl]carbamoyl]-4-pyridyl]amino]ethyl] phenyl]-2-methyl-propanoate (step 1) (494 mg, 0.94 mmol) in DCM (12 mL) under $N_2$ and the mixture was stirred at room temperature overnight. The resulting mixture was diluted with water (20 mL) and extracted with DCM (30 mL). The organic extract was dried over $Na_2SO_4$ and concentrated in vacuo. Purification of the crude residue by C18 reverse phase chromatography eluting with 10-100% water (+0.1% formic acid)/MeCN (+0.1% formic acid) afforded the title compound as an off-white solid.

LC-MS (Method G): Rt 1.02 min; MS m/z 482.2, 484.1=[M+H]+ (100% @215 nm)

$^1$H NMR (500 MHz, DMSO-d6) δ 10.86 (s, 1H), 9.39 (s, 1H), 8.51 (d, J=5.5 Hz, 1H), 8.19 (d, J=2.0 Hz, 1H), 7.84 (dd, J=5.5, 2.2 Hz, 1H), 7.67 (s, 1H), 7.38 (s, 1H), 3.94 (s, 2H), 1.46 (s, 6H), 1.32-1.28 (m, 2H), 1.21-1.17 (m, 2H).

Step 3: 4-[[2-[2-Chloro-5-hydroxy-4-(2-hydroxy-1,1-dimethyl-ethyl)phenyl]acetyl]amino]-N-[1-(trifluoromethyl)cyclopropyl]pyridine-2-carboxamide To a cooled (−78° C.) solution of 4-[[2-(5-chloro-3,3-dimethyl-2-oxo-benzofuran-6-yl)acetyl]amino]-N-[1-(trifluoromethyl)cyclopropyl]pyridine-2-carboxamide (step 2) (197 mg, 0.41 mmol) in THF (4 mL) was added 4M $LiBH_4$ in THF (0.11 mL, 0.45 mmol). The resulting mixture was stirred for 5 min then allowed to warm gradually to room temperature over 1 h.

The mixture was poured onto ice cold 1M HCl (50 mL), allowed to stand for 20 min and then diluted with EtOAc (50 mL) and water (20 mL). The phases were separated and the aqueous portion was extracted with EtOAc (50 mL). The combined organic extracts were washed with saturated $NaHCO_3$ solution (2×50 mL), brine (50 mL), dried over $Na_2SO_4$ and concentrated in vacuo. Purification of the crude residue by C18 reverse phase chromatography eluting with 10-100% water (+0.1% formic acid)/MeCN (+0.1% formic acid) afforded the title compound as an off-white solid.

LC-MS (Method A): Rt 3.12 min; MS m/z 486.2, 488.1=[M+H]+ (99% @215 nm)

$^1$H NMR (500 MHz, DMSO-d6) δ 10.82 (s, 1H), 9.69 (s, 1H), 9.40 (s, 1H), 8.51 (d, J=5.5 Hz, 1H), 8.23 (d, J=2.0 Hz, 1H), 7.85 (dd, J=5.5, 2.2 Hz, 1H), 7.13 (s, 1H), 6.80 (s, 1H), 4.77 (s, 1H), 3.75 (s, 2H), 3.61 (s, 2H), 1.33-1.28 (m, 2H), 1.26 (s, 6H), 1.22-1.17 (m, 2H).

Example 14.1

4-[[2-[5-Hydroxy-4-(2-hydroxy-1,1-dimethyl-ethyl)-2-methyl-phenyl]acetyl]amino]-N-[1-(trifluoromethyl)cyclopropyl]pyridine-2-carboxamide

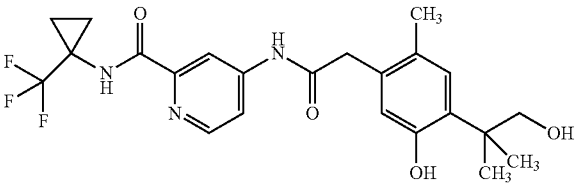 [SMILES: Cc1cc(C(C)(C)CO)c(O)cc1CC(=O)Nc1ccnc(C(=O)NC2(C(F)(F)F)CC2)c1]

Step 1: Methyl 2-[5-bromo-2-methoxy-4-[2-oxo-2-[[2-[[1-(trifluoromethyl)cyclopropyl] carbamoyl]-4-pyridyl]amino]ethyl]phenyl]-2-methyl-propanoate

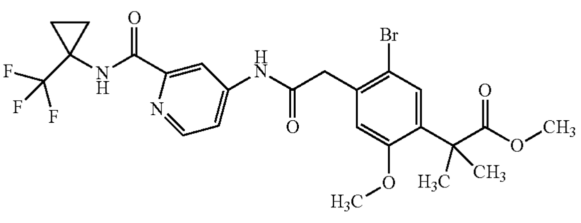 [SMILES: COC(=O)C(C)(C)c1cc(Br)c(CC(=O)Nc2ccnc(C(=O)NC3(C(F)(F)F)CC3)c2)cc1OC]

The title compound was prepared from 2-[2-bromo-5-methoxy-4-(2-methoxy-1,1-dimethyl-2-oxo-ethyl)phenyl] acetic acid (Intermediate Q) and 4-amino-N-[1-(trifluoromethyl)cyclopropyl]pyridine-2-carboxamide (Intermediate A) analogously Example 14 steps 1.

LC-MS (Method H): Rt 1.53 min; MS m/z 573.4=[M+H]+ (99% @215 nm)

$^1$H NMR (500 MHz, DMSO-d6) δ 10.87 (s, 1H), 9.40 (s, 1H), 8.51 (d, J=5.5 Hz, 1H), 8.21 (d, J=2.0 Hz, 1H), 7.85 (dd, J=5.5, 2.2 Hz, 1H), 7.41 (s, 1H), 7.12 (s, 1H), 3.90 (s, 2H), 3.72 (s, 3H), 3.55 (s, 3H), 1.42 (s, 6H), 1.32-1.29 (m, 2H), 1.22-1.16 (m, 2H).

Step 2: Methyl 2-[2-methoxy-5-methyl-4-[2-oxo-2-[[2-[[1-(trifluoromethyl)cyclopropyl] carbamoyl]-4-pyridyl]amino]ethyl]phenyl]-2-methyl-propanoate

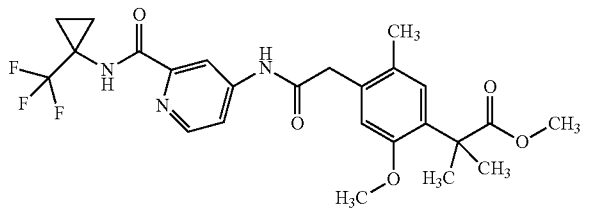 [SMILES: COC(=O)C(C)(C)c1cc(C)c(CC(=O)Nc2ccnc(C(=O)NC3(C(F)(F)F)CC3)c2)cc1OC]

Methyl 2-[5-bromo-2-methoxy-4-[2-oxo-2-[[2-[[1-(trifluoromethyl)cyclopropyl]carbamoyl]-4-pyridyl]amino] ethyl]phenyl]-2-methyl-propanoate (step 1) (75%, 655 mg, 0.86 mmol) was dissolved in 1,4-dioxane (15 mL) and 2,4,6-trimethyl-1,3,5,2,4,6-trioxatriborinane (50%, 0.29 mL, 1.03 mmol), $Pd(dppf)_2Cl_2$ (31 mg, 0.04 mmol) and $K_2CO_3$ (237 mg, 1.72 mmol) were added. The reaction mixture was degassed for 5 min and left to stir at 110° C. for 18 h. The resulting mixture was diluted with EtOAc (40 mL) and washed with water (30 mL), brine (30 mL), dried over $Na_2SO_4$ and concentrated in vacuo. Purification by C18 reverse phase chromatography eluting with 0-100% MeCN in water afforded the title compound.

LC-MS (Method G): Rt 1.01 min; MS m/z 508.30=[M+H]+ (79% @215 nm)

$^1$H NMR (400 MHz, DMSO-d6) δ 10.77 (s, 1H), 9.38 (s, 1H), 8.50 (d, J=5.5 Hz, 1H), 8.20 (d, J=2.0 Hz, 1H), 7.86 (dd, J=5.5, 2.1 Hz, 1H), 7.06 (s, 1H), 6.90 (s, 1H), 3.72 (s, 2H), 3.67 (s, 3H), 3.52 (s, 3H), 2.22 (s, 3H), 1.39 (s, 6H), 1.32-1.28 (m, 2H), 1.21-1.15 (m, 2H).

Step 3: N-[1-(Trifluoromethyl)cyclopropyl]-4-[[2-(3,3,5-trimethyl-2-oxo-benzofuran-6-yl)acetyl] amino]pyridine-2-carboxamide

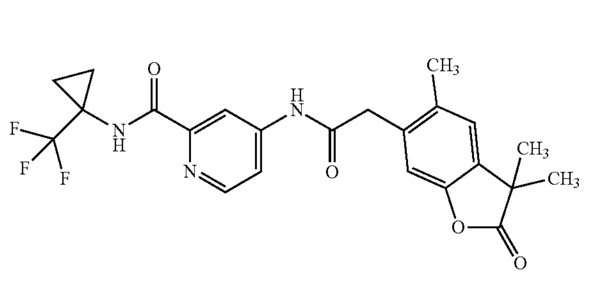 [SMILES: Cc1cc2c(cc1CC(=O)Nc1ccnc(C(=O)NC3(C(F)(F)F)CC3)c1)OC(=O)C2(C)C]

The title compound was prepared from methyl 2-[2-methoxy-5-methyl-4-[2-oxo-2-[[2-[[1-(trifluoromethyl)cyclopropyl]carbamoyl]-4-pyridyl]amino]ethyl]phenyl]-2-methyl-propanoate (step 2) and 1M $BBr_3$ in DCM analogously to Example 14 step 2.

LC-MS (Method G): Rt 1.02 min; MS m/z 462.2=[M+H]+ (93% @215 nm)

$^1$H NMR (500 MHz, DMSO-d6) δ 10.79 (s, 1H), 9.39 (s, 1H), 8.50 (d, J=5.5 Hz, 1H), 8.20 (d, J=1.9 Hz, 1H), 7.85 (dd, J=5.5, 2.2 Hz, 1H), 7.28 (s, 1H), 7.16 (s, 1H), 3.79 (s, 2H), 2.27 (s, 3H), 1.42 (s, 6H), 1.32-1.27 (m, 2H), 1.21-1.16 (m, 2H).

Step 4: 4-[[2-[5-Hydroxy-4-(2-hydroxy-1,1-dimethyl-ethyl)-2-methyl-phenyl]acetyl]amino]-N-[1-(trifluoromethyl)cyclopropyl]pyridine-2-carboxamide The title compound was prepared from N-[1-(trifluoromethyl)cyclopropyl]-4-[[2-(3,3,5-trimethyl-2-oxo-benzofuran-6-yl)acetyl]amino]pyridine-2-carboxamide (step 3) and 4M $LiBH_4$ analogously to Example 14 step 3.

LC-MS (Method A): Rt 3.04 min; MS m/z 466.3=[M+H]+ (98% @215 nm)

$^1$H NMR (500 MHz, DMSO-d6) δ 10.73 (s, 1H), 9.39 (s, 1H), 9.15 (s, 1H), 8.50 (d, J=5.5 Hz, 1H), 8.22 (d, J=1.9 Hz, 1H), 7.85 (dd, J=5.5, 2.2 Hz, 1H), 6.92 (s, 1H), 6.64 (s, 1H), 4.71 (s, 1H), 3.59 (s, 2H), 3.58 (s, 2H), 2.15 (s, 3H), 1.32-1.28 (m, 2H), 1.25 (s, 6H), 1.21-1.17 (m, 2H).

Example 15

N-(3,3-Difluoro-1-methyl-cyclobutyl)-4-[[2-[2-fluoro-5-hydroxy-4-(2-hydroxy-1,1-dimethyl-ethyl) phenyl]acetyl]amino]pyridine-2-carboxamide

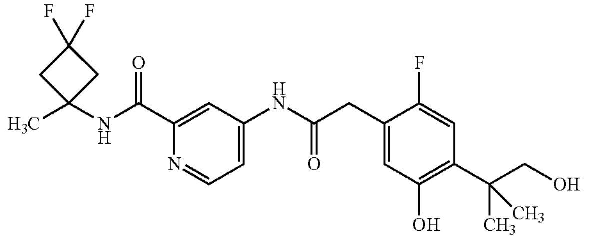 [SMILES: CC1(NC(=O)c2cc(NC(=O)Cc3cc(O)c(C(C)(C)CO)cc3F)ccn2)CC(F)(F)C1]

4-Amino-N-(3,3-difluoro-1-methyl-cyclobutyl)pyridine-2-carboxamide (Intermediate AE) (67 mg, 0.28 mmol) and 2-(5-fluoro-3,3-dimethyl-2-oxo-benzofuran-6-yl)acetic acid (Intermediate U) (60 mg, 0.25 mmol) in DMF (2.5 mL) were treated with DIPEA (0.13 mL, 0.74 mmol) and 50% T3P® solution in EtOAc (0.59 mL, 0.49 mmol) and the mixture stirred for 3 h. The resulting mixture was diluted with EtOAc (20 mL) and washed with brine (2×20 mL), dried over $Na_2SO_4$ and concentrated in vacuo. The residue was dissolved in THF (2.5 mL), cooled to −78° C. and treated with 4M $LiBH_4$ in THF (60 µL, 0.25 mmol). The mixture was allowed to warm to 0° C. and stirred for 4 h. The reaction was quenched by adding dropwise to an ice-cold solution of 1M HCl and extracted with EtOAc (3×20 mL). The combined organic extracts were washed with saturated aqueous sodium bicarbonate (30 mL), dried over $Na_2SO_4$ and concentrated in vacuo. Purification of the crude material by preparative HPLC (acidic pH, early elution method) afforded the title compound as a colourless solid.

LC-MS (Method A): Rt 3.02 min; MS m/z 466.3=[M+H]+ (99% @215 nm)

$^1$H NMR (500 MHz, DMSO-d6) δ 10.78 (s, 1H), 9.39 (br. s, 1H), 9.04 (s, 1H), 8.49 (d, J=5.5 Hz, 1H), 8.18 (d, J=1.9 Hz, 1H), 7.83 (dd, J=5.5, 2.2 Hz, 1H), 6.90 (d, J=12.1 Hz, 1H), 6.72 (d, J=7.0 Hz, 1H), 4.75 (br. s, 1H), 3.65 (s, 2H), 3.60 (s, 2H), 3.12-3.00 (m, 2H), 2.74-2.64 (m, 2H), 1.52 (s, 3H), 1.25 (s, 6H).

Example 15.1

4-[[2-[2-Chloro-5-hydroxy-4-(2-hydroxy-1,1-dimethyl-ethyl)phenyl]acetyl]amino]-N-(1,1-dimethyl-prop-2-ynyl)pyridine-2-carboxamide

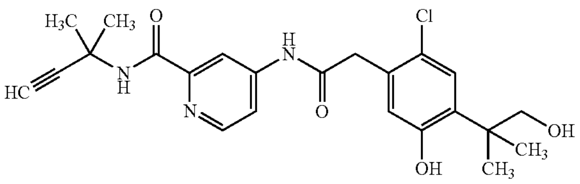 [SMILES: C#CC(C)(C)NC(=O)c1cc(NC(=O)Cc2cc(O)c(C(C)(C)CO)cc2Cl)ccn1]

The title compound was prepared from 4-amino-N-(1,1-dimethylprop-2-ynyl)pyridine-2-carboxamide (Intermediate AD) and 2-(5-chloro-3,3-dimethyl-2-oxo-benzofuran-6-yl) acetic acid (Intermediate T) analogously to Example 15.

LC-MS (Method A): Rt 3.07 min; MS m/z 444.3, 446.3=[M+H]+ (100% @215 nm)

$^1$H NMR (500 MHz, DMSO-d6) δ 10.82 (s, 1H), 9.68 (s, 1H), 8.48 (d, J=5.5 Hz, 1H), 8.33 (s, 1H), 8.21 (d, J=1.9 Hz, 1H), 7.83 (dd, J=5.5, 2.2 Hz, 1H), 7.12 (s, 1H), 6.80 (s, 1H), 4.76 (s, 1H), 3.74 (s, 2H), 3.61 (s, 2H), 3.22 (s, 1H), 1.64 (s, 6H), 1.25 (s, 6H).

Example 15.2

4-[[2-[2-Chloro-5-hydroxy-4-(2-hydroxy-1,1-dimethyl-ethyl)phenyl]acetyl]amino]-N-(3,3-difluoro-1-methyl-cyclobutyl)pyridine-2-carboxamide

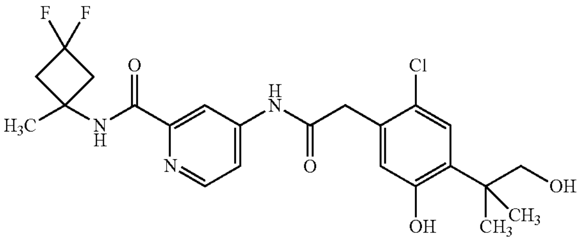 [SMILES: CC1(NC(=O)c2cc(NC(=O)Cc3cc(O)c(C(C)(C)CO)cc3Cl)ccn2)CC(F)(F)C1]

The title compound was prepared from 4-amino-N-(3,3-difluoro-1-methyl-cyclobutyl)pyridine-2-carboxamide (Intermediate AE) and 2-(5-chloro-3,3-dimethyl-2-oxo-benzofuran-6-yl)acetic acid (Intermediate T) analogously to Example 15.

LC-MS (Method A): Rt 3.18 min; MS m/z 482.3, 484.3=[M+H]+ (99% @215 nm)

$^1$H NMR (500 MHz, DMSO-d6) δ 10.79 (s, 1H), 9.68 (s, 1H), 9.04 (s, 1H), 8.49 (d, J=5.5 Hz, 1H), 8.19 (d, J=1.9 Hz, 1H), 7.83 (dd, J=5.5, 2.2 Hz, 1H), 7.12 (s, 1H), 6.80 (s, 1H), 4.76 (t, J=5.2 Hz, 1H), 3.74 (s, 2H), 3.61 (d, J=4.9 Hz, 2H), 3.12-3.00 (m, 2H), 2.74-2.63 (m, 2H), 1.52 (s, 3H), 1.25 (s, 6H).

Example 15.3

4-[[2-[2-Chloro-5-hydroxy-4-(2-hydroxy-1,1-dimethyl-ethyl)phenyl]acetyl]amino]-N-[1-(difluoromethyl)cyclopropyl]pyridine-2-carboxamide

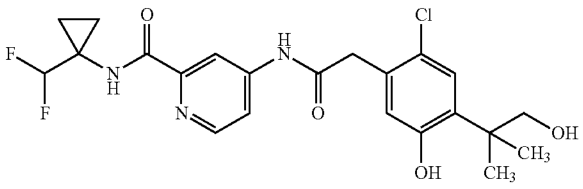 [SMILES: CC(C)(CO)c1cc(Cl)c(CC(=O)Nc2ccnc(C(=O)NC3(C(F)F)CC3)c2)cc1O]

The title compound was prepared from 2-(5-chloro-3,3-dimethyl-2-oxo-benzofuran-6-yl)acetic acid (Intermediate T) and 4-amino-N-[1-(difluoromethyl)cyclopropyl]pyridine-2-carboxamide (Intermediate AC) analogously to Example 15.

LC-MS (Method A): Rt 2.96 min; MS m/z 468.2, 470.2=[M+H]+ (100% @215 nm)

$^1$H NMR (400 MHz, DMSO-d6) δ 10.80 (s, 1H), 9.68 (s, 1H), 9.08 (s, 1H), 8.49 (d, J=5.5 Hz, 1H), 8.21 (d, J=2.1 Hz, 1H), 7.83 (dd, J=5.5, 2.1 Hz, 1H), 7.12 (s, 1H), 6.80 (s, 1H), 6.08 (t, J=57.1 Hz, 1H), 4.75 (s, 1H), 3.74 (s, 2H), 3.61 (s, 2H), 1.25 (s, 6H), 1.11-1.05 (m, 2H), 1.06-0.99 (m, 2H).

Example 15.4

N-[1-(Difluoromethyl)cyclopropyl]-4-[[2-[2-fluoro-5-hydroxy-4-(2-hydroxy-1,1-dimethyl-ethyl)phenyl]acetyl]amino]pyridine-2-carboxamide

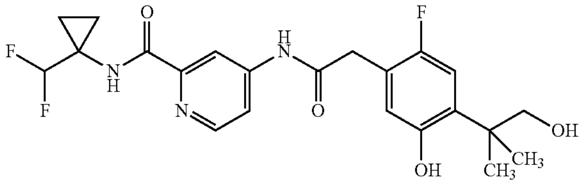 [SMILES: CC(C)(CO)c1cc(F)c(CC(=O)Nc2ccnc(C(=O)NC3(C(F)F)CC3)c2)cc1O]

The title compound was prepared from 2-(5-fluoro-3,3-dimethyl-2-oxo-benzofuran-6-yl)acetic acid (Intermediate U) and 4-amino-N-[1-(difluoromethyl)cyclopropyl]pyridine-2-carboxamide (Intermediate AC) analogously to Example 15.

LC-MS (Method A): Rt 2.78 min; MS m/z 452.3=[M+H]+ (94% @215 nm)

$^1$H NMR (500 MHz, DMSO-d6) δ 10.79 (s, 1H), 9.38 (br. s, 1H), 9.09 (s, 1H), 8.49 (d, J=5.5 Hz, 1H), 8.21 (d, J=1.9 Hz, 1H), 7.83 (dd, J=5.5, 2.2 Hz, 1H), 6.90 (d, J=12.1 Hz, 1H), 6.72 (d, J=7.0 Hz, 1H), 6.08 (t, J=57.1 Hz, 1H), 4.75 (br. s, 1H), 3.64 (s, 2H), 3.60 (s, 2H), 1.25 (s, 6H), 1.11-1.05 (m, 2H), 1.05-1.00 (m, 2H).

Example 16

N-(1,1-Dimethylprop-2-ynyl)-4-[[2-[2-fluoro-5-hydroxy-4-(2-hydroxy-1,1-dimethyl-ethyl)phenyl]acetyl]amino]pyridine-2-carboxamide

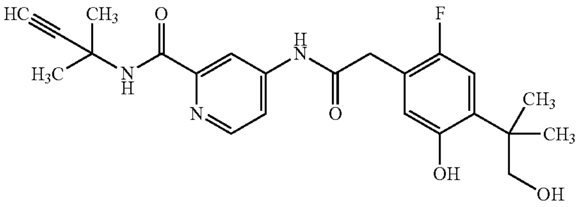 [SMILES: C#CC(C)(C)NC(=O)c1cc(NC(=O)Cc2cc(O)c(C(C)(C)CO)cc2F)ccn1]

Step 1: N-(1,1-Dimethylprop-2-ynyl)-4-[[2-(5-fluoro-3,3-dimethyl-2-oxo-benzofuran-6-yl)acetyl]amino]pyridine-2-carboxamide

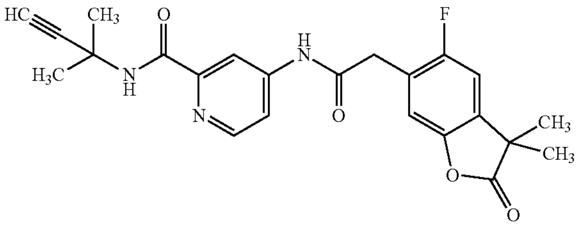 [SMILES: C#CC(C)(C)NC(=O)c1cc(NC(=O)Cc2cc3c(cc2F)C(C)(C)C(=O)O3)ccn1]

A solution of 4-amino-N-(1,1-dimethylprop-2-ynyl)pyridine-2-carboxamide (Intermediate AD) (176 mg, 0.87 mmol), DIPEA (0.21 mL, 1.18 mmol), 2-(5-fluoro-3,3-dimethyl-2-oxo-benzofuran-6-yl)acetic acid (Intermediate U) (94%, 200 mg, 0.79 mmol) and 50% T3P® solution in EtOAc (0.56 mL, 0.95 mmol) in DMF (5 mL) was stirred at room temperature overnight. The resulting mixture was diluted with EtOAc (10 mL) and washed with brine (20 mL). The organic portion was dried over $Na_2SO_4$ and concentrated in vacuo to afford the title compound as a white solid. This was used in the next step without further purification.

LC-MS (Method G): Rt 0.98 min; MS m/z 424.3=[M+H]+ (92% @215 nm)

Step 2: N-(1,1-Dimethylprop-2-ynyl)-4-[[2-[2-fluoro-5-hydroxy-4-(2-hydroxy-1,1-dimethyl-ethyl)phenyl]acetyl]amino]pyridine-2-carboxamide To a cooled (−78° C.), stirred solution of N-(1,1-dimethylprop-2-ynyl)-4-[[2-(5-fluoro-3,3-dimethyl-2-oxo-benzofuran-6-yl)acetyl]amino]pyridine-2-carboxamide (step 1) (92%, 330 mg, 0.72 mmol) in THF (10 mL) was added 4M $LiBH_4$ in THF (215 μL, 0.86 mmol) and the mixture was stirred at −78° C. for 1 h and then at room temperature for 3 h. The resulting mixture was cooled to 0° C. and the reaction was quenched with 1M HCl (10 mL). The mixture was diluted with EtOAc (10 mL) and the layers were separated. The aqueous portion was re-extracted with EtOAc (2×10 mL) and the combined organic extracts were dried over $Na_2SO_4$ and concentrated in vacuo. Purification of the crude product by C18 reverse phase chromatography eluting with 10-100% MeCN in water (+0.1% formic acid) followed by recrystallisation from MeCN afforded the title compound as a white solid.

LC-MS (Method C): Rt 2.97 min; MS m/z 426.5=[M−H]− (100% @215 nm)

$^1$H NMR (400 MHz, DMSO-d6) δ 10.79 (s, 1H), 9.37 (bs, 1H), 8.48 (d, J=5.5 Hz, 1H), 8.32 (s, 1H), 8.20 (d, J=1.9 Hz, 1H), 7.83 (dd, J=5.5, 2.2 Hz, 1H), 6.90 (d, J=12.1 Hz, 1H), 6.72 (d, J=7.0 Hz, 1H), 4.75 (bs, 1H), 3.65 (s, 2H), 3.60 (s, 2H), 3.21 (s, 1H), 1.65 (s, 6H), 1.25 (s, 6H).

Example 16.1

4-[[2-[2-Fluoro-5-hydroxy-4-(2-hydroxy-1,1-dimethyl-ethyl)phenyl]acetyl]amino]-N-(4-methyltetrahydropyran-4-yl)pyridine-2-carboxamide

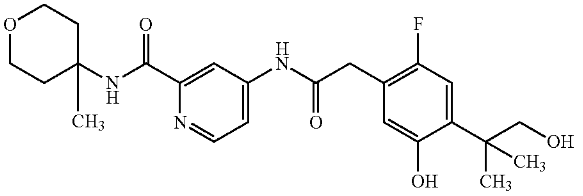 [SMILES: CC1(NC(=O)c2cc(NC(=O)Cc3cc(O)c(C(C)(C)CO)cc3F)ccn2)CCOCC1]

The title compound was prepared from 2-(5-fluoro-3,3-dimethyl-2-oxo-benzofuran-6-yl)acetic acid (Intermediate U) and 4-amino-N-(4-methyltetrahydropyran-4-yl)pyridine-2-carboxamide (Intermediate AF) analogously to Example 16 steps 1 and 2.

LC-MS (Method A): Rt 2.66 min; MS m/z 460.3=[M+H]+ (100% @215 nm)

$^1$H NMR (400 MHz, DMSO-d6) δ 10.79 (s, 1H), 9.38 (s, 1H), 8.49 (d, J=5.6 Hz, 1H), 8.20 (d, J=1.8 Hz, 1H), 8.12 (s, 1H), 7.83 (dd, J=5.5, 2.2 Hz, 1H), 6.91 (d, J=12.1 Hz, 1H), 6.73 (d, J=7.0 Hz, 1H), 4.75 (br. s, 1H), 3.70-3.57 (m, 6H), 3.55-3.47 (m, 2H), 2.24-2.16 (m, 2H), 1.68-1.58 (m, 2H), 1.43 (s, 3H), 1.26 (s, 6H).

Example 16.2

N-(1-Cyano-1-methyl-ethyl)-4-[[2-[2-fluoro-5-hydroxy-4-(2-hydroxy-1,1-dimethyl-ethyl)phenyl]acetyl]amino]pyridine-2-carboxamide

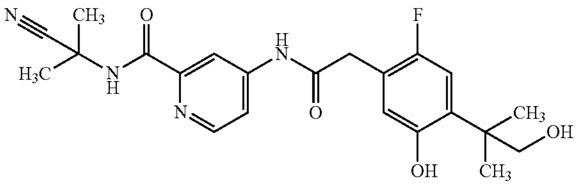 [SMILES: CC(C)(C#N)NC(=O)c1cc(NC(=O)Cc2cc(O)c(C(C)(C)CO)cc2F)ccn1]

The title compound was prepared from 2-(5-fluoro-3,3-dimethyl-2-oxo-benzofuran-6-yl)acetic acid (Intermediate U) and 4-amino-N-(1-cyano-1-methyl-ethyl)pyridine-2-carboxamide (Intermediate AB) analogously to Example 16 steps 1 and 2.

LC-MS (Method A): Rt 2.65 min; MS m/z 429.4=[M+H]+ (98% @215 nm)

$^1$H NMR (500 MHz, DMSO-d6) δ 10.83 (s, 1H), 9.39 (s, 1H), 8.84 (s, 1H), 8.52 (d, J=5.5 Hz, 1H), 8.23 (d, J=2.0 Hz, 1H), 7.86 (dd, J=5.5, 2.2 Hz, 1H), 6.90 (d, J=12.1 Hz, 1H), 6.73 (d, J=7.0 Hz, 1H), 4.75 (s, 1H), 3.66 (s, 2H), 3.60 (s, 2H), 1.72 (s, 6H), 1.25 (s, 6H).

Example 16.3

4-[[2-[2-Fluoro-5-hydroxy-4-(2-hydroxy-1-methyl-ethyl)phenyl]acetyl]amino]-N-(4-methyltetrahydro-pyran-4-yl)pyridine-2-carboxamide

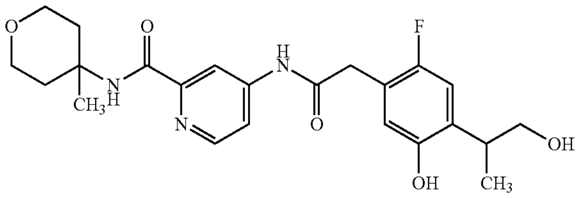 [SMILES: CC(CO)c1cc(F)c(CC(=O)Nc2ccnc(C(=O)NC3(C)CCOCC3)c2)cc1O]

The title compound was prepared from 2-(5-fluoro-3-methyl-2-oxo-3H-benzofuran-6-yl)acetic acid (Intermediate UA) and 4-amino-N-(4-methyltetrahydropyran-4-yl)pyridine-2-carboxamide (Intermediate AF) analogously to Example 16 steps 1 and 2.

LC-MS (Method A): Rt 2.34 min; MS m/z 446.3=[M+H]+ (99% @215 nm)

$^1$H NMR (500 MHz, DMSO-d6) δ 10.79 (s, 1H), 9.25 (s, 1H), 8.49 (d, J=5.5 Hz, 1H), 8.20 (d, J=1.9 Hz, 1H), 8.12 (s, 1H), 7.82 (dd, J=5.5, 2.2 Hz, 1H), 6.88 (d, J=11.0 Hz, 1H), 6.75 (d, J=6.8 Hz, 1H), 4.64 (t, J=5.3 Hz, 1H), 3.68-3.61 (m, 4H), 3.57-3.48 (m, 3H), 3.38-3.34 (m, 1H), 3.18-3.08 (m, 1H), 2.24-2.17 (m, 2H), 1.67-1.59 (m, 2H), 1.43 (s, 3H), 1.13 (d, J=7.0 Hz, 3H).

Example 16.4

4-[[2-[2,6-Difluoro-3-hydroxy-4-(2-hydroxy-1,1-dimethyl-ethyl)phenyl]acetyl]amino]-N-[1-(trifluoromethyl)cyclopropyl]pyridine-2-carboxamide

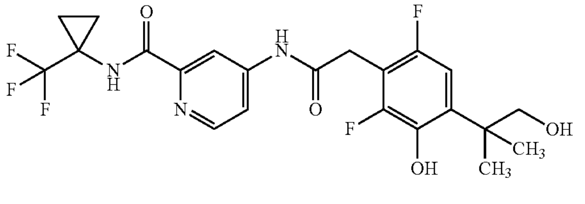 [SMILES: CC(C)(CO)c1cc(F)c(CC(=O)Nc2ccnc(C(=O)NC3(C(F)(F)F)CC3)c2)c(F)c1O]

The title compound was prepared from 4-amino-N-[1-(trifluoromethyl)cyclopropyl]pyridine-2-carboxamide (Intermediate A) and 2-(5,7-difluoro-3,3-dimethyl-2-oxo-benzofuran-6-yl)acetic acid (Intermediate V) analogously to Example 16 steps 1 and 2.

LC-MS (Method A): Rt 3.04 min; MS m/z 488.3=[M+H]+ (99% @215 nm)

$^1$H NMR (400 MHz, DMSO-d6) δ 10.88 (s, 1H), 9.51 (br. s, 1H), 9.38 (s, 1H), 8.51 (d, J=5.6 Hz, 1H), 8.18 (d, J=2.1 Hz, 1H), 7.84 (dd, J=5.5, 2.2 Hz, 1H), 6.82 (dd, J=11.8, 1.7 Hz, 1H), 5.07 (br. s, 1H), 3.77 (s, 2H), 3.63 (s, 2H), 1.32-1.24 (m, 8H), 1.22-1.15 (m, 2H).

Example 17

4-[[2-[2-Fluoro-5-hydroxy-4-[2,2,2-trifluoro-1-(hydroxymethyl)ethyl]phenyl]acetyl] amino]N-[1-(trifluoromethyl)cyclopropyl]pyridine-2-carboxamide

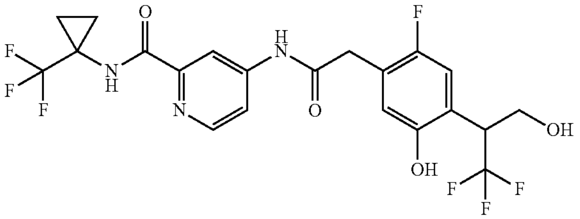 [SMILES: O=C(Cc1cc(O)c(C(CO)C(F)(F)F)cc1F)Nc1ccnc(C(=O)NC2(C(F)(F)F)CC2)c1]

Step 1: 4-[[2-[5-Benzyloxy-4-[1-[[tert-butyl(dimethyl)silyl]oxymethyl]-2,2,2-trifluoro-ethyl]-2-fluoro-phenyl]acetyl]amino]-N-[1-(trifluoromethyl) cyclopropyl]pyridine-2-carboxamide tert-Butyl-chloro-dimethyl-silane (41 mg, 0.27 mmol) was added to a mixture of 2-[5-benzyloxy-2-fluoro-4-[2,2,2-trifluoro-1-(hydroxymethyl)ethyl]phenyl]acetic acid (Intermediate R) (51 mg, 0.14 mmol) and imidazole (23 mg, 0.34 mmol) in DMF (1.5 mL) and the resulting mixture was stirred at room temperature overnight. Additional Imidazole (23 mg, 0.34 mmol) and tert-butyl-chloro-dimethyl-silane (41 mg, 0.27 mmol) were added and stirring continued for a further 30 min. More imdazole (46 mg) and tert-butyl-chloro-dimethyl-silane (82 mg) were added and stirring continued for 30 min. The resulting mixture was diluted with EtOAc (10 mL) and saturated ammonium chloride solution (10 mL) and the phases were separated. The aqueous portion was extracted with EtOAc (10 mL) and the combined organic extracts were dried over $Na_2SO_4$ and concentrated in vacuo. The residue was dissolved in in 1,4-dioxane (1.5 mL) and treated with 4-amino-N-[1-(trifluoromethyl)cyclopropyl]pyridine-2-carboxamide (Intermediate A) (40 mg, 0.16 mmol), DIPEA (47.95 μL, 0.27 mmol) followed by 50% T3P® solution in EtOAc (0.1 mL, 0.16 mmol) and the resulting mixture was stirred at room temperature for 45 min. The resulting mixture was diluted with EtOAc (15 mL) and water (15 mL) and the phases were separated. The aqueous portion was extracted with EtOAc (10 mL) and the combined organic extracts were dried over $Na_2SO_4$ and concentrated in vacuo. Purification of the crude material by chromatography on silica eluting with 0-50% EtOAc in heptanes afforded the title compound as a colourless oil.

LC-MS (Method H): Rt 2.10 min; MS m/z 714.5=[M+H]+ (98% @215 nm)

$^1$H NMR (500 MHz, DMSO-d6) δ 10.84 (s, 1H), 9.40 (s, 1H), 8.51 (d, J=5.5 Hz, 1H), 8.20 (d, J=1.9 Hz, 1H), 7.84 (dd, J=5.5, 2.2 Hz, 1H), 7.45-7.41 (m, 2H), 7.40-7.35 (m, 2H), 7.35-7.30 (m, 1H), 7.28 (d, J=10.4 Hz, 1H), 7.25 (d, J=6.4 Hz, 1H), 5.15.15-5.08 (m, 2H), 4.21-4.11 (m, 1H), 4.07-4.01 (m, 1H), 3.98-3.93 (m, 1H), 3.80 (s, 2H), 1.31-1.17 (m, 4H), 0.80 (s, 9H), −0.02 (s, 3H), −0.04 (s, 3H).

Step 2: 4-[[2-[2-Fluoro-5-hydroxy-4-[2,2,2-trifluoro-1-(hydroxymethyl)ethyl]phenyl]acetyl] amino]-N-[1-(trifluoromethyl)cyclopropyl]pyridine-2-carboxamide 4M HCl in dioxane (0.5 mL, 2.0 mmol) was added to mixture of 4-[[2-[5-benzyloxy-4-[1-[[tert-butyl(dimethyl)silyl]oxymethyl]-2,2,2-trifluoro-ethyl]-2-fluoro-phenyl] acetyl]amino]-N-[1-(trifluoromethyl)cyclopropyl]pyridine-2-carboxamide (step 1) (46 mg, 0.06 mmol) in MeOH (0.5 mL). The mixture was stirred at room temperature for 15 min and then concentrated in vacuo azeotroping with EtOH (2×5 mL). The residue was dissolved in EtOH (3 mL) and placed under a nitrogen atmosphere. 10% Pd/C (6.85 mg, 0.01 mmol) was added and the reaction mixture was stirred under a hydrogen atmosphere for 2 h. The resulting mixture was filtered through a Celite® pad rinsing through with 9:1 EtOAc:MeOH. The filtrate was concentrated in vacuo and purification of the crude material by C18 reverse phase chromatography eluting with 10-100% MeCN/water (+0.1% formic acid) afforded the title compound as an off-white solid.

LC-MS (Method A): Rt 2.91 min; MS m/z 510.0=[M+H]+ (99% @215 nm)

$^1$H NMR (500 MHz, DMSO-d6) δ 10.84 (s, 1H), 9.80 (s, 1H), 9.39 (s, 1H), 8.51 (d, J=5.5 Hz, 1H), 8.21 (d, J=2.0 Hz, 1H), 7.84 (dd, J=5.5, 2.2 Hz, 1H), 7.08 (d, J=10.6 Hz, 1H), 6.87 (d, J=6.7 Hz, 1H), 5.11 (t, J=4.9 Hz, 1H), 4.11-4.00 (m, 1H), 3.93-3.86 (m, 1H), 3.82-3.75 (m, 1H), 3.71 (s, 2H), 1.33-1.25 (m, 2H), 1.24-1.15 (m, 2H).

Example 18

4-[[2-[2-Chloro-6-fluoro-3-hydroxy-4-(1-hydroxy-1-methyl-ethyl)phenyl]acetyl]amino]-N-[1-(trifluoromethyl)cyclopropyl]pyridine-2-carboxamide

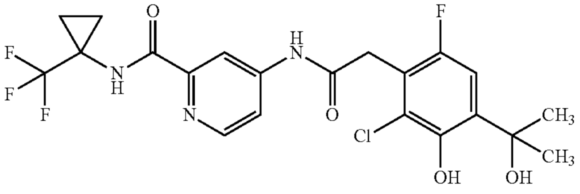 [SMILES: CC(C)(O)c1cc(F)c(CC(=O)Nc2ccnc(C(=O)NC3(C(F)(F)F)CC3)c2)c(Cl)c1O]

N-Chlorosuccinimide (59 mg, 0.44 mmol) was added to a mixture of 4-[[2-[2-fluoro-5-hydroxy-4-(1-hydroxy-1-methyl-ethyl)phenyl]acetyl]amino]-N-[1-(trifluoromethyl)cyclopropyl]pyridine-2-carboxamide (Example 2) (100 mg, 0.22 mmol) in DMF (2 mL) and the mixture was stirred at room temperature for 18 h. Additional N-chlorosuccinimide (59 mg, 0.44 mmol) was added and stirring continued for 24 h. The resulting mixture was diluted with EtOAc (10 mL) and 1:1 brine:water (10 mL) and the phases were separated. The organic portion was dried over $Na_2SO_4$ and concentrated in vacuo to give the crude product as a yellow oil. Purification of the oil by C18 reverse phase chromatography eluting with 10-100% MeCN/water (+0.1% formic acid) afforded the title compound as an off-white solid.

LC-MS (Method A): Rt 3.16 min; MS m/z 490.3=[M+H]+ (100% @215 nm)

$^1$H NMR (500 MHz, DMSO-d6) δ 10.93 (s, 1H), 9.39 (s, 1H), 8.50 (d, J=5.5 Hz, 1H), 8.18 (d, J=2.0 Hz, 1H), 7.83 (dd, J=5.5, 2.2 Hz, 1H), 7.06 (d, J=10.8 Hz, 1H), 3.88 (s, 2H), 1.52 (s, 6H), 1.32-1.26 (m, 2H), 1.21-1.15 (m, 2H).

Example 19

4-[[2-[2-Chloro-5-hydroxy-4-(1-hydroxy-1-methyl-ethyl)phenyl]acetyl]amino]-N-[1-(trifluoromethyl)cyclopropyl]pyridine-2-carboxamide

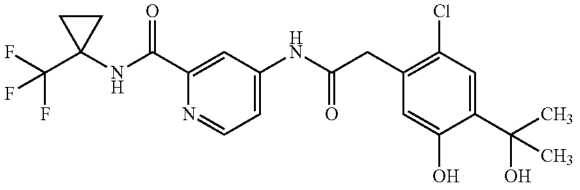 [SMILES: CC(C)(O)c1cc(Cl)c(CC(=O)Nc2ccnc(C(=O)NC3(C(F)(F)F)CC3)c2)cc1O]

Step 1: 4-[[2-[5-Benzyloxy-2-chloro-4-(1-hydroxy-1-methyl-ethyl)phenyl]acetyl]amino]-N-[1-(trifluoromethyl)cyclopropyl]pyridine-2-carboxamide

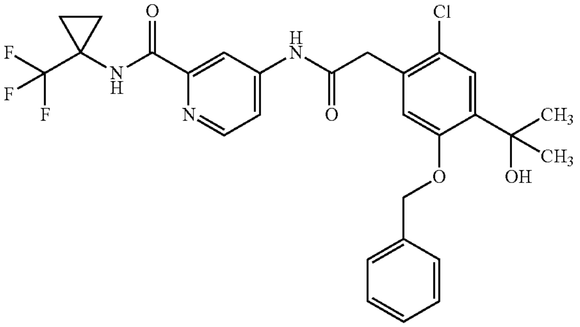 [SMILES: CC(C)(O)c1cc(Cl)c(CC(=O)Nc2ccnc(C(=O)NC3(C(F)(F)F)CC3)c2)cc1OCc1ccccc1]

To a solution of 2-[5-benzyloxy-2-chloro-4-(1-hydroxy-1-methyl-ethyl)phenyl]acetic acid (Intermediate BE) (150 mg, 0.45 mmol), 4-amino-N-[1-(trifluoromethyl)cyclopropyl]pyridine-2-carboxamide (Intermediate A) (100 mg, 0.41 mmol) and DIPEA (178 µL, 1.02 mmol) in 1,4-dioxane (1 mL) was added 50% T3P® solution in EtOAc (364 µL, 0.61 mmol) and the mixture was stirred at ambient temperature for 2 h then allowed to stand over the weekend. The resulting mixture was partitioned between DCM (5 mL) and water (5 mL) and the organics were separated via filtration through a hydrophobic PTFE fritted tube. The filtrate was concentrated in vacuo and purification of the residue by chromatography on silica eluting with 0-100% EtOAc in heptanes followed by 0-100% MeOH in EtOAc afforded the title compound as a pale yellow powdery solid.

LC-MS (Method G): Rt 1.05 min; MS m/z 562.2, 564.2=[M+H]+ (91% @215 nm)

$^1$H NMR (500 MHz, DMSO-$d_6$) δ 10.83 (s, 1H), 9.40 (s, 1H), 8.52 (d, J=5.6 Hz, 1H), 8.21 (d, J=2.0 Hz, 1H), 7.85 (dd, J=5.5, 2.2 Hz, 1H), 7.59 (s, 1H), 7.49-7.44 (m, 2H), 7.43-7.37 (m, 2H), 7.36-7.31 (m, 1H), 7.19 (s, 1H), 5.15 (s, 1H), 5.11 (s, 2H), 3.86 (s, 2H), 1.47 (s, 6H), 1.33-1.28 (m, 2H), 1.22-1.17 (m, 2H).

Step 2: 4-[[2-[2-Chloro-5-hydroxy-4-(1-hydroxy-1-methyl-ethyl)phenyl]acetyl]amino]-N-[1-(trifluoromethyl)cyclopropyl]pyridine-2-carboxamide To 4-[[2-[5-benzyloxy-2-chloro-4-(1-hydroxy-1-methyl-ethyl)phenyl]acetyl]amino]-N-[1-(trifluoromethyl)cyclopropyl]pyridine-2-carboxamide (196 mg, 0.35 mmol) (step 1) and 10% Pd/C (20 mg, 0.35 mmol) under an atmosphere of nitrogen was added degassed EtOH (3.5 mL) and the mixture was purged with nitrogen and then placed under a hydrogen atmosphere for 60 min. Further 10% Pd/C (20 mg, 0.35 mmol) was added then the reaction was again purged with nitrogen and placed under a hydrogen atmosphere for a further 65 min. The resulting mixture was diluted with MeOH (~10 mL) and filtered through Celite®, washing through with further MeOH. The filtrate was concentrated in vacuo and the residue was purified by chromatography on silica eluting with 0-100% EtOAc in heptanes and 0-100% MeOH in EtOAc followed by preparative HPLC (acidic pH, early elution method) using water/MeCN with 0.1% formic acid. The combined product fractions were concentrated in vacuo to remove the bulk of the organic solvents and the aqueous residue was treated with saturated aq. $NaHCO_3$ (10 mL). The mixture was extracted with EtOAc (2×15 mL) and the combined organic extracts were dried over $Na_2SO_4$ and concentrated in vacuo to afford the title compound as a white crystalline solid.

LC-MS (Method A): Rt 3.11 min; MS m/z 472.2, 474.2=[M+H]+ (100% @215 nm)

UPLC (MSQ1, 7MIN_HIRES_UPLC) 100%; Rt 3.11 mins; MS m/z 472.2, 474.2=[M+H]+

1H NMR (500 MHz, DMSO-d6) δ 10.82 (s, 1H), 9.40 (s, 1H), 8.51 (d, J=5.5 Hz, 1H), 8.22 (d, J=2.0 Hz, 1H), 7.84 (dd, J=5.5, 2.2 Hz, 1H), 7.35 (s, 1H), 6.79 (s, 1H), 3.76 (s, 2H), 1.49 (s, 6H), 1.33-1.28 (m, 2H), 1.22-1.17 (m, 2H).

Example 20

4-[[2-[2-Fluoro-5-hydroxy-4-(2-hydroxy-1-methyl-ethyl)phenyl]acetyl]amino]-N-[1-(trifluoromethyl) cyclopropyl]pyridine-2-carboxamide

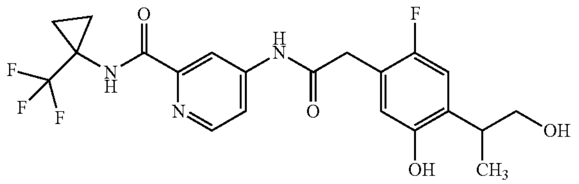 [SMILES: CC(CO)c1cc(F)c(CC(=O)Nc2ccnc(C(=O)NC3(C(F)(F)F)CC3)c2)cc1O]

Step 1: Methyl 2-[2-benzyloxy-5-fluoro-4-[2-oxo-2-[[2-[[1-(trifluoromethyl)cyclopropyl] carbamoyl]-4-pyridyl]amino]ethyl]phenyl]propanoate A solution of [(E)-1-methoxyprop-1-enoxy]-trimethyl-silane (130 μL, 0.71 mmol) in degassed DMF (2 mL) was added to a mixture of 4-[[2-(5-benzyloxy-4-bromo-2-fluoro-phenyl)acetyl]amino]-N-[1-(trifluoromethyl)cyclopropyl] pyridine-2-carboxamide (Example 13, step 1) (200 mg, 0.35 mmol), $ZnF_2$ (37 mg, 0.35 mmol) and $Pd(P^tBu_3)_2$ (18 mg, 0.04 mmol) under nitrogen and the resulting mixture was heated to 80° C. for 16 h. The resulting mixture was diluted with EtOAc (20 mL) and washed with water (2×20 mL), brine (2×20 mL), dried over $Na_2SO_4$ and concentrated in vacuo. The resulting crude material was purified by chromatography on silica eluting with 0-100% EtOAc in heptanes to afford the title compound as a white solid.

LC-MS (Method G): Rt 1.09 min; MS m/z 574.2=[M+H]+ (83% @215 nm)

$^1H$ NMR (500 MHz, DMSO-d6) δ 10.82 (s, 1H), 9.39 (s, 1H), 8.51 (d, J=5.5 Hz, 1H), 8.20 (d, J=2.0 Hz, 1H), 7.84 (dd, J=5.5, 2.2 Hz, 1H), 7.43-7.35 (m, 4H), 7.33-7.29 (m, 1H), 7.14 (d, J=6.3 Hz, 1H), 7.06 (d, J=10.2 Hz, 1H), 5.10-5.04 (m, 2H), 3.98 (q, J=7.2 Hz, 1H), 3.77 (s, 2H), 3.51 (s, 3H), 1.37 (d, J=7.2 Hz, 3H), 1.32-1.28 (m, 2H), 1.21-1.17 (m, 2H).

Step 2: 4-[[2-[5-Benzyloxy-2-fluoro-4-(2-hydroxy-1-methyl-ethyl)phenyl]acetyl]amino]-N-[1-(trifluoromethyl)cyclopropyl]pyridine-2-carboxamide

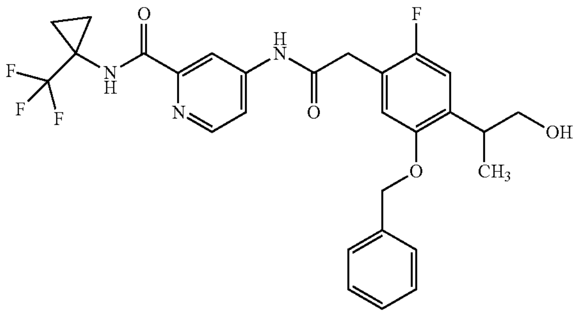 [SMILES: CC(CO)c1cc(F)c(CC(=O)Nc2ccnc(C(=O)NC3(C(F)(F)F)CC3)c2)cc1OCc1ccccc1]

A cooled (−78° C.) solution of methyl 2-[2-benzyloxy-5-fluoro-4-[2-oxo-2-[[2-[[1-(trifluoromethyl) cyclopropyl]carbamoyl]-4-pyridyl]amino]ethyl]phenyl]propanoate (step 1) (83%, 100 mg, 0.14 mmol) in THF (10 mL) under an inert atmosphere was treated with a solution of 2.4M $LiAlH_4$ in THF (121 μL, 0.29 mmol) and the mixture was allowed to stir at −78° C. for 1.5 h and then warmed to 0° C. The reaction was quenched with water and allowed to warm to room temperature. The resulting mixture was diluted with water (25 mL) and EtOAc (25 mL). The layers were separated and the organic portion was washed with a saturated Rochelles salt solution (10 mL), brine (10 mL), dried over $Na_2SO_4$ and concentrated in vacuo. The crude material was purified by C18 reverse phase chromatography eluting with 10-100% MeCN/water (+0.1% formic acid). The product fractions were concentrated in vacuo to afford a colourless oil. The oil was azeotroped with MeOH and concentrated under high vacuum to afford the title compound as a light yellow solid.

LC-MS (Method G): Rt 1.00 min; MS m/z 546.2=[M+H]+ (90% @215 nm)

$^1H$ NMR (500 MHz, DMSO-d6) δ 10.79 (s, 1H), 9.39 (s, 1H), 8.50 (d, J=5.5 Hz, 1H), 8.19 (d, J=2.0 Hz, 1H), 7.84 (dd, J=5.5, 2.2 Hz, 1H), 7.47-7.41 (m, 2H), 7.40-7.35 (m, 2H), 7.35-7.28 (m, 1H), 7.08 (d, J=6.5 Hz, 1H), 7.00 (d, J=10.8 Hz, 1H), 5.07 (s, 2H), 4.66-4.61 (m, 1H), 3.74 (s, 2H), 3.58-3.52 (m, 1H), 3.30-3.22 (partial obscured m, 2H), 1.32-1.26 (m, 2H), 1.22-1.17 (m, 2H), 1.14 (d, J=7.0 Hz, 3H).

Step 3: 4-[[2-[2-Fluoro-5-hydroxy-4-(2-hydroxy-1-methyl-ethyl)phenyl]acetyl]amino]-N-[1-(trifluoromethyl)cyclopropyl]pyridine-2-carboxamide The title compound was prepared from 4-[[2-[5-benzyloxy-2-fluoro-4-(2-hydroxy-1-methyl-ethyl)phenyl]acetyl] amino]-N-[1-(trifluoromethyl)cyclopropyl]pyridine-2-carboxamide (step 2) and 10% Pd—C analogously to Example 2 step 2.

LC-MS (Method A): Rt 2.70 min; MS m/z 456.3=[M+H]+ (96% @215 nm)

$^1$H NMR (500 MHz, DMSO-d6) δ 10.80 (s, 1H), 9.38 (s, 1H), 9.26 (s, 1H), 8.50 (d, J=5.5 Hz, 1H), 8.21 (d, J=2.0 Hz, 1H), 7.84 (dd, J=5.5, 2.2 Hz, 1H), 6.87 (d, J=11.0 Hz, 1H), 6.75 (d, J=6.7 Hz, 1H), 4.66-4.61 (m, 1H), 3.65 (s, 2H), 3.57-3.51 (m, 1H), 3.17-3.08 (m, 1H), 1.32-1.28 (m, 2H), 1.21-1.16 (m, 2H), 1.13 (d, J=7.0 Hz, 3H). Signal at ~3.3-3.4 hidden under water peak but observed in HSQC (below).

Examples 20a and 20b

Chiral separation of racemic 4-[[2-[2-fluoro-5-hydroxy-4-(2-hydroxy-1-methyl-ethyl)phenyl]acetyl]amino]-N-[1-(trifluoromethyl)cyclopropyl]pyridine-2-carboxamide (Example 20) using Supercritical Fluid Chromatography [15% IPA:85% $CO_2$ with Chiralpak AD-H 10×250 mm column at 15 mL/min] afforded the individual enantiomers:

Example 20a

4-[[2-[2-Fluoro-5-hydroxy-4-[(1S)-2-hydroxy-1-methyl-ethyl]phenyl]acetyl]amino]-N-[1-(trifluoromethyl)cyclopropyl]pyridine-2-carboxamide or 4-[[2-[2-fluoro-5-hydroxy-4-[(1R)-2-hydroxy-1-methyl-ethyl]phenyl]acetyl]amino]-N-[1-(trifluoromethyl)cyclopropyl]pyridine-2-carboxamide

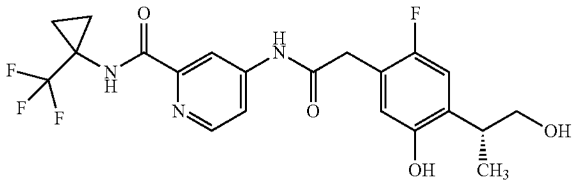

(R)-Isomer

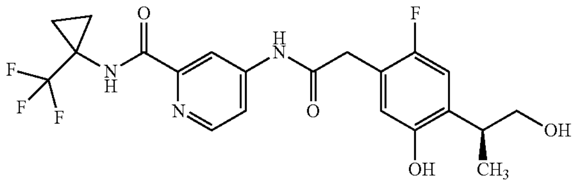

(S)-Isomer

First eluted peak: SFC retention time=17.13 min

LC-MS (Method A): Rt 2.69 min; MS m/z 456.3=[M+H]+ (91% @215 nm)

$^1$H NMR (500 MHz, DMSO-d6) δ 10.80 (s, 1H), 9.39 (s, 1H), 9.21 (br. s, 1H), 8.50 (d, J=5.5 Hz, 1H), 8.21 (d, J=2.0 Hz, 1H), 7.84 (dd, J=5.5, 2.2 Hz, 1H), 6.87 (d, J=11.0 Hz, 1H), 6.74 (d, J=6.8 Hz, 1H), 4.65 (br. s, 1H), 3.65 (s, 2H), 3.53 (dd, J=10.2, 5.6 Hz, 1H), 3.40-3.30 (obscured m, 1H), 3.14-3.10 (m, 1H), 1.32-1.28 (m, 2H), 1.21-1.17 (m, 2H), 1.13 (d, J=7.0 Hz, 3H).

Example 20b

4-[[2-[2-Fluoro-5-hydroxy-4-[(1 S)-2-hydroxy-1-methyl-ethyl]phenyl]acetyl]amino]-N-[1-(trifluoromethyl)cyclopropyl]pyridine-2-carboxamide or 4-[[2-[2-fluoro-5-hydroxy-4-[(1R)-2-hydroxy-1-methyl-ethyl]phenyl]acetyl]am no]-N-[1-(trifluoromethyl)cyclopropyl]pyridine-2-carboxamide

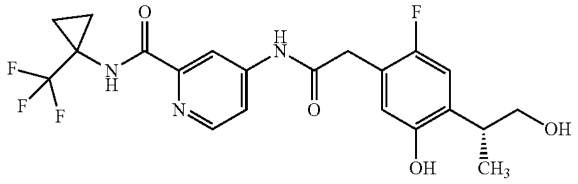

(R)-Isomer

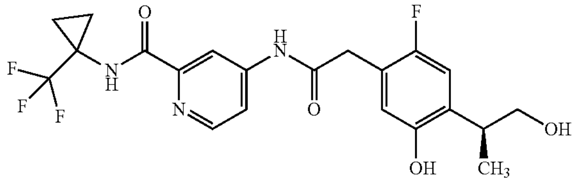

(S)-Isomer

Second eluted peak: SFC retention time=20.28 min

LC-MS (Method A): Rt 2.69 min; MS m/z 456.3=[M+H]+ (99% @215 nm)

$^1$H NMR (500 MHz, DMSO-d6) δ 10.80 (s, 1H), 9.39 (s, 1H), 9.25 (br. s, 1H), 8.50 (d, J=5.5 Hz, 1H), 8.21 (d, J=2.1 Hz, 1H), 7.84 (dd, J=5.5, 2.2 Hz, 1H), 6.87 (d, J=11.0 Hz, 1H), 6.74 (d, J=6.7 Hz, 1H), 4.65 (br. s, 1H), 3.65 (s, 2H), 3.53 (dd, J=10.2, 5.6 Hz, 1H), 3.40-3.30 (obscured m, 1H), 3.15-3.10 (m, 1H), 1.31-1.28 (m, 2H), 1.20-1.17 (m, 2H), 1.13 (d, J=7.0 Hz, 3H).

Preparation of Intermediates

Intermediate A

4-Amino-N-[1-(trifluoromethyl)cyclopropyl]pyridine-2-carboxamide

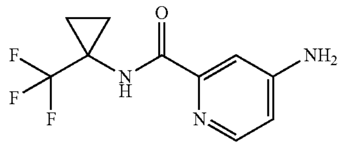 [SMILES: Nc1ccnc(C(=O)NC2(C(F)(F)F)CC2)c1]

4-Aminopyridine-2-carboxylic acid (1 g, 7.24 mmol) in DMF (36.2 mL) was treated with TEA (3.68 mL, 26.43 mmol), 1-(trifluoromethyl)cyclopropanamine hydrochloride (1.29 g, 7.96 mmol) followed by TBTU (3.14 g, 9.77 mmol) and stirred at room temperature for 4 days. The resulting mixture was filtered and the solid washed with DMF (2×30 mL). The filtrate was concentrated in vacuo and the crude residue dissolved in EtOAc (300 mL) and washed with sat. $NaHCO_3$ solution (2×300 mL). The aqueous portion was re-extracted with EtOAc (30 mL) and the combined organic extracts were washed with brine (2×160 mL), dried over $Na_2SO_4$ and concentrated in vacuo. Purification by C18 reverse column chromatography eluting with 10-100% MeCN in water afforded the title compound as an off-white solid.

LC-MS (Method F): Rt 1.32 mins; MS m/z 246.1=[M+H]+ (100% @215 nm)

$^1$H NMR (500 MHz, DMSO-$d_6$) δ 9.13 (s, 1H), 8.02 (d, J=5.6 Hz, 1H), 7.20 (d, J=2.3 Hz, 1H), 6.61 (dd, J=5.6, 2.4 Hz, 1H), 6.36 (s, 2H), 1.32-1.22 (m, 2H), 1.21-1.11 (m, 2H).

Intermediate AB

4-Amino-N-(1-cyano-1-methyl-ethyl)pyridine-2-carboxamide

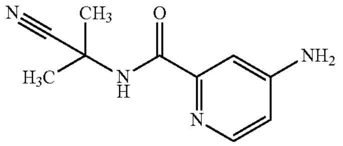

The title compound was prepared from 4-aminopyridine-2-carboxylic acid and 2-amino-2-methyl-propanenitrile hydrochloride analogously to Intermediate A.

LC-MS (Method E): Rt 0.35 mins; MS m/z 205.0=[M+H]+ (100% @215 nm)

$^1$H NMR (400 MHz, DMSO-d6) δ 8.60 (s, 1H), 8.03 (d, J=5.6 Hz, 1H), 7.21 (d, J=2.3 Hz, 1H), 6.62 (dd, J=5.6, 2.4 Hz, 1H), 6.40 (s, 2H), 1.70 (s, 6H).

Intermediate AC

4-Amino-N-[1-(difluoromethyl)cyclopropyl]pyridine-2-carboxamide

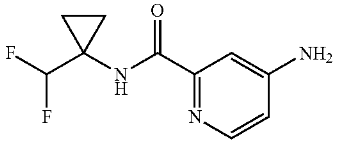 [SMILES: Nc1ccnc(C(=O)NC2(C(F)F)CC2)c1]

The title compound was prepared from 4-aminopyridine-2-carboxylic acid and 1-(difluoromethyl)cyclopropanamine hydrochloride analogously to Intermediate A.

LC-MS (Method I): Rt 0.39 min; MS m/z 228.0=[M+H]+ (100% @215 nm)

$^1$H NMR (400 MHz, DMSO-d6) δ 8.85 (s, 1H), 8.00 (d, J=5.6 Hz, 1H), 7.19 (d, J=2.1 Hz, 1H), 6.60 (dd, J=5.6, 2.4 Hz, 1H), 6.36 (s, 2H), 6.05 (t, J=57.2 Hz, 1H), 1.09-1.03 (m, 2H), 1.03-0.97 (m, 2H).

Intermediate AD

4-Amino-N-(1,1-dimethylprop-2-ynyl)pyridine-2-carboxamide

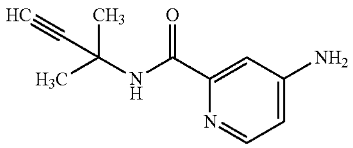

The title compound was prepared from 4-aminopyridine-2-carboxylic acid and 2-methylbut-3-yn-2-amine analogously to Intermediate A.

LC-MS (Method I): Rt 0.42 min; MS m/z 203.9=[M+H]+ (100% @215 nm)

$^1$H NMR (400 MHz, DMSO-d6) δ 8.23 (s, 1H), 7.99 (d, J=5.6 Hz, 1H), 7.19 (d, J=2.3 Hz, 1H), 6.58 (dd, J=5.6, 2.4 Hz, 1H), 6.36 (s, 2H), 3.19 (s, 1H), 1.62 (s, 6H).

Intermediate AE

4-Amino-N-(3,3-difluoro-1-methyl-cyclobutyl)pyridine-2-carboxamide

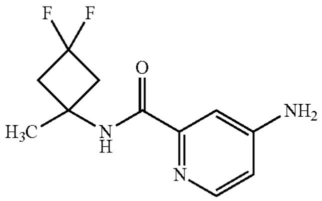 [SMILES: CC1(NC(=O)c2cc(N)ccn2)CC(F)(F)C1]

The title compound was prepared from 3,3-difluoro-1-methyl-cyclobutanamine hydrochloride and 4-aminopyridine-2-carboxylic acid analogously to Intermediate A.

LC-MS (Method G): Rt 0.63 min; MS m/z 242.2=[M+H]+ (98% @215 nm)

$^1$H NMR (400 MHz, DMSO-d6) δ 8.79 (s, 1H), 8.01 (d, J=5.6 Hz, 1H), 7.18 (d, J=2.2 Hz, 1H), 6.59 (dd, J=5.6, 2.4 Hz, 1H), 6.32 (br. s, 2H), 3.11-2.96 (m, 2H), 2.72-2.59 (m, 2H), 1.50 (s, 3H).

Intermediate AF

4-Amino-N-(4-methyltetrahydropyran-4-yl)pyridine-2-carboxamide

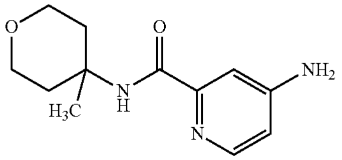 [SMILES: CC1(NC(=O)c2cc(N)ccn2)CCOCC1]

The title compound was prepared from 4-methyltetrahydropyran-4-amine hydrochloride and 4-aminopyridine-2-carboxylic acid analogously to Intermediate A.

LC-MS (Method I): Rt 0.36 min; MS m/z 236.0=[M+H]+ (93% @215 nm)

$^1$H NMR (500 MHz, DMSO-d6) δ 8.08 (s, 1H), 8.00 (d, J=5.6 Hz, 1H), 7.18 (d, J=2.2 Hz, 1H), 6.58 (dd, J=5.6, 2.4 Hz, 1H), 6.34 (s, 2H), 3.67-3.60 (m, 2H), 3.51-3.45 (m, 2H), 2.18-2.12 (m, 2H), 1.63-1.56 (m, 2H), 1.39 (s, 3H).

Intermediate B

2-[5-Benzyloxy-2-fluoro-4-(1-hydroxy-1-methyl-ethyl)phenyl]acetic acid

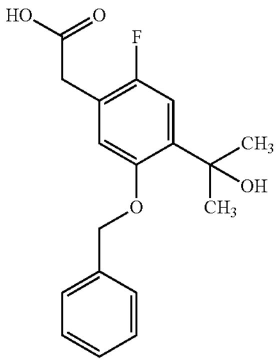 [SMILES: CC(C)(O)c1cc(F)c(CC(=O)O)cc1OCc1ccccc1]

Step 1: (3-Bromo-4-fluoro-phenyl) acetate

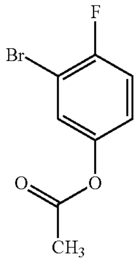

A cooled (0° C.) solution of 3-bromo-4-fluoro-phenol (5 g, 26.18 mmol) and TEA (6.86 mL, 49.22 mmol) in DCM (100 mL) was treated dropwise with acetyl chloride (2.61 mL, 36.65 mmol) and the mixture was stirred at room temperature for 45 min. The resulting mixture was diluted with DCM (100 mL) and washed sequentially with 0.5M HCl (120 mL), water (120 mL), sat. $NaHCO_3$ (120 mL) and brine (120 mL). The organic portion was dried over $Na_2SO_4$ and concentrated in vacuo to afford the title compound as a tan solid.

LC-MS (Method E): Rt 1.14 min (85% @215 nm)

$^1$H NMR (500 MHz, DMSO-d6) δ 7.59 (dd, J=6.0, 2.8 Hz, 1H), 7.43 (t, J=8.8 Hz, 1H), 7.26-7.17 (m, 1H), 2.26 (s, 3H).

Step 2:
1-(4-Bromo-5-fluoro-2-hydroxy-phenyl)ethanone

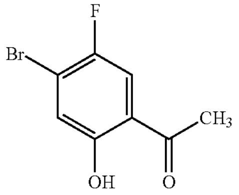

A mixture of (3-bromo-4-fluoro-phenyl) acetate (step 1) (90%, 6.3 g, 24.33 mmol) and aluminium trichloride (5.84 g, 43.8 mmol) was stirred at 165° C. for 3 h. The melt was allowed to cool to room temperature and the resulting solid was suspended in DCM (100 mL). 2N HCl (100 mL) was added and the insoluble material was removed by filtration through Celite® (filter material). The layers were separated and the aqueous portion was re-extracted with DCM (60 mL). The combined organic extracts were washed with water (140 mL), brine (140 mL), dried over $Na_2SO_4$ and concentrated in vacuo. The crude material was purified by chromatography on silica eluting with 0-30% EtOAc in heptanes to afford the title compound as an off-white solid.

LC-MS (Method E): Rt 1.17 min (96% @215 nm)

$^1$H NMR (500 MHz, DMSO-d6) δ 11.62 (s, 1H), 7.79 (d, J=9.4 Hz, 1H), 7.33 (d, J=5.8 Hz, 1H), 2.61 (s, 3H).

Step 3:
1-(2-Benzyloxy-4-bromo-5-fluoro-phenyl)ethanone

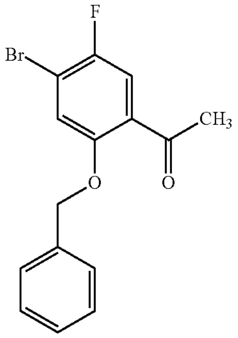 [SMILES: CC(=O)c1cc(F)c(Br)cc1OCc1ccccc1]

Benzyl bromide (3.23 mL, 27.19 mmol) was added to a stirred mixture of 1-(4-bromo-5-fluoro-2-hydroxy-phenyl) ethanone (step 2) (96%, 5.5 g, 22.66 mmol) and $K_2CO_3$ (7.83 g, 56.65 mmol) in DMF (25 mL) and the mixture was stirred at 80° C. for 1 hour. The resulting mixture was allowed to cool to room temperature and partitioned between EtOAc (150 mL) and water (150 mL). The aqueous layer was further extracted with EtOAc (100 mL). The combined organic extracts were washed with water (2×150 mL), brine (150 mL), dried over $Na_2SO_4$ and concentrated in vacuo. The crude material was purified by chromatography on silica eluting with 0-60% EtOAc in heptanes to afford the title compound as an off-white solid.

LC-MS (Method E): Rt 1.35 min (87% @215 nm)

$^1$H NMR (500 MHz, DMSO-d6) δ 7.65 (d, J=5.5 Hz, 1H), 7.55-7.46 (m, 3H), 7.44-7.40 (m, 2H), 7.39-7.35 (m, 1H), 5.26 (s, 2H), 2.49 (s, 3H).

Step 4: 2-(2-Benzyloxy-4-bromo-5-fluoro-phenyl) propan-2-ol

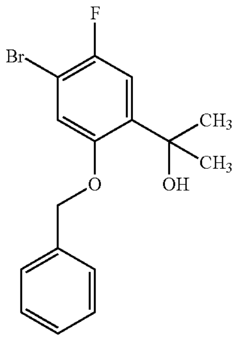 [SMILES: CC(C)(O)c1cc(F)c(Br)cc1OCc1ccccc1]

To a stirred solution of 1-(2-benzyloxy-4-bromo-5-fluoro-phenyl)ethanone (step 3) (90%, 100 mg, 0.28 mmol) in THF (1 mL) at −78° C. was added bromo(methyl)magnesium (3M in $Et_2O$) (121 μL, 0.36 mmol). The dry ice bath was removed and the mixture was stirred at room temperature for 1 hour. The resulting mixture was diluted with sat. aq. $NH_4Cl$ (10 mL) and EtOAc (10 mL). The organic layer was separated, dried over $Na_2SO_4$ and concentrated in vacuo to afford the title compound as a pale yellow solid.

LC-MS (Method E): Rt 1.31 mins; MS m/z 320.9, 322.9 [M+H−$H_2O$]+ (95% @215 nm)

$^1$H NMR (400 MHz, DMSO-d6) δ 7.57-7.27 (m, 7H), 5.23 (s, 1H), 5.14 (s, 2H), 1.45 (s, 6H).

Step 5: 2-[5-Benzyloxy-2-fluoro-4-(1-hydroxy-1-methyl-ethyl)phenyl]acetic acid

To a stirred solution of potassium 3-ethoxy-3-oxo-propanoate (75 mg, 0.44 mmol) and 2-(2-benzyloxy-4-bromo-5-fluoro-phenyl)propan-2-ol (step 4) (100 mg, 0.29 mmol) in toluene (2 mL) was added DMAP (3.6 mg, 0.03 mmol). The resulting mixture was degassed for 5 min. Diallyldipalladium dichloride (2.2 mg, 0.01 mmol) and BINAP (11.0 mg, 0.02 mmol) were added and the sealed reaction mixture was stirred at 140° C. for 3.5 h. The resulting mixture was concentrated in vacuo and the residue dissolved in THF (3 mL). The insoluble material was removed by filtration and the filtrate was diluted with MeOH (0.5 mL) and treated with 2M aq LiOH solution (0.44 mL, 0.88 mmol). The resulting mixture was stirred at room temperature for 16 h. The mixture was diluted with 2M NaOH (10 mL) and extracted with EtOAc (3×10 mL). The organic extracts were discarded and the aqueous portion was acidified to pH 3 using 2M aq. HCl. The mixture was extracted with EtOAc (3×10 mL) and the combined organic extracts were dried over $Na_2SO_4$ and concentrated in vacuo to the title compound as an off-white solid.

LC-MS (Method E): Rt 1.10 mins; MS m/z 301.0 [M+H−$H_2O$]+ (93% @215 nm)

$^1$H NMR (500 MHz, DMSO-d6) δ 12.40 (s, 1H), 7.49-7.45 (m, 2H), 7.45-7.40 (m, 2H), 7.37-7.33 (m, 1H), 7.31 (d, J=11.5 Hz, 1H), 7.05 (d, J=6.3 Hz, 1H), 5.08 (s, 1H), 5.06 (s, 2H), 3.57 (s, 2H), 1.46 (s, 6H).

Intermediate BA

2-[5-Benzyloxy-2-fluoro-4-(2,2,2-trifluoro-1-hydroxy-1-methyl-ethyl)phenyl]acetic acid

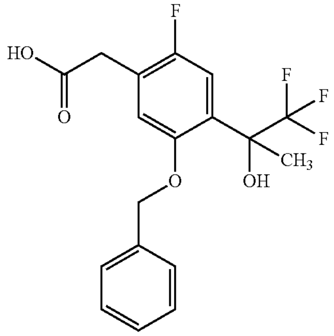 [SMILES: CC(O)(c1cc(F)c(CC(=O)O)cc1OCc1ccccc1)C(F)(F)F]

Step 1: [1-(2-benzyloxy-4-bromo-5-fluoro-phenyl)-2,2,2-trifluoro-1-methyl-ethoxy]-trimethyl-silane

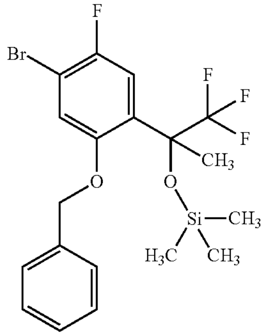 [SMILES: CC(O[Si](C)(C)C)(c1cc(F)c(Br)cc1OCc1ccccc1)C(F)(F)F]

To a stirred solution of trimethyl(trifluoromethyl)silane (257 μL, 1.74 mmol) in THF (1 mL) at −50° C. was added a solution of 1-(2-benzyloxy-4-bromo-5-fluoro-phenyl) ethanone (Intermediate B step 3) (90%, 500 mg, 1.39 mmol) in THF (1 mL) followed by TBAF (2.5 mg, 0.01 mmol). The reaction mixture was stirred at −50° C. for 30 min then allowed to warm to room temperature for 1 hour. The resulting mixture was diluted with EtOAc (10 mL) and water (10 mL). The organic layer was separated, washed with water (10 mL), dried over $Na_2SO_4$ and concentrated in vacuo to ford the title compound as a yellow oil.

LC-MS (Method H): Rt 2.03 mins; (85% @215 nm)

$^1$H NMR (500 MHz, Chloroform-d) δ 7.38 (d, J=10.3 Hz, 1H), 7.31-7.11 (m, 5H), 6.99 (d, J=5.7 Hz, 1H), 4.88 (s, 2H), 1.79 (s, 3H), 0.05 (s, 9H).

Step 2: 2-[5-Benzyloxy-2-fluoro-4-(2,2,2-trifluoro-1-hydroxy-1-methyl-ethyl)phenyl]acetic acid The title compound was prepared from [1-(2-benzyloxy-4-bromo-5-fluoro-phenyl)-2,2,2-trifluoro-1-methyl-ethoxy]-trimethyl-silane (step 1) and potassium 3-ethoxy-3-oxo-propanoate analogously to Intermediate B step 5.

LC-MS (Method E): Rt 1.18 mins; MS m/z 743.2 [2M−H]− (100% @215 nm)

$^1$H NMR (500 MHz, DMSO-d6) δ 12.60 (s (br), 1H), 7.47-7.39 (m, 5H), 7.37-7.31 (m, 1H), 7.19 (d, J=6.4 Hz, 1H), 6.59 (s, 1H), 5.10-5.03 (m, 2H), 3.61 (s, 2H), 1.78 (s, 3H).

Intermediate BB

2-[5-Benzyloxy-4-(1-cyclopropyl-1-hydroxy-ethyl)-2-fluoro-phenyl]acetic acid

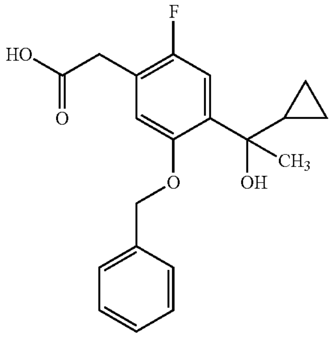 [SMILES: CC(O)(c1cc(F)c(CC(=O)O)cc1OCc1ccccc1)C1CC1]

The title compound was prepared from 1-(2-benzyloxy-4-bromo-5-fluoro-phenyl)ethanone (Intermediate B step 3) and bromo(cyclopropyl)magnesium solution (1M in Me-THF) analogously to Intermediate B steps 4 and 5.

LC-MS (Method E): Rt 1.23 mins; MS m/z 345.1 [M+H]+ (86% @215 nm)

$^1$H NMR (500 MHz, DMSO-d6) δ 12.47 (s (br), 1H), 7.49-7.45 (m, 2H), 7.43-7.39 (m, 2H), 7.36-7.32 (m, 1H), 7.23 (d, J=11.5 Hz, 1H), 7.06 (d, J=6.4 Hz, 1H), 5.08 (s, 2H), 4.64 (s, 1H), 3.56 (s, 2H), 1.64-1.58 (m, 1H), 1.54 (s, 3H), 0.50-0.42 (m, 1H), 0.24-0.16 (m, 2H), 0.06-0.00 (m, 1H).

Intermediate BC

2-[5-benzyloxy-2-fluoro-4-(1-hydroxy-1-methyl-propyl)phenyl]acetic acid

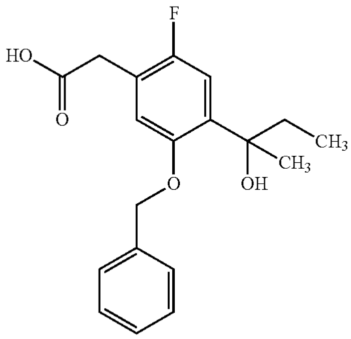 [SMILES: CCC(C)(O)c1cc(F)c(CC(=O)O)cc1OCc1ccccc1]

The title compound was prepared from 1-(2-benzyloxy-4-bromo-5-fluoro-phenyl)ethanone (Intermediate B step 3) and bromo(ethyl)magnesium solution (1M in THF) analogously to Intermediate B steps 4 and 5.

LC-MS (Method E): Rt 1.17 mins; MS m/z 315.1 [M+H−$H_2O$]+ (96% @215 nm)

$^1$H NMR (500 MHz, DMSO-$d_6$) δ 12.43 (br. s, 1H), 7.47-7.39 (m, 4H), 7.37-7.32 (m, 1H), 7.28 (d, J=11.6 Hz, 1H), 7.04 (d, J=6.3 Hz, 1H), 5.05 (s, 2H), 4.85 (s, 1H), 3.59-3.54 (m, 2H), 2.02 (dq, J=14.8, 7.4 Hz, 1H), 1.65 (dq, J=14.5, 7.3 Hz, 1H), 1.44 (s, 3H), 0.61 (t, J=7.4 Hz, 3H).

Intermediate BD

2-[5-Benzyloxy-4-(1-hydroxy-1-methyl-ethyl)-2-methyl-phenyl]acetic acid

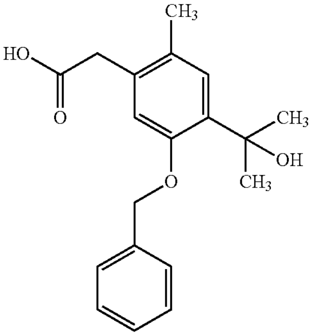 [SMILES: Cc1cc(C(C)(C)O)c(OCc2ccccc2)cc1CC(=O)O]

Step 1: 1-(2-Benzyloxy-4-bromo-5-methyl-phenyl)ethanone

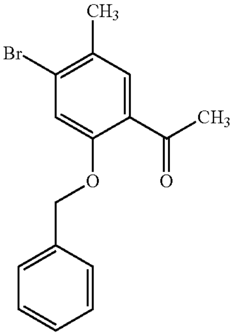 [SMILES: CC(=O)c1cc(C)c(Br)cc1OCc1ccccc1]

The title compound was prepared from 1-(4-bromo-2-hydroxy-5-methyl-phenyl)ethanone and bromomethylbenzene analogously to Intermediate B step 3.

LC-MS (Method G): Rt 1.18 min; MS m/z 319.0, 321.0= [M+H]+ (98% @215 nm)

$^1$H NMR (400 MHz, DMSO-d6) δ 7.56-7.46 (m, 4H), 7.45-7.39 (m, 2H), 7.38-7.33 (m, 1H), 5.24 (s, 2H), 2.48 (s, 3H), 2.30 (s, 3H).

Step 2: 2-(2-Benzyloxy-4-bromo-5-methyl-phenyl)propan-2-ol

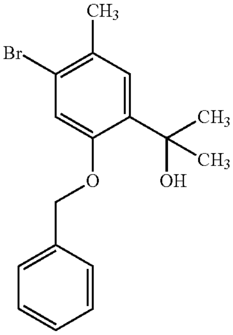 [SMILES: Cc1cc(C(C)(C)O)c(OCc2ccccc2)cc1Br]

A cooled (0° C.) suspension of cerium trichloride (2.27 g, 9.21 mmol) in THF (100 mL) was treated with 3M methyl magnesium bromide in ether (3.07 mL, 9.21 mmol) and stirred for 1 h. 1-(2-Benzyloxy-4-bromo-5-methyl-phenyl) ethanone (step 1) (98%, 2 g, 6.14 mmol) was added in one portion and the reaction mixture was stirred at 0° C. for 90 min. The reaction was quenched with the addition of water (150 mL) followed by EtOAc (100 mL). The organics were separated, washed with water (100 mL), brine (100 mL), dried over $Na_2SO_4$ and concentrated in vacuo. The crude material was purified by chromatography on silica eluting with 0-100% EtOAc in heptanes to afford the title compound as a colourless oil.

LC-MS (Method G): Rt 1.16 min; MS m/z 317.1, 319.1=[M−$H_2O$+H]+ (100% @215 nm)

$^1$H NMR (400 MHz, DMSO-d6) δ 7.54 (s, 1H), 7.47-7.39 (m, 4H), 7.37-7.31 (m, 1H), 7.22 (s, 1H), 5.12 (s, 2H), 5.02 (s, 1H), 2.27 (s, 3H), 1.45 (s, 6H).

Step 3: 2-[5-Benzyloxy-4-(1-hydroxy-1-methyl-ethyl)-2-methyl-phenyl]acetic acid

The title compound was prepared from 2-(2-benzyloxy-4-bromo-5-methyl-phenyl)propan-2-ol (step 2) and potassium 3-ethoxy-3-oxo-propanoate analogously to Intermediate B step 5.

LC-MS (Method G): Rt 0.87 min; MS m/z 297.2=[M−$H_2O$+H]+ (95% @215 nm)

$^1$H NMR (400 MHz, DMSO-d6) δ 12.32 (br. s, 1H), 7.49-7.44 (m, 2H), 7.44-7.38 (m, 2H), 7.38-7.31 (m, 2H), 6.92 (s, 1H), 5.05 (s, 2H), 4.86 (s, 1H), 3.52 (s, 2H), 2.16 (s, 3H), 1.46 (s, 6H).

Intermediate BE

2-[5-Benzyloxy-2-chloro-4-(1-hydroxy-1-methyl-ethyl)phenyl]acetic acid

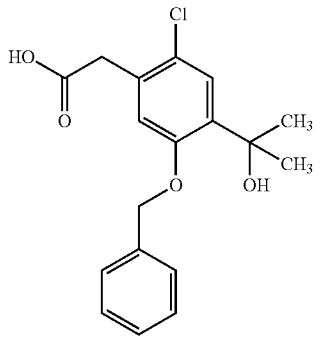 [SMILES: CC(C)(O)c1cc(Cl)c(CC(=O)O)cc1OCc1ccccc1]

Step 1: (3-Bromo-4-chloro-phenyl) acetate

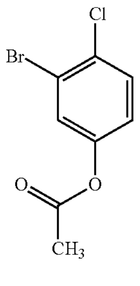

A cooled (ice bath) solution of 3-bromo-4-chloro-phenol (5.0 g, 24.1 mmol) and TEA (6.31 mL, 36.15 mmol) in DCM (75 mL) was treated dropwise with acetyl chloride (2.4 mL, 33.74 mmol) in DCM (25 mL) and stirred at room temperature for 1 h. The resulting mixture was washed with 0.5M HCl (100 mL), 1:1 saturated $NaHCO_3$/water (100 mL), dried over $Na_2SO_4$, and concentrated in vacuo to afford the title compound as a brown oil.

LC-MS (Method E): Rt 1.22 min; no ionisation (90% @215 nm)

$^1$H NMR (400 MHz, DMSO-d6) δ 7.68 (d, J=8.9 Hz, 1H), 7.66 (d, J=2.8 Hz, 1H), 7.23 (dd, J=8.7, 2.7 Hz, 1H), 2.27 (s, 3H).

Step 2:
1-(4-Bromo-5-chloro-2-hydroxy-phenyl)ethanone

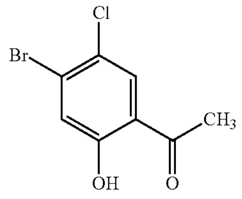

A mixture of (3-bromo-4-chloro-phenyl) acetate (step 1) (6.35 g, 25.47 mmol) and aluminium trichloride (6.11 g, 45.84 mmol) under nitrogen was heated to 165° C. for 3 h. The resulting melt was cooled to 130° C., toluene (50 mL) was added and the mixture was heated to reflux to dissolve the solids for 1 h. The resulting mixture was cooled to room temperature then EtOAc (10 mL) and 0.5M HCl (40 mL) were added and the mixture stirred with a secondary stirrer. The organics were separated and the aqueous was re-extracted with EtOAc (20 mL). The combined organic extracts were washed with brine, dried over $Na_2SO_4$ and concentrated in vacuo. The residue was treated with heptane (25 mL) and the resultant suspension was filtered, washed with further heptane and dried under suction to afford the title compound as a tan crystalline solid.

LC-MS (Method E): Rt 1.26 min; no ionisation (96% @215 nm)

$^1$H NMR (500 MHz, DMSO-d6) δ 11.76 (s, 1H), 7.97 (s, 1H), 7.41 (s, 1H), 2.62 (s, 3H).

Step 3:
1-(2-Benzyloxy-4-bromo-5-chloro-phenyl)ethanone

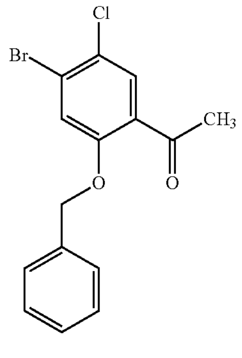 [SMILES: CC(=O)c1cc(Cl)c(Br)cc1OCc1ccccc1]

1-(4-Bromo-5-chloro-2-hydroxy-phenyl)ethanone (step 2) (96%, 3.56 g, 13.69 mmol) and 1-(4-bromo-5-chloro-2-hydroxy-phenyl)ethanone (78%, 2.35 g, 7.33 mmol) were dissolved in DMF (30 mL) and treated with $K_2CO_3$ (11.62 g, 84.1 mmol) and benzyl bromide (4.5 mL, 37.85 mmol). The reaction mixture was stirred at room temperature for 18 h. The resulting mixture was filtered through Celite®, washing with MeOH and the filtrate was concentrated in vacuo. The residue was partitioned between 4:1 EtOAc/heptane (150 mL) and water (100 mL). The organic portion was separated, washed with water (100 mL), dried over $Na_2SO_4$ and concentrated in vacuo. The residue was purified by chromatography on silica eluting with a gradient of 0 to 30% EtOAc in heptanes. The product fractions were concentrated in vacuo and recrystallisation of the residue from 1:1 TBME/heptane (20 mL) afforded the title compound as a brown crystalline solid.

LC-MS (Method G): Rt 1.19 min; (76% @215 nm)

$^1$H NMR (500 MHz, Chloroform-d) δ 7.83 (s, 1H), 7.44-7.40 (m, 5H), 7.32 (s, 1H), 5.14 (s, 2H), 2.55 (s, 3H).

Step 4: 2-(2-Benzyloxy-4-bromo-5-chloro-phenyl)propan-2-ol

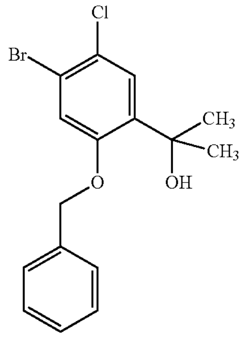 [SMILES: CC(C)(O)c1cc(Cl)c(Br)cc1OCc1ccccc1]

A cooled (−78° C.) solution of 1-(2-benzyloxy-4-bromo-5-chloro-phenyl)ethanone (step 3) (1.29 g, 3.8 mmol) in THF (25 mL) was treated with methyl magnesium bromide (3M in $Et_2O$) (1.65 mL, 4.94 mmol) and allowed to warm to room temperature, stirring for 1.5 h. The resulting mixture was cooled to 0° C. and treated with 10% aq $NH_4Cl$ (10 mL) and EtOAc (10 mL). The organic portion was separated, dried over $Na_2SO_4$ and concentrated in vacuo. Purification of the crude material by chromatography on basic silica eluting with a gradient of 0 to 50% EtOAc in heptanes afforded the title compound as a light tan oil which crystallised on standing.

LC-MS (Method G): Rt 1.17 min; MS m/z 337.0, 339.0=[M+H−$H_2O$]+ (68% @215 nm)

$^1$H NMR (500 MHz, Chloroform-d) δ 7.47 (s, 1H), 7.45-7.36 (m, 5H), 7.21 (s, 1H), 5.10 (s, 2H), 3.45 (s, 1H), 1.58 (s, 6H).

Step 5: 2-[5-Benzyloxy-2-chloro-4-(1-hydroxy-1-methyl-ethyl)phenyl]acetic acid 2-(2-Benzyloxy-4-bromo-5-chloro-phenyl)propan-2-ol (step 4) (1.04 g, 2.91 mmol), potassium 3-ethoxy-3-oxo-propanoate (991 mg, 5.82 mmol), diallyldipalladium dichloride (106 mg, 0.29 mmol), BINAP (362 mg, 0.58 mmol) and DMAP (36 mg, 0.29 mmol) were suspended in toluene (9.7 mL) and heated in a sealed tube to 140° C. for 18 h. The reaction solvent was concentrated in vacuo and the resulting residue was treated with MeOH (20 mL) and 2M aq. LiOH (4.37 mL, 8.73 mmol) then stirred at room temperature for 3 h. Further 2M aq. LiOH (4.37 mL, 8.73 mmol) and MeOH (10 mL) were added and stirring continued for an additional 2 h. The mixture was concentrated in vacuo to remove the bulk of the organics and the aqueous residue was diluted with water (20 mL) and DCM (30 mL). The aqueous portion was separated, washed with DCM and acidified with 2M $KHSO_4$ (25 mL). The mixture was extracted with DCM (2×30 mL) and the combined organic extracts were dried over $Na_2SO_4$ and concentrated in vacuo. The crude material was purified by chromatography on silica eluting with 0 to 100% EtOAc in heptanes followed by 0 to 100% MeOH in EtOAc. The product fractions were concentrated in vacuo and the residue was dissolved in 1:1 DMSO/MeOH (1.2 mL). Purification of the crude material by preparative HPLC (acidic pH, early elution method) afforded the title compound as a white crystalline solid LC-MS (Method E): Rt 1.12 min; MS m/z 316.9, 318.9=[M+H−$H_2O$]+ (100% @215 nm)

$^1$H NMR (400 MHz, DMSO-d6) δ 7.57 (s, 1H), 7.50-7.45 (m, 2H), 7.45-7.39 (m, 2H), 7.38-7.33 (m, 1H), 7.15 (s, 1H), 5.11 (s, 1H), 5.09 (s, 2H), 3.65 (s, 2H), 1.45 (s, 6H).

Intermediate C

2-[5-Benzyloxy-4-(1-cyano-1-methyl-ethyl)-2-fluoro-phenyl]acetic acid

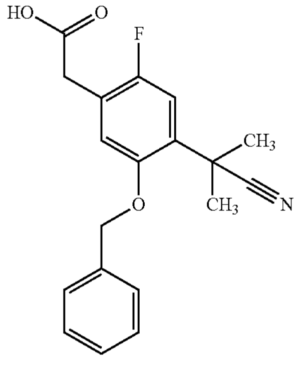 [SMILES: CC(C)(C#N)c1cc(F)c(CC(=O)O)cc1OCc1ccccc1]

Step 1: Methyl 4-bromo-5-fluoro-2-triisopropylsilyloxy-benzoate

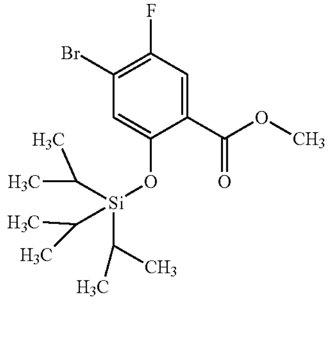 [SMILES: COC(=O)c1cc(F)c(Br)cc1O[Si](C(C)C)(C(C)C)C(C)C]

A stirred mixture of methyl 4-bromo-5-fluoro-2-hydroxy-benzoate (3 g, 12.05 mmol), TEA (3.69 mL, 26.5 mmol) and DMAP (147 mg, 1.2 mmol) in DCM (20 mL) under nitrogen was treated dropwise with triisopropylsilyl chloride (3.09 mL, 14.46 mmol) and the mixture was stirred at room temperature overnight. The resulting mixture was diluted with water (20 mL) and the organic layer was separated, dried over $Na_2SO_4$ and concentrated in vacuo to afford the title compound as a yellow oil.

LC-MS (Method H): Rt 2.09 mins; MS m/z 405.1, 407.1=[M+H]+ (97% @215 nm)

$^1$H NMR (500 MHz, DMSO-d6) δ 7.61 (d, J=8.8 Hz, 1H), 7.12 (d, J=5.6 Hz, 1H), 3.81-3.74 (m, 3H), 1.29 (hept, J=7.3 Hz, 3H), 1.05 (d, J=7.6 Hz, 18H).

Step 2: (4-Bromo-5-fluoro-2-triisopropylsilyloxy-phenyl)methanol

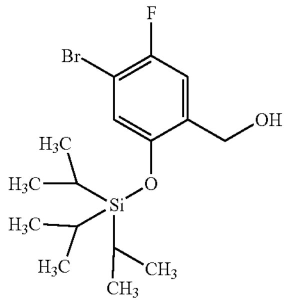 [SMILES: CC(C)[Si](Oc1cc(Br)c(F)cc1CO)(C(C)C)C(C)C]

A stirred solution of methyl 4-bromo-5-fluoro-2-triisopropylsilyloxy-benzoate (step 1) (76%, 5.4 g, 10.12 mmol) in THF (100 mL) was treated with 4M $LiBH_4$ in THF (7.59 mL, 30.37 mmol) and the mixture was stirred at room temperature overnight.

The mixture was cooled (0° C.) and the reaction was quenched carefully with ice (20 mL) stirring for 30 min then allowed to warm to room temperature. EtOAc (20 mL) was added and the organic layer was separated, dried over $Na_2SO_4$ and concentrated in vacuo. Purification of the crude material by chromatography on silica (Biotage® Isolera 55 g KP-NH) eluting with 0-100% EtOAc in heptanes afforded the title compound as a yellow oil.

LC-MS (Method H): Rt 1.60 mins; MS m/z 400.1=[M+Na]+ (90% @215 nm)

$^1$H NMR (500 MHz, DMSO-d6) δ 7.28 (d, J=9.5 Hz, 1H), 6.92 (d, J=5.7 Hz, 1H), 5.32 (t, J=5.2 Hz, 1H), 4.48 (d, J=4.4 Hz, 2H), 1.28 (dq, J=14.5, 7.5 Hz, 3H), 1.09-1.03 (m, 18H).

Step 3: [5-Bromo-2-(chloromethyl)-4-fluoro-phenoxy]-triisopropyl-silane

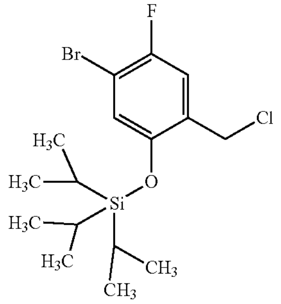 [SMILES: CC(C)[Si](Oc1cc(Br)c(F)cc1CCl)(C(C)C)C(C)C]

A cooled (0° C.), stirred solution of (4-bromo-5-fluoro-2-triisopropylsilyloxy-phenyl)methanol (4.8 g, 12.72 mmol) and DMF (941 μL, 12.14 mmol) in DCM (80 mL) was treated dropwise with thionyl chloride (2.24 mL, 30.88 mmol) in DCM (40 mL) and the mixture was stirred at room temperature for 2 h.

The solvents were removed in vacuo and the residue was diluted with EtOAc (100 mL). The mixture was washed with saturated $NaHCO_3$ (100 mL), brine (30 mL), dried over $Na_2SO_4$ and concentrated in vacuo. Purification of the crude material by chromatography on silica eluting with 0-100% EtOAc in heptanes afforded the title compound as a yellow oil.

LC-MS (Method H): Rt 2.12 min (87% @215 nm)

$^1$H NMR (400 MHz, DMSO-d6) δ 7.51 (d, J=9.0 Hz, 1H), 7.02 (d, J=5.8 Hz, 1H), 4.66 (s, 2H), 1.35 (hept, J=7.4 Hz, 3H), 1.08 (d, J=7.5 Hz, 18H).

Step 4: 2-(4-Bromo-5-fluoro-2-hydroxy-phenyl)acetonitrile

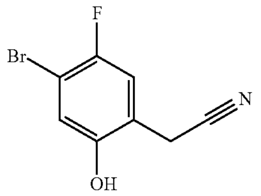 [SMILES: N#CCc1cc(F)c(Br)cc1O]

Sodium cyanide (576 mg, 11.75 mmol) was added to a solution of [5-bromo-2-(chloromethyl)-4-fluoro-phenoxy]-triisopropyl-silane (step 3) (3.1 g, 7.83 mmol) in DMF (20 mL) and the mixture was stirred at room temperature overnight. The resulting mixture was diluted with EtOAc (20 mL) and washed with sat. sodium carbonate (30 mL), brine (50 mL), dried over $Na_2SO_4$ and concentrated in vacuo. Purification of the crude material by chromatography on silica eluting with 0-100% EtOAc in heptanes afforded the title compound as a yellow solid.

LC-MS (Method E): Rt 1.04 mins; MS m/z 227.8, 229.8=[M−H]− (98% @215 nm)

$^1$H NMR (500 MHz, DMSO-d6) δ 10.43 (s, 1H), 7.30 (d, J=9.1 Hz, 1H), 7.08 (d, J=6.1 Hz, 1H), 3.78 (s, 2H).

Step 5: 2-(2-Benzyloxy-4-bromo-5-fluoro-phenyl)acetonitrile

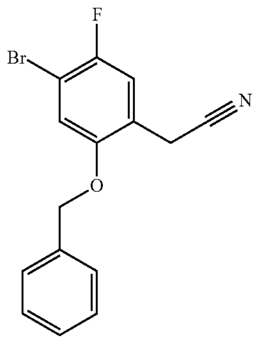 [SMILES: N#CCc1cc(F)c(Br)cc1OCc1ccccc1]

Benzyl bromide (614 μL, 5.16 mmol) was added to a stirred mixture of 2-(4-bromo-5-fluoro-2-hydroxy-phenyl) acetonitrile (step 4) (990 mg, 4.3 mmol) and $K_2CO_3$ (1.49 g, 10.76 mmol) in DMF (10 mL) and the mixture was stirred at 80° C. for 1 hour. The resulting mixture was allowed to cool to room temperature and partitioned between EtOAc (20 mL) and water (50 mL). The layers were separated and the aqueous portion was further extracted with EtOAc (10 mL). The combined organic extracts were washed with brine (50 mL), dried over $Na_2SO_4$ and concentrated in vacuo. Purification by chromatography on silica eluting with 0-100% EtOAc in heptanes afforded the title compound as a yellow oil.

LC-MS (Method E): Rt 1.30 min (68% @215 nm)

$^1$H NMR (400 MHz, DMSO-d6) δ 7.56-7.45 (m, 3H), 7.46-7.37 (m, 3H), 7.40-7.32 (m, 1H), 5.22 (s, 2H), 3.90 (s, 2H).

Step 6: 2-(2-Benzyloxy-4-bromo-5-fluoro-phenyl)-2-methyl-propanenitrile

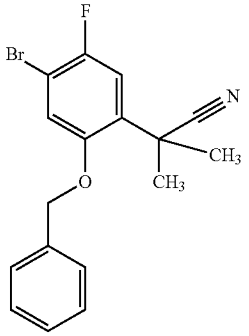 [SMILES: CC(C)(C#N)c1cc(F)c(Br)cc1OCc1ccccc1]

To a cooled (0° C.) solution of 2-(2-benzyloxy-4-bromo-5-fluoro-phenyl)acetonitrile (0.51 g, 1.59 mmol) in DMF (10 mL) under nitrogen was added methyl iodide (100%, 0.2 mL, 3.19 mmol) followed by NaH, (60% dispersion in mineral oil, 127 mg, 3.19 mmol). The mixture was allowed to warm to room temperature and stirred overnight. The resulting mixture was carefully poured onto ice (20 mL), EtOAc (20 mL) was added and the mixture was stirred for 20 min. The organic portion was separated, dried over $Na_2SO_4$ and concentrated in vacuo. The residual DMF was removed by drying in a high vacuum oven at 40° C. overnight to afford the title compound as a yellow oil.

LC-MS (Method E): Rt 1.37 mins; MS m/z 347.9, 350.0=[M+H]+ (66% @215 nm)

$^1$H NMR (500 MHz, DMSO-d6) δ 7.56 (m, 2H), 7.53 (d, J=6.0 Hz, 1H), 7.45-7.38 (m, 2H), 7.38-7.32 (m, 2H), 5.27 (s, 2H), 1.69 (s, 6H).

Step 7: 2-[5-Benzyloxy-4-(1-cyano-1-methyl-ethyl)-2-fluoro-phenyl]acetic acid

The title compound was prepared from potassium 3-ethoxy-3-oxo-propanoate and 2-(2-benzyloxy-4-bromo-5-fluoro-phenyl)-2-methyl-propanenitrile (step 6) analogously to Intermediate B step 5.

LC-MS (Method E): Rt 1.20 mins; MS m/z 328.0=[M+H]+ (48% @215 nm)

$^1$H NMR (400 MHz, DMSO-d6) δ 12.50 (s, 1H), 7.61-7.54 (m, 2H), 7.45-7.37 (m, 2H), 7.39-7.31 (m, 1H), 7.24 (d, J=6.5 Hz, 1H), 7.15 (d, J=10.9 Hz, 1H), 5.19 (s, 2H), 3.62 (s, 2H), 1.69 (s, 6H).

Intermediate CA

2-[4-[1-(Acetoxymethyl)cyclobutyl]-5-benzyloxy-2-fluoro-phenyl]acetic acid

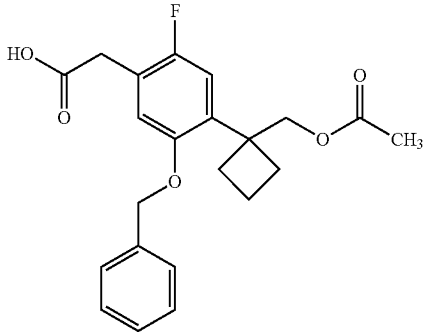 [SMILES: CC(=O)OCC1(c2cc(F)c(CC(=O)O)cc2OCc2ccccc2)CCC1]

Step 1: 1-(2-Benzyloxy-4-bromo-5-fluoro-phenyl) cyclobutanecarbonitrile

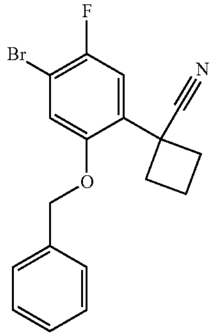 [SMILES: N#CC1(c2cc(F)c(Br)cc2OCc2ccccc2)CCC1]

To a cooled (0° C.) suspension of NaH (60% dispersion in mineral oil, 394 mg, 9.84 mmol) in DMF (15 mL) was added a solution of 2-(2-benzyloxy-4-bromo-5-fluoro-phenyl)acetonitrile (Intermediate C step 5) (1.5 g, 4.69 mmol) in DMF (5 mL). The mixture was stirred for 15 min and then treated dropwise with a solution of 1,3-dibromopropane (523 μL, 5.15 mmol) in DMF (5 mL) over 10 min. The mixture was allowed to warm to room temperature and stirred for 2 h The reaction was quenched with saturated aqueous $NH_4Cl$ solution (100 mL) and extracted with DCM (100 mL). The combined organic extracts were washed with brine (100 mL), dried over $Na_2SO_4$ and concentrated in vacuo. Purification of the crude material by chromatography on silica eluting with 0-50% TBME in heptanes afforded the title compound as a colourless crystalline solid.

LC-MS (Method G): Rt 1.18 min; MS m/z 360.1, 362.0=[M+H]+ (99% @215 nm)

$^1$H NMR (400 MHz, DMSO-d6) δ 7.53-7.46 (m, 3H), 7.45-7.39 (m, 2H), 7.39-7.32 (m, 2H), 5.21 (s, 2H), 2.67-2.53 (m, 4H), 2.29-2.17 (m, 1H), 1.92-1.83 (m, 1H).

Step 2: 1-(2-Benzyloxy-4-bromo-5-fluoro-phenyl) cyclobutanecarbaldehyde

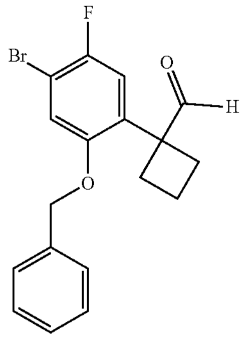 [SMILES: O=CC1(c2cc(F)c(Br)cc2OCc2ccccc2)CCC1]

To a cooled (−78° C.) solution of 1-(2-benzyloxy-4-bromo-5-fluoro-phenyl)cyclobutane carbonitrile (step 1) (99%, 556 mg, 1.53 mmol) in THF (7.5 mL) was added 1.2M DIBAL in toluene (1.91 mL, 2.29 mmol) and the mixture was allowed to warm to 0° C. and maintained at 0° C. overnight. The resulting mixture was cooled to −78° C. and treated with a further 0.5 equiv. of 1.2M DIBAL in toluene and allowed to warm to −40° C. The reaction was quenched by addition of 1M HCl (2 mL) at −30° C. then warmed to room temperature and stirred for 30 min. The resulting mixture was diluted with EtOAc (30 mL) and washed with sat. $NaHCO_3$ (30 mL) solution and brine (30 mL). The organics were dried over $Na_2SO_4$ and concentrated in vacuo. The crude residue purified by chromatography on silica eluting with 0-50% TBME in heptanes to afford the title compound as a colourless oil, which crystallised on standing at room temperature.

LC-MS (Method G): Rt 1.23 min; (97% @215 nm)

$^1$H NMR (400 MHz, DMSO-d6) δ 9.61 (s, 1H), 7.42-7.30 (m, 6H), 7.26 (d, J=9.4 Hz, 1H), 5.07 (s, 2H), 2.40-2.32 (m, 2H), 2.00-1.90 (m, 1H), 1.86-1.78 (m, 1H), 2.56-2.45 (obscured m, 2H)

Step 3: [1-(2-Benzyloxy-4-bromo-5-fluoro-phenyl) cyclobutyl]methanol

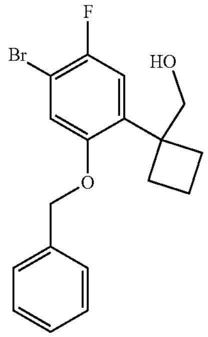 [SMILES: OCC1(c2cc(F)c(Br)cc2OCc2ccccc2)CCC1]

To a cooled (0° C.) solution of 1-(2-benzyloxy-4-bromo-5-fluoro-phenyl)cyclobutane carbaldehyde (step 2) (97%, 200 mg, 0.53 mmol) in MeOH (2.5 mL) was added $NaBH_4$ (21 mg, 0.56 mmol) and the mixture stirred for 30 min. The reaction was quenched by addition of sat. $NaHCO_3$ solution (20 mL) and extracted with EtOAc (3×20 mL). The combined organic extracts were washed with brine (30 mL), dried over $Na_2SO_4$ and concentrated to afford the title compound as a colourless oil which crystallised on standing at room temperature.

LC-MS (Method G): Rt 1.17 min; MS m/z 363.1, 365.1=[M−H]− (99% @215 nm)

$^1$H NMR (400 MHz, DMSO-d6) δ 7.45-7.38 (m, 4H), 7.36-7.32 (m, 1H), 7.29 (d, J=5.9 Hz, 1H), 6.88 (d, J=9.7 Hz, 1H), 5.07 (s, 2H), 4.62 (t, J=5.8 Hz, 1H), 3.62 (d, J=5.7 Hz, 2H), 2.25-2.11 (m, 4H), 1.97-1.89 (m, 1H), 1.74-1.66 (m, 1H).

Step 4: [1-(2-Benzyloxy-4-bromo-5-fluoro-phenyl) cyclobutyl]methyl acetate

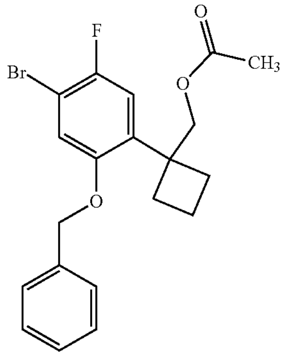 [SMILES: CC(=O)OCC1(c2cc(F)c(Br)cc2OCc2ccccc2)CCC1]

To a solution of [1-(2-benzyloxy-4-bromo-5-fluoro-phenyl)cyclobutyl]methanol (step 3) (99%, 191 mg, 0.52 mmol), TEA (99 μL, 0.57 mmol) and DMAP (6.32 mg, 0.05 mmol) in DCM (3 mL) was added acetic anhydride (54 μL, 0.57 mmol) and the mixture stirred at room temperature overnight. The resulting mixture was diluted with DCM (20 mL) and washed with 1M HCl (15 mL), brine (15 mL), dried over $Na_2SO_4$ and concentrated in vacuo to afford the title compound as a colourless oil.

LC-MS (Method E): Rt 1.55 min; (95% @215 nm)

$^1$H NMR (400 MHz, DMSO-d6) δ 7.45-7.38 (m, 4H), 7.36-7.31 (m, 2H), 6.98 (d, J=9.6 Hz, 1H), 5.09 (s, 2H), 4.31 (s, 2H), 2.33-2.25 (m, 2H), 2.17-2.10 (m, 2H), 2.07-1.98 (m, 1H), 1.88 (s, 3H), 1.78-1.69 (m, 1H).

Step 5: tert-Butyl 2-[4-[1-(acetoxymethyl)cyclobutyl]-5-benzyloxy-2-fluoro-phenyl]acetate

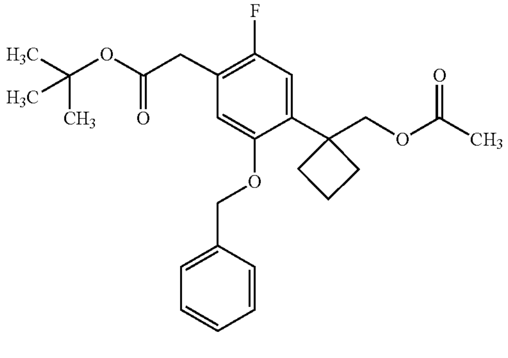 [SMILES: CC(=O)OCC1(c2cc(F)c(CC(=O)OC(C)(C)C)cc2OCc2ccccc2)CCC1]

To a solution of [1-(2-benzyloxy-4-bromo-5-fluoro-phenyl)cyclobutyl]methyl acetate (step 4) (170 mg, 0.42 mmol) in THF (1.5 mL) was added Pd(dba)$_2$ (12 mg, 0.02 mmol) and Q-Phos (15 mg, 0.02 mmol). The mixture was degassed for 5 min then 0.5M bromo-(2-tert-butoxy-2-oxo-ethyl)zinc in THF (1.25 mL, 0.63 mmol) was added and the mixture was heated at 60° C. for 2 h. After cooling to room temperature, the resulting mixture was diluted with EtOAc (10 mL) and washed with sat. $NaHCO_3$ (10 mL) solution, brine (10 mL), dried over $Na_2SO_4$ and concentrated in vacuo. Purification of the crude residue by chromatography on silica eluting with 0-50% TBME in heptanes afforded the title compound as a pale orange oil.

LC-MS (Method E): Rt 1.57 min; MS m/z 465.2 [M+Na]+ (72% @215 nm)

$^1$H NMR (400 MHz, DMSO-d6) δ 7.45-7.38 (m, 4H), 7.35-7.31 (m, 1H), 7.00 (d, J=6.4 Hz, 1H), 6.79 (d, J=10.5 Hz, 1H), 5.02 (s, 2H), 4.31 (s, 2H), 3.56 (s, 2H), 2.34-2.26 (m, 2H), 2.17-2.11 (m, 2H), 2.05-1.97 (m, 1H), 1.88 (s, 3H), 1.77-1.70 (m, 1H), 1.40 (s, 9H).

Step 6: 2-[4-[1-(Acetoxymethyl)cyclobutyl]-5-benzyloxy-2-fluoro-phenyl]acetic acid To a cooled (0° C.) solution of tert-butyl 2-[4-[1-(acetoxymethyl)cyclobutyl]-5-benzyloxy-2-fluoro-phenyl]acetate (step 5) (90%, 192 mg, 0.39 mmol) in DCM (1.5 mL) was added TFA (0.5 mL, 6.53 mmol) and the mixture was allowed to warm to room temperature, stirring for a further 2 h. The resulting mixture was concentrated in vacuo and the crude product was azeotroped with DCM to afford the title compound as an orange oil.

LC-MS (Method E): Rt 1.31 min; MS m/z 409.1 [M+Na]+ (94% @215 nm)

Intermediate CB

2-[4-[4-(Acetoxymethyl)tetrahydropyran-4-yl]-5-benzyloxy-2-fluoro-phenyl]acetic acid

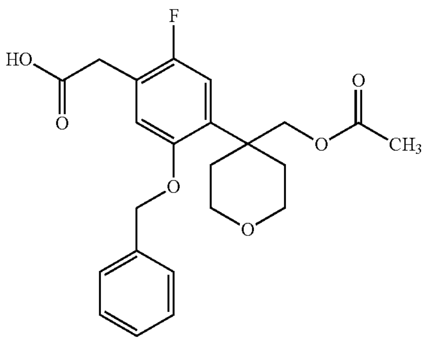 [SMILES: CC(=O)OCC1(c2cc(F)c(CC(=O)O)cc2OCc2ccccc2)CCOCC1]

Step 1: 4-(2-Benzyloxy-4-bromo-5-fluoro-phenyl)tetrahydropyran-4-carbonitrile

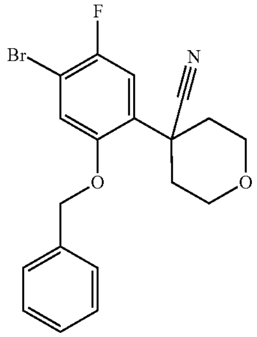 [SMILES: N#CC1(c2cc(F)c(Br)cc2OCc2ccccc2)CCOCC1]

The title compound was prepared from 2-(2-benzyloxy-4-bromo-5-fluoro-phenyl)acetonitrile (Intermediate C step 5) and 1-bromo-2-(2-bromoethoxy)ethane analogously to Intermediate C step 6.

LC-MS (Method G): Rt 1.11 min; MS m/z 390.1, 392.1=[M+H]+ (95% @215 nm)

$^1$H NMR (400 MHz, Chloroform-d) δ 7.52-7.50 (m, 1H), 7.45-7.35 (m, 4H), 7.18 (d, J=5.8 Hz, 1H), 7.09 (d, J=9.5 Hz, 1H), 5.18 (s, 2H), 4.06-3.99 (m, 2H), 3.91 (td, J=12.2, 1.6 Hz, 2H), 2.36-2.27 (m, 2H), 2.09-1.99 (m, 2H).

Step 2: [4-(2-Benzyloxy-4-bromo-5-fluoro-phenyl)tetrahydropyran-4-yl]methanol

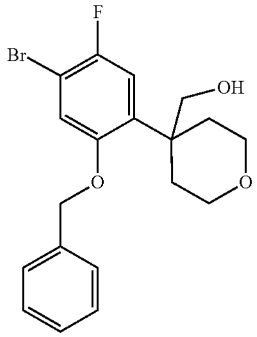 [SMILES: OCC1(c2cc(F)c(Br)cc2OCc2ccccc2)CCOCC1]

To a stirred solution of 4-(2-benzyloxy-4-bromo-5-fluoro-phenyl)tetrahydropyran-4-carbonitrile (step 1) (1.85 g, 4.74 mmol) in DCM (50 mL) at −78° C. was added dropwise 1M DIBAL in hexane (5.21 mL, 5.21 mmol) and the mixture was stirred at −78° C. for 1 h. The reaction was quenched dropwise addition of MeOH, the diluted with saturated aqueous Rochelle's salt (10 mL), water (30 mL) and the phases were separated. The organic phase was washed with 1M HCl (30 mL), dried over $Na_2SO_4$ and concentrated in vacuo. The crude solid was dissolved in DCM (50 mL) and re-treated with 1M DIBAL in hexane (5.21 mL, 5.21 mmol) at −78° C. and left to stir overnight. Additional 1 M DIBAL in hexane (3.0 mL, 3.0 mmol) was added at −78° C. and stirred for 40 min. The reaction was quenched with dropwise addition of MeOH leading to the formation of a 'hydrogel-like' material. The mixture was diluted with further DCM (30 mL), physically broken up, filtered through a sinter funnel and concentrated in vacuo. The filter cake was dissolved in 1 M NaOH (200 mL) and stirred for 2 h. The aqueous layer was extracted with TBME (2×100 mL) and the combined organic extracts were concentrated in vacuo. Purification by chromatography on silica eluting with 0-100% EtOAc in heptanes afforded the title compound as an off-white gum.

LC-MS (Method G): Rt 1.02 min; MS m/z 395.1, 397.2=[M+H]+ (78% @215 nm)

$^1$H NMR (400 MHz, DMSO-d6) δ 7.46-7.28 (m, 6H), 7.16 (d, J=11.2 Hz, 1H), 5.12 (s, 2H), 4.49 (t, J=5.6 Hz, 1H), 3.71-3.58 (m, 4H), 3.43-3.35 (m, 2H), 2.23-2.14 (m, 2H), 1.84-1.75 (m, 2H).

Step 3: [4-(2-Benzyloxy-4-bromo-5-fluoro-phenyl)tetrahydropyran-4-yl]methyl acetate

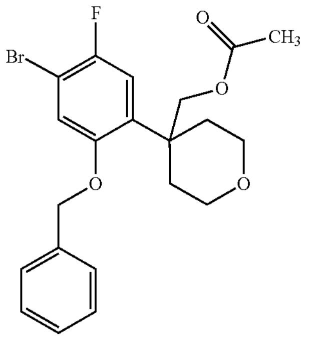 [SMILES: CC(=O)OCC1(c2cc(F)c(Br)cc2OCc2ccccc2)CCOCC1]

To a cooled (0° C.) solution of [4-(2-benzyloxy-4-bromo-5-fluoro-phenyl)tetrahydropyran-4-yl]methanol (step 2) (574 mg, 1.45 mmol) in DCM (10 mL) was added TEA (507 μL, 2.9 mmol) followed by DMAP (17.73 mg, 0.15 mmol) and acetic anhydride (274 μL, 2.9 mmol) and the reaction mixture was allowed to warm to room temperature and stirred overnight. The resulting mixture was diluted with DCM (20 mL) and washed with water (2×15 mL). The organic portion was dried over $Na_2SO_4$ and concentrated in vacuo. Purification by C18 reverse phase chromatography eluting with 10-100% MeCN in water (+0.1% formic acid) afforded the title compound as a pale yellow gum.

LC-MS (Method E): Rt 1.42 min; (100% @215 nm)

$^1$H NMR (500 MHz, DMSO-d6) δ 7.47-7.38 (m, 5H), 7.39-7.31 (m, 1H), 7.25 (d, J=11.0 Hz, 1H), 5.14 (s, 2H), 4.37 (s, 2H), 3.65 (ddd, J=11.5, 5.7, 3.6 Hz, 2H), 3.41 (ddd, J=11.5, 8.9, 2.5 Hz, 2H), 2.27-2.19 (m, 2H), 1.87-1.77 (m, 5H).

Step 4: tert-Butyl 2-[4-[4-(acetoxymethyl)tetrahydropyran-4-yl]-5-benzyloxy-2-fluoro-phenyl]acetate

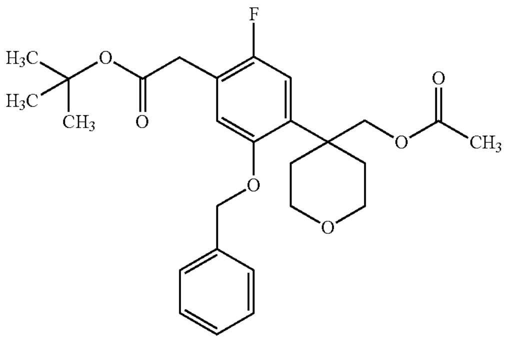 [SMILES: CC(=O)OCC1(c2cc(F)c(CC(=O)OC(C)(C)C)cc2OCc2ccccc2)CCOCC1]

The title compound was prepared from [4-(2-benzyloxy-4-bromo-5-fluoro-phenyl)tetrahydropyran-4-yl]methyl acetate (step 3) and 0.5M bromo-(2-tert-butoxy-2-oxo-ethyl)zinc in THF analogously to Intermediate CA step 5.

LC-MS (Method G): Rt 1.17 min; MS m/z 495.2=[M+Na]+ (99% @215 nm)

$^1$H NMR (400 MHz, DMSO-d6) δ 7.48-7.43 (m, 2H), 7.43-7.37 (m, 2H), 7.38-7.30 (m, 1H), 7.10 (d, J=6.7 Hz, 1H), 7.05 (d, J=11.9 Hz, 1H), 5.07 (s, 2H), 4.37 (s, 2H), 3.69-3.60 (m, 2H), 3.58 (s, 2H), 3.46-3.36 (m, 2H), 2.29-2.19 (m, 2H), 1.88-1.78 (m, 5H), 1.40 (s, 9H).

Step 5: 2-[4-[4-(Acetoxymethyl)tetrahydropyran-4-yl]-5-benzyloxy-2-fluoro-phenyl]acetic acid The title compound was prepared from tert-butyl 2-[4-[4-(acetoxymethyl)tetrahydropyran-4-yl]-5-benzyloxy-2-fluoro-phenyl]acetate (step 4) and TFA analogously to Intermediate CA step 6.

LC-MS (Method G): Rt 0.91 min; MS m/z 439.2=[M+Na]+ (99% @215 nm)

$^1$H NMR (500 MHz, DMSO-d6) δ 12.51 (br. s, 1H), 7.48-7.43 (m, 2H), 7.43-7.38 (m, 2H), 7.38-7.31 (m, 1H), 7.14 (d, J=6.7 Hz, 1H), 7.04 (d, J=11.8 Hz, 1H), 5.06 (s, 2H), 4.37 (s, 2H), 3.65 (ddd, J=11.3, 5.5, 3.5 Hz, 2H), 3.59 (s, 2H), 3.46-3.38 (m, 2H), 2.27-2.19 (m, 2H), 1.87-1.79 (m, 5H).

Intermediate D

2-[5-Benzyloxy-4-(1-cyanocyclopropyl)-2-fluoro-phenyl]acetic acid

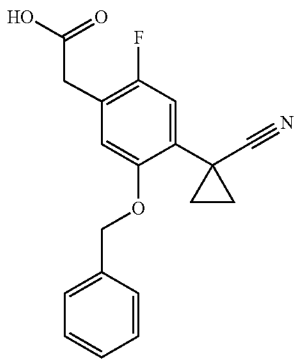 [SMILES: N#CC1(c2cc(F)c(CC(=O)O)cc2OCc2ccccc2)CC1]

Step 1: 1-(2-Benzyloxy-4-bromo-5-fluoro-phenyl)cyclopropanecarbonitrile

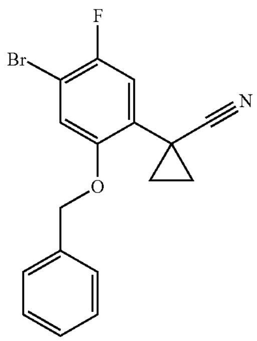 [SMILES: N#CC1(c2cc(F)c(Br)cc2OCc2ccccc2)CC1]

To solid potassium hydroxide (210 mg, 3.75 mmol) was added 60% aq. potassium hydroxide (779 mg, 3.28 mmol) followed by 2-(2-benzyloxy-4-bromo-5-fluoro-phenyl)acetonitrile (Intermediate C step 5) (500 mg, 1.56 mmol) and tetrabutylammonium bromide (5 g, 15.62 mmol). The resulting mixture was treated dropwise with 1,2-dibromoethane (0.27 mL, 3.12 mmol) (exotherm observed and temperature was maintained at 50° C. by external cooling) and stirring continued at 50° C. overnight. The resulting mixture was diluted with water (15 mL) and extracted with EtOAc (2×10 mL). The organic extracts were combined, dried over $Na_2SO_4$ and concentrated in vacuo. Purification of the crude material by chromatography on silica eluting with 0-100% EtOAc in heptanes afforded the title compound as a yellow solid.

LC-MS (Method E): Rt 1.33 min (100% @215 nm)

$^1H$ NMR (500 MHz, DMSO-d6) δ 7.55 (d, J=7.1 Hz, 2H), 7.48 (d, J=5.9 Hz, 1H), 7.47-7.39 (m, 3H), 7.35 (t, J=7.3 Hz, 1H), 5.28 (s, 2H), 1.64-1.58 (m, 2H), 1.41-1.35 (m, 2H).

Step 2: 2-[5-Benzyloxy-4-(1-cyanocyclopropyl)-2-fluoro-phenyl]acetic acid

The title compound was prepared from 1-(2-benzyloxy-4-bromo-5-fluoro-phenyl)cyclopropanecarbonitrile (step 1) and potassium 3-ethoxy-3-oxo-propanoate analogously to Intermediate B step 5 substituting toluene with mesitylene as the solvent.

LC-MS (Method E): Rt 1.12 mins; MS m/z 326.1=[M+H]+ (71% @215 nm)

$^1H$ NMR (500 MHz, DMSO-d6) δ 12.55 (s, 1H), 7.57 (d, J=7.1 Hz, 2H), 7.45-7.38 (m, 2H), 7.38-7.32 (m, 1H), 7.20 (d, J=9.8 Hz, 1H), 7.17 (d, J=6.4 Hz, 1H), 5.20 (s, 2H), 3.60 (s, 2H), 1.62-1.55 (m, 2H), 1.38-1.32 (m, 2H).

Intermediate E

2-[5-Benzyloxy-4-(1,1-dimethyl-2-morpholino-ethyl)-2-fluoro-phenyl]acetic acid

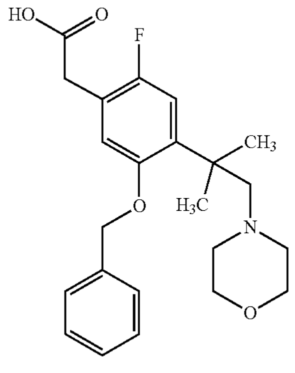 [SMILES: CC(C)(CN1CCOCC1)c1cc(F)c(CC(=O)O)cc1OCc1ccccc1]

Step 1: 2-(2-Benzyloxy-4-bromo-5-fluoro-phenyl)-2-methyl-propanal

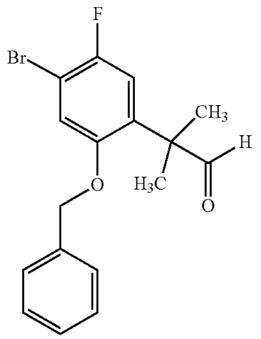 [SMILES: CC(C)(C=O)c1cc(F)c(Br)cc1OCc1ccccc1]

To a solution of 2-(2-benzyloxy-4-bromo-5-fluoro-phenyl)-2-methyl-propanenitrile (Intermediate C step 6) (80% purity, 1 g, 2.30 mmol) in DCM (20 mL) at −78° C. was added 1M DIBAL in hexane (6.03 mL, 6.03 mmol). The mixture was allowed to slowly warm to room temperature and was stirred overnight. The reaction was quenched with 1M HCl (50 mL) and stirred for 30 min. The organic layer was separated, dried over $Na_2SO_4$ and concentrated in vacuo. Purification of the crude material by chromatography on silica eluting with 0-30% EtOAc in heptanes afforded the title compound as a white solid.

LC-MS (Method E): Rt 1.40 min (99% @215 nm)

$^1H$ NMR (400 MHz, DMSO-d6) δ 9.46 (s, 1H), 7.46 (d, J=6.0 Hz, 1H), 7.44-7.37 (m, 1H), 7.41-7.28 (m, 5H), 5.12 (s, 2H), 1.31 (s, 6H).

Step 2: 4-[2-(2-Benzyloxy-4-bromo-5-fluoro-phenyl)-2-methyl-propyl]morpholine

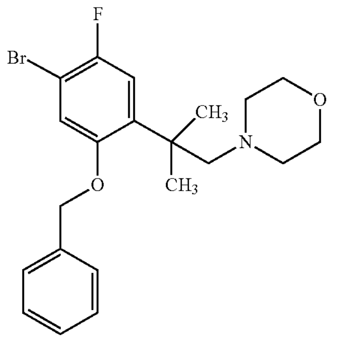 [SMILES: CC(C)(CN1CCOCC1)c1cc(F)c(Br)cc1OCc1ccccc1]

To a solution of 2-(2-benzyloxy-4-bromo-5-fluoro-phenyl)-2-methyl-propanal (step 1) (520 mg, 1.48 mmol) and AcOH (127 μL, 2.22 mmol) in THF (10 mL) was added morpholine (256 μL, 2.96 mmol) and sodium triacetoxyborohydride (377 mg, 1.78 mmol) and the resulting mixture was stirred at room temperature for 16 h. The resulting mixture was diluted with EtOAc (10 mL) and saturated sodium bicarbonate solution (20 mL). The phases were separated and the organic portion was washed with brine (20 mL), dried over $Na_2SO_4$ and concentrated in vacuo. Purification of the crude material by chromatography on silica eluting with 0-100% EtOAc in heptanes afforded the title compound as a colourless oil.

LC-MS (Method E): Rt 0.99 mins; MS m/z 422.1, 424.1=[M+H]+ (100% @215 nm)

$^1$H NMR (500 MHz, DMSO-d6) δ 7.52-7.46 (m, 2H), 7.43 (t, J=7.5 Hz, 2H), 7.40-7.33 (m, 1H), 7.34 (d, J=6.2 Hz, 1H), 7.14 (d, J=10.9 Hz, 1H), 5.12 (s, 2H), 3.40-3.34 (m, 4H), 2.59 (s, 2H), 2.21-2.11 (m, 4H), 1.26 (s, 6H).

Step 3: 2-[5-Benzyloxy-4-(1,1-dimethyl-2-morpholino-ethyl)-2-fluoro-phenyl]acetic acid The title compound was prepared from 4-[2-(2-benzyloxy-4-bromo-5-fluoro-phenyl)-2-methyl-propyl]morpholine (step 1) and potassium 3-ethoxy-3-oxo-propanoate analogously to Intermediate B step 5 substituting toluene with mesitylene as the solvent.

LC-MS (Method E): Rt 0.90 mins; MS m/z 402.5=[M+H]+ (83% @215 nm)

$^1$H NMR (400 MHz, DMSO-d6) δ 7.54-7.47 (m, 2H), 7.47-7.38 (m, 2H), 7.40-7.31 (m, 1H), 7.05 (d, J=6.7 Hz, 1H), 6.93 (d, J=11.8 Hz, 1H), 5.04 (s, 2H), 3.51 (s, 2H), 3.42-3.34 (m, 4H), 2.60 (s, 2H), 2.22-2.10 (m, 4H), 1.26 (s, 6H).

Intermediate F 2-(2-Bromo-4-tert-butyl-5-methoxy-phenyl)acetic acid

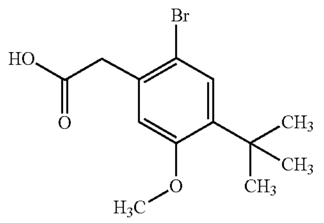

Step 1: (4-tert-Butyl-3-methoxy-phenyl)methanol

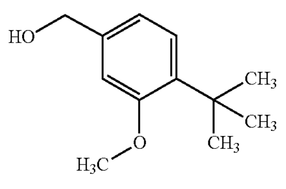

1M borane in THF (134.45 mL, 134.45 mmol) was added to a stirred solution of 4-tert-butyl-3-methoxy-benzoic acid (10 g, 48.02 mmol) in THF (100 mL) and the mixture was stirred at 50° C. for 1 hour. After cooling to room temperature, the resulting mixture was quenched cautiously with MeOH (10 mL) and the volatile solvents were removed in vacuo. Additional MeOH (10 mL) was added and the mixture was concentrated in vacuo to afford the title compound as a pale yellow oil.

LC-MS (Method E): Rt 1.14 min (97% @215 nm)

$^1$H NMR (500 MHz, DMSO-d6) δ 7.14 (d, J=7.9 Hz, 1H), 6.94 (s, 1H), 6.81 (d, J=7.8 Hz, 1H), 5.12 (s, 1H), 4.46 (s, 2H), 3.79 (s, 3H), 1.32 (s, 9H).

Step 2: 1-tert-Butyl-4-(chloromethyl)-2-methoxy-benzene

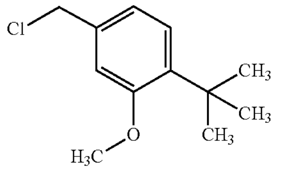

Thionyl chloride (6.09 mL, 83.88 mmol) in DCM (40 mL) was added dropwise to a cooled (0° C.) solution of (4-tert-butyl-3-methoxy-phenyl)methanol (step 1) (97%, 8.4 g, 41.94 mmol) and DMF (3.25 mL, 41.94 mmol) in DCM (80 mL) and the mixture was stirred at room temperature for 1 hour. The resulting mixture was concentrated in vacuo and the residue was partitioned between EtOAc (100 mL) and saturated $NaHCO_3$ (100 mL). The phases were separated and the organic portion was washed with brine (30 mL), dried over $Na_2SO_4$ and concentrated in vacuo to afford the title compound as a yellow oil.

LC-MS (Method E): Rt 1.38 min (79% @215 nm)

$^1$H NMR (500 MHz, DMSO-d6) δ 7.20 (d, J=7.9 Hz, 1H), 7.04 (d, J=1.7 Hz, 1H), 6.94 (dd, J=7.9, 1.7 Hz, 1H), 4.71 (s, 2H), 3.81 (s, 3H), 1.32 (s, 9H).

Step 3: 2-(4-tert-Butyl-3-methoxy-phenyl)acetonitrile

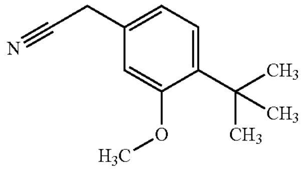

Sodium cyanide (1.88 g, 38.33 mmol) was added to a solution of 1-tert-butyl-4-(chloromethyl)-2-methoxy-benzene (step 2) (79%, 8.6 g, 31.94 mmol) in DMF (100 mL) and the mixture was stirred at room temperature overnight. The resulting mixture was diluted with EtOAc (100 mL) and washed with saturated aqueous sodium carbonate (300 mL), brine (50 mL), dried over $Na_2SO_4$ and concentrated in vacuo to afford the title compound as a brown oil.

LC-MS (Method E): Rt 1.25 min (84% @215 nm)

$^1$H NMR (500 MHz, DMSO-d6) δ 7.21 (d, J=7.9 Hz, 1H), 6.94 (d, J=1.5 Hz, 1H), 6.86 (dd, J=7.9, 1.7 Hz, 1H), 3.95 (s, 2H), 3.81 (s, 3H), 1.31 (s, 9H).

Step 4: 2-(4-tert-Butyl-3-methoxy-phenyl)acetic acid

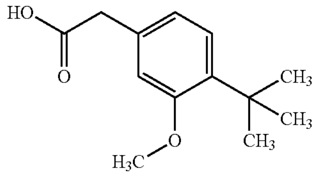 [SMILES: COc1cc(CC(=O)O)ccc1C(C)(C)C]

To a solution of 2-(4-tert-butyl-3-methoxy-phenyl)acetonitrile (step 3) (84%, 8.0 g, 33.06 mmol) in water (50 mL) was added lithium hydroxide hydrate (9.27 g, 165.29 mmol) and the mixture was heated at reflux overnight. After cooling to room temperature, the resulting mixture was acidified with conc. HCl solution and extracted with DCM (2×30 mL). The combined organic extracts were dried over $Na_2SO_4$ and concentrated in vacuo to afford the title compound as a pale yellow solid.

LC-MS (Method E): Rt 1.13 min (88% @215 nm)

$^1$H NMR (400 MHz, DMSO-d6) δ 12.27 (s, 1H), 7.13 (d, J=7.9 Hz, 1H), 6.86 (d, J=1.6 Hz, 1H), 6.75 (dd, J=7.9, 1.7 Hz, 1H), 3.78 (s, 3H), 3.50 (s, 2H), 1.31 (s, 9H).

Step 5: 2-(2-Bromo-4-tert-butyl-5-methoxy-phenyl)acetic acid 2-(4-tert-Butyl-3-methoxy-phenyl)acetic acid (step 4) (340 mg, 1.53 mmol) in acetic acid (2.19 mL) was treated with bromine (176 μL, 3.06 mmol) and stirred for 90 min. The reaction was quenched with saturated aqueous sodium thiosulfate and the resulting mixture was diluted with water (10 mL) and extracted with EtOAc (3×30 mL). The combined organic extracts were dried over $Na_2SO_4$ and concentrated in vacuo. Purification of the crude material by C18 reverse phase chromatography eluting with 10-100% MeCN in water afforded the title compound as a colourless solid.

LC-MS (Method E): Rt 1.24 min (97% @215 nm)

$^1$H NMR (500 MHz, DMSO-d6) δ 12.43 (s, 1H), 7.28 (s, 1H), 7.04 (s, 1H), 3.79 (s, 3H), 3.65 (s, 2H), 1.31 (s, 9H).

Intermediate G 2-(4-tert-Butyl-2-fluoro-5-methoxy-phenyl)acetic acid

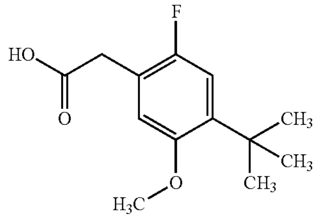 [SMILES: COc1cc(CC(=O)O)c(F)cc1C(C)(C)C]

2-(2-Fluoro-5-methoxy-phenyl)acetic acid (585 mg, 3.17 mmol) was treated with concentrated sulfuric acid (677 μL, 12.7 mmol) and tert-butanol (1.21 mL, 12.7 mmol) and stirred for 3 h. The reaction mixture was concentrated in vacuo. During transfer of material MeOH was used, which resulted in the formation of the methyl ester. The residue was purified by C18 reverse phase chromatography eluting with 10-100% MeCN in water. The resulting material was dissolved in 2M LiOH (7 mL) and THF (7 mL) and stirred for 2 h. The volatile solvents were removed in vacuo and the aqueous solution was acidified with 1M HCl. The suspension was extracted with DCM (3×20 mL) and the combined organic extracts were dried over $Na_2SO_4$ and concentrated in vacuo to afford the title compound as a pale yellow solid.

LC-MS (Method E): Rt 1.17 mins; MS m/z 239.0=[M−H]− (96% @215 nm)

$^1$H NMR (500 MHz, DMSO-d6) δ 12.42 (s, 1H), 6.94 (d, J=7.0 Hz, 1H), 6.92 (d, J=1.9 Hz, 1H), 3.77 (s, 3H), 3.57-3.53 (m, 2H), 1.31 (s, 9H).

Intermediate H

4-[2-(4-Bromo-2-fluoro-5-methoxyphenyl)acetamido]-N-[1-(trifluoromethyl)cyclo propyl]pyridine-2-carboxamide

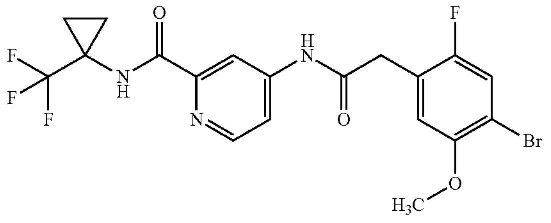 [SMILES: COc1cc(CC(=O)Nc2ccnc(C(=O)NC3(C(F)(F)F)CC3)c2)c(F)cc1Br]

To a solution of 2-(4-bromo-2-fluoro-5-methoxy-phenyl) acetic acid (Intermediate U step 1) (99%, 15.5 g, 58.33 mmol) in DMF (150 mL) was added DIPEA (15.28 mL, 87.5 mmol) and 4-amino-N-[1-(trifluoromethyl)cyclopropyl] pyridine-2-carboxamide (Intermediate A) (15.02 g, 61.25 mmol) and the mixture was cooled to 0° C. 50% T3P® solution in EtOAc (41.67 mL, 70. mmol) was added dropwise over 5 min and the reaction mixture was allowed to warm to room temperature gradually and stirred for 4 h. The resulting mixture was diluted with EtOAc (200 mL) and washed with brine (500 mL). The aqueous wash was back-extracted with EtOAc (200 mL) and the combined organic portions were washed with sat. $NaHCO_3$ (200 mL) and 1M HCl (200 mL). A precipitate formed which was filtered, washed with EtOAc (100 mL) and dried to yield a white solid. The solid was suspended in EtOAc (200 mL) and sat. $NaHCO_3$ (500 mL) was added. After stirring vigorously for 30 min, the organic layer was separated, dried over $Na_2SO_4$ and concentrated in vacuo to afford the title compound as a white solid.

LC-MS (Method G): Rt 1.01 min; MS m/z 490.0, 492.0=[M+H]+ (100% @215 nm)

1H NMR (500 MHz, DMSO-d6) δ 10.83 (s, 1H), 9.39 (s, 1H), 8.50 (d, J=5.6 Hz, 1H), 8.19 (d, J=1.8 Hz, 1H), 7.84 (dd, J=5.5, 2.2 Hz, 1H), 7.53 (d, J=8.8 Hz, 1H), 7.18 (d, J=6.6 Hz, 1H), 3.83 (s, 3H), 3.81 (s, 2H), 1.36-1.23 (m, 2H), 1.22-1.12 (m, 2H).

Intermediate I

4-[[2-(4-Bromo-2-fluoro-5-methoxy-phenyl)acetyl]amino]-N-tert-butyl-pyridine-2-carboxamide

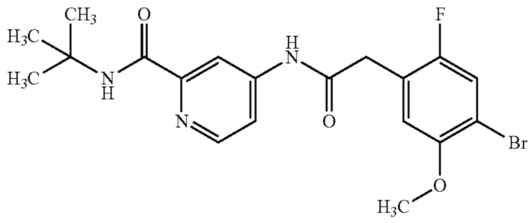 [SMILES: COc1cc(CC(=O)Nc2ccnc(C(=O)NC(C)(C)C)c2)c(F)cc1Br]

Step 1: Methyl 4-[[2-(4-bromo-2-fluoro-5-methoxy-phenyl)acetyl]amino]pyridine-2-carboxylate

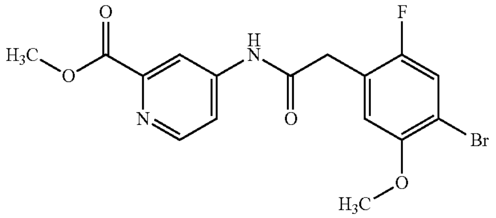 [SMILES: COC(=O)c1cc(NC(=O)Cc2cc(OC)c(Br)cc2F)ccn1]

To a stirred solution of 2-(4-bromo-2-fluoro-5-methoxy-phenyl)acetic acid (Intermediate U step 1)) (91%, 2.92 g, 10.09 mmol), methyl 4-aminopyridine-2-carboxylate (1.54 g, 10.09 mmol) and DIPEA (5.29 mL, 30.26 mmol) in 1,4-dioxane (20 mL) was added 50% T3P® solution in EtOAc (6.6 mL, 11.1 mmol) and the mixture was stirred at room temperature for 17 h. The resulting mixture was diluted with EtOAc (100 mL) and water (100 mL). The phases were separated and the aqueous layer was further extracted with EtOAc (60 mL). The organic extracts were combined, washed with water (2×100 mL), brine (100 mL), dried over $Na_2SO_4$ and concentrated in vacuo. The crude material was purified by chromatography on silica eluting with 0-100% EtOAc to afford the title compound as an off-white solid.

LC-MS (Method E): Rt 1.05 mins; MS m/z 397.0, 399.0=[M+H]+ (99% @215 nm)

$^1$H NMR (500 MHz, DMSO-d6) δ 10.82 (s, 1H), 8.55 (d, J=5.5 Hz, 1H), 8.29 (d, J=1.9 Hz, 1H), 7.76 (dd, J=5.5, 2.2 Hz, 1H), 7.52 (d, J=8.9 Hz, 1H), 7.17 (d, J=6.6 Hz, 1H), 3.86 (s, 3H), 3.82 (s, 3H), 3.80 (s, 2H).

Step 2: 4-[[2-(4-Bromo-2-fluoro-5-methoxy-phenyl)acetyl]amino]pyridine-2-carboxylic acid

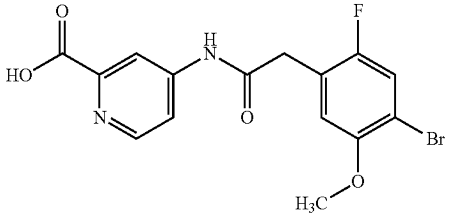 [SMILES: COc1cc(CC(=O)Nc2ccnc(C(=O)O)c2)c(F)cc1Br]

2M aq. LiOH (7.55 mL, 15.11 mmol) was added to a stirred solution of methyl 4-[[2-(4-bromo-2-fluoro-5-methoxy-phenyl)acetyl]amino]pyridine-2-carboxylate (step 1) (2 g, 5.04 mmol) in THF (10 mL) and the mixture was stirred at room temperature for 1 hour. The volatile solvent was removed in vacuo and the resulting aqueous layer was acidified to pH 3 with 1M aqueous HCl. The precipitate was collected by filtration and dried in a vacuum oven at 40° C. for 8 h to afford the title compound as an off-white solid.

LC-MS (Method E): Rt 0.91 mins; MS m/z 382.9, 384.9=[M+H]+ (97% @215 nm)

$^1$H NMR (500 MHz, DMSO-d6) δ 11.10 (s, 1H), 8.55 (d, J=5.6 Hz, 1H), 8.31 (d, J=2.0 Hz, 1H), 7.84 (dd, J=5.6, 2.1 Hz, 1H), 7.52 (d, J=8.8 Hz, 1H), 7.21 (d, J=6.5 Hz, 1H), 3.84 (s, 2H), 3.83 (s, 3H).

Step 3: 4-[[2-(4-Bromo-2-fluoro-5-methoxy-phenyl)acetyl]amino]-N-tert-butyl-pyridine-2-carboxamide To a solution of 4-[[2-(4-bromo-2-fluoro-5-methoxy-phenyl)acetyl]amino]pyridine-2-carboxylic acid (step 2) (930 mg, 2.43 mmol), 2-methylpropan-2-amine (306 μL, 2.91 mmol) and DIPEA (636 μL, 3.64 mmol) in DMF (5 mL) was added HATU (1 g, 2.67 mmol) and the mixture was stirred at room temperature for 1 hour. The resulting mixture was concentrated in vacuo and the residue partitioned between EtOAc (10 mL) and water (10 mL). The phases were separated and the organic portion was washed with water (2×10 mL), brine (10 mL), dried over $Na_2SO_4$ and concentrated in vacuo. The crude material was purified by chromatography on silica eluting with 0-100% EtOAc in heptanes to afford the title compound as an off-white solid.

LC-MS (Method E): Rt 1.28 mins; MS m/z 438.1, 440.0=[M+H]+ (100% @215 nm)

$^1$H NMR (500 MHz, DMSO-d6) δ 10.80 (s, 1H), 8.46 (d, J=5.5 Hz, 1H), 8.17 (d, J=1.9 Hz, 1H), 8.03 (s, 1H), 7.80 (dd, J=5.5, 2.2 Hz, 1H), 7.53 (d, J=8.8 Hz, 1H), 7.18 (d, J=6.6 Hz, 1H), 3.83 (s, 3H), 3.81 (s, 2H), 1.40 (s, 9H).

Intermediate J

Triethylammonium bis(catecholato)iodomethylsilicate

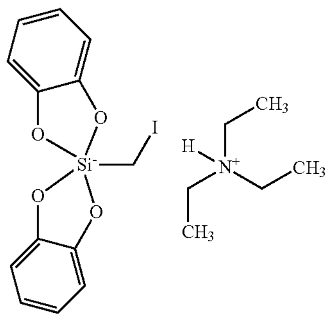

This compound was prepared according to the procedure described in J. Am. Chem. Soc. 2018, 140, 8037-8047. Redox-Neutral Photocatalytic Cyclopropanation via Radical/Polar Crossover.

Intermediate K 2-(4-tert-Butyl-2-chloro-5-methoxy-phenyl)acetic acid

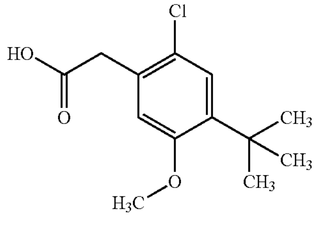 [SMILES: COc1cc(CC(=O)O)c(Cl)cc1C(C)(C)C]

Step 1: 2-(2-Chloro-5-methoxy-phenyl)acetic acid

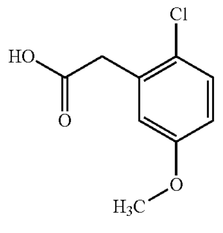

To a stirred solution of 2-(3-methoxyphenyl)acetic acid (10 g, 60.18 mmol) in DCM (301 mL) was added triphenylphosphine sulfide (1.77 g, 6.02 mmol) followed by N-chlorosuccinimide (9.64 g, 72.22 mmol) and the reaction mixture was stirred at room temperature for 20 hours. The resulting mixture was filtered through a silica plug washing through with TBME (2×500 mL). The filtrate was concentrated in vacuo and the residue dissolved in 1M NaOH (1 L) solution, stirring vigorously for 10 min. The aqueous mixture was extracted with TBME (2×200 mL) to remove the organic impurities, then acidified to pH 1 using 6 M HCl and extracted with DCM (2×200 mL). The DCM extracts were washed with brine, dried over $Na_2SO_4$ and concentrated in vacuo. The crude material was purified further by hot filtration from boiling heptanes. The solids were suspended in heptanes (1 L) and heated to reflux until all solids had dissolved while an insoluble oily residue remained. The product crystallised from the hot heptane solution once decanted away from the insoluble oily impurity. The crystallised solid was filtered and dried in a vacuum oven to afford the title compound as a pale yellow crystalline solid.

LC-MS (Method E): Rt 1.00 min; (98% @215 nm)

$^1$H NMR (400 MHz, DMSO-d6) δ 12.43 (s, 1H), 7.32 (d, J=8.8 Hz, 1H), 6.99 (d, J=3.1 Hz, 1H), 6.87 (dd, J=8.8, 3.1 Hz, 1H), 3.74 (s, 3H), 3.66 (s, 2H).

Step 2: 2-(4-tert-butyl-2-chloro-5-methoxy-phenyl)acetic acid

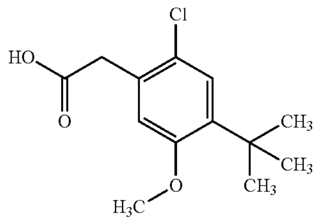 [SMILES: COc1cc(CC(=O)O)c(Cl)cc1C(C)(C)C]

2-(2-Chloro-5-methoxy-phenyl)acetic acid (step 1) (20.0 g, 99.69 mmol) in DCE (498.45 mL) was treated with t-butanol (114.41 mL, 1196.29 mmol) followed by concentrated sulfuric acid (63.77 mL, 1196.29 mmol) added dropwise via a dropping funnel over 40 min at room temperature and stirred for 1 hr. Additional t-butanol (38 mL) and concentrated sulfuric acid (21 mL) were added at 90 minute intervals until the full consumption of starting material was observed. The layers were separated, then the sulphuric acid layer was extracted with DCE (2×200 mL), and the combined DCE layers were concentrated in vacuo (heating at 60° C. and high vacuum required). The resulting solid was triturated with heptane followed by 1M HCl and then washed with water to afford the title compound as an off-white solid.

LC-MS (Method A): Rt 3.65 min; (98% @215 nm)

1H NMR (500 MHz, DMSO-d6) δ 12.42 (br. s, 1H), 7.14 (s, 1H), 7.03 (s, 1H), 3.80 (s, 3H), 3.64 (s, 2H), 1.31 (s, 9H).

Intermediate L

2-[5-Benzyloxy-2-fluoro-4-(2-hydroxy-1,1-dimethyl-ethyl)phenyl]acetic acid

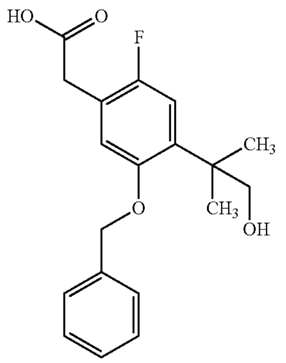 [SMILES: CC(C)(CO)c1cc(F)c(CC(=O)O)cc1OCc1ccccc1]

Step 1: 2-(2-Benzyloxy-4-bromo-5-fluoro-phenyl)-2-methyl-propan-1-ol

Sodium borohydride (96.17 mg, 2.54 mmol) was added to a stirred solution of 2-(2-benzyloxy-4-bromo-5-fluoro-phenyl)-2-methyl-propanal (Intermediate E step 1) (72%, 620 mg, 1.27 mmol) in MeOH (10 mL) and the mixture was stirred at room temperature overnight. The solvent was removed in vacuo then treated with saturated aq. $NH_4Cl$ (20 mL), stirring for 30 min. EtOAc (20 mL) was added and the organic portion was separated, dried over $Na_2SO_4$ and concentrated in vacuo to afford the title compound as a colourless oil.

LC-MS (Method E): Rt 1.32 mins; MS m/z 351.0, 353.0=[M−H]− (89% @215 nm)

$^1$H NMR (500 MHz, DMSO-d6) δ 7.50-7.45 (m, 2H), 7.46-7.39 (m, 2H), 7.39-7.32 (m, 1H), 7.33 (d, J=6.2 Hz, 1H), 7.18 (d, J=11.1 Hz, 1H), 5.13 (s, 2H), 4.59 (t, J=5.5 Hz, 1H), 3.59 (d, J=5.4 Hz, 2H), 1.23 (s, 6H).

Step 2: [2-(2-Benzyloxy-4-bromo-5-fluoro-phenyl)-2-methyl-propyl]acetate

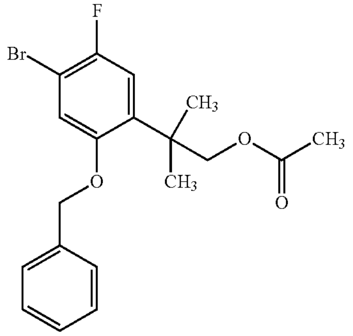 [SMILES: CC(=O)OCC(C)(C)c1cc(F)c(Br)cc1OCc1ccccc1]

A solution of 2-(2-benzyloxy-4-bromo-5-fluoro-phenyl)-2-methyl-propan-1-ol (step 1) (85%, 520 mg, 1.25 mmol) in DCM (10 mL) was treated with DMAP (15 mg, 0.13 mmol), acetic anhydride (237 μL, 2.5 mmol) and TEA (349 μL, 2.5 mmol) and the mixture was stirred at room temperature for 4 h. The resulting mixture was washed with saturated $Na_2CO_3$ (20 mL) and the organic layer was separated, dried over $Na_2SO_4$ and concentrated in vacuo. Purification of the crude material by chromatography on silica eluting with 0-100% EtOAc in heptanes afforded the title compound as a colourless oil.

LC-MS (Method E): Rt 1.47 min (94% @215 nm)

$^1$H NMR (500 MHz, DMSO-d6) δ 7.49-7.44 (m, 2H), 7.42 (t, J=7.4 Hz, 2H), 7.40-7.32 (m, 2H), 7.17 (d, J=10.8 Hz, 1H), 5.15 (s, 2H), 4.28 (s, 2H), 1.90 (s, 3H), 1.30 (s, 6H).

Step 3: 2-[5-Benzyloxy-2-fluoro-4-(2-hydroxy-1,1-dimethyl-ethyl)phenyl]acetic acid The title compound was prepared from potassium 3-ethoxy-3-oxo-propanoate and [2-(2-benzyloxy-4-bromo-5-fluoro-phenyl)-2-methyl-propyl]acetate (step 2) analogously to Intermediate B step 5.

LC-MS (Method E): Rt 1.16 mins; MS m/z 663.4=[2M−H]− (96% @215 nm)

$^1$H NMR (500 MHz, DMSO-d6) δ 12.44 (br. s, 1H), 7.50-7.47 (m, 2H), 7.44-7.40 (m, 2H), 7.37-7.33 (m, 1H), 7.05 (d, J=6.7 Hz, 1H), 6.99 (d, J=11.9 Hz, 1H), 5.05 (s, 2H), 4.56 (t, J=5.3 Hz, 1H), 3.59 (d, J=5.1 Hz, 2H), 3.55 (s, 2H), 1.24 (s, 6H).

Intermediate M

2-[5-Benzyloxy-4-(4-cyanotetrahydropyran-4-yl)-2-fluoro-phenyl]acetic acid

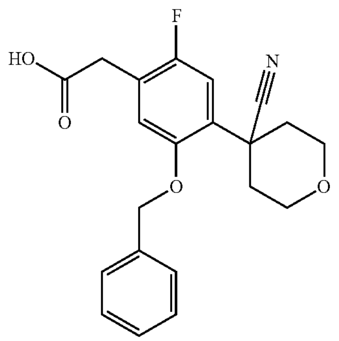 [SMILES: N#CC1(c2cc(F)c(CC(=O)O)cc2OCc2ccccc2)CCOCC1]

Step 1: 4-(2-benzyloxy-4-bromo-5-fluoro-phenyl)tetrahydropyran-4-carbonitrile

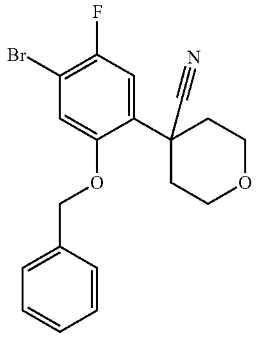 [SMILES: N#CC1(c2cc(F)c(Br)cc2OCc2ccccc2)CCOCC1]

To a cooled (0° C.) solution of 2-(2-benzyloxy-4-bromo-5-fluoro-phenyl)acetonitrile (Intermediate C step 5) (1 g, 3.12 mmol) in DMF (40 mL) under nitrogen was added NaH (60% dispersion in mineral oil, 262 mg, 6.56 mmol). After stirring for 5 min, the mixture was treated dropwise over 10 min with 1-bromo-2-(2-bromoethoxy)ethane (0.8 g, 3.44 mmol). The reaction mixture was allowed to warm to room temperature, stirred for 1 h and then heated to 65° C. for 2 h. The resulting mixture was cooled to 0° C. and the reaction quenched by careful addition of water (10 mL) under nitrogen. Further water (200 mL) addition yielded a precipitate which was stirred at room temperature for 20 min. The solid was collected by filtration, washed with water (200 mL) and dried a vacuum oven at 40° C. for 3 h to afford the title compound as a beige solid.

LC-MS (Method E): Rt 1.33 mins; MS (90% @215 nm)

$^1$H NMR (500 MHz, DMSO-d6) δ 7.54 (d, J=6.3 Hz, 3H), 7.43-7.31 (m, 4H), 5.29 (s, 2H), 3.98-3.92 (m, 2H), 3.66 (t, J=11.5 Hz, 2H), 2.29 (d, J=12.6 Hz, 2H), 1.99 (td, J=13.1, 4.2 Hz, 2H).

Step 2: 2-[5-Benzyloxy-4-(4-cyanotetrahydropyran-4-yl)-2-fluoro-phenyl]acetic acid To a solution of 4-(2-benzyloxy-4-bromo-5-fluoro-phenyl)tetrahydropyran-4-carbonitrile (step 1) (90%, 750 mg, 1.73 mmol) in THF (10 mL) was added $Pd(dba)_2$ (20 mg, 0.03 mmol) followed by Q-Phos (25 mg, 0.03 mmol). The mixture was sparged with nitrogen for 10 min and treated with 0.5M bromo-(2-tert-butoxy-2-oxo-ethyl)zinc in THF (3.46 mL, 1.73 mmol) was added. After stirring at 50° C. under nitrogen for 1.5 h, further portions of $Pd(dba)_2$ (20 mg, 0.03 mmol) and Q-Phos (25 mg, 0.03 mmol) were added and stirring continued at 60° C. overnight. The resulting was diluted with EtOAc (25 mL) and washed with water (20 mL), 1M HCl (20 mL), dried over $Na_2SO_4$ and concentrated in vacuo. Purification of the crude material by chromatography on silica eluting with 0-100% EtOAc in heptanes afforded a yellow oil. The oil was dissolved in DCM (15 mL), treated with TFA (1.99 mL, 25.94 mmol) and stirred at room temperature overnight. The resulting mixture was concentrated in vacuo and the crude residue was dissolved in EtOAc (25 mL). The organic mixture was washed with 2M NaOH (2×25 mL). The basic aqueous washes were combined, re-acidified with 6M HCl to pH 4-5 and then back extracted with EtOAc (3×25 mL). The combined organic extracts were dried over $Na_2SO_4$ and concentrated in vacuo to afford the title compound as a pale yellow oil.

LC-MS (Method E): Rt 1.12 mins; MS m/z 370.1=[M+H]+ (97% @215 nm)

$^1$H NMR (500 MHz, DMSO-d6) δ 7.55 (d, J=7.2 Hz, 2H), 7.43-7.38 (m, 2H), 7.35-7.31 (m, 1H), 7.24 (d, J=6.4 Hz, 1H), 7.15 (d, J=10.9 Hz, 1H), 5.20 (s, 2H), 3.98-3.92 (m, 2H), 3.66 (t, J=11.6 Hz, 2H), 3.59 (s, 2H), 2.29 (d, J=12.7 Hz, 2H), 2.03-1.96 (m, 2H).

Intermediate N

2-[5-Benzyloxy-2-fluoro-4-[2-(trifluoromethyl)oxetan-2-yl]phenyl]acetic acid

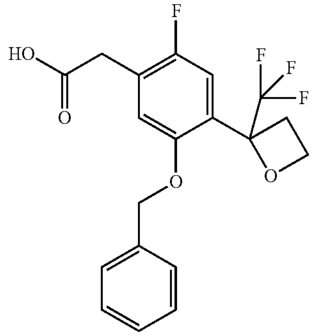 [SMILES: O=C(O)Cc1cc(OCc2ccccc2)c(C2(C(F)(F)F)CCO2)cc1F]

Step 1: Methyl 2-benzyloxy-4-bromo-5-fluoro-benzoate

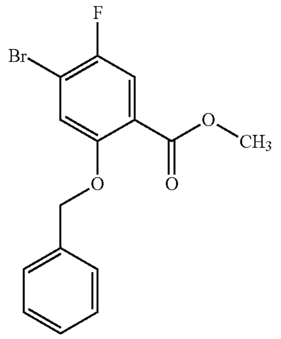 [SMILES: COC(=O)c1cc(F)c(Br)cc1OCc1ccccc1]

Benzyl bromide (2.29 mL, 19.27 mmol) was added to a stirred mixture of methyl 4-bromo-5-fluoro-2-hydroxy-benzoate (4 g, 16.06 mmol) and $K_2CO_3$ (5.55 g, 40.16 mmol) in DMF (50 mL) and the reaction mixture was stirred at 80° C. for 1 hour. After cooling to room temperature, the resulting mixture was partitioned between EtOAc (150 mL) and water (150 mL). The organic portion was separated and the aqueous layer was further extracted with EtOAc (50 mL). The combined organics were washed with water (2×50 mL), brine (150 mL), dried over $Na_2SO_4$ and concentrated in vacuo. Purification by chromatography on silica eluting with 0-60% EtOAc in heptanes afforded the title compound as a colourless oil.

LC-MS (Method E): Rt 1.37 min; (99% @215 nm)

$^1$H NMR (500 MHz, DMSO-d6) δ 7.66 (d, J=8.8 Hz, 1H), 7.62 (d, J=5.6 Hz, 1H), 7.50-7.44 (m, 2H), 7.44-7.37 (m, 2H), 7.36-7.29 (m, 1H), 5.23 (s, 2H), 3.81 (s, 3H).

Step 2: (2-Benzyloxy-4-bromo-5-fluoro-phenyl)methanol

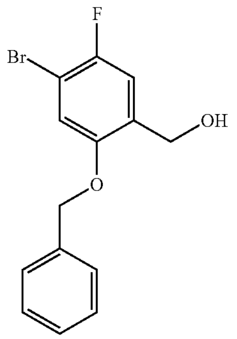 [SMILES: OCc1cc(F)c(Br)cc1OCc1ccccc1]

To a stirred solution of methyl 2-benzyloxy-4-bromo-5-fluoro-benzoate (step 1) (5.4 g, 15.92 mmol) in THF (100 mL) was added $LiBH_4$ (11.94 mL, 47.77 mmol) and the reaction mixture was stirred at room temperature overnight. A further portion of $LiBH_4$ (11.94 mL, 47.77 mmol) was added and stirring continued overnight. The resulting mixture was quenched with ice (~50 mL), stirred for 30 min and then EtOAc (50 mL) was added. The organic layer was separated, dried over $Na_2SO_4$ and concentrated in vacuo to afford the title compound as a yellow oil.

LC-MS (Method E): Rt 1.24 min; (94% @215 nm)

$^1$H NMR (500 MHz, DMSO-$d_6$) δ 7.46-7.36 (m, 4H), 7.37-7.30 (m, 2H), 7.30 (d, J=9.4 Hz, 1H), 5.29 (t, J=5.6 Hz, 1H), 5.14 (s, 2H), 4.49 (d, J=5.6 Hz, 2H).

Step 3: 1-(2-Benzyloxy-4-bromo-5-fluoro-phenyl)-2,2,2-trifluoro-ethanol

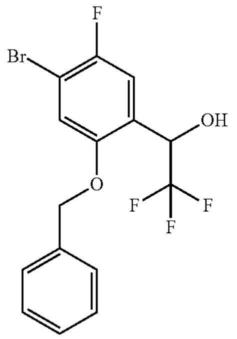 [SMILES: OC(c1cc(F)c(Br)cc1OCc1ccccc1)C(F)(F)F]

To a solution of (2-benzyloxy-4-bromo-5-fluoro-phenyl)methanol (step 2) (1 g, 3.21 mmol) in toluene (50 mL) was added manganese dioxide (1.1 g, 12.86 mmol). The reaction mixture was stirred at 90° C. for 1 hour and then left to stir at room temperature overnight. The resulting mixture was filtered through Celite® (filter material) and washed with toluene. The filtrate was concentrated in vacuo and the residue was re-dissolved in THF (25 mL) and treated with trimethyl(trifluoromethyl)silane (914 mg, 6.43 mmol). After stirring for 5 min, 1M TBAF in THF (47 μL, 0.16 mmol) was added and the mixture was stirred at room temperature for 2 h. The resulting mixture was cooled to 0° C. and 2M HCl (20 mL) was added. After stirring at room temperature for 1 hour, the mixture was partitioned between EtOAc (100 mL)

and water (100 mL). The phases were separated and the organics were washed with brine (2×50 mL), dried over $Na_2SO_4$ and concentrated in vacuo. The crude product was purified by chromatography on silica eluting with 0-50% EtOAc in heptanes to afford the title compound as a yellow oil.

LC-MS (Method E): Rt 1.39 min; (98% @215 nm)

$^1H$ NMR (500 MHz, DMSO-$d_6$) δ 7.52 (d, J=5.7 Hz, 1H), 7.44-7.33 (m, 6H), 6.99 (d, J=6.0 Hz, 1H), 5.44-5.36 (m, 1H), 5.19 (s, 2H).

Step 4: 1-(2-Benzyloxy-4-bromo-5-fluoro-phenyl)-2,2,2-trifluoro-ethanone

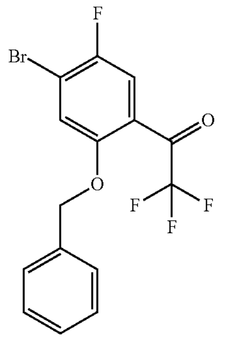 [SMILES: O=C(c1cc(F)c(Br)cc1OCc1ccccc1)C(F)(F)F]

To a solution of 1-(2-benzyloxy-4-bromo-5-fluoro-phenyl)-2,2,2-trifluoro-ethanol (step 3) (700 mg, 1.85 mmol) in DCM (40 mL) was added Dess-Martin periodinane (979 mg, 2.31 mmol) followed by TFA (0.14 mL, 1.85 mmol) and the mixture was stirred at room temperature for 5 h. The resulting reaction mixture was filtered and washed through with DCM (~20 mL). The filtrate was washed with sat. $NaHCO_3$ (2×25 mL), dried over $Na_2SO_4$ and concentrated in vacuo. Purification by chromatography on silica eluting with 0-100% EtOAc in heptanes afforded the title compound.

LC-MS (Method G): Rt 1.16 min; MS m/z 375.1, 377.1=[M+H]+ (70% @215 nm)

$^1H$ NMR (500 MHz, DMSO-$d_6$) δ 7.81 (d, J=5.5 Hz, 1H), 7.68 (d, J=8.5 Hz, 1H), 7.45-7.32 (m, 5H), 5.28 (s, 2H).

Step 5: 2-(2-Benzyloxy-4-bromo-5-fluoro-phenyl)-2-(trifluoromethyl)oxetane

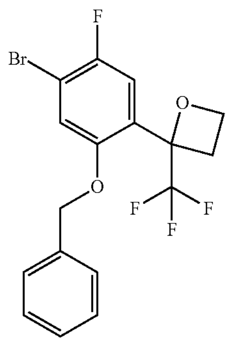 [SMILES: Fc1cc(C2(C(F)(F)F)CCO2)c(OCc2ccccc2)cc1Br]

Trimethylsulfoxonium iodide (490 mg, 2.23 mmol) and potassium t-butoxide (250 mg, 2.23 mmol) were dissolved in DMSO (10 mL) and stirred for 10 min. To this mixture was added dropwise a solution of 1-(2-benzyloxy-4-bromo-5-fluoro-phenyl)-2,2,2-trifluoro-ethanone (step 4) (70%, 400 mg, 0.74 mmol) in DMSO (2 mL) and the mixture was stirred at room temperature under an inert atmosphere for 7 h. The resulting mixture was diluted in EtOAc (50 mL) and washed with water (2×25 mL), brine (25 mL), dried over $Na_2SO_4$ and concentrated in vacuo. Purification by chromatography on silica eluting with 0-100% EtOAc in heptanes afforded the title compound as a light yellow solid.

LC-MS (Method E): Rt 1.53 min; (95% @215 nm)

$^1H$ NMR (500 MHz, DMSO-$d_6$) δ 7.58 (d, J=5.7 Hz, 1H), 7.44-7.39 (m, 4H), 7.38-7.33 (m, 1H), 7.25 (d, J=9.0 Hz, 1H), 5.17 (s, 2H), 4.72-4.66 (m, 1H), 4.51 (dt, J=9.3, 5.9 Hz, 1H), 3.15 (dt, J=12.6, 8.7 Hz, 1H), 3.04-2.97 (m, 1H).

Step 6: 2-[5-Benzyloxy-2-fluoro-4-[2-(trifluoromethyl)oxetan-2-yl]phenyl]acetic acid The title compound was prepared from 2-(2-benzyloxy-4-bromo-5-fluoro-phenyl)-2-(trifluoromethyl) oxetane (step 5) and 0.5M bromo-(2-tert-butoxy-2-oxo-ethyl)zinc in THF analogously to Intermediate M step 2.

LC-MS (Method G): Rt 1.02 min; MS m/z 767.3=[2M−H]− (90% @215 nm)

$^1H$ NMR (400 MHz, DMSO-$d_6$) δ 12.60 (br. s, 1H), 7.46-7.31 (m, 5H), 7.25 (d, J=6.1 Hz, 1H), 7.07 (d, J=10.0 Hz, 1H), 5.09 (s, 2H), 4.74-4.65 (m, 1H), 4.53-4.46 (m, 1H), 3.65 (s, 2H), 3.19-3.10 (m, 1H), 3.06-2.97 (m, 1H).

Intermediate O 2-(4-Bromo-2-fluoro-5-methoxyphenyl)acetonitrile

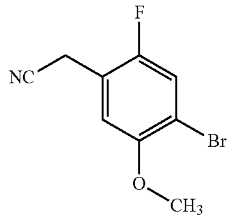

Step 1: 2-Bromo-4-fluoro-5-methylphenol

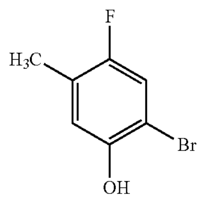

To a solution of 4-fluoro-3-methylphenol (10 g, 79.3 mmol) in DCM (79 mL) at −78° C. was added dropwise bromine (4.09 mL, 79.3 mmol). After 1 hour, 1M aqueous sodium thiosulfate was added and the mixture allowed to warm to room temperature. The organic layer was separated, dried over $Na_2SO_4$ and concentrated in vacuo to afford the title compound as a pale yellow solid. Regioselectivity >10:1.

$^1$H NMR (400 MHz, Chloroform-d) δ 7.12 (d, J=8.6 Hz, 1H), 6.84 (dd, J=6.8, 0.9 Hz, 1H), 5.27 (s, 1H), 2.20 (dd, J=2.1, 0.8 Hz, 3H).

Step 2: 1-Bromo-5-fluoro-2-methoxy-4-methylbenzene

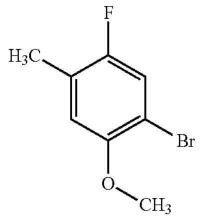

Iodomethane (7.3 mL, 117 mmol) was added dropwise to a mixture of 2-bromo-4-fluoro-5-methylphenol (step 1) (16 g, 78.0 mmol) and potassium carbonate (21.6 g, 156 mmol) in DMF (156 mL) and the mixture was stirred vigorously overnight. After filtration, the filtrate was partitioned between water and $Et_2O$. The phases were separated, and the organic phase was washed with water (×3), brine, dried over $MgSO_4$ and concentrated in vacuo. The residue was purified by chromatography on silica eluting with n-pentane to afford the title compound as a pale yellow oil.

$^1$H NMR (400 MHz, Chloroform-d) δ 7.21 (d, J=8.6 Hz, 1H), 6.72-6.68 (m, 1H), 3.85 (s, 3H), 2.24 (dd, J=2.1, 0.7 Hz, 3H).

Step 3: 1-Bromo-4-(bromomethyl)-5-fluoro-2-methoxybenzene

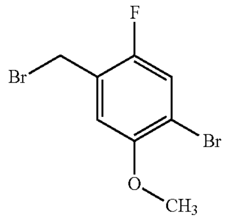

To stirred solution of 1-bromo-5-fluoro-2-methoxy-4-methylbenzene (step 2) (2 g, 9.13 mmol) in $CCl_4$ (45.7 mL) was added N-bromosuccinimide (1.63 g, 9.13 mmol) and azobisisobutyronitrile (150 mg, 0.913 mmol) at room temperature. The resulting mixture was heated to reflux for 3 h. After cooling to room temperature, the mixture was poured onto ice cold water and extracted with DCM (×2). The combined organic layers were dried over $Na_2SO_4$ and concentrated in vacuo. The crude product was purified by chromatography on silica eluting with 0-10% EtOAc in cyclohexane to afford the title compound as an off-white solid.

$^1$H NMR (400 MHz, Chloroform-d) δ 7.30 (d, J=8.7 Hz, 1H), 6.88 (d, J=6.4 Hz, 1H), 4.46 (d, J=1.2 Hz, 2H), 3.89 (s, 3H).

Step 4: 2-(4-Bromo-2-fluoro-5-methoxyphenyl)acetonitrile

To a solution of 1-bromo-4-(bromomethyl)-5-fluoro-2-methoxybenzene (step 3) (4.38 g, 14.7 mmol) in 10:1 DMF:water (34 mL) was added KCN (1.05 g, 16.2 mmol) and tetrabutylammonium bromide (5.21 g, 16.2 mmol) and reaction mixture was stirred at room temperature for 16 h. The resulting mixture was diluted with water (100 mL) and extracted with $Et_2O$ (3×50 mL). The combined organic extracts were washed with 50% sat. $NaHCO_3$ (3×100 mL), dried over $Na_2SO_4$ and concentrated in vacuo. The crude product was purified by chromatography on silica eluting with 0-100% EtOAc in cyclohexane to afford the title compound as a yellow solid.

$^1$H NMR (400 MHz, Chloroform-d) δ 7.26 (d, J=8.7 Hz, 1H), 6.86 (d, J=6.4 Hz, 1H), 3.84 (s, 3H), 3.69-3.64 (m, 2H).

Intermediate P 2-(6-Fluoro-4,4-dimethyl-2-oxo-chroman-7-yl)acetic acid

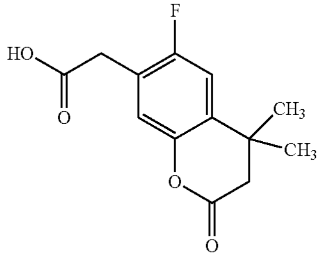 [SMILES: CC1(C)CC(=O)Oc2cc(CC(=O)O)c(F)cc21]

Step 1: 2-(2-Fluoro-5-hydroxy-phenyl)acetic acid

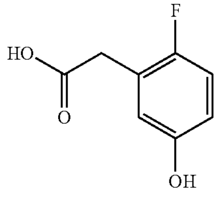 [SMILES: O=C(O)Cc1cc(O)ccc1F]

A solution of 2-(2-fluoro-5-methoxy-phenyl)acetic acid (2.0 g, 10.86 mmol) in DCM (30 mL) and 1M $BBr_3$ in DCM (21.72 mL, 21.72 mmol) was stirred at room temperature overnight. A further portion of 1M $BBr_3$ in DCM (21.72 mL, 21.72 mmol) was added and the reaction mixture was stirred at room temperature over the weekend. The resulting precipitate was filtered, washed with DCM (100 mL) and dried in vacuo to afford the title compound as a pale yellow solid.

LC-MS (Method G): Rt 0.52 min; MS m/z 339.1=(85% @215 nm)

$^1$H NMR (500 MHz, DMSO-d6) δ 12.37 (s, 1H), 9.30 (s, 1H), 6.94 (t, J=9.1 Hz, 1H), 6.72-6.65 (m, 1H), 6.67-6.59 (m, 1H), 3.50 (s, 2H).

Step 2: Methyl 2-(6-fluoro-4,4-dimethyl-2-oxo-chroman-7-yl)acetate

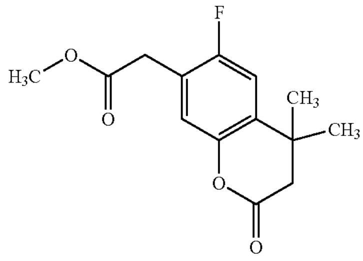

A solution of 2-(2-fluoro-5-hydroxy-phenyl)acetic acid (step 1) (85%, 710 mg, 3.55 mmol) and methyl 3-methylbut-2-enoate (714 mg, 6.26 mmol) in methanesulfonic acid (5.42 mL, 83.46 mmol) was stirred at 70° C. for 40 h. After cooling to room temperature, the mixture was poured onto ice (20 g) and EtOAc (30 mL) was added. The organic layer was separated, dried over $Na_2SO_4$ and concentrated in vacuo. Purification by chromatography on silica eluting with 0-100% EtOAc in heptanes followed by 0-100% MeOH in EtOAc and then C18 reverse phase chromatography eluting with 10-100% MeCN in water (+0.1% formic acid) afforded the title compound as a pale yellow solid.

LC-MS (Method E): Rt 1.14 min; (100% @215 nm)

$^1$H NMR (500 MHz, DMSO-d6) δ 7.27 (d, J=10.3 Hz, 1H), 7.11 (d, J=6.5 Hz, 1H), 3.73 (s, 2H), 3.63 (s, 3H), 2.73 (s, 2H), 1.27 (s, 6H).

Step 3: 2-(6-Fluoro-4,4-dimethyl-2-oxo-chroman-7-yl)acetic acid

To a solution of lithium hydroxide (189 mg, 7.89 mmol) in water (2 mL) was added methyl 2-(6-fluoro-4,4-dimethyl-2-oxo-chroman-7-yl)acetate (step 2) (420 mg, 1.58 mmol) in THF (2 mL) and the reaction mixture was stirred at room temperature for 4 h. The resulting mixture was concentrated in vacuo to remove the organics and then diluted with EtOAc (20 mL). The mixture was acidified with 1M HCl to pH 1 and the organic portion was separated, dried over $Na_2SO_4$ and concentrated in vacuo to afford title compound as a pale yellow solid.

LC-MS (Method I: Rt 0.28 min; MS m/z 251.3=[M−H]− (100% @215 nm)

$^1$H NMR (500 MHz, DMSO-d6) δ 12.53 (s, 1H), 7.25 (d, J=10.3 Hz, 1H), 7.09 (d, J=6.5 Hz, 1H), 3.61 (s, 2H), 2.72 (s, 2H), 1.27 (s, 6H).

Intermediate Q

2-[2-Bromo-5-methoxy-4-(2-methoxy-1,1-dimethyl-2-oxo-ethyl)phenyl]acetic acid

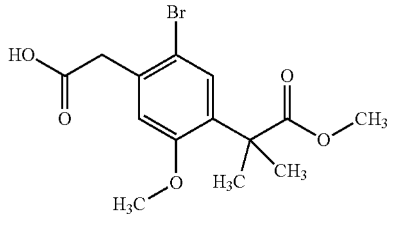 [SMILES: COC(=O)C(C)(C)c1cc(Br)c(CC(=O)O)cc1OC]

A cooled (0° C.) solution of methyl 2-[4-(2-tert-butoxy-2-oxo-ethyl)-2-methoxy-phenyl]-2-methyl-propanoate (Intermediate T step 3) (811 mg, 2.52 mmol) in MeCN (10 mL) was treated dropwise with a bromine (0.17 mL, 3.02 mmol) over a period of 10 min. The resulting mixture was allowed to warm to room temperature gradually without removing the ice bath and then left to stir for 16 h. Aqueous saturated sodium sulphite solution (20 mL) was added slowly to the mixture and stirred for 10 min. The resulting solution was diluted with brine (50 mL) and extracted with EtOAc (50 mL). The organic portion was separated, dried over $Na_2SO_4$ and concentrated in vacuo. Purification by chromatography on silica eluting with 0-70% EtOAc in hepanes afforded the title compound as an off-white gum.

LC-MS (Method H): Rt 1.31 min; MS m/z 345, 347=[M+H]+ (96% @215 nm)

$^1$H NMR (500 MHz, DMSO-$d_6$) δ 12.53 (br. s, 1H), 7.38 (s, 1H), 7.06 (s, 1H), 3.70 (s, 3H), 3.68 (s, 2H), 3.53 (s, 3H), 1.40 (s, 6H).

Intermediate R

2-[5-Benzyloxy-2-fluoro-4-[2,2,2-trifluoro-1-(hydroxymethyl)ethyl]phenyl]acetic acid

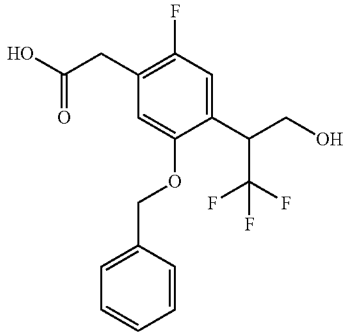 [SMILES: O=C(O)Cc1cc(OCc2ccccc2)c(C(CO)C(F)(F)F)cc1F]

Step 1: 4-Bromo-5-fluoro-2-methoxy-benzaldehyde

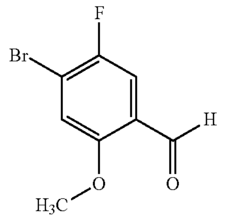

To a cooled (0° C.) solution of 2-bromo-1-fluoro-4-methoxy-benzene (7.35 g, 35.85 mmol) in dry DCM (125 mL) was added $TiCl_4$ (3.94 mL, 35.85 mmol) and the mixture was stirred at 0° C. for 15 min. Dichloro(methoxy)methane (4.87 mL, 53.78 mmol) was added followed by additional $TiCl_4$ (3.94 mL, 35.85 mmol) and the reaction mixture was stirred for 1 h. The resulting mixture was poured onto ice water (~300 mL), stirred vigorously for 15 min and the phases were separated. The aqueous portion was extracted with DCM (150 mL) and the combined organic extracts were dried over $Na_2SO_4$ and concentrated in vacuo. The residue was suspended in hot EtOAc (100 mL) and filtered through a sinter pad rinsing through with EtOAc. The filtrate was concentrated in vacuo and the residue was recrystalised from EtOAc (~20 mL) to afford the title compound as a white crystalline solid.

LC-MS (Method G): Rt 0.92 min; (97% @215 nm)

$^1$H NMR (400 MHz, DMSO-d6) δ 10.27-10.22 (m, 1H), 7.64 (d, J=5.3 Hz, 1H), 7.55 (d, J=8.4 Hz, 1H), 3.95 (s, 3H).

Step 2: 4-Bromo-5-fluoro-2-hydroxy-benzaldehyde

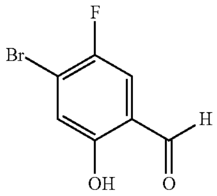 [SMILES: O=Cc1cc(F)c(Br)cc1O]

To a cooled (0° C.) solution of 4-bromo-5-fluoro-2-methoxy-benzaldehyde (step 1) (4.0 g, 17.17 mmol) in dry DCM (60 mL) was added dropwise 1M $BBr_3$ in DCM (25.75 mL, 25.75 mmol). The reaction mixture was allowed to warm to room temperature and stirred for 18 h.

The resulting mixture was cooled to 0° C., water (50 mL) was slowly added and the mixture was stirred vigorously for 10 min. The phases were separated and the aqueous was extracted with DCM (50 mL). The combined organic extracts were concentrated in vacuo to give a pale purple solid which was dissolved in EtOAc (30 mL). Saturated sodium bicarbonate solution (30 mL) was added and the mixture was stirred vigorously for 10 min. The phases were separated and the organic portion was washed with brine (30 mL), dried over $Na_2SO_4$ and concentrated in vacuo to afford the title compound as a pale beige solid.

LC-MS (Method E): Rt 1.14 min; (100% @215 nm)

MS18, no ionisation, RT=1.14, UV 100%

$^1$H NMR (400 MHz, DMSO-d6) δ 10.63 (br. s, 1H), 10.23-10.20 (m, 1H), 7.50 (d, J=8.6 Hz, 1H), 7.31 (d, J=5.6 Hz, 1H).

Step 3: 2-Benzyloxy-4-bromo-5-fluoro-benzaldehyde

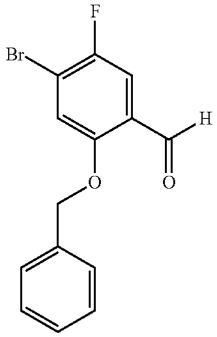 [SMILES: O=Cc1cc(F)c(Br)cc1OCc1ccccc1]

To a mixture of 4-bromo-5-fluoro-2-hydroxy-benzaldehyde (step 2) (100%, 3.68 g, 16.81 mmol) and $K_2CO_3$ (4.65 g, 33.61 mmol) in MeCN (75 mL) was added bromomethylbenzene (2.2 mL, 18.49 mmol) and the mixture was stirred at room temperature for 4 h 30 min. The resulting mixture was diluted with EtOAc (300 mL) and water (300 mL) and the phases were separated. The organic portion was washed with water (2×200 mL), brine (200 mL), dried over $Na_2SO_4$ and concentrated in vacuo to give the crude product as a pale orange solid. The solid was dissolved in the minimum volume of boiling heptanes (30 mL) and allowed to cool to room temperature. The resulting crystalline solid was filtered, washing with heptanes (2×5 mL) and dried in vacuo to afford the title compound as a beige crystalline solid.

LC-MS (Method G): Rt 1.12 min; MS m/z 307.0, 309.0=[M−H]− (100% @215 nm)

$^1$H NMR (500 MHz, DMSO-d6) δ 10.30-10.28 (m, 1H), 7.77 (d, J=5.3 Hz, 1H), 7.57 (d, J=8.4 Hz, 1H), 7.52-7.49 (m, 2H), 7.44-7.39 (m, 2H), 7.38-7.33 (m, 1H), 5.32 (s, 2H).

Step 4: 1-Benzyloxy-5-bromo-2-(2,2-difluorovinyl)-4-fluoro-benzene

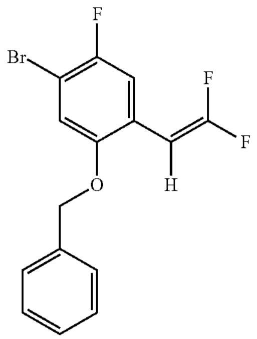 [SMILES: FC(F)=Cc1cc(F)c(Br)cc1OCc1ccccc1]

A mixture of 2-benzyloxy-4-bromo-5-fluoro-benzaldehyde (step 3) (3.95 g, 12.78 mmol) and triphenyl phosphine (4.02 g, 15.33 mmol) in DMF (25 mL) was placed under a nitrogen atmosphere and heated to 100° C. To this mixture was added dropwise sodium 2-chloro-2,2-difluoro-acetate (2.92 g, 19.17 mmol) in DMF (10 mL) and stirring continued at 100° C. for 40 min. The resulting mixture was diluted with EtOAc (200 mL) and 1:1 water:brine (200 mL) and the phases were separated. The organic portion was washed with brine (2×100 mL), dried over $Na_2SO_4$ and concentrated in vacuo to give the crude product as an orange/brown oil. Purification of the oil by chromatography on silica eluting with 0-15% EtOAc in heptanes afforded the title compound as a colourless oil.

LC-MS (Method H): Rt 1.87 min; (100% @215 nm)

$^1$H NMR (400 MHz, DMSO-d6) δ 7.49-7.44 (m, 3H), 7.43-7.38 (m, 2H), 7.38-7.32 (m, 2H), 5.73 (dd, J=26.7, 3.7 Hz, 1H), 5.17 (s, 2H).

Step 5: 2-(2-Benzyloxy-4-bromo-5-fluoro-phenyl)-3,3,3-trifluoro-propanoic acid

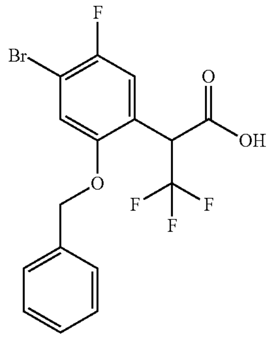 [SMILES: O=C(O)C(c1cc(F)c(Br)cc1OCc1ccccc1)C(F)(F)F]

Cesium fluoride (4.45 g, 29.29 mmol) was added to a 3 neck flask equipped with a magnetic stirrer bar. The flask was placed under vacuum with excessive heating (heat gun) to ensure the solids are suitably dry. During the drying process the vessel was purged with nitrogen and re-evacuated several times. The flask was allowed to sit under vacuum for 1 hour at 100° C. After allowing the flask to cool to room temperature, the flask was placed under a nitrogen atmosphere and a solution of 1-benzyloxy-5-bromo-2-(2,2-difluorovinyl)-4-fluoro-benzene (step 4) (3.35 g, 9.76 mmol) in dry DMSO (75 mL) was added. The vessel was placed under a $CO_2$ atmosphere (3× cycles of filling and evacuating, 1 atm pressure $CO_2$ filling from a lecture bottle) and stirred vigorously at 55° C. overnight. The resulting mixture was diluted with water (300 mL) and EtOAc (300 mL) and the phases were separated. The organic portion was washed with water (300 mL), brine (300 mL), dried over $Na_2SO_4$ and concentrated in vacuo. The crude product was purified by C18 reverse phase chromatography eluting with 10-100% MeCN in water (+0.1% formic acid) to afford the title compound as a pale yellow solid.

LC-MS (Method H): Rt 1.33 min; MS m/z 361.0, 363.0=[M−$CO_2$−H] (98% @215 nm)

$^1$H NMR (400 MHz, DMSO-d6) δ 13.56 (br. s, 1H), 7.56 (d, J=5.9 Hz, 1H), 7.46-7.37 (m, 5H), 7.36-7.31 (m, 1H), 5.25-5.16 (m, 2H), 5.05 (q, J=9.3 Hz, 1H).

Step 6: Methyl 2-(2-benzyloxy-4-bromo-5-fluoro-phenyl)-3,3,3-trifluoro-propanoate

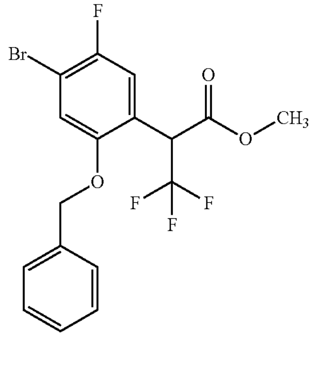 [SMILES: COC(=O)C(c1cc(F)c(Br)cc1OCc1ccccc1)C(F)(F)F]

A cooled (0° C.) mixture of 2-(2-benzyloxy-4-bromo-5-fluoro-phenyl)-3,3,3-trifluoro-propanoic acid (step 5) (763 mg, 1.87 mmol) in MeOH (20 mL) was treated dropwise with $SOCl_2$ (1360 μL, 18.75 mmol) and heated to 50° C. for 4 h. The resulting mixture was concentrated in vacuo azeotroping with DCM (10 mL) and THF (10 mL) to afford the title compound as a brown/orange oil.

LC-MS (Method E): Rt 1.47 min; (97% @215 nm)

$^1$H NMR (400 MHz, DMSO-d6) δ 7.58 (d, J=5.9 Hz, 1H), 7.43-7.38 (m, 5H), 7.37-7.31 (m, 1H), 5.27-5.14 (m, 3H), 3.57 (s, 3H).

Step 7: 2-(2-Benzyloxy-4-bromo-5-fluoro-phenyl)-3,3,3-trifluoro-propan-1-ol

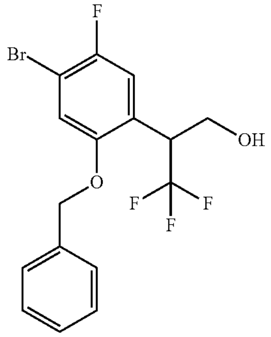 [SMILES: OCC(c1cc(F)c(Br)cc1OCc1ccccc1)C(F)(F)F]

To a cooled (−78° C.) solution of methyl 2-(2-benzyloxy-4-bromo-5-fluoro-phenyl)-3,3,3-trifluoro-propanoate (step 6) (97%, 720 mg, 1.66 mmol) in THF (16 mL) was added dropwise 4M $LiBH_4$ in THF (0.41 mL, 1.66 mmol) and the mixture was stirred for 30 min. Additional 4M $LiBH_4$ in THF (0.41 mL, 1.66 mmol) was added and the mixture was stirred for 1 h. The reaction was quenched by the dropwise addition of saturated $NH_4Cl$ solution (10 mL) and the resulting mixture was diluted with EtOAc (80 mL) and water. The phases were separated and the organic portion was washed with brine (80 mL), dried over $Na_2SO_4$ and concentrated in vacuo to give a yellow oil. Purification of the oil by chromatography on silica eluting with 0-40% EtOAc in heptanes afforded the title compound as a colourless oil.

LC-MS (Method G): Rt 1.11 min; MS m/z 391.1, 393.1=[M+H]+ (99% @215 nm)

$^1$H NMR (500 MHz, DMSO-d6) δ 7.49 (d, J=6.0 Hz, 1H), 7.46-7.41 (m, 3H), 7.40-7.33 (m, 3H), 5.18 (s, 2H), 5.16 (t, J=5.7 Hz, 1H), 4.21-4.09 (m, 1H), 3.96-3.89 (m, 1H), 3.88-3.81 (m, 1H).

Step 8: [2-(2-Benzyloxy-4-bromo-5-fluoro-phenyl)-3,3,3-trifluoro-propoxy]-tert-butyl-dimethyl-silane

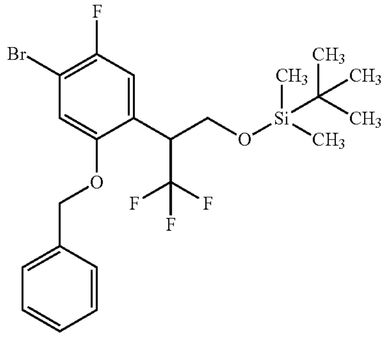 [SMILES: CC(C)(C)[Si](C)(C)OCC(c1cc(F)c(Br)cc1OCc1ccccc1)C(F)(F)F]

t-Butyldimethylsilyl chloride (70 mg, 0.46 mmol) was added to a mixture of 2-(2-benzyloxy-4-bromo-5-fluoro-phenyl)-3,3,3-trifluoro-propan-1-ol (step 7) (99%, 123 mg, 0.31 mmol) and imidazole (42 mg, 0.62 mmol) in DCM (3 mL) and the reaction mixture was stirred at room temperature for 4 h. The resulting mixture was diluted with DCM (10 mL) and water (10 mL) and the phases were separated. The aqueous was extracted with DCM (10 mL) and the combined organic extracts were dried over $Na_2SO_4$ and concentrated in vacuo. Purification of the crude product by chromatography on silica eluting with 0-20% EtOAc in heptanes afforded the title compound as a colourless oil.

LC-MS (Method H): Rt 2.21 min; (98% @215 nm)

$^1$H NMR (500 MHz, DMSO-d6) δ 7.52 (d, J=6.0 Hz, 1H), 7.47 (d, J=9.6 Hz, 1H), 7.44-7.38 (m, 4H), 7.37-7.33 (m, 1H), 5.20 (d, J=11.9 Hz, 1H), 5.16 (d, J=11.9 Hz, 1H), 4.21-4.11 (m, 1H), 4.05 (dd, J=10.8, 5.9 Hz, 1H), 3.99 (dd, J=10.8, 6.0 Hz, 1H), 0.78 (s, 9H), −0.03 (s, 3H), −0.05 (s, 3H).

Step 9: tert-Butyl 2-[5-benzyloxy-4-[1-[[tert-butyl(dimethyl)silyl]oxymethyl]-2,2,2-trifluoro-ethyl]-2-fluoro-phenyl]acetate

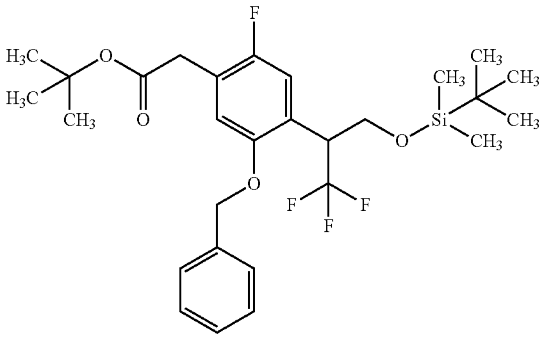 [SMILES: CC(C)(C)OC(=O)Cc1cc(OCc2ccccc2)c(C(CO[Si](C)(C)C(C)(C)C)C(F)(F)F)cc1F]

The title compound was prepared from [2-(2-benzyloxy-4-bromo-5-fluoro-phenyl)-3,3,3-trifluoro-propoxy]-tert-butyl-dimethyl-silane (step 8) and 0.5M bromo-(2-tert-butoxy-2-oxo-ethyl)zinc in THF analogously to Intermediate M step 2.

LC-MS (Method H): Rt 2.26 min; MS m/z 487.2=[M+H]+ (81% @215 nm)

$^1$H NMR (500 MHz, DMSO-d6) δ 7.45-7.37 (m, 4H), 7.36-7.32 (m, 1H), 7.25 (d, J=10.4 Hz, 1H), 7.16 (d, J=6.4 Hz, 1H), 5.12 (d, J=11.8 Hz, 1H), 5.08 (d, J=11.9 Hz, 1H), 4.20-4.11 (m, 1H), 4.03 (dd, J=10.8, 6.0 Hz, 1H), 3.97 (dd, J=10.8, 5.9 Hz, 1H), 3.60 (s, 2H), 1.38 (s, 9H), 0.79 (s, 9H), −0.03 (s, 3H), −0.05 (s, 3H).

Step 10: 2-[5-Benzyloxy-2-fluoro-4-[2,2,2-trifluoro-1-(hydroxymethyl)ethyl]phenyl]acetic acid TFA (938 μL, 12.25 mmol) was added to a mixture of tert-butyl 2-[5-benzyloxy-4-[1-[[tert-butyl(dimethyl)silyl]oxymethyl]-2,2,2-trifluoro-ethyl]-2-fluoro-phenyl]acetate (step 9) (90%, 12 mg, 0.2 mmol) in DCM (3 mL) and the reaction mixture was stirred at room temperature for 5 h. The resulting mixture was concentrated in vacuo then azeotroped with DCM (3×5 mL). The crude product was purified by C18 reverse phase chromatography eluting with 10-100% MeCN/water (+0.1% formic acid) to afford the title compound as a colourless oil.

LC-MS (Method E): Rt 1.19 min; MS m/z 355.1=[M+H−$H_2O$]+ (100% @215 nm)

$^1$H NMR (500 MHz, DMSO-d6) δ 12.51 (br s, 1H), 7.47-7.39 (m, 4H), 7.37-7.32 (m, 1H), 7.21 (d, J=10.4 Hz, 1H), 7.18 (d, J=6.4 Hz, 1H), 5.14 (t, J=5.2 Hz, 1H), 5.09 (s, 2H), 4.19-4.09 (m, 1H), 3.96-3.90 (m, 1H), 3.85-3.79 (m, 1H), 3.61 (s, 2H).

Intermediate S 2-(5-Benzyloxy-4-bromo-2-fluoro-phenyl)acetic acid

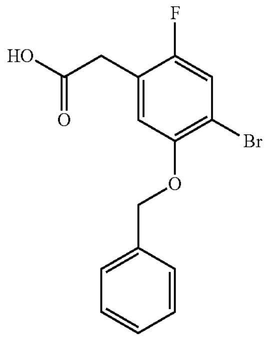 [SMILES: O=C(O)Cc1cc(OCc2ccccc2)c(Br)cc1F]

Step 1: 2-(4-Bromo-2-fluoro-5-hydroxy-phenyl)acetic acid

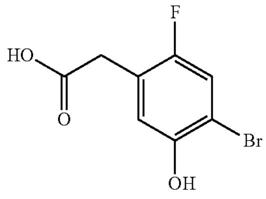 [SMILES: O=C(O)Cc1cc(O)c(Br)cc1F]

1M $BBr_3$ in DCM (28.51 mL, 28.51 mmol) was added dropwise to a cooled (0° C.), stirred suspension of 2-(4-bromo-2-fluoro-5-methoxy-phenyl)acetic acid (Intermediate U step 1) (2.5 g, 9.5 mmol) in DCM (30 mL). After 30 mins, the ice bath was removed and the reaction mixture was stirred at room temperature for 3 h. The resulting mixture was concentrated in vacuo and the residue was partitioned between EtOAc (100 mL) and water (100 mL). The organic layer was separated, washed with water (100 mL), dried over $Na_2SO_4$ and concentrated in vacuo. The crude material was purified by C18 reverse phase chromatography eluting with MeCN in water (+0.1% formic acid) to afford the title compound as an off-white solid.

$^1H$ NMR (500 MHz, DMSO-d6) δ 10.43 (br s, 1H), 7.36 (d, J=9.1 Hz, 1H), 6.89 (d, J=6.9 Hz, 1H), 3.52-3.49 (m, 2H). 90% purity by $^1H$ NMR.

Step 2: Benzyl 2-(5-benzyloxy-4-bromo-2-fluoro-phenyl)acetate

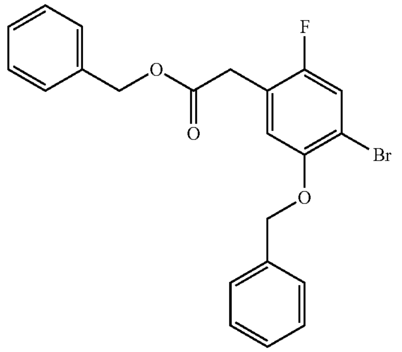 [SMILES: O=C(Cc1cc(OCc2ccccc2)c(Br)cc1F)OCc1ccccc1]

The title compound was prepared from 2-(4-bromo-2-fluoro-5-hydroxy-phenyl)acetic acid (step 1) and bromomethylbenzene analogously to Intermediate R step 3.

LC-MS (Method E): Rt 1.52 min; (88% @215 nm)

$^1H$ NMR (400 MHz, DMSO-d6) δ 7.56 (d, J=8.9 Hz, 1H), 7.50-7.45 (m, 2H), 7.43-7.31 (m, 8H), 7.28 (d, J=6.6 Hz, 1H), 5.14 (s, 2H), 5.12 (s, 2H), 3.78 (d, J=1.1 Hz, 2H).

Step 3: 2-(5-Benzyloxy-4-bromo-2-fluoro-phenyl)acetic acid

The title compound was prepared from benzyl 2-(5-benzyloxy-4-bromo-2-fluoro-phenyl)acetate (step 2) and lithium hydroxide analogously to Intermediate P step 3.

LC-MS (Method G): Rt 0.99 min; MS m/z 675.1, 677.1, 679.1=[2M−H]− (84% @215 nm)

$^1H$ NMR (400 MHz, DMSO-d6) δ 12.55 (br. s, 1H), 7.53 (d, J=8.9 Hz, 1H), 7.50-7.46 (m, 2H), 7.43-7.38 (m, 2H), 7.37-7.32 (m, 1H), 7.26 (d, J=6.7 Hz, 1H), 5.14 (s, 2H), 3.60 (d, J=1.2 Hz, 2H).

Intermediate T 2-(5-Chloro-3,3-dimethyl-2-oxo-benzofuran-6-yl)acetic acid

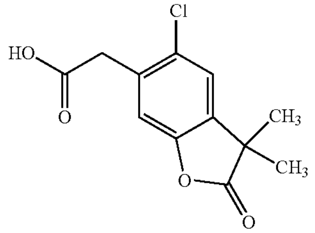 [SMILES: CC1(C)C(=O)Oc2cc(CC(=O)O)c(Cl)cc21]

Step 1: Methyl 2-(4-bromo-2-methoxy-phenyl)acetate

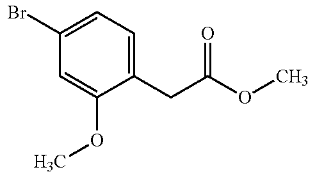

Concentrated sulfuric acid (350 μL, 6.3 mmol) was added dropwise to a stirred solution of 2-(4-bromo-2-methoxy-phenyl)acetic acid (7.25 g, 29.6 mmol) in MeOH (70 mL). The reaction mixture was heated to 70° C. for 3 h and then left to stand at room temperature overnight. The resulting mixture was concentrated in vacuo and the residue was dissolved in EtOAc (100 mL). The mixture was washed with $NaHCO_3$ (50 mL), the aqueous wash was further extracted with EtOAc (20 mL×2). The combined organic extracts were washed with brine (50 mL), dried over $Na_2SO_4$ and concentrated in vacuo to afford the title compound as an orange oil.

LC-MS (Method G): Rt 0.96 min; (90% @215 nm)

$^1H$ NMR (500 MHz, DMSO-d6) δ 7.17 (d, J=1.8 Hz, 1H), 7.15 (d, J=8.0 Hz, 1H), 7.10 (dd, J=8.0, 1.9 Hz, 1H), 3.77 (s, 3H), 3.59 (s, 3H), 3.58 (s, 2H).

Step 2: Methyl 2-(4-bromo-2-methoxy-phenyl)-2-methyl-propanoate

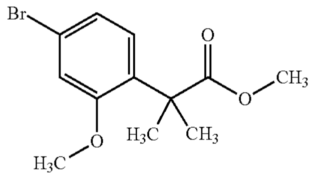 [SMILES: COC(=O)C(C)(C)c1ccc(Br)cc1OC]

A cooled (−78° C.) solution of diisopropylamine (20.7 mL, 147.5 mmol) in THF (104.21 mL) was treated with 1.8M BuLi in hexanes (80.6 mL, 145.1 mmol). After stirring for 10 min, methyl 2-(4-bromo-2-methoxy-phenyl)acetate (step 1) (90%, 5 g, 17.4 mmol) and methyl 2-(4-bromo-2-methoxy-phenyl)acetate (step 1) (80%, 10.3 g, 31.8 mmol) in THF (50 mL) and methyl iodide (12.2 mL, 196.7 mmol) were added and the reaction mixture was allowed to warm to room temperature and stirred for 2 days. Additional THF (100 mL) was added and the mixture was cooled to 0° C. and treated with 2M LDA in THF (30 mL, 60.0 mmol) and MeI (1.6 mL, 19.2 mmol). After stirring at 0° C. for 2 h, the resulting mixture was partitioned between EtOAc (500 mL) and saturated aqueous ammonium chloride (500 mL). The phases were separated and the aqueous was further extracted with EtOAc (2×300 mL). The combined organic extracts were dried over $Na_2SO_4$ and concentrated in vacuo. Purification of the crude material by chromatography on silica eluting with 0-25% EtOAc in heptanes afforded the title compound as a pale yellow oil.

LC-MS (Method H): Rt 1.51 min; MS m/z 286.8, 288.8=[M+H]+ (92% @215 nm)

$^1H$ NMR (400 MHz, DMSO-d6) δ 7.22 (d, J=8.2 Hz, 1H), 7.18-7.10 (m, 2H), 3.74 (s, 3H), 3.52 (s, 3H), 1.39 (s, 6H).

Step 3: Methyl 2-[4-(2-tert-butoxy-2-oxo-ethyl)-2-methoxy-phenyl]-2-methyl-propanoate

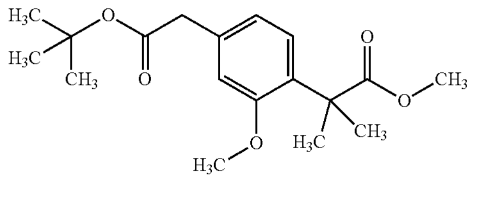 [SMILES: COC(=O)C(C)(C)c1ccc(CC(=O)OC(C)(C)C)cc1OC]

Methyl 2-(4-bromo-2-methoxy-phenyl)-2-methyl-propanoate (step 2) (2.0 g, 6.97 mmol), $Pd(dba)_2$ (200 mg, 0.35 mmol) and Q-Phos (248 mg, 0.35 mmol) were suspended in THF (40 mL) then the reaction was degassed with nitrogen for 5 min. 0.5M bromo-(2-tert-butoxy-2-oxo-ethyl)zinc in THF (20.9 mL, 10.45 mmol) was added and the reaction mixture was heated at 60° C. for 2.5 h. After cooling to room temperature, the mixture was partitioned between EtOAc (75 mL) and saturated $NaHCO_3$ (50 mL). The organic portion was separated, dried over $Na_2SO_4$ and concentrated in vacuo. The residue was purified by chromatography on silica eluting with 0-100% EtOAc in heptanes followed by 0-100% DCM in heptanes then 0-100% MeOH in DCM. The residue was dissolved in 1:1 DMSO/MeOH (1.2 mL) and purified by mass directed LC-MS using eluting with water/MeCN with 0.1% formic acid to afford the title compound as a light red oil.

LC-MS (Method G): Rt 1.13 min; MS m/z 345.2=[M+Na]+ (95% @215 nm)

$^1$H NMR (500 MHz, DMSO-d6) δ 7.20 (d, J=7.9 Hz, 1H), 6.86 (d, J=1.5 Hz, 1H), 6.81 (dd, J=7.8, 1.6 Hz, 1H), 3.69 (s, 3H), 3.53-3.51 (m, 5H), 1.42 (s, 9H), 1.40 (s, 6H).

Step 4: Methyl 2-[4-(2-tert-butoxy-2-oxo-ethyl)-5-chloro-2-methoxy-phenyl]-2-methyl-propanoate

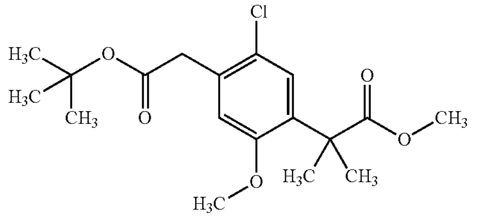 [SMILES: COC(=O)C(C)(C)c1cc(Cl)c(CC(=O)OC(C)(C)C)cc1OC]

Methyl 2-[4-(2-tert-butoxy-2-oxo-ethyl)-2-methoxy-phenyl]-2-methyl-propanoate (step 3) (1.2 g, 3.72 mmol) in DCM (18.6 mL) was treated with triphenylphosphine sulfide (110 mg, 0.37 mmol) and N-chlorosuccinimide (596 mg, 4.47 mmol) and stirred for 1 h. The reaction was quenched with saturated aqueous sodium thiosulfate (20 mL) and the phases separated. The aqueous layer was extracted with DCM (2×20 mL) and the combined organic extracts were dried over $Na_2SO_4$ and concentrated in vacuo. Purification by chromatography on silica eluting with 0-50% TBME in heptanes afforded the title compound as a pale yellow oil.

LC-MS (Method G): Rt 1.24 min; MS m/z 379.2, 381.2=[M+Na]+ (95% @215 nm)

$^1$H NMR (400 MHz, DMSO-d6) δ 7.25 (s, 1H), 7.04 (s, 1H), 3.71 (s, 3H), 3.65 (s, 2H), 3.53 (s, 3H), 1.42 (s, 9H), 1.41 (s, 6H).

Step 5: 2-[2-Chloro-5-methoxy-4-(2-methoxy-1,1-dimethyl-2-oxo-ethyl)phenyl]acetic acid

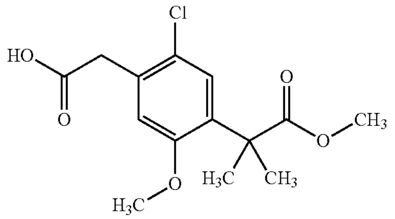 [SMILES: COC(=O)C(C)(C)c1cc(Cl)c(CC(=O)O)cc1OC]

Methyl 2-[4-(2-tert-butoxy-2-oxo-ethyl)-5-chloro-2-methoxy-phenyl]-2-methyl-propanoate (step 4) (95%, 1.37 g, 3.63 mmol) in DCM (15 mL) was treated with TFA (5.0 mL, 65.34 mmol) and stirred at room temperature for 2 h. The resulting mixture was concentrated in vacuo and azeotroped once with DCM (20 mL). The residue was dissolved in EtOAc (20 mL) and washed with water (2×10 mL). The organic layer was dried over $Na_2SO_4$ and concentrated in vacuo to afford the title compound as an off-white solid.

LC-MS (Method G): Rt 0.90 min; MS m/z 301.1, 303.1=[M+H]+ (95% @215 nm)

$^1$H NMR (400 MHz, DMSO-d6) δ 12.45 (br. s, 1H), 7.25 (s, 1H), 7.05 (s, 1H), 3.70 (s, 3H), 3.67 (s, 2H), 3.54 (s, 3H), 1.41 (s, 6H).

Step 6: 2-(5-Chloro-3,3-dimethyl-2-oxo-benzofuran-6-yl)acetic acid

A cooled (0° C.) solution of 2-[2-chloro-5-methoxy-4-(2-methoxy-1,1-dimethyl-2-oxo-ethyl)phenyl]acetic acid (step 5) (95%, 1.02 g, 3.22 mmol) in DCM (32.2 mL) was treated with 1M $BBr_3$ in DCM (0.93 mL, 9.67 mmol) then allowed to warm to room temperature and stirred for 20 h. The reaction was quenched with water, phases were separated and the aqueous phase was extracted with EtOAc (3×20 mL). The combined organic extracts were dried over $Na_2SO_4$ and concentrated in vacuo. Purification by C18 reverse phase chromatography eluting with 10-100% MeCN in water (+0.1% formic acid) afforded the title compound as a colourless solid.

LC-MS (Method G): Rt 0.97 min; (98% @215 nm)

$^1$H NMR (400 MHz, DMSO-d6) δ 12.53 (s, 1H), 7.64 (s, 1H), 7.33 (s, 1H), 3.74 (s, 2H), 1.45 (s, 6H).

Intermediate U 2-(5-Fluoro-3,3-dimethyl-2-oxo-benzofuran-6-yl) acetic acid

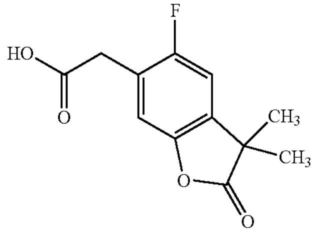 [SMILES: CC1(C)C(=O)Oc2cc(CC(=O)O)c(F)cc21]

Step 1: 2-(4-Bromo-2-fluoro-5-methoxy-phenyl)acetic acid

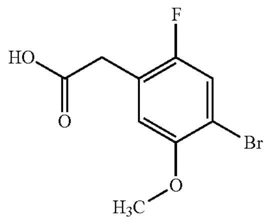

To a cooled (0° C.) solution of 2-(2-fluoro-5-methoxy-phenyl)acetic acid (45 g, 244.4 mmol) in MeCN (1.2 L) was added dropwise a solution of bromine (12.63 mL, 244.9 mmol) in MeCN (100 mL) over a period of 10 min. The resulting mixture was allowed to warm to room temperature gradually without removing the ice bath (~1.5 h). Additional bromine (4.21 mL, 81.64 mmol) in MeCN (50 mL) was added dropwise to the mixture at 0° C. which was stirred at room temperature for a further 3.5 h. Further bromine (4.21 mL, 81.64 mmol) in MeCN (50 mL) was added at room temperature and mixture was stirred at room temperature for 30 min. The reaction was quenched carefully with saturated aqueous sodium sulfite (~700 mL) until the bright orange colour had disappeared. The colourless solution was diluted with brine (200 mL) and EtOAc (200 mL), stirred vigorously for 10 min. The organic layer was separated and the aqueous layer was extracted further with EtOAc (200 mL). Organic layers were combined, dried over $Na_2SO_4$ and concentrated in vacuo to obtain the crude product as a white solid. The crude product was recrystallised by dissolving the solid in AcOH (700 mL), then treated with water (4 L). The mixture was stirred to mix the solvents whereupon crystals gradually appeared. The mixture was kept at room temperature for 1 h and then at 0° C. for 3 h. Filtration followed by vacuum drying at 40° C. afforded the title compound as a fluffy white solid.

LC-MS (Method E): Rt 1.07 min; (99% @215 nm)

$^1$H NMR (500 MHz, DMSO-d6) δ 12.55 (brs, 1H), 7.50 (d, J=8.9 Hz, 1H), 7.13 (d, J=6.6 Hz, 1H), 3.81 (s, 3H), 3.61 (d, J=1.3 Hz, 2H).

Step 2: Benzyl 2-(4-bromo-2-fluoro-5-methoxy-phenyl)acetate

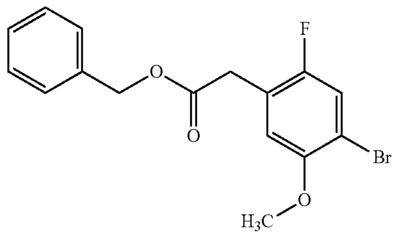 [SMILES: COc1cc(CC(=O)OCc2ccccc2)c(F)cc1Br]

A mixture of 2-(4-bromo-2-fluoro-5-methoxy-phenyl) acetic acid (step 1) (15 g, 57.02 mmol) and $K_2CO_3$ (15.76 g, 114.0 mmol) in DMF (140 mL) was treated with benzylbromide (7.45 mL, 62.7 mmol) and stirred at room temperature for 18 h. The resulting mixture was filtered and concentrated in vacuo. The residue was dissolved in EtOAc (300 mL) and sequentially washed with brine (200 mL) and saturated aqueous sodium bicarbonate (2×200 mL). The organic layer was dried over $Na_2SO_4$ and concentrated in vacuo. Purification by chromatography on silica eluting with 0-20% EtOAc in heptanes afforded the title compound as a colourless solid.

LC-MS (Method G): Rt 1.13 min; (95% @215 nm)

$^1$H NMR (500 MHz, DMSO-d6) δ 7.53 (d, J=8.9 Hz, 1H), 7.40-7.31 (m, 5H), 7.15 (d, J=6.6 Hz, 1H), 5.14 (s, 2H), 3.81-3.78 (m, 5H).

Step 3: Methyl 2-[4-(2-benzyloxy-2-oxo-ethyl)-5-fluoro-2-methoxy-phenyl]-2-methyl-propanoate

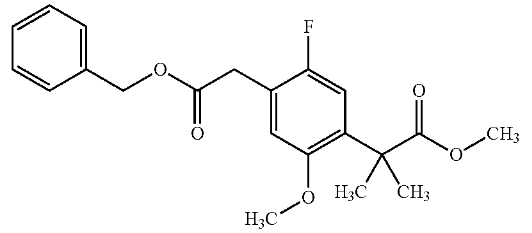 [SMILES: COC(=O)C(C)(C)c1cc(F)c(CC(=O)OCc2ccccc2)cc1OC]

Benzyl 2-(4-bromo-2-fluoro-5-methoxy-phenyl)acetate (step 2) (5.0 g, 14.16 mmol), $ZnF_2$ (1.1 g, 10.62 mmol) and $Pd(P^tBu_3)_2$ (0.36 g, 0.71 mmol) were added to a reaction vessel and placed under a nitrogen atmosphere. A solution of (1-methoxy-2-methyl-prop-1-enoxy)-trimethyl-silane (5.75 mL, 28.31 mmol) in degassed DMF (50 mL) was added and the reaction mixture was heated to 80° C. for 18 h. The resulting mixture was filtered and concentrated in vacuo. The residue was dissolved in EtOAc (100 mL) and washed with brine (2×50 mL) and the organic layer was dried over $Na_2SO_4$ and concentrated in vacuo. Purification by chromatography on silica eluting with 0-30% EtOAc in heptanes the title compound as a pale yellow oil.

LC-MS (Method A): Rt 3.99 min; MS m/z 375.3=[M+H]+ (92% @215 nm)

$^1$H NMR (400 MHz, DMSO-d6) δ 7.40-7.30 (m, 5H), 7.09 (d, J=11.0 Hz, 1H), 6.98 (d, J=6.5 Hz, 1H), 5.14 (s, 2H), 3.76 (s, 2H), 3.66 (s, 3H), 3.53 (s, 3H), 1.40 (s, 6H).

Step 4: 2-(5-Fluoro-3,3-dimethyl-2-oxo-benzofuran-6-yl)acetic acid

1M $BBr_3$ in DCM (34.13 mL, 34.1 mmol) was added to a cooled (0° C.) mixture of methyl 2-[4-(2-benzyloxy-2-oxo-ethyl)-5-fluoro-2-methoxy-phenyl]-2-methyl-propanoate (step 3) (92%, 2777 mg, 6.83 mmol) in dry DCM (60 mL). The resulting mixture was allowed to warm to room temperature and stirred for 4.5 h. The reaction mixture was re-cooled to 0° C. and water (50 mL) was added. Stirring continued whilst gradually warming to room temperature over 30 min. The resulting mixture was diluted with DCM (80 mL) and water (80 mL) and the phases were separated. The aqueous was extracted with EtOAc (80 mL) then the combined organic extracts were dried over $Na_2SO_4$ and concentrated in vacuo to give the crude product as a brown oil. Purification of the crude product by C18 reverse phase chromatography eluting with 10-100% MeCN/water (+0.1% formic acid) afforded the title compound as a pale yellow solid.

LC-MS (Method H): Rt 1.19 min; (98% @215 nm)

$^1$H NMR (500 MHz, DMSO-d6) δ 12.56 (br. s, 1H), 7.42 (d, J=8.9 Hz, 1H), 7.25 (d, J=5.8 Hz, 1H), 3.64 (d, J=1.5 Hz, 2H), 1.44 (s, 6H).

Intermediate UA 2-(5-Fluoro-3-methyl-2-oxo-3H-benzofuran-6-yl) acetic acid

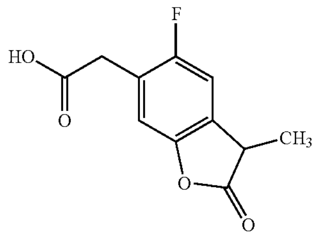 [SMILES: CC1C(=O)Oc2cc(CC(=O)O)c(F)cc21]

Step 1: Methyl 2-[4-(2-benzyloxy-2-oxo-ethyl)-5-fluoro-2-methoxy-phenyl]propanoate

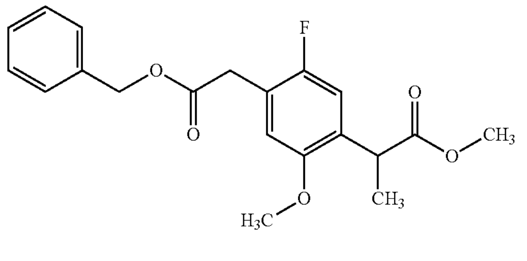 [SMILES: COC(=O)C(C)c1cc(F)c(CC(=O)OCc2ccccc2)cc1OC]

The title compound was prepared from benzyl 2-(4-bromo-2-fluoro-5-methoxy-phenyl)acetate (Intermediate U step 2) and [(E)-1-methoxyprop-1-enoxy]-trimethyl-silane analogously to Intermediate U step 3.

LC-MS (Method E): Rt 1.37 min; MS m/z 361.2=[M+H]+ (97% @215 nm)

$^1$H NMR (500 MHz, DMSO-d6) δ 7.39-7.30 (m, 5H), 7.02 (d, J=10.2 Hz, 1H), 6.99 (d, J=6.3 Hz, 1H), 5.14 (s, 2H), 3.93 (q, J=7.2 Hz, 1H), 3.76 (s, 2H), 3.71 (s, 3H), 3.57 (s, 3H), 1.34 (d, J=7.2 Hz, 3H).

Step 2: 2-(5-Fluoro-3-methyl-2-oxo-3H-benzofuran-6-yl)acetic acid

The title compound was prepared from methyl 2-[4-(2-benzyloxy-2-oxo-ethyl)-5-fluoro-2-methoxy-phenyl]propanoate (step 1) and 1M $BBr_3$ in DCM analogously to Intermediate U step 4.

LC-MS (Method A): Rt 2.08 min; (88% @215 nm)

$^1$H NMR (500 MHz, DMSO-d6) δ 12.56 (br s, 1H), 7.33 (d, J=8.9 Hz, 1H), 7.20 (d, J=5.9 Hz, 1H), 4.03 (q, J=7.5 Hz, 1H), 3.63 (d, J=1.2 Hz, 2H), 1.45 (d, J=7.6 Hz, 3H).

Intermediate V 2-(5,7-Difluoro-3,3-dimethyl-2-oxo-benzofuran-6-yl)acetic acid

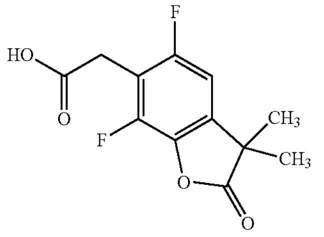 [SMILES: CC1(C)C(=O)Oc2c1cc(F)c(CC(=O)O)c2F]

Step 1: 2-(2,6-Difluoro-3-hydroxy-phenyl)acetic acid

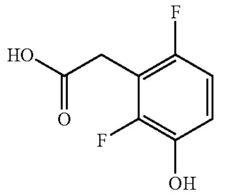 [SMILES: O=C(O)Cc1c(F)ccc(O)c1F]

To a solution of 2-(2,6-difluoro-3-methoxy-phenyl)acetic acid (850 mg, 4.2 mmol) in DCM (30 mL) was added 1M $BBr_3$ in DCM (6.31 mL, 6.31 mmol) and the mixture was stirred at room temperature for 1 h then allowed to stand at room temperature for 5 days. The resulting mixture was poured onto water (30 mL) and 1M NaOH (aq) (~20 mL) was added. The biphasic mixture was stirred vigorously for 30 min at room temperature and the layers were separated. The aqueous portion was acidified to pH1-2 by the dropwise addition of 6M HCl then extracted with EtOAc (2×30 mL). The combined organic extracts were dried over $Na_2SO_4$ and concentrated in vacuo to afford the title compound as a white solid.

LC-MS (Method G): Rt 0.50 min; (100% @215 nm)

$^1$H NMR (500 MHz, DMSO-d6) δ 12.61 (br. s, 1H), 9.74 (s, 1H), 6.89-6.83 (m, 2H), 3.58 (s, 2H).

Step 2: 2-(4-Bromo-2,6-difluoro-3-hydroxy-phenyl)acetic acid

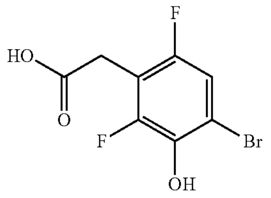 [SMILES: O=C(O)Cc1c(F)cc(Br)c(O)c1F]

To a cooled (0° C.) mixture of 2-(2,6-difluoro-3-hydroxy-phenyl)acetic acid (step 1) (940 mg, 5. mmol) in chloroform (30 mL) was added DIPEA (1.75 mL, 9.99 mmol) and the resulting mixture was stirred vigorously for 10 min. N-Bromosuccinimide (889 mg, 5. mmol) was added and the mixture was stirred at 0° C. for 20 min. The resulting mixture was diluted with EtOAc (150 mL) and 1M HCl (150 mL) and the phases were separated. The aqueous portion was extracted with EtOAc (150 mL) and the combined organic extracts were dried over $Na_2SO_4$ and concentrated in vacuo. Purification of the crude product by C18 reverse phase chromatography eluting with 10-100% MeCN/water (+0.1% formic acid) afforded the title compound as a pale orange solid.

LC-MS (Method G): Rt 0.70 min; MS m/z 264.9, 266.9=[M−H]− (100% @215 nm)

$^1$H NMR (400 MHz, DMSO-d6) δ 12.73 (br. s, 1H), 10.27 (br. s, 1H), 7.35 (dd, J=8.8, 2.2 Hz, 1H), 3.59 (s, 2H).

Step 3: Benzyl 2-(3-benzyloxy-4-bromo-2,6-difluoro-phenyl)acetate

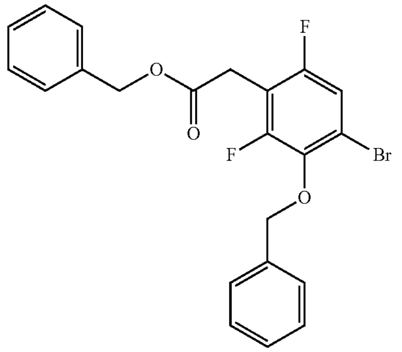 [SMILES: O=C(Cc1c(F)cc(Br)c(OCc2ccccc2)c1F)OCc1ccccc1]

To a solution of 2-(4-bromo-2,6-difluoro-3-hydroxy-phenyl)acetic acid (step 2) (896 mg, 3.35 mmol) in DMF (25 mL) was added $K_2CO_3$ (1391 mg, 10.06 mmol) and bromomethylbenzene (0.88 mL, 7.38 mmol) and the mixture was stirred at room temperature for 16 h. The resulting mixture was diluted with EtOAc (150 mL) and water (150 mL) and the phases were separated. The organic portion was washed with brine (150 mL), dried over $Na_2SO_4$ and concentrated in vacuo. Purification of the crude product by chromatography on silica eluting with 0-25% EtOAc in heptanes afforded the title compound as a pale yellow oil.

LC-MS (Method G): Rt 1.30 min; (99% @215 nm)

$^1$H NMR (500 MHz, DMSO-d6) δ 7.56 (dd, J=8.8, 2.1 Hz, 1H), 7.49-7.46 (m, 2H), 7.42-7.31 (m, 8H), 5.16 (s, 2H), 5.02 (s, 2H), 3.82 (s, 2H).

Step 4: Methyl 2-[2-benzyloxy-4-(2-benzyloxy-2-oxo-ethyl)-3,5-difluoro-phenyl]-2-methyl-propanoate

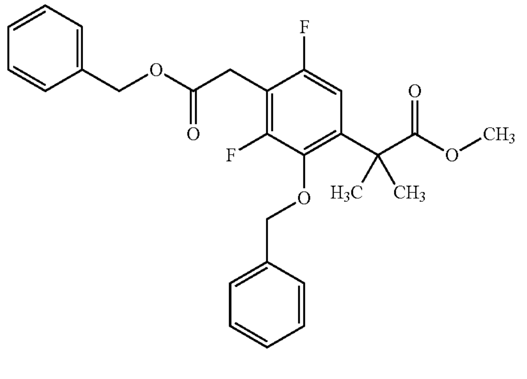 [SMILES: COC(=O)C(C)(C)c1cc(F)c(CC(=O)OCc2ccccc2)c(F)c1OCc1ccccc1]

The title compound was prepared from benzyl 2-(3-benzyloxy-4-bromo-2,6-difluoro-phenyl)acetate (step 3) and (1-methoxy-2-methyl-prop-1-enoxy)-trimethyl-silane analogously to Intermediate U step 3.

LC-MS (Method A): Rt 4.66 min; MS m/z 469.3=[M+H]+ (49% @215 nm)

Step 5: 2-(5,7-Difluoro-3,3-dimethyl-2-oxo-benzofuran-6-yl)acetic acid

The title compound was prepared from methyl 2-[2-benzyloxy-4-(2-benzyloxy-2-oxo-ethyl)-3,5-difluoro-phenyl]-2-methyl-propanoate (step 4) and 1M $BBr_3$ in DCM analogously to Intermediate U step 4.

LC-MS (Method G): Rt 0.82 min; (100% @215 nm)

$^1$H NMR (500 MHz, DMSO-d6) δ 12.75 (br. s, 1H), 7.39 (dd, J=8.3, 1.2 Hz, 1H), 3.68 (s, 2H), 1.49 (s, 6H).

Intermediate W

2-[4-[1-(Acetoxymethyl)cyclopropyl]-5-benzyloxy-2-fluoro-phenyl]acetic acid

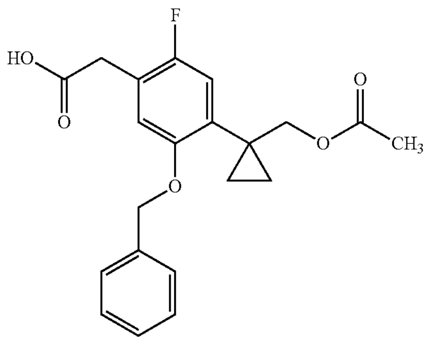 [SMILES: CC(=O)OCC1(c2cc(F)c(CC(=O)O)cc2OCc2ccccc2)CC1]

Step 1: 1-Benzyloxy-5-bromo-2-(chloromethyl)-4-fluoro-benzene

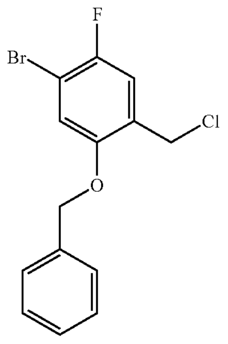 [SMILES: Fc1cc(CCl)c(OCc2ccccc2)cc1Br]

To a cooled (0° C.), stirred solution of (2-benzyloxy-4-bromo-5-fluoro-phenyl)methanol (Intermediate N, step 2) (11.6 g, 37.28 mmol) in DCM (100 mL) and DMF (2.89 mL, 37.28 mmol) at was added dropwise thionyl chloride (5.41 mL, 74.56 mmol) in DCM (20 mL) and the mixture was stirred at room temperature for 2 h. The solvents were removed in vacuo and the residue was diluted with EtOAc (150 mL) and washed with saturated $NaHCO_3$ (3×100 mL). The organic portion was washed further with brine (2×100 mL), dried over $Na_2SO_4$ and concentrated in vacuo to afford the title compound as a yellow solid.

LC-MS (Method E): Rt 1.43 min; (99% @215 nm)

$^1H$ NMR (500 MHz, DMSO-d6) δ 7.54-7.45 (m, 4H), 7.43-7.39 (m, 2H), 7.37-7.32 (m, 1H), 5.22 (s, 2H), 4.71 (s, 2H).

Step 2: 2-(2-Benzyloxy-4-bromo-5-fluoro-phenyl) acetonitrile

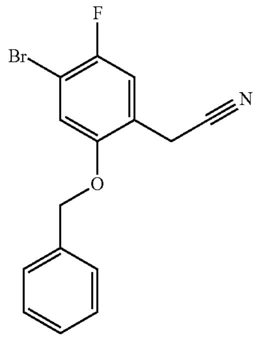 [SMILES: N#CCc1cc(F)c(Br)cc1OCc1ccccc1]

To a solution of 1-benzyloxy-5-bromo-2-(chloromethyl)-4-fluoro-benzene (step 1) (3.7 g, 11.23 mmol) in DMF (50 mL) was added sodium cyanide (0.63 g, 12.91 mmol) and the mixture was stirred at room temperature overnight. The resulting mixture was diluted with EtOAc (50 mL) and washed with sat. sodium carbonate (100 mL) and brine (50 mL). The organic layer was separated, dried over $Na_2SO_4$ and concentrated in vacuo to afford the title compound as a yellow solid.

LC-MS (Method G): Rt 1.09 min; MS m/z 318.0, 320.0=[M+H]+ (97% @215 nm)

$^1H$ NMR (500 MHz, DMSO-d6) δ 7.54-7.48 (m, 2H), 7.48 (d, J=5.8 Hz, 1H), 7.45-7.37 (m, 3H), 7.38-7.32 (m, 1H), 5.22 (s, 2H), 3.90 (s, 2H).

Step 3: 1-(2-Benzyloxy-4-bromo-5-fluoro-phenyl) cyclopropanecarbonitrile

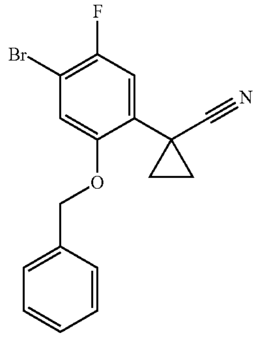

To a mixture of potassium hydroxide (2209 mg, 39.37 mmol) in water (1.3 mL) was added 2-(2-benzyloxy-4-bromo-5-fluoro-phenyl)acetonitrile (step 2) (3.4 g, 10.62 mmol) and tetrabutylammonium bromide (34.23 g, 106.2 mmol). The resulting mixture was treated dropwise with 1,2-dibromoethane (1.83 mL, 21.24 mmol) where a strong exothermic effect was observed and the temperature was kept at 50° C. (external cooling). After stirring at 50° C. overnight, the resulting mixture was diluted with brine (100 mL) and extracted with EtOAc (2×30 mL). The combined organic extracts were dried over $Na_2SO_4$ and concentrated in vacuo. Purification of the crude product by chromatography on silica eluting with 0-60% EtOAc in heptanes afforded the title compound as a pale yellow solid.

LC-MS (Method E): Rt 1.39 min; MS m/z 346.0, 348.0=[M+H]+ (99% @215 nm)

$^1H$ NMR (500 MHz, DMSO-d6) δ 7.58-7.52 (m, 2H), 7.48 (d, J=5.9 Hz, 1H), 7.46-7.39 (m, 3H), 7.38-7.31 (m, 1H), 5.28 (s, 2H), 1.64-1.58 (m, 2H), 1.41-1.35 (m, 2H).

Step 4: [1-(2-Benzyloxy-4-bromo-5-fluoro-phenyl) cyclopropyl]methanol

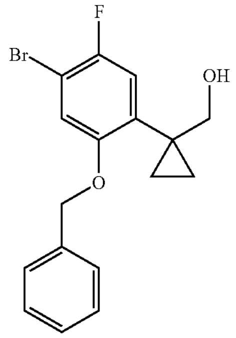 [SMILES: OCC1(c2cc(F)c(Br)cc2OCc2ccccc2)CC1]

To a stirred, cooled (0° C.) solution of 1-(2-benzyloxy-4-bromo-5-fluoro-phenyl)cyclopropanecarbonitrile (step 3) (2 g, 5.78 mmol) in DCM (50 mL) was added dropwise 1M DIBAL in hexane (17.33 mL, 17.33 mmol) and the reaction mixture was stirred at 0° C. for 1 h and then at room temperature overnight. A further portion of 1M DIBAL in hexane (17.33 mL, 17.33 mmol) was added and stirring continued at room temperature overnight. The reaction was quenched cautiously with 1M HCl (20 mL) and stirred for 30 min. The organic portion was separated, dried over $Na_2SO_4$ and concentrated in vacuo. Purification of the crude product by chromatography on silica eluting with 0-100% EtOAc in heptanes followed by 0-100% MeOH in EtOAc afforded the title compound as a brown oil.

LC-MS (Method E): Rt 1.32 min; MS m/z 682.0, 684.9, 686.0=[2M−$H_2O$] (78% @215 nm)

$^1H$ NMR (500 MHz, DMSO-d6) δ 7.49-7.44 (m, 2H), 7.45-7.37 (m, 2H), 7.36-7.31 (m, 1H), 7.31 (d, J=5.9 Hz, 1H), 7.16 (d, J=9.3 Hz, 1H), 5.16 (s, 2H), 4.53 (t, J=5.9 Hz, 1H), 3.45 (d, J=5.8 Hz, 2H), 0.81-0.74 (m, 2H), 0.69-0.63 (m, 2H).

Step 5: [1-(2-Benzyloxy-4-bromo-5-fluoro-phenyl)cyclopropyl]methyl acetate

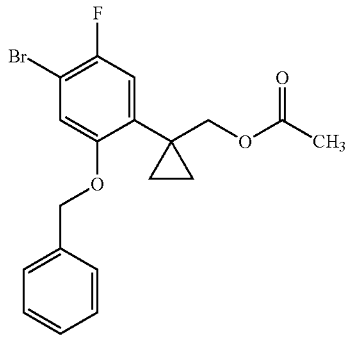 [SMILES: CC(=O)OCC1(c2cc(F)c(Br)cc2OCc2ccccc2)CC1]

To a stirred solution of [1-(2-benzyloxy-4-bromo-5-fluoro-phenyl)cyclopropyl]methanol (step 4) (700 mg, 1.99 mmol) in DCM (10 mL) was added DMAP (24 mg, 0.2 mmol), acetic anhydride (0.38 mL, 3.99 mmol) and TEA (0.56 mL, 3.99 mmol) and the mixture was stirred at room temperature for 2 h. The reaction was quenched with saturated aqueous $Na_2CO_3$ solution (20 mL) and the organic portion was separated, dried over $Na_2SO_4$ and concentrated in vacuo to afford the title compound as a brown oil.

LC-MS (Method G): Rt 1.22 min; (89% @215 nm)

$^1$H NMR (500 MHz, DMSO-d6) δ 7.51-7.45 (m, 2H), 7.45-7.38 (m, 2H), 7.38-7.32 (m, 2H), 7.20 (d, J=9.2 Hz, 1H), 5.18 (s, 2H), 4.09 (s, 2H), 1.88 (s, 3H), 0.96-0.87 (m, 2H), 0.86-0.79 (m, 2H).

Step 6: 2-[4-[1-(Acetoxymethyl)cyclopropyl]-5-benzyloxy-2-fluoro-phenyl]acetic acid The title compound was prepared from [1-(2-benzyloxy-4-bromo-5-fluoro-phenyl)cyclopropyl]methyl acetate (step 5) and 0.5M bromo-(2-tert-butoxy-2-oxo-ethyl)zinc in THF analogously to Intermediate M step 2.

LC-MS (Method G): Rt 0.98 min; MS m/z 395.2=[M+Na]+ (82% @215 nm)

$^1$H NMR (500 MHz, DMSO-d6) δ 12.45 (s, 1H), 7.52-7.47 (m, 2H), 7.45-7.38 (m, 2H), 7.37-7.30 (m, 1H), 7.05 (d, J=6.4 Hz, 1H), 7.00 (d, J=10.0 Hz, 1H), 5.10 (s, 2H), 4.09 (s, 2H), 3.57 (s, 2H), 1.88 (s, 3H), 0.92-0.86 (m, 2H), 0.85-0.75 (m, 2H).

Biological Examples

In the Examples below, the compounds of the invention are compared with Examples 93.4 and 91 of our earlier application PCT/GB2019/050209. These compounds are as follows:

Example 93.4 of PCT/GB2019/050209

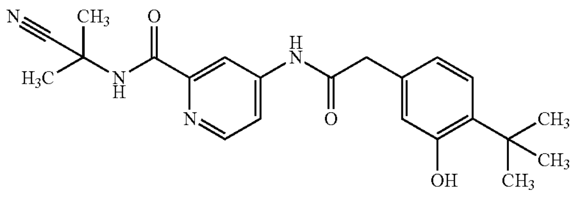 [SMILES: CC(C)(C#N)NC(=O)c1cc(NC(=O)Cc2ccc(C(C)(C)C)c(O)c2)ccn1]

Example 91 of PCT/GB2019/050209

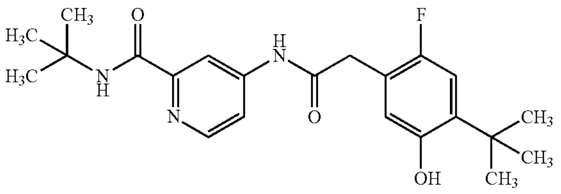 [SMILES: CC(C)(C)NC(=O)c1cc(NC(=O)Cc2cc(O)c(C(C)(C)C)cc2F)ccn1]

Example 21

Automated Whole-Cell Patch Clamp Assay to Detect TMEM16A Activity in Recombinant Cells Cell Culture and Preparation Fisher rat thyroid (FRT) cells stably expressing human TMEM16A (TMEM16Aabc variant; Dr Luis Galietta, Insituto Giannina, Italy) were cultured in T-75 flasks in Hams F-12 media with Coon's modification (Sigma) supplemented with 10% (v/v) foetal bovine serum, penicillin-streptomycin (10,000 U/mL/10000 μg/mL), G-418 (750 μg/mL), L-glutamine (2 mM) and sodium bicarbonate solution (7.5% v/v). At ~90% confluence cells were harvested for experiments by detachment with a 2:1 (v/v) mixture of Detachin (BMS Biotechnology) and 0.25% (w/v) trypsin-EDTA. Cells were diluted to a density of 3.5-4.5×$10^6$ cells/mL with media consisting of CHO-S-SFM II (Sigma), 25 mM HEPES (Sigma) and Soy bean trypsin inhibitor (Sigma).

Whole-Cell Patch Clamp Recording

FRT-TMEM16A cells were whole-cell patch clamped using an automated planar patch clamp system (Qpatch, Sophion). Briefly, once high resistance (GOhm) seals were established between the cells and the planar recording array the patch was ruptured using suction pulses to establish the whole-cell recording configuration of the patch clamp technique. The assay employed the following solutions (all reagents Sigma): Intracellular solution (mM): N-methyl-D-glucamine 130, $CaCl_2$ 18.2, $MgCl_2$ 1, HEPES 10, EGTA 10, BAPTA 20, Mg-ATP 2, pH 7.25, 325 mOsm with sucrose.

Extracellular solution (mM): N-methyl-D-glucamine 130, $CaCl_2$ 2, $MgCl_2$ 1, HEPES 10, pH 7.3, 320 mOsm with sucrose.

The intracellular solution buffers intracellular calcium at levels required to give ~20% activation of the maximal TMEM16A mediated current ($E0_{20}$ for calcium ions). Cells were voltage clamped at a holding potential of −70mV and a combined voltage step (to +70 mV)/ramp (−90 my to +90 mV) was applied at 0.05 Hz. After a period of current stabilisation test compounds, solubilised in 100% (v/v) DMSO and subsequently diluted into extracellular solution, were applied to generate a cumulative concentration response curve. Each concentration of test compound was incubated for 5 minutes before addition of the next concentration. After the final concentration was tested a supramaximal concentration of either a known active positive modulator or the TMEM16A inhibitor, CaCCinhA01 (Del La Fuente et al, 2008) was added to define the upper and lower limits of the assay.

Compound activity was quantified by measuring the increase in current upon compound addition and expressing this as a percentage increase of baseline TMEM16A current level. Percentage increases in current were determined for each concentration and the data plotted as a function of concentration using either the Qpatch software or Graphpad Prism v6.05 providing the concentration which gave 50% of its maximal effect ($EC_{50}$) and maximum efficacy (percentage of baseline increase).

The method of calculating the results is illustrated in FIG. 1, which shows an example trace from the Qpatch TMEM16A assay. In FIG. 1, $I_{BL}$ equals baseline current, $I_{[\#1]}$ equals the peak current during test compound concentration 1 incubation period and so on.

Peak TMEM16A current at +70 mV was plotted as a function of time over the assay period. Baseline current ($I_{BL}$) was measured after a period of stabilisation. The increase in current for each compound addition was determined by taking the peak current during the incubation period and subtracting the current from the previous recording period and then expressing this as a percentage of the baseline current (% potentiation). For test compound concentration 1 in FIG. 1 this is:

$$(I_{[\#1]} - I_{BL}/I_{BL}) \times 100$$

For each additional concentration tested the increase in current was determined by subtracting the current from the previous incubation period and normalising the baseline value—for test concentration 2 in FIG. 1 this is:

$$(I_{[\#2]} - I_{[\#1]}/I_{BL}) \times 100$$

The values for each test concentration were plotted as a cumulative function of concentration eg. for test concentration two this would be the sum of the peak changes measured during concentration one plus concentration two.

The results obtained for the example compounds are shown in Table 2, from which it can be seen that the compounds of the present invention are capable of significantly increasing the TMEM16A current level.

TABLE 2

QPatch TMEM16A (minimum n = 2) $EC_{50}$

| Example | % Potentiation @ 3.33 uM Avg | QPatch TMEM16A $EC_{50}$ (μM) |
|---|---|---|
| 91 of PCT/GB2019/050209 | | 0.055 |
| 93.4 of PCT/GB2019/050209 | 476 | 0.064 |
| 1 | 247.69 | 0.038 |
| 1.1 | 118 | 0.026 |
| 1.2 | 149.26 | 0.045 |
| 1.3 | 380.31 | 0.104 |
| 1.3a | 223.74 | 0.187 |
| 1.3b | 70.906 | 0.042 |
| 1.4 | 200.04 | 0.037 |
| 1.5 | 147.57 | 0.065 |
| 1.6 | 120.9 | 0.040 |
| 1.6a | 372.08 | 0.061 |
| 1.6b | 219.92 | 0.327 |
| 1.7 | 202.06 | 0.025 |
| 2 | 243.21 | 0.064 |
| 2.1 | 350.22 | 0.466 |
| 2.2 | 355.83 | 0.150 |
| 2.3 | 72.13 | 0.052 |
| 2.4 | 356.44 | 0.069 |

TABLE 2-continued

QPatch TMEM16A (minimum n = 2) $EC_{50}$

| Example | % Potentiation @ 3.33 uM Avg | QPatch TMEM16A $EC_{50}$ (μM) |
|---|---|---|
| 2.5 | 111.8 | Not determined |
| 2.6 | 270.23 | 0.030 |
| 2.7 | 309.32 | 0.219 |
| 2.8 | 301.84 | 0.077 |
| 2.9 | 294.99 | 0.149 |
| 2.10 | 434.25 | 0.030 |
| 2.11 | 390.42 | 0.064 |
| 2.11a | 193.13 | 0.014 |
| 2.11b | 144.37 | 0.049 |
| 2.12 | 209.38 | 0.042 |
| 2.13 | 339.06 | 0.037 |
| 2.14 | 121.65 | 0.027 |
| 2.15 | 412.89 | 0.279 |
| 2.16 | 227.3 | 0.076 |
| 3 | 352.65 | 0.132 |
| 4 | 185.57 | 0.029 |
| 5 | 335.29 | 0.043 |
| 6 | 513.47 | 0.099 |
| 7 | 83.6 | 0.068 |
| 7.1 | 433.05 | 0.015 |
| 8 | 240.3 | 0.046 |
| 9 | 378.14 | 0.088 |
| 10 | 310.23 | 0.052 |
| 10.1 | 250.35 | 0.057 |
| 10.2 | 251.62 | 0.052 |
| 11 | 207.85 | 0.043 |
| 12 | 150.15 | 0.118 |
| 12.1 | 405.58 | 0.052 |
| 12.2 | 141.53 | 0.238 |
| 12.3 | 97.234 | 0.238 |
| 12.4 | 341.6 | 0.214 |
| 13 | 195.86 | 0.221 |
| 14 | 489.99 | 0.033 |
| 14.1 | 232.64 | 0.045 |
| 15 | 113.02 | 0.014 |
| 15.1 | 190.16 | 0.041 |
| 15.2 | 194.81 | 0.036 |
| 15.3 | 249.64 | 0.036 |
| 15.4 | 226.33 | 0.060 |
| 16 | 74.547 | 0.019 |
| 16.1 | 213.82 | 0.181 |
| 16.2 | 294.78 | 0.115 |
| 16.3 | 139.6 | 0.407 |
| 16.4 | 280.47 | 0.018 |
| 17 | 374.02 | 0.093 |
| 18 | 314.59 | 0.268 |
| 19 | 244.19 | 0.046 |
| 20 | 294.73 | 0.100 |
| 20a | 321.29 | 0.195 |
| 20b | 283.84 | 0.063 |

It can be seen that the majority of the compounds have $EC_{50}$ values similar to those of Compounds 91 and 93.4 of PCT/GB2019/050209 and indeed in some cases the activity is improved.

Example 22

Physicochemical Assays

Kinetic Solubility Determinations

Test compounds (10 μL; 20 mM DMSO solution) were added to sterile water (190 μL) in triplicate and shaken at 300 rpm at room temperature. After 90 min. the test compounds were filtered by centrifuge (5 min. at 3000 rpm) to obtain the aqueous filtrate. Acetonitrile (20 μL) was dispensed into clean 96-well UV/VIS analysis plate and aqueous filtrate (80 μL) added and the plate analysed for test compound concentration using a Molecular Devices SPECTRAmax® plus microplate reader at the following wavelengths: (280, 300, 320, 340, 360, 800 nm). A second diluted analysis plate (10-fold) was prepared by adding aqueous filtrate (10 μL) to 95% water 5% DMSO (90 μL) and the plate shaken for 10 min. The diluted filtrate (80 μL) was then added to acetonitrile (20 μL) and the plate analysed. as previously. The results obtained were quantified against a standard calibration curve prepared for each test sample and the results controlled by analysis of the reference control compounds (Ketoconazole, nifedipine, β-estradiol and diphenylimidazole)

Log D (pH7.4 Shake Flask)

All compounds were tested in a 'cassette' containing a mixture of 4 test compounds each initially dissolved in DMSO at 5 mMolar. Phosphate buffer (1 M) was diluted to 20 mM with deionised water and adjusted to pH 7.4 with phosphoric acid or sodium hydroxide. 1-octanol and phosphate buffer (20 mM) were saturated overnight by tumbling. The two phases were separated using a separation funnel. 5 μL of 5 mM compound cassette was added to 495 μL of octanol-saturated buffer and 495 μL buffer saturated octanol in a 96-well plate (top concentration 50 μM). Plate was shaken for 1 h and centrifuged at 25° C. for 5 min. 200 μL of each phase was transferred to a separate plate. The octanol layer was sampled first to avoid cross contamination. 5 μL of the solutions were transferred to 495 μL of quench solution* (max concentration 0.5 μM). In addition, 40 μL of buffer solution was added to 360 μL of quench solvent (max concentration 5 μM). Samples were analysed by LC-MS/MS. Benchmarking against a calibration curve for each compound and with reference to the control compounds sulpride, diclofenac, chlorpromazine and tamoxifen.
*Quench solution was a 1:3:1 mixture (v/v/v) of Acetonitrile containing 0.1% formic acid and imipramine/labetalol, 200 nM:Acetonitrile:Water.

The results for the Log D and kinetic solubility assays are shown in Table 3. Compounds which have an mLog D value at pH 7.4 of 5 or less are generally sufficiently soluble for pharmaceutical formulation. Table 3 shows that mLog D values of the example compounds all fall within this range. It is preferred that the mLog D value is 4.2 or less and almost all of the example compounds fall within this range.

TABLE 3

Log D and High Throughput (HT) kinetic solubility data

| Example | mLogD (pH 7.4) | Kinetic solubility (mg/ml) |
|---|---|---|
| 93.4 of PCT/GB2019/050209 | >4.1 | 0.037 |
| 91 of PCT/GB2019/050209 | >4.5 | 0.01 |
| 1 | >4.2 | n/d |
| 1.1 | >4.0 | 0.006 |
| 1.2 | >4.5 | 0.003 |
| 1.3 | 3.9 | 0.035 |
| 1.3a | >4.0 | 0.032 |
| 1.3b | 4.0 | 0.033 |
| 1.4 | >4.1 | n/d |
| 1.5 | 3.7 | 0.011 |
| 1.6 | 3.8 | 0.074 |
| 1.6a | 3.8 | 0.069 |
| 1.6b | 3.6 | 0.096 |
| 1.7 | >4 | n/d |
| 2 | 3.1 | 0.152 |
| 2.1 | 2.4 | 0.32 |
| 2.2 | >4.2 | 0.042 |
| 2.3 | 2.9 | 0.069 |
| 2.4 | 3.7 | n/d |

TABLE 3-continued

Log D and High Throughput (HT) kinetic solubility data

| Example | mLogD (pH 7.4) | Kinetic solubility (mg/ml) |
|---|---|---|
| 2.5 | 2.7 | 0.327 |
| 2.6 | 3.2 | 0.142 |
| 2.7 | 3.0 | 0.164 |
| 2.8 | 3.6 | 0.068 |
| 2.9 | 2.5 | 0.057 |
| 2.10 | 4.2 | n/d |
| 2.11 | 3.6 | 0.116 |
| 2.11a | n/d | 0.131 |
| 2.11b | 3.3 | 0.118 |
| 2.12 | 3.2 | 0.027 |
| 2.13 | 3.3 | 0.067 |
| 2.14 | n/d | 0.099 |
| 2.15 | 2.7 | 0.081 |
| 2.16 | 2.7 | 0.047 |
| 3 | 3.9 | n/d |
| 4 | 3.8 | 0.029 |
| 5 | >4.0 | 0.017 |
| 6 | >4.0 | 0.012 |
| 7 | 3.3 | 0.167 |
| 7.1 | >4.2 | 0.018 |
| 8 | >4.0 | 0.037 |
| 9 | 3.5 | 0.072 |
| 10 | >4.0 | n/d |
| 10.1 | 3.7 | 0.256 |
| 10.2 | 3.7 | 0.011 |
| 11 | 3.7 | 0.12 |
| 12 | 2.4 | 0.044 |
| 12.1 | 3.1 | 0.218 |
| 12.2 | 2.6 | 0.296 |
| 13 | 2.7 | 0.207 |
| 14 | 3.9 | 0.09 |
| 14.1 | 3.4 | 0.154 |
| 15 | 3.5 | 0.089 |
| 15.1 | >4.0 | 0.051 |
| 15.2 | >4.2 | 0.044 |
| 15.3 | 3.4 | 0.164 |
| 15.4 | 3.1 | 0.207 |
| 16 | 3.5 | 0.073 |
| 16.1 | 3.2 | 0.225 |
| 16.2 | 2.1 | 0.136 |
| 16.3 | 2.5 | 0.338 |
| 16.4 | 3.6 | 0.075 |
| 17 | 3.3 | 0.292 |
| 18 | 3.5 | 0.014 |
| 19 | 3.0 | 0.128 |
| 20 | 2.3 | 0.381 |
| 20a | 2.7 | n/d |
| 20b | 2.8 | n/d |

n/d = not determined

Example 23

Permeability Assays

PAMPA

Parallel artificial membrane permeability assay (PAMPA) permeability data is a useful tool to predict passive permeability through biological lipid membranes. High passive permeability (>10×$10^{-6}$ cm/s) as determined by this assay indicates that the compound is likely to have absorption properties which make it suitable for oral administration. Passive permeability (>0.1 and <10×$10^{-6}$ cm/s) may still give good absorption properties. Many examples in Table 4 have higher Pe than 10×$10^{-6}$ cm/s, All Test compounds were formulated in DMSO to 20 mM. Final concentration of all compounds in the assay was 200 μM with final DMSO concentration of 1%. The following reference controls were used: Antipyrine, Carbamazepine, Propranolol, Ranitidine and Ketoprofen.

Test compounds were diluted to 200 μM in system buffer at pH 5.0, 6.2 and 7.4. The solutions were filtered and 150 μL transferred to a High Sensitivity 96 well UV plate. This was analysed by UV as the reference plate. A 200 μL sample of the 200 μM solution was transferred to the 'donor' plate of the PAMPA plon sandwich plate system. 200 μL of acceptor sink buffer was transferred to the 'acceptor' plate which had been previously treated with GIT-O lipid solution across the well filter. Donor and acceptor plates were sandwiched and kept in a humid environment at room temperature for 16 hours. On completion of the incubation the donor and acceptor plates were separated. 150 μL of solution was transferred from each of the donor and acceptor PAMPA sandwich plates into High Sensitivity 96 well UV plates for analysis by UV. Passive permeability (Pe $10^{-6}$ cm/second) was determined for each compound tested. Control compounds were compared with historic and literature values to ensure assay functionality. The results are shown in Table 4.

TABLE 4

| PAMPA Assay Data | | | |
|---|---|---|---|
| Example | PAMPA Pe (pH 7.4) ($\times10^{-6}$ cm/s) | PAMPA Pe (pH 6.2) ($\times10^{-6}$ cm/s) | PAMPA Pe (pH 5.0) ($\times10^{-6}$ cm/s) |
| 93.4 of PCT/GB2019/050209 | 36.4 | 38.4 | 30.9 |
| 91 of PCT/GB2019/050209 | n/d | n/d | n/d |
| 1 | 37.0 | 34.6 | 32.0 |
| 1.1 | n/d | n/d | n/d |
| 1.2 | n/d | n/d | n/d |
| 1.3 | 48.8 | 43.9 | 37.3 |
| 1.3a | n/d | 37.9 | 28.9 |
| 1.3b | 37.9 | 33.7 | 28.2 |
| 1.4 | 32.9 | 37.7 | n/d |
| 1.5 | 44.1 | 46.2 | 41.7 |
| 1.6 | 0.1 | 0.1 | 0.1 |
| 1.6a | n/d | n/d | n/d |
| 1.6b | 11.8 | 18.9 | n/d |
| 1.7 | n/d | n/d | n/d |
| 2 | 15.6 | 15.7 | 22.2 |
| 2.1 | 14.3 | 13.5 | 14.1 |
| 2.2 | 1.3 | 6.9 | 26.9 |
| 2.3 | 0.9 | 4.4 | 19.1 |
| 2.4 | n/d | n/d | n/d |
| 2.5 | 19.7 | 18.4 | 12.6 |
| 2.6 | 18.3 | 24.8 | 25.9 |
| 2.7 | 11.4 | 13.6 | 5.7 |
| 2.8 | 22.7 | 21.4 | 15.6 |
| 2.9 | 7.4 | 9.1 | 8.8 |
| 2.10 | 30.9 | 17.9 | 0.1 |
| 2.11 | 5.8 | 5.1 | 5.0 |
| 2.11a | 16.6 | 16.4 | 16.9 |
| 2.11b | 18.4 | 17.0 | 16.9 |
| 2.12 | n/d | n/d | n/d |
| 2.13 | 15.3 | 19.8 | 33.0 |
| 2.14 | 28.7 | 26.7 | 30.0 |
| 2.15 | 3.3 | 3.7 | 4.1 |
| 2.16 | 11.5 | 16.4 | 16.0 |
| 3 | n/d | n/d | n/d |
| 4 | 40.2 | 39.2 | 39.0 |
| 5 | 27.7 | 39.1 | 31.2 |
| 6 | n/d | n/d | n/d |
| 7 | 20.1 | 20.6 | 24.1 |
| 7.1 | n/d | 6.2 | 2.9 |
| 8 | 0.8 | n/d | 0.1 |
| 9 | 28.8 | 19.4 | 14.0 |
| 10 | n/d | n/d | n/d |
| 10.1 | n/d | n/d | n/d |
| 10.2 | 29.4 | n/d | 28.3 |
| 11 | n/d | n/d | 9.7 |
| 12 | 12.5 | n/d | 13.3 |
| 12.1 | 12.1 | 11.7 | 11.9 |
| 12.2 | 1.6 | 0.8 | 1.0 |

TABLE 4-continued

| PAMPA Assay Data | | | |
|---|---|---|---|
| Example | PAMPA Pe (pH 7.4) ($\times10^{-6}$ cm/s) | PAMPA Pe (pH 6.2) ($\times10^{-6}$ cm/s) | PAMPA Pe (pH 5.0) ($\times10^{-6}$ cm/s) |
| 13 | 11.1 | 12.6 | 12.0 |
| 14 | 1.7 | 1.1 | 1.0 |
| 14.1 | 2.9 | 2.8 | 2.2 |
| 15 | 20.1 | 15.1 | 15.3 |
| 15.1 | 12.3 | 13.4 | 12.6 |
| 15.2 | 15.7 | 12.0 | 14.2 |
| 15.3 | 16.6 | 14.0 | 13.3 |
| 15.4 | 14.0 | 14.3 | 12.2 |
| 16 | 21.7 | 17.3 | 17.4 |
| 16.1 | 14.1 | 15.9 | 2.2 |
| 16.2 | 9.9 | 9.6 | 8.9 |
| 16.3 | 9.2 | 7.5 | 6.2 |
| 16.4 | 14.0 | 13.5 | 12.5 |
| 17 | 0.9 | 0.3 | 0.2 |
| 18 | n/d | 0.1 | n/d |
| 19 | 16.1 | 15.5 | 14.2 |
| 20 | 10.2 | 9.0 | 12.8 |
| 20a | 10.7 | 11.7 | 10.6 |
| 20b | n/d | n/d | n/d |

n/d = not determined

Caco-2 Permeability Assay

Caco2 permeability data provides a measure of a compound's permeability, and its potential for efflux by P-glycoprotein. In general, a high apical to basolateral permeability ($>1\times10^{-6}$ cm/s) combined with a low propensity for efflux (ratio <10) can indicate that a compound has good potential for oral absorption. This assay therefore provides an indication of which compounds are likely to be suitable for oral administration. Many of the examples in Table 5 show permeability $>1\times10^{-6}$ cm/s and efflux ratios <10.

Caco-2 cells were purchased from ATCC and passaged to create a bank of cells. Cells were not used post 20 passages.

All test and reference compounds (metoprolol (passive permeability) and atenolol (pgp substrate)) were formulated in DMSO to 20 mM.

96-well plates were seeded with 9x103 Caco-2 cells/well in DMEM, 10% FBS, 1% NEAA, 1% pen/strep and maintained at 37° C., in a highly humidified atmosphere of 95% air and 5% $CO_2$. Plates were ready for use on day 21.

10 mM DMSO stock test compounds were diluted to 1 mM in DMSO. Two replicates of each test compound were included in every assay. Final concentration of donor solution was 10 μM.

Assay transport buffer (25 mM HEPES/Hanks Balanced Salt Solution (HBSS), pH7.4) was prepared to wash the cells, create lucifer yellow (LY) stock solutions, receiver solutions and blanks for the transport assay. Final concentration of LY was 10 μM. Basolateral wells were treated with 250 μL of 10 μM dosing drug solution or 250 μL Transport Buffer. Apical wells were treated with 75 μL drug dosing solution or 75 μL Transport Buffer. The two plates were sandwiched together and cells were incubated with test compounds for 2 hours, shaking at 50 rpm, 37° C., 0% $CO_2$.

A calibration curve was prepared for each compound; DMSO stock solutions were serially diluted from 300 μM to 100 μM, 30 μM, 10 μM, 3 μM, 1 μM and 0.3 μM in DMSO. 2 μL of each concentration was diluted into 198 μL of Sample Quench Solution (50% acetonitrile containing 500 nM tolbutamide). 50 μL of each calibration solution was then diluted in 50 μL Dosing Buffer (modified HBSS containing LY). Finally this plate was diluted 1:10 using a Janus robot in Robot Dilution Quench Solution (35% acetonitrile containing 250 nM tolbutamide).

Following a 2 h incubation, 50 μL of sample was removed from each well (apical and basolateral) and added to the T2 sample plate. Lucifer Yellow fluorescence was analysed using Spectrafluor Plus featuring the XFluor software to determine membrane integrity.

Fluorescence was measured at the following wavelengths: λ excitation (nm), λ emission (nm): 485, 535. The gain was set appropriately for each individual assay.

Following the fluorescence plate read, 50 μL Sample Quench Solution was then added to the T2 sample plate. Plates were diluted 1:10 and/or 1:100 into opaque 384-well plates using a Janus Robot. 1:100 dilution transfers were created sequentially directly from 1:10 dilutions. All dilutions were created using Robot Dilution Quench Solution (35% acetonitrile containing 250 nM tolbutamide). All samples were analysed by LC-MS/MS.

The results obtained were quantified against a standard calibration curve prepared for each test sample and the results controlled by analysis of the reference control compounds. The results are shown in Table 5.

TABLE 5

Caco-2 Permeability Data

| Example | Caco-2 A-B Papp ($\times 10^{-6}$ cm/s) | Caco-2 B-A Papp ($\times 10^{-6}$ cm/s) | Caco-2 Efflux Ratio |
|---|---|---|---|
| 93.4 of PCT/GB2019/050209 | <30% | <30% | n/d |
| 91 of PCT/GB2019/050209 | Poor calibration curve | Poor calibration curve | n/d |
| 1.2 | n/d | n/d | n/d |
| 1.3 | 2.8 | 2.5 | 0.9 |
| 1.3a | n/d | n/d | n/d |
| 1.3b | n/d | n/d | n/d |
| 1.4 | n/d | n/d | n/d |
| 1.5 | n/d | n/d | n/d |
| 1.6 | 0.6 | 4.7 | 8.4 |
| 1.6a | 0.6 | 3.1 | 5.6 |
| 1.6b | 0.6 | 6.2 | 9.6 |
| 1.7 | n/d | n/d | n/d |
| 2 | 3.2 | 5.7 | 1.8 |
| 2.1 | 2.3 | 12.1 | 5.2 |
| 2.2 | n/d | n/d | n/d |
| 2.3 | n/d | n/d | n/d |
| 2.4 | n/d | n/d | n/d |
| 2.5 | n/d | n/d | n/d |
| 2.6 | 2.2 | 5.3 | 2.4 |
| 2.7 | n/d | n/d | n/d |
| 2.8 | 3.7 | 5.7 | 1.6 |
| 2.9 | 0.5 | 5.5 | 10.0 |
| 2.10 | n/d | n/d | n/d |
| 2.11 | 4.7 | 4.7 | 1.0 |
| 2.11a | n/d | n/d | n/d |
| 2.11b | 2.4 | 3.3 | 1.4 |
| 2.12 | 6.5 | 6.5 | 1.0 |
| 2.13 | 2.4 | 6.1 | 2.6 |
| 2.14 | n/d | n/d | n/d |
| 2.15 | 0.2 | 8.9 | 37.1 |
| 2.16 | 2.0 | 9.0 | 4.6 |
| 3 | n/d | n/d | n/d |
| 4 | n/d | n/d | n/d |
| 5 | n/d | n/d | n/d |
| 6 | n/d | n/d | n/d |
| 7 | 4.5 | 6.7 | 1.5 |
| 7.1 | n/d | n/d | n/d |
| 8 | n/d | n/d | n/d |
| 9 | n/d | n/d | n/d |
| 10 | n/d | n/d | n/d |
| 10.1 | n/d | n/d | n/d |
| 10.2 | n/d | n/d | n/d |
| 11 | 2.4 | 5.5 | 2.3 |

TABLE 5-continued

Caco-2 Permeability Data

| Example | Caco-2 A-B Papp ($\times 10^{-6}$ cm/s) | Caco-2 B-A Papp ($\times 10^{-6}$ cm/s) | Caco-2 Efflux Ratio |
|---|---|---|---|
| 12 | 0.0 | 6.9 | 149.7 |
| 12.1 | 0.1 | 6.0 | 52.2 |
| 12.2 | n/d | n/d | n/d |
| 13 | 0.9 | 8.8 | 9.5 |
| 14 | 1.8 | 4.9 | 2.8 |
| 14.1 | 2.1 | 6.0 | 2.8 |
| 15 | 2.0 | 8.5 | 4.3 |
| 15.1 | 1.1 | 6.5 | 6.1 |
| 15.2 | n/d | n/d | n/d |
| 15.3 | 0.4 | 7.2 | 19.8 |
| 15.4 | 1.2 | 8.7 | 7.2 |
| 16 | 0.9 | 7.0 | 8.1 |
| 16.1 | 0.5 | 13.7 | 29.9 |
| 16.2 | 1.0 | 11.9 | 11.8 |
| 16.3 | 0.6 | 11.5 | 18.9 |
| 16.4 | n/d | n/d | n/d |
| 17 | 0.4 | 7.8 | 20.7 |
| 18 | 2.8 | 7.7 | 2.8 |
| 19 | 3.9 | 6.5 | 1.7 |
| 20 | 1.4 | 9.4 | 6.7 |
| 20a | n/d | n/d | n/d |
| 20b | n/d | n/d | n/d |

n/d = not determined

Example 24

Metabolic Stability Assays

Microsomal Stability

Microsomes (human) were obtained from Bioreclamation.

All Test and reference control compounds (raloxifene, diclofenac, terfenadine, propranolol, dextromethorphan and metoprolol) were dissolved to create a 100 μM stock (final concentrations; 91.5% Acetonitrile: 8.5% DMSO). Final test compound concentration in incubation was 1 μM (<0.1% DMSO).

The assay buffer is prepared from Potassium phosphate solutions 1 and 2 by combination to form a pH 7.42 solution at 37° C. Solution 1: 17.4 g potassium phosphate dibasic anhydrous ($K_2HPO_4$, 0.1 M) dissolved in 1 L deionised water. Solution 2: 13.6 g potassium phosphate monobasic anhydrous ($KH_2PO_4$, 0.1 M) dissolved in 1 L deionised water. pH7.4 with 2 mM magnesium chloride. NADPH (10 mM) is prepared in deionised water.

Microsomes (all species) were removed from the −80° C. thawed at 37° C. Microsomes were diluted in assay buffer to achieve a final protein concentration of 0.5 mg/mL and 1 mM NADPH.

The following procedure was completed on a Perkin Elmer Janus robotic platform in 96 well format: The microsomal incubation plate was transferred to a heater shaker at 300 rpm and solution heated to 37° C. for 10 min pre-warm. A no co-factor control at 0 and 45 min and one replicates of each test compound was included in every assay. Microsomes were incubated at 37° C., on a shaker set at 300 rpm throughout the assay. At each timepoint (0, 5, 15, 30, 45 min) 50 μL of sample was removed from the 96-well and added to 200 μL of quench solution (Acetonitrile containing 0.1% formic acid and imipramine/labetalol, 200 nM). Samples were diluted 1:1 with water using the Janus Robot and analysed by LC-MS/MS. The results obtained were quantified against a standard calibration curve prepared for each test sample and the results controlled by analysis of the reference control compounds.

The human microsome clearance rates for Compounds 91 and 93.4 of PCT/GB2019/050209 are 32.8 and 51 μL/min/mg respectively. For compounds intended for oral administration, however, it is advantageous for the microsome clearance rates to be significantly lower, as this improves the likelihood of achieving low first pass clearance, thus enhancing the oral bioavailability and increasing the systemic half-life of the compound, and reducing the dose required for efficacy and/or making the compounds suitable for once or twice daily dosing. Several of the Example compounds did indeed have significantly lower clearance rates than Compounds 91 and 93.4 of PCT/GB2019/050209 as shown in Table 6.

TABLE 6

Microsome clearance data

| Example | Human Microsome $CI_{int}$ (μL/min/mg) |
|---|---|
| 93.4 of PCT/GB2019/050209 | 32.8 |
| 91 of PCT/GB2019/050209 | 51.0 |
| 1 | 43.7 |
| 1.1 | 16.6 |
| 1.2 | 126.2 |
| 1.3 | 12.0 |
| 1.3a | 13.9 |
| 1.3b | 12.4 |
| 1.4 | 53.0 |
| 1.5 | 18.0 |
| 1.6 | 20.5 |
| 1.6a | 23.9 |
| 1.6b | 20.7 |
| 1.7 | 20.2 |
| 2 | <10.0 |
| 2.1 | <10.0 |
| 2.2 | 249.7 |
| 2.3 | 232.8 |
| 2.4 | 106.7 |
| 2.5 | 500.0 |
| 2.6 | 10.7 |
| 2.7 | <10.0 |
| 2.8 | <10.0 |
| 2.9 | 31.6 |
| 2.10 | 29.9 |
| 2.11 | 11.9 |
| 2.11a | 13.8 |
| 2.11b | 10.9 |
| 2.12 | <10.0 |
| 2.13 | 11.7 |
| 2.14 | n/d |
| 2.15 | 29.5 |
| 2.16 | <10.0 |
| 3 | 15.4 |
| 4 | 14.5 |
| 5 | 24.7 |
| 6 | 14.5 |
| 7 | 18.9 |
| 7.1 | 44.4 |
| 8 | 15.7 |
| 9 | <10.0 |
| 10 | 31.6 |
| 10.1 | 22.5 |
| 10.2 | 24.7 |
| 11 | 36.3 |
| 12 | <10.0 |
| 12.1 | 15.5 |
| 12.2 | <10.0 |
| 13 | <10.0 |
| 14 | <10.0 |

TABLE 6-continued

Microsome clearance data

| Example | Human Microsome $CI_{int}$ (μL/min/mg) |
|---|---|
| 14.1 | 12.7 |
| 15 | <10.0 |
| 15.1 | 10.4 |
| 15.2 | <10.0 |
| 15.3 | <10.0 |
| 15.4 | <10.0 |
| 16 | <10.0 |
| 16.1 | 135.7 |
| 16.2 | <10.0 |
| 16.3 | 63.7 |
| 16.4 | <10.0 |
| 17 | <10.0 |
| 18 | <10.0 |
| 19 | <10.0 |
| 20 | 12.0 |
| 20a | <10.0 |
| 20b | <10.0 |

n/d = not determined.

Hepatic Stability

Cryopreserved hepatocytes (human) were obtained from Bioreclamation.

Test compounds and reference controls (raloxifene, diclofenac, terenadine, propranolol, dextromethorphan and metoprolol) were dissolved in a 100 μM stock was prepared by diluting 5 μL of 4 mM (DMSO) in 195 μL of 50:50 DMSO:hepatocyte buffer. Final test compound concentration in incubation was 1 μM.

The hepatocyte buffer was prepared (Williams E media containing phenol red and Glutamax™, 15 mM HEPES, warmed to 37° C., pH7.4 with NaOH). Hepatocyte cells (all main species) were removed from liquid nitrogen, thawed in a waterbath, decanted into 50 mL of pre-warmed Cryopreserved Hepatocyte Recovery Media (LifeTechnologies) and centrifuged. Supernatant fraction was removed, cells were re-suspended in hepatocyte buffer and counted by trypan blue exclusion. Cell viability of >80% was required for all assays.

Cells were re-suspended to 1×106/mL and 198 μL cell suspension added to each 96-well. 2 μL of 100 μM compound stock solution was added to relevant wells to initiate the incubation. A no cell control and two replicates of each test compound was included in every assay. Cells were incubated at 37° C., on a shaker set at 300 rpm. At each timepoint (0, 15, 30, 45, 60, 90 min) 20 μL of sample was removed from the 96-well and added to 80 μL of quench solution (Acetonitrile containing 0.1% formic acid and imipramine/labetalol, 200 nM). Samples were diluted 1:1 with water using the Janus Robot and analysed by LC-MS/MS. The results obtained were quantified against a standard calibration curve prepared for each test sample and the results controlled by analysis of the reference control compounds.

The results are shown in Table 7. Again, it is advantageous for compounds intended for oral administration to have low in vitro hepatocyte clearance as this improves the likelihood of achieving low first pass clearance which, in turn, enhances the oral bioavailability lowers the dose need for efficacy and increases the systemic half-life, making the compounds potentially suitable for once or twice daily dosing. Table 5 below shows the example compounds for which the human hepatocyte clearance data was comparable with or, in some cases, more favourable than the data for Compounds 91 and 93.4 of PCT/GB2019/050209.

TABLE 7

| Hepatocyte clearance data | |
|---|---|
| Example | Human Hepatocyte $CI_{int}$ (μL/min/million cells) |
| 93.4 of PCT/GB2019/050209 | 24.1 |
| 91 of PCT/GB2019/050209 | 15.6 |
| 1 | 26.1 |
| 1.1 | 18.0 |
| 1.2 | 38.7 |
| 1.3 | 22.4 |
| 1.3a | 27.2 |
| 1.3b | 23.4 |
| 1.4 | 20.8 |
| 1.5 | 20.0 |
| 1.6 | 28.2 |
| 1.6a | 20.7 |
| 1.6b | 30.7 |
| 1.7 | 11.4 |
| 2 | 6.6 |
| 2.1 | 7.9 |
| 2.2 | 125.3 |
| 2.3 | 72.0 |
| 2.4 | 69.8 |
| 2.5 | 120.1 |
| 2.6 | 7.1 |
| 2.7 | 45.4 |
| 2.8 | 12.4 |
| 2.9 | 10.4 |
| 2.10 | 11.3 |
| 2.11 | 10.3 |
| 2.11a | 15.5 |
| 2.11b | 6.3 |
| 2.12 | 16.9 |
| 2.13 | 6.3 |
| 2.14 | 13.1 |
| 2.15 | 3.2 |
| 2.16 | 5.8 |
| 3 | 65.3 |
| 4 | 19.6 |
| 5 | 33.3 |
| 6 | 14.0 |
| 7 | 14.9 |
| 7.1 | 149.6 |
| 8 | 20.9 |
| 9 | 24.5 |
| 10 | 15.8 |
| 10.1 | 10.8 |
| 10.2 | 13.9 |
| 11 | 131.6 |
| 12 | 3.7 |
| 12.1 | 7.3 |
| 12.2 | 7.8 |
| 13 | 7.8 |
| 14 | 8.3 |
| 14.1 | 9.1 |
| 15 | 7.8 |
| 15.1 | 13.3 |
| 15.2 | 9.9 |
| 15.3 | 8.6 |
| 15.4 | 6.7 |
| 16 | 8.1 |
| 16.1 | 15.2 |
| 16.2 | 5.2 |
| 16.3 | 5.8 |
| 16.4 | 12.5 |
| 17 | 7.2 |
| 18 | 6.9 |
| 19 | 10.5 |
| 20 | 6.7 |
| 20a | 7.2 |
| 20b | 32.2 |

REFERENCES

Accurso F J, Moss R B, Wilmott R W, Anbar R D, Schaberg A E, Durham T A, Ramsay B W; TIGER-1 Investigator Study Group (2011) Denufosol tetrasodium in patients with cystic fibrosis and normal to mildly impaired lung function. Am J Respir Crit Care Med, 183(5):627-634.

Boucher R C (2007) Evidence for airway surface dehydration as the initiating event in CF airway disease. J Intern Med., 261(1):5-16.

Caputo A, Caci E, Ferrera L, Pedemonte N, Barsanti C, Sondo E, Pfeffer U, Ravazzolo R, Zegarra-Moran O & Galietta L J (2008) TMEM16A, a membrane protein associated with calcium-dependent chloride channel activity. Science, 322(5901):590-594.

Del La Fuente R, Namkung W, Mills A & Verkman A S (2008) Small molecule screen identifies inhibitors of a human intestinal calcium-activated chloride channel. Mol Pharmacol, 73(3):758-768.

Gupta D, Bhatia D, Dave V, Sutariya V & Gupta S V (2018) Salts of Therapeutic Agents: Chemical, Physicochemical, and Biological Considerations. Molecules, 23, 1719.

Kellerman D, Rossi Mospan A, Engels J, Schaberg A, Gorden J & Smiley L (2008) Denufosol: a review of studies with inhaled P2Y(2) agonists that led to Phase 2. Pulm Pharmacol Ther, 21(4):600-607.

Kunzelmann K & Mall M (2003) Pharmacotherapy of the ion transport defect in cystic fibrosis: role of purinergic receptor agonists and other potential therapeutics. Am J Respir Med, 2(4):299-309.

Matsui H, Grubb B R, Tarran R, Randell S H, Gatzy J T, Davis C W and Boucher R C (1998) Evidence for periciliary liquid layer depletion, not abnormal ion composition, in the pathogenesis of cystic fibrosis airways disease. Cell, 95(7):1005-15.

Moss R B (2013) Pitfalls of drug development: lessons learned from trials of denufosol in cystic fibrosis. J Pediatr, 162(4):676-680.

Pedemonte N & Galietta L J (2014) Structure and function of TMEM16 proteins (anoctamins). Physiol Rev, 94(2):419-459.

Pezzulo A A, Tang X X, Hoegger M J, Abou Alaiwa M H, Ramachandran S, Moninger T O, Karp P H, Wohlford-Lenan C L, Haagsman H P, van Eijk M, Banfi B, Horswill A R, Stoltz D A, McCray P B Jr, Welsh M J & Zabner J (2012) reduced airway surface pH impairs bacterial killing in the porcine cystic fibrosis lung. Nature, 487(7405):109-113.

Yang Y D, Cho H, Koo J Y, Tak M H, Cho Y, Shim W S, Park S P, Lee J, Lee B, Kim B M, Raouf R, Shin Y K & Oh U (2008) TMEM16 confers receptor-activated calcium-dependent chloride conductance. Nature, 455(7217):1210-1215.

The invention claimed is:

1. A compound of general formula (I) or a pharmaceutically acceptable salt thereof:

(I)

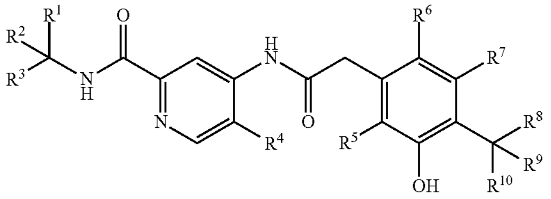

wherein:

$R^1$ is selected from methyl, fluoromethyl, difluoromethyl, trifluoromethyl, chlorodifluoromethyl, dichlorofluoromethyl, ethynyl and CN; or $R^2$ is selected from methyl and $CH_2OH$;

$R^3$ is selected from H and methyl; or $R^2$ and $R^3$ together with the carbon atom to which they are attached form a 3- to 10-membered carbocyclic or oxygen-containing heterocyclic ring system, either of which is optionally substituted, in addition to the $R^1$ group, with one or more substituents selected from OH, halo, $C_{1-4}$ alkyl, $C_{1-4}$ alkyl substituted with one or more OH substituents, and $C_{1-4}$ haloalkyl; or when $R^2$ and $R^3$ together with the carbon atom to which they are attached form a 4- to 6-membered carbocyclic ring substituted, in addition to the $R^1$ group, with OH, halo, methyl or $CH_2OH$, $R^1$ may also be H; or when $R^2$ and $R^3$ together with the carbon atom to which they are attached form a 4- to 6-membered carbocyclic ring, which is unsubstituted apart from the $R^1$ group; $R^1$ may also be $CH_2OH$; or $R^1$, $R^2$ and $R^3$ together with the carbon atom to which they are attached combine to form a 5- to 8-membered bridged carbocyclic or heterocyclic ring system optionally substituted with one or more substituents selected from OH, halo, $C_{1-4}$ alkyl and $C_{1-4}$ haloalkyl;

$R^4$ is H or halo;

each of $R^5$ and $R^7$ is independently selected from H, halo, $C_{1-3}$ alkyl and $C_{1-3}$ haloalkyl;

$R^6$ is selected from halo, CN and $C_{1-4}$ alkyl optionally substituted with one or more substituents selected from halo and OH;

$R^8$ is methyl or ethyl, either of which is optionally substituted with one or more halogen substituents;

$R^9$ is OH, $CH_2OH$ or methyl or ethyl, either of which is optionally substituted with one or more halogen substituents; or $R^8$ and $R^9$ together with the carbon atom to which they are attached form either a 3- to 6-membered cycloalkyl or oxygen-containing heterocyclic ring optionally substituted, in addition to the $R^{10}$ group, with one or more substituents selected from OH, F and $CH_2OH$; or an ethenyl group optionally substituted with one or two halogen substituents;

$R^{10}$ is selected from H, CN, OH, cycloalkyl optionally substituted with OH, and $C_{1-4}$ alkyl optionally substituted with one or more substituents selected from halo, OH and a 3- to 6-membered cycloalkyl or heterocyclic group, either of which is optionally substituted with OH; or $R^8$, $R^9$ and $R^{10}$ together with the carbon atom to which they are attached form a 5- to 8-membered fused or bridged carbocyclic ring system optionally substituted with one or more substituents selected from OH, F and $CH_2OH$;

provided that:

i. when $R^5$ and $R^7$ are H and $R^6$ is H or F, $R^1$, $R^2$, $R^3$, $R^8$, $R^9$ and $R^{10}$ are not all methyl; and ii. when $R^2$, $R^3$, $R^8$, $R^9$ and $R^{10}$ are all methyl, $R^5$, $R^6$ and $R^7$ are not all H; and iii. when $R^1$ is CN and $R^2$ and $R^3$ together with the carbon atom to which they are attached form a 3- to 10-membered oxygen-containing heterocyclic ring, $R^8$, $R^9$ and $R^{10}$ are not all methyl; and iv. $R^9$ and $R^{10}$ are not both OH.

2. A compound according to claim 1, wherein either:

$R^8$ and $R^9$ together with the carbon atom to which they are attached form a 3- to 6-membered cycloalkyl or oxygen-containing heterocyclic ring substituted, in addition to the $R^{10}$ group, with one or more $CH_2OH$ substituents and optionally with one or more further substituents selected from OH and F; or $R^8$ and $R^9$ together with the carbon atom to which they are attached form a 3- to 6-membered cycloalkyl or oxygen-containing heterocyclic ring optionally substituted, in addition to the $R^{10}$ group, with one or more substituents selected from OH and F; and $R^{10}$ is CN or $C_{1-4}$ alkyl substituted with one or more substituents selected from OH, a 3- to 6-membered cycloalkyl group optionally substituted with OH and a 3- to 6-membered heterocyclic group optionally substituted with OH; or $R^8$ and $R^9$ together with the carbon atom to which they are attached form an ethenyl group optionally substituted with one or two halogen substituents; or $R^8$, $R^9$ and $R^{10}$ together with the carbon atom to which they are attached form a 5- to 8-membered fused or bridged carbocyclic ring system substituted with one or more $CH_2OH$ substituents and optionally with one or more further substituents selected from OH and F.

3. A compound according to claim 2, wherein either:

$R^8$ and $R^9$ together with the carbon atom to which they are attached form a 3- to 6-membered cycloalkyl or oxygen-containing heterocyclic ring system which is unsubstituted except for the $R^{10}$ group; and $R^{10}$ is selected from CN and $CH_2OH$; or $R^8$, $R^9$ and $R^{10}$ together with the carbon atom to which they are attached form a 5- to 8-membered fused or bridged carbocyclic ring system substituted with $CH_2OH$.

4. A compound according to claim 1, wherein:

$R^8$ is methyl or ethyl, either of which is optionally substituted with one or more halogen substituents; and $R^9$ is OH, $CH_2OH$ or methyl or ethyl, either of which is optionally substituted with one or more halogen substituents; or $R^8$ and $R^9$ together with the carbon atom to which they are attached form a 3- to 6-membered cycloalkyl or oxygen-containing heterocyclic ring optionally substituted, in addition to the $R^{10}$ group, with one or more substituents selected from OH and F, and $R^{10}$ is H, OH or $C_{1-4}$ alkyl optionally substituted with one or more halo substituents; or $R^8$, $R^9$ and $R^{10}$ together with the carbon atom to which they are attached form a 5- to 8-membered fused or bridged carbocyclic ring system optionally substituted with one or more substituents selected from OH and F.

5. A compound according to claim 4, wherein:

$R^8$ is methyl or ethyl, $R^9$ is OH or $CH_2OH$ and $R^{10}$ is methyl or ethyl;

$R^8$ is methyl or ethyl, $R^9$ is methyl or ethyl and $R^{10}$ is OH or $C_{1-4}$ alkyl substituted with OH; or $R^8$, $R^9$ and $R^{10}$ are all methyl.

6. A compound according to claim 1, wherein $R^1$ is methyl, difluoromethyl, trifluoromethyl, ethynyl or CN.

7. A compound according to claim 1, wherein either:

$R^2$ is methyl and/or $R^3$ is H or methyl; or $R^2$ and $R^3$ together with the carbon atom to which they are attached form a 3- to 6-membered cycloalkyl or oxygen-containing heterocyclic ring system, optionally substituted, in addition to $R^1$, with one or more substituents selected from OH, halo, $C_{1-4}$ alkyl and $C_{1-4}$ haloalkyl; or $R^1$ is H and $R^2$ and $R^3$ together with the carbon atom to which they are attached form a 4- to 6-membered carbocyclic ring substituted with OH; or $R^1$ is trifluoromethyl; and $R^2$ and $R^3$ together with the carbon atom to which they are attached form a cyclopropyl ring which is unsubstituted except for $R^1$.

8. A compound according to claim 1, wherein:

$R^4$ is H; and/or each of $R^5$ and $R^7$ is H; and/or $R^6$ is halo, CN, $CH_3$, $CF_3$, $CHF_2$, $CH_2F$ or $CH_2OH$.

9. A compound selected from:

4-[[2-(4-tert-Butyl-2-fluoro-5-hydroxy-phenyl)acetyl]amino]-N-(1-methylcyclopropyl)pyridine-2-carboxamide (Compound 1);

4-[2-(4-tert-Butyl-2-fluoro-5-hydroxy-phenyl)acetyl]amino]-N-(1,1-dimethylprop-2-ynyl)pyridine-2-carboxamide (Compound 1.1);

4-[[2-(4-tert-Butyl-2-fluoro-5-hydroxy-phenyl)acetyl]amino]-N-(1-ethynylcyclopentyl)pyridine-2-carboxamide (Compound 1.2);

4-[[2-(4-tert-Butyl-2-fluoro-5-hydroxy-phenyl)acetyl]amino]-N-(1-cyanoethyl)pyridine-2-carboxamide (Compound 1.3);

4-[[2-(4-tert-Butyl-2-fluoro-5-hydroxy-phenyl)acetyl]amino]-N-[(1R)-1-cyanoethyl]pyridine-2-carboxamide (Compound 1.3a/b);

4-[[2-(4-tert-butyl-2-fluoro-5-hydroxy-phenyl)acetyl]amino]-N-[(1S)-1-cyanoethyl]pyridine-2-carboxamide (Compound 1.3 a/b);

4-[[2-(4-tert-Butyl-2-fluoro-5-hydroxy-phenyl)acetyl]amino]-N-(1-cyano-1-methyl-ethyl)pyridine-2-carboxamide (Compound 1.4);

4-[[2-(4-tert-Butyl-2-fluoro-5-hydroxy-phenyl)acetyl]amino]-N-(1-cyanocyclopropyl)pyridine-2-carboxamide (Compound 1.5);

4-[[2-(4-tert-Butyl-2-fluoro-5-hydroxy-phenyl)acetyl]amino]-N-(1-cyano-2-hydroxy-1-methyl-ethyl)pyridine-2-carboxamide (Compound 1.6);

4-[[2-(4-tert-Butyl-2-fluoro-5-hydroxy-phenyl)acetyl]amino]-N-[(1R)-1-cyano-2-hydroxy-1-methyl-ethyl]pyridine-2-carboxamide (Compound 1.6 a/b);

4-[[2-(4-tert-butyl-2-fluoro-5-hydroxy-phenyl)acetyl]amino]-N-[(1S)-1-cyano-2-hydroxy-1-methyl-ethyl]pyridine-2-carboxamide (Compound 1.6 a/b);

4-[[2-(4-tert-Butyl-2-fluoro-5-hydroxy-phenyl)acetyl]amino]-N-[1-(trifluoromethyl)cyclopropyl]pyridine-2-carboxamide (Compound 1.7);

4-[[2-[2-Fluoro-5-hydroxy-4-(1-hydroxy-1-methyl-ethyl)phenyl]acetyl]amino]-N-[1-(trifluoromethyl)cyclopropyl]pyridine-2-carboxamide (Compound 2);

N-(1-Cyano-1-methyl-ethyl)-4-[[2-[2-fluoro-5-hydroxy-4-(1-hydroxy-1-methyl-ethyl)phenyl]acetyl]amino]pyridine-2-carboxamide (Compound 2.1);

N-tert-Butyl-4-[[2-[4-(1-cyano-1-methyl-ethyl)-2-fluoro-5-hydroxy-phenyl]acetyl]amino]pyridine-2-carboxamide (Compound 2.2);

4-[[2-[4-(1-Cyano-1-methyl-ethyl)-2-fluoro-5-hydroxy-phenyl]acetyl]amino]-N-[1-(trifluoromethyl)cyclopropyl]pyridine-2-carboxamide (Compound 2.3);

N-tert-Butyl-4-[2-[4-(1-cyanocyclopropyl)-2-fluoro-5-hydroxy-phenyl]acetyl]amino]pyridine-2-carboxamide (Compound 2.4);

N-(1-Cyano-1-methyl-ethyl)-4-[2-[4-(1,1-dimethyl-2-morpholino-ethyl)-2-fluoro-5-hydroxy-phenyl]acetyl]amino]pyridine-2-carboxamide (Compound 2.5);

4-[[2-[2-fluoro-5-hydroxy-4-(2-hydroxy-1,1-dimethyl-ethyl) phenyl]acetyl]amino]-N-[1-(trifluoromethyl)cyclopropyl]pyridine-2-carboxamide (Compound 2.6);

N-(1-Cyano-1-methyl-ethyl)-4-[[2-[2-fluoro-5-hydroxy-4-(2,2,2-trifluoro-1-hydroxy-1-methyl-ethyl)phenyl]acetyl]amino]pyridine-2-carboxamide (Compound 2.7);

4-[[2-[4-(1-Cyclopropyl-1-hydroxy-ethyl)-2-fluoro-5-hydroxy-phenyl]acetyl]amino]-N-[1-(trifluoromethyl)cyclopropyl]pyridine-2-carboxamide (Compound 2.8);

4-[[2-[4-(4-Cyanotetrahydropyran-4-yl)-2-fluoro-5-hydroxy-phenyl]acetyl]amino]-N-[1-(trifluoromethyl)cyclopropyl]pyridine-2-carboxamide (Compound 2.9);

4-[[2-[2-Fluoro-5-hydroxy-4-[2-(trifluoromethyl) oxetan-2-yl]phenyl]acetyl]amino]-N-[1-(trifluoromethyl)cyclopropyl]pyridine-2-carboxamide (Compound 2.10);

4-[[2-[2-Fluoro-5-hydroxy-4-(1-hydroxy-1-methyl-propyl)phenyl]acetyl]amino]-N-[1-(trifluoromethyl)cyclopropyl]pyridine-2-carboxamide (Compound 2.11);

4-[[2-[2-Fluoro-5-hydroxy-4-[(1S)-1-hydroxy-1-methyl-propyl]phenyl]acetyl]amino]-N-[1-(trifluoromethyl)cyclopropyl]pyridine-2-carboxamide (Compound 2.11 a/b);

4-[[2-[2-fluoro-5-hydroxy-4-[(1R)-1-hydroxy-1-methyl-propyl]phenyl]acetyl]amino]-N-[1-(trifluoromethyl)cyclopropyl]pyridine-2-carboxamide (Compound 2.11 a/b);

4-[[2-[5-Hydroxy-4-(1-hydroxy-1-methyl-ethyl)-2-methyl-phenyl]acetyl]amino]-N-[1-(trifluoromethyl)cyclopropyl]pyridine-2-carboxamide (Compound 2.12);

4-[[2-[2-Fluoro-5-hydroxy-4-[1-(hydroxymethyl)cyclobutyl]phenyl]acetyl]amino]-N-[1-(trifluoromethyl)cyclopropyl]pyridine-2-carboxamide (Compound 2.13);

N-(1-Cyano-1-methyl-ethyl)-4-[[2-[2-fluoro-5-hydroxy-4-[2-(trifluoromethyl)oxetan-2-yl]phenyl]acetyl]amino]pyridine-2-carboxamide (Compound 2.14);

4-[[2-[2-Fluoro-5-hydroxy-4-[4-(hydroxymethyl)tetrahydropyran-4-yl] phenyl]acetyl]amino]-N-[1-(trifluoromethyl)cyclopropyl]pyridine-2-carboxamide (Compound 2.15);

4-[[2-[2-Fluoro-5-hydroxy-4-[1-(hydroxymethyl)cyclopropyl]phenyl]acetyl]amino]-N-[1-(trifluoromethyl)cyclopropyl]pyridine-2-carboxamide (Compound 2.16);

4-[[2-(4-tert-Butyl-2-fluoro-5-hydroxy-phenyl)acetyl]amino]-N-(1-cyano-1-methyl-ethyl)-5-fluoro-pyridine-2-carboxamide (Compound 3);

N-(1-Cyanocyclopropyl)-4-[[2-[2-deuterio-6-fluoro-3-hydroxy-4-[2,2,2-trideuterio-1,1-bis(trideuteriomethyl)ethyl]phenyl]acetyl]amino]pyridine-2-carboxamide (Compound 4);

N-(1-Cyano-1-methyl-ethyl)-4-[2-[2-fluoro-5-hydroxy-4-(1-methylcyclo butyl)phenyl]acetyl]amino]pyridine-2-carboxamide (Compound 5);

N-tert-Butyl-4-[[2-(4-tert-butyl-5-hydroxy-2-isopropyl-phenyl)acetyl]amino]pyridine-2-carboxamide (Compound 6);

N-tert-Butyl-4-[[2-[2-fluoro-5-hydroxy-4-(1-hydroxy-1-methyl-ethyl)phenyl]acetyl]amino]pyridine-2-carboxamide (Compound 7);

4-[[2-(2-Fluoro-5-hydroxy-4-isopropenyl-phenyl)acetyl]amino]-N-[1-(trifluoromethyl) cyclopropyl]pyridine-2-carboxamide (Compound 7.1);

N-tert-Butyl-4-[[2-[2-fluoro-5-hydroxy-4-(1-methylcyclopropyl)phenyl]acetyl]amino]pyridine-2-carboxamide (Compound 8);

N-(1-Cyanocyclopropyl)-4-[[2-[2-fluoro-5-hydroxy-4-[1-(trifluoromethyl) cyclopropyl]phenyl]acetyl]amino] pyridine-2-carboxamide (Compound 9);

4-[[2-(4-tert-Butyl-2-chloro-5-hydroxy-phenyl)acetyl] amino]-N-(1-cyano-1-methyl-ethyl)pyridine-2-carboxamide (Compound 10);

4-[[2-(4-tert-Butyl-2-chloro-5-hydroxy-phenyl)acetyl] amino]-N-[1-(trifluoromethyl) cyclopropyl]pyridine-2-carboxamide (Compound 10.1);

4-[[2-(4-tert-Butyl-2-chloro-5-hydroxy-phenyl)acetyl] amino]-N-(1-cyanocyclopropyl) pyridine-2-carboxamide (Compound 10.2);

4-[[2-[2-Fluoro-5-hydroxy-4-(3-hydroxy-1,1-dimethyl-propyl) phenyl]acetyl]amino]-N-[1-(trifluoromethyl) cyclopropyl]pyridine-2-carboxamide (Compound 11);

N-(4-Cyanotetrahydropyran-4-yl)-4-[[2-[2-fluoro-5-hydroxy-4-(2-hydroxy-1,1-dimethyl-ethyl)phenyl]acetyl] amino]pyridine-2-carboxamide (Compound 12);

4-[[2-[2-Fluoro-5-hydroxy-4-(2-hydroxy-1,1-dimethyl-ethyl) phenyl]acetyl]amino]-N-[3-(trifluoromethyl) oxetan-3-yl]pyridine-2-carboxamide (Compound 12.1);

4-[[2-[2-Fluoro-5-hydroxy-4-(2-hydroxy-1,1-dimethyl-ethyl) phenyl]acetyl]amino]-N-[(1S,2S)-2-hydroxycyclopentyl]pyridine-2-carboxamide (Compound 12.2);

4-[[2-[2-Fluoro-5-hydroxy-4-(2-hydroxy-1,1-dimethyl-ethyl) phenyl]acetyl]amino]-N-(2-hydroxy-1,1-dimethyl-ethyl)pyridine-2-carboxamide (Compound 12.3);

4-[[2-[2-Fluoro-5-hydroxy-4-(2-hydroxy-1,1-dimethyl-ethyl) phenyl]acetyl]amino]-N-[1-(hydroxymethyl)cyclobutyl]pyridine-2-carboxamide (Compound 12.4);

4-[[2-[2-Fluoro-5-hydroxy-4-(4-hydroxytetrahydropyran-4-yl) phenyl]acetyl]amino]-N-[1-(trifluoromethyl) cyclopropyl]pyridine-2-carboxamide (Compound 13);

4-[[2-[2-Chloro-5-hydroxy-4-(2-hydroxy-1,1-dimethyl-ethyl) phenyl]acetyl]amino]-N-[1-(trifluoromethyl)cyclopropyl]pyridine-2-carboxamide (Compound 14);

4-[[2-[5-Hydroxy-4-(2-hydroxy-1,1-dimethyl-ethyl)-2-methyl-phenyl]acetyl]amino]-N-[1-(trifluoromethyl) cyclopropyl]pyridine-2-carboxamide (Compound 14.1);

N-(3,3-Difluoro-1-methyl-cyclobutyl)-4-[[2-[2-fluoro-5-hydroxy-4-(2-hydroxy-1,1-dimethyl-ethyl)phenyl] acetyl]amino]pyridine-2-carboxamide (Compound 15);

4-[[2-[2-Chloro-5-hydroxy-4-(2-hydroxy-1,1-dimethyl-ethyl) phenyl]acetyl]amino]-N-(1,1-dimethylprop-2-ynyl)pyridine-2-carboxamide (Compound 15.1);

4-[[2-[2-Chloro-5-hydroxy-4-(2-hydroxy-1,1-dimethyl-ethyl) phenyl]acetyl]amino]-N-(3,3-difluoro-1-methyl-cyclobutyl)pyridine-2-carboxamide (Compound 15.2);

4-[[2-[2-Chloro-5-hydroxy-4-(2-hydroxy-1,1-dimethyl-ethyl) phenyl]acetyl]amino]-N-[1-(difluoromethyl)cyclopropyl]pyridine-2-carboxamide (Compound 15.3);

N-[1-(Difluoromethyl)cyclopropyl]-4-[[2-[2-fluoro-5-hydroxy-4-(2-hydroxy-1,1-dimethyl-ethyl)phenyl]acetyl] amino]pyridine-2-carboxamide (Compound 15.4);

N-(1,1-Dimethylprop-2-ynyl)-4-[[2-[2-fluoro-5-hydroxy-4-(2-hydroxy-1,1-dimethyl-ethyl)phenyl]acetyl] amino]pyridine-2-carboxamide (Compound 16);

4-[[2-[2-Fluoro-5-hydroxy-4-(2-hydroxy-1,1-dimethyl-ethyl)phenyl]acetyl]amino]-N-(4-methyltetrahydropyran-4-yl)pyridine-2-carboxamide (Compound 16.1);

N-(1-Cyano-1-methyl-ethyl)-4-[[2-[2-fluoro-5-hydroxy-4-(2-hydroxy-1,1-dimethyl-ethyl)phenyl]acetyl] amino]pyridine-2-carboxamide (Compound 16.2);

4-[[2-[2-Fluoro-5-hydroxy-4-(2-hydroxy-1-methyl-ethyl) phenyl]acetyl]amino]-N-(4-methyltetrahydropyran-4-yl)pyridine-2-carboxamide (Compound 16.3);

4-[[2-[2,6-Difluoro-3-hydroxy-4-(2-hydroxy-1,1-dimethyl-ethyl)phenyl]acetyl]amino]-N-[1-(trifluoromethyl)cyclopropyl]pyridine-2-carboxamide (Compound 16.4);

4-[[2-[2-Fluoro-5-hydroxy-4-[2,2,2-trifluoro-1-(hydroxymethyl)ethyl]phenyl]acetyl]amino]-N-[1-(trifluoromethyl)cyclopropyl]pyridine-2-carboxamide (Compound 17);

4-[[2-[2-Chloro-6-fluoro-3-hydroxy-4-(1-hydroxy-1-methyl-ethyl)phenyl]acetyl]amino]-N-[1-(trifluoromethyl)cyclopropyl]pyridine-2-carboxamide (Compound 18);

4-[[2-[2-Chloro-5-hydroxy-4-(1-hydroxy-1-methyl-ethyl)phenyl]acetyl]amino]-N-[1-(trifluoromethyl)cyclopropyl]pyridine-2-carboxamide (Compound 19);

4-[[2-[2-Fluoro-5-hydroxy-4-(2-hydroxy-1-methyl-ethyl) phenyl]acetyl]amino]-N-[1-(trifluoromethyl)cyclopropyl]pyridine-2-carboxamide (Compound 20);

4-[[2-[2-Fluoro-5-hydroxy-4-[(1S)-2-hydroxy-1-methyl-ethyl]phenyl]acetyl]amino]-N-[1-(trifluoromethyl)cyclopropyl]pyridine-2-carboxamide (Compound 20a/b);

4-[[2-[2-fluoro-5-hydroxy-4-[(1R)-2-hydroxy-1-methyl-ethyl]phenyl]acetyl]amino]-N-[1-(trifluoromethyl)cyclopropyl]pyridine-2-carboxamide (Compound 20a/b);

and salts and solvates of the above.

10. The compound of claim 9 which is 4-[[2-(4-tert-Butyl-2-fluoro-5-hydroxy-phenyl)acetyl]amino]-N-(1-cyanocyclopropyl)pyridine-2-carboxamide (Compound 1.5); or a salt or solvate thereof.

11. The compound of claim 9 which is N-(1-Cyanocyclopropyl)-4-[[2-[2-deuterio-6-fluoro-3-hydroxy-4-[2,2,2-trideuterio-1,1-bis(trideuteriomethyl)ethyl]phenyl]acetyl] amino]pyridine-2-carboxamide (Compound 4); or a salt or solvate thereof.

12. The compound of claim 9 which is 4-[[2-[2-Fluoro-5-hydroxy-4-[2,2,2-trifluoro-1-(hydroxymethyl)ethyl]phenyl]acetyl]amino]-N-[1-(trifluoromethyl)cyclopropyl]pyridine-2-carboxamide (Compound 17); or a salt or solvate thereof.

13. The compound of claim 9 which is 4-[[2-(4-tert-Butyl-2-chloro-5-hydroxy-phenyl)acetyl]amino]-N-[1-(trifluoromethyl)cyclopropyl]pyridine-2-carboxamide (Compound 10.1); or a salt or solvate thereof.

14. A pharmaceutical composition comprising a compound according to a claim 1 and a pharmaceutically acceptable excipient.

* * * * *